US008065092B2

(12) United States Patent
Khan et al.

(10) Patent No.: US 8,065,092 B2
(45) Date of Patent: *Nov. 22, 2011

(54) METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

(75) Inventors: Javed Khan, Derwood, MD (US); Markus Ringnér, Lund (SE); Carsten Peterson, Lund (SE); Paul Meltzer, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/858,674

(22) Filed: Aug. 18, 2010

(65) Prior Publication Data

US 2010/0312486 A1 Dec. 9, 2010

Related U.S. Application Data

(63) Continuation of application No. 11/928,901, filed on Oct. 30, 2007, now Pat. No. 7,783,431, which is a continuation of application No. 10/133,937, filed on Apr. 25, 2002, now Pat. No. 7,774,143.

(51) Int. Cl.
G06F 19/00 (2011.01)
G06F 17/10 (2006.01)
G06N 3/00 (2006.01)
G06G 7/00 (2006.01)
G06G 7/58 (2006.01)

(52) U.S. Cl. .................. 702/19; 702/13; 702/15; 703/2; 703/11

(58) Field of Classification Search .................... None
See application file for complete search history.

(56) References Cited

U.S. PATENT DOCUMENTS

| 6,794,137 B2 | 9/2004 | Blumenberg |
| 7,062,384 B2 | 6/2006 | Rocke et al. |
| 7,229,774 B2 | 6/2007 | Chinnaiyan et al. |
| 7,341,552 B2 | 3/2008 | Zhang et al. |
| 7,370,021 B2 | 5/2008 | Reeve et al. |
| 7,384,736 B2 | 6/2008 | Hakonarson |
| 7,402,388 B2 | 7/2008 | Gillis et al. |
| 7,402,399 B2 | 7/2008 | Mukherjeei et al. |
| 7,774,143 B2 | 8/2010 | Khan et al. |
| 7,783,431 B2 | 8/2010 | Khan et al. |
| 2003/0207278 A1 | 11/2003 | Khan et al. |
| 2004/0009154 A1 | 1/2004 | Khan et al. |
| 2008/0181896 A1 | 7/2008 | Khan et al. |

OTHER PUBLICATIONS

Agilent Technology Webpage, dated Aug. 16, 2007.
Ancoca et al., "On the statistical assessment of classifiers using DNA microarray data", *BMC Bioinformatics*, 7:387 (2006).
Blast Alignment between GenBank Accession No. NM_000612 and SEQ ID No. 72, dated Aug. 16, 2007.
Chen et al., "Diagnosis of the Small Round Blue Cell Tumors Using Multiplex Polymerase Chain Reaction", *Journal of Molecular Diagnostics*, 9(1):80-88 (2007).
Cover page of Nature Medicine, vol. 7, No. 6, Jun. 2001.
ECgene Summary for CCND1 available via URL: <genome.ewha.ac.kr/cgi-bin/ECquery.cgi?organism=human&query=CCND1>, printed May 29, 2008.
ECgene Summary for IGF2 available via URL: <genome.ewha.ac.kr/cgi-bin/ECquery.cgi?organism=human&query=IGF2>, printed May 29, 2008.
Furey et al., *Bioinformatics*, 16(10):906-914 (2000).
GenBank Accession No. N54901, dated Jan. 28, 1997.
GenBank Accession No. NM_000612, dated Oct. 31, 2000.
GenBank Sequence Revision History page printed Aug. 15, 2007.
GeneCard Database Record IGF2 printed Aug. 15, 2007.
GeneCard for IGF2 via URL: <genecards.org/cgi-bin/carddisp.pl?gene=IGF2&snp=93#snp>, printed May 29, 2008.
GeneCard for CCND1 available via URL: <genecards.org/cgi-bin/carddisp.pl?gene=Ccnd1&snp=97#snp>, printed May 29, 2008.
Golub et al., "Molecular Classification of Cancer: Class Discovery and Class Prediction by Gene Expression Monitoring", Science, 286:531-537 (1999).
Gruvberger et al., "Estrogen Receptor Status in Breast Cancer is Associated with Remarkably Distinct Gene Expression Patterns", Cancer Research, 61:5979-5984 (2001).
Herrero et al., *Bioinformatics*, 17(2):126-136 (2001).
Image Consortium Record printed Aug. 15, 2007.
Image Id. No. record printed Sep. 21, 2006.
Kim et al., "ECgene: genome annotation for alternative splicing", *Nucleic Acids Research*, 33:D75-D79 (2005).
Khan et al., "Classification and diagnostic prediction of cancers using gene expression profiling and artificial neural networks", Nature Medicine, 7(6):673-679 (2001).
Kwon et al., "DNA Microarray Data Analysis for Cancer Classification Based on Stepwise Discriminant Analysis and Bayesian Decision Theory", Genome Informatics, 12:252-254 (2001).
Li et al., Human Pathology, 2008, 39:1792-1801.
Mateos et al., "Supervised Neural Networks for Clustering Conditions in DNA Array Data after Reducing Noise by Clustering Gene Expression Profiles", *Microarray data analysis II*, Kluwer Academic Publ., pp. 91-103 (2002).
Muller et al., *IEEE Transactions on Neural Networks*, 12(2):181-201 (2001).

(Continued)

*Primary Examiner* — Lori A Clow
(74) *Attorney, Agent, or Firm* — Merchant & Gould P.C.

(57) ABSTRACT

A method of diagnosing, predicting, or prognosticating about a disease that includes obtaining experimental data, wherein the experimental data is high dimensional data, filtering the data, reducing the dimensionality of the data through use of one or more methods, training a supervised pattern recognition method, ranking individual data points from the data, wherein the ranking is dependent on the outcome of the supervised pattern recognition method, choosing multiple data points from the data, wherein the choice is based on the relative ranking of the individual data points, and using the multiple data points to determine if an unknown set of experimental data indicates a diseased condition, a predilection for a diseased condition, or a prognosis about a diseased condition.

27 Claims, 9 Drawing Sheets

OTHER PUBLICATIONS

NHGRI Protocol, http://www.nhgri.hih.gov/DIR/LGG/SK/HTML/protocol.html, 27 pages (Apr. 25, 2002).
Peterson et al., "JETNET 3.0—A versatile artificial neural network package", Computer Physics Communications, 81:185-220 (1994).
Raychaudhuri et al., Pacific Symposium on Biocomputing (2000) pp. 455-466.
Raychaudhuri et al., *Trends in Biotechnology*, 19(5):189-193 (2001).
Sequence Alignment printed Sep. 11, 2006.
Sperduti et al., "Supervised Neural Networks for the Classification of Structures", IEEE Transaction on Neural Networks, 8(3):714-735 (1997).
Tips for cDNA sequences printed Sep. 21, 2006.
Tusher et al., "Significance analysis of microarrays applied to the ionizing radiation response", PNAS, 98(9):5116-5121 (2001).
U.S. Appl. No. 10/133,937 Office Action dated Jan. 22, 2009.
U.S. Appl. No. 10/159,563 Office Action dated Feb. 12, 2009.
U.S. Appl. No. 10/159,653 Form PTO-892 from Office Action dated Jun. 10, 2008, should be U.S. Appl. No. 10/159,563.
Van Gelder et al., "Amplified RNA synthesized from limited quantities of heterogeneous cDNA", Proc. Natl. Acad. Sci. USA, 87(5):1663-1667 (1990).
Wang et al., Human Genetics, 2006, 120:297-300.

METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

CROSS REFERENCE TO RELATED APPLICATIONS

This application is a continuation of U.S. application Ser. No. 11/928,901, filed on Oct. 30, 2007, now U.S. Pat. No. 7,783,431, which is a continuation application of Ser. No. 10/133,937, filed on Apr. 25, 2002, now U.S. Pat. No. 7,774,143, which applications are incorporated herein by reference.

STATEMENT OF GOVERNMENT RIGHTS

The work performed during the development of this invention utilized U.S. Government Funds. The government has certain rights in the invention.

FIELD OF THE INVENTION

The invention relates generally to the use of supervised pattern recognition methods to classify and diagnose disease. More specifically, the invention relates to the use of supervised pattern recognition methods, such as artificial neural networks for the classification, diagnosis, prognosis and prediction of disease using high dimensional data, such as gene expression profiling data.

BACKGROUND OF THE INVENTION

Disease is generally diagnosed based on a myriad of factors, both objective and subjective, including but not limited to symptoms, laboratory test values, demographic factors and environmental factors. Diagnosis relies on a clinician such as a physician or a veterinarian being able to identify and evaluate the relevant factors. Often this task can be difficult, and becomes exceedingly more so as the number of factors to be considered increases.

An example of a disease whose diagnosis is difficult is tumors. Tumors are currently diagnosed on the basis of clinical presentation, routine histology, immunohistochemistry and electron microscopy. However the histological appearance may not reveal the genetic aberrations or underlying biologic processes that contribute to the malignancy. Monitoring global gene expression levels using DNA microarrays would provide an additional tool for elucidating tumor biology as well as the potential for molecular diagnostic classification of cancers. Several studies have demonstrated that gene expression profiling using DNA microarrays is able to classify tumors with a high accuracy, and discover new cancer classes.

A specific type of tumors which could benefit is the small, round blue cell tumors (SRBCTs) of childhood as a model. SRBCTs include, neuroblastoma (NB), rhabdomyosarcoma (RMS), non-Hodgkin lymphoma (NHL) and the Ewing family of tumors (EWS), are so named because of their similar appearance on routine histology. However, accurate diagnosis of SRBCTs is essential because the treatment options, responses to therapy, and prognoses vary widely depending on the diagnosis. As their name implies, these cancers are difficult to distinguish by light microscopy, and currently no single test can precisely distinguish these cancers.

In clinical practice, several techniques are used for diagnosis, including immunohistochemistry, cytogenetics, interphase fluorescence in situ hybridization and reverse transcription (RT)-PCR. Immunohistochemistry allows the detection of protein expression, but it can only examine one protein at a time. Molecular techniques such as RT-PCR are used increasingly for diagnostic confirmation following the discovery of tumor-specific translocations such as EWS-FLI1; t(11;22)(q24;q12) in EWS, and the PAX3-FKHR; t(2;13) (q35;q14) in alveolar rhabdomyosarcoma (ARMS). However, molecular markers do not always provide a definitive diagnosis, as on occasion there is failure to detect the classical translocations, due to either technical difficulties or the presence of variant translocations.

An example of a diagnostic method replete with such problems is the diagnostic method for Ewing sarcoma. Ewing sarcoma is diagnosed by immunohistochemical evidence of MIC2 expression and lack of expression of the leukocyte common antigen CD45 (excluding lymphoma), muscle-specific actin or myogenin (excluding RMS). However, reliance on detection of MIC2 alone can lead to incorrect diagnosis as MIC2 expression occurs occasionally in other tumor types including RMS and NHL.

One objective factor that can, in certain circumstances, be entirely predictive of a diseased state is the genetic makeup of the individual. Genetic makeup of an individual can also be considered in terms f the level of expression of the genes of that individual through gene expression data.

DNA microarray technology is a recently developed high throughput technology for monitoring gene expression at the transcription level. Its use is akin to performing tens of thousands of northern blots simultaneously, and has the potential for parallel integration of the expression levels of an entire genome. A DNA microarray consists of DNA probes immobilized on a solid support such as a glass microscope slide. The DNA probes can be double stranded cDNA or short (25 mers) or long (50-70 mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 mers) sets are commercially available for human, mouse and other organisms (www.cgen.com, www.operon.com).

Another technique for fabricating oligonucleotides microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink jet onto glass surfaces.

One method of utilizing gene expression data from microarrays is given by Tusher et al., PNAS 98(9) p. 5116-21, April, 2001. The method of Tusher et al. is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

DNA microarrays would be an invaluable tool for disease diagnosis. Gene-expression profiling using DNA microarrays permits a simultaneous analysis of multiple markers, and can be used for example to categorize cancers into subgroups. The only limitation associated with the use of DNA microarrays is the vast amount of data generated thereby. A method that would allow for the easy and automated use of DNA microarray data in disease diagnosis is therefore desirable. Despite the many statistical techniques to analyze gene-expression data, none so far has been rigorously tested for their ability to accurately distinguish diseases belonging to several diagnostic categories. Such methods have also not been used to extract the genes or features that are the most important for the classification performance. Such genes would also generally be those that are of use to biologists and physicians as offering avenues to research in investigating cures.

Therefore, there remains a need for a method of using gene expression data to diagnose, predict, or prognosticate about a disease condition.

However, these other methods have not been used to extract the genes or features that are most important for the classification performance and which also will be of interest to cancer biologists.

SUMMARY OF THE INVENTION

In accordance with the invention, there is provided a method of diagnosing, predicting, and/or prognosticating about a disease including obtaining experimental data, wherein the experimental data includes high dimensional data, filtering noise from the data, reducing the dimensionality of the data by using one or more methods of analysis, training a supervised pattern recognition and/or classification method, ranking individual data from the overall data based on the relevance of the individual data to the diagnosis, prediction, prognosis or classification, choosing multiple individual data members, wherein the choice is based on the relative ranking of the individual data, and using the chosen data to determine if an unknown set of experimental data indicates a particular diseased condition, prognosis, prediction, or classification.

The invention offers a method of diagnostic classification of cancers from their gene-expression signatures and also identifies the genes that contributed to this classification. One embodiment of the method diagnoses SRBCTs of childhood, which occasionally present diagnostic difficulties.

The invention also offers a method of diagnosing, predicting, and/or prognosticating about SRBCTs including obtaining gene expression data, filtering noise from the gene expression data, reducing the dimensionality of the data by using principal component analysis (PCA), training an ANN, ranking the individual genes from the gene expression data, choosing multiple genes from the gene expression data, wherein the choice is based on the relative ranking of the individual genes and using the chosen genes to determine if an unknown set of gene expression data indicates a particular diseased condition, prognosis, and/or a prediction.

Methods of the invention can be utilized in a number of different applications. For example, diagnostic chips can be fabricated based on the identification of the diagnostic genes. Such chips would be very useful in clinical settings, as it would allow clinicians to diagnose cancers from a relatively small set of genes instead of purchasing entire gene sets.

Methods of the invention can also be used to define which patients with the same types of cancers are likely to respond to treatment. This would allow a physician to intensify treatment for those with a more negative prognosis based on their gene expression profiles as detected utilizing a method of the invention.

Methods of the invention can also be used for identifying pharmaceutical targets. Pharmaceutical companies can utilize methods of the invention to determine which genes to target in efforts to target specific diseases.

Methods of the invention can also be utilized as a research tool for analyzing all types of gene expression data including cDNA and oligonucleotide microarray data.

Methods of the invention can also be utilized to identify and rank, by importance, the genes that contribute to a diagnosis. A minimal set of genes that can correctly classify and identify diagnostic categories can also be determined using methods of the invention.

Methods of the invention identify the most significant genes, by calculating the sensitivity of the classification to a change in the expression level of each gene. A list of genes, ranked by their significance to the classification, is produced thereby. In an embodiment of the invention utilized for classifying SRBCTs the most important 96 genes reduced the misclassifications to zero. This allows for cost effective fabrication of SRBCT subarrays for diagnostic use. When a method of the invention used the 96 genes on 25 unknown samples, all 20 samples of SRBCTs and 5 non-SRBCTs were correctly classified.

One embodiment of the invention calibrates ANN models on the expression profiles of 63 SRBCTs of 4 diagnostic categories. Preferred embodiments of the invention utilize linear (that is no hidden layers) ANN models because of the high performance achieved. Methods of the invention may utilize other linear methods as well, and methods of the invention can easily accommodate nonlinear features of expression data if required. Hidden layers will be utilized for non linear data. Preferably, both tumor samples and cell line samples are used in order to compensate for heterogeneity within unknown samples (which contain both malignant and stromal cells) based on possible artifacts due to growth of cell lines in tissue culture.

Data from such samples is complementary, because tumor tissue, though complex, provides a gene-expression pattern representative of tumor growth in vivo, while cell lines contain a uniform malignant population without stromal contamination. Despite using only neuroblastoma (NB) cell lines for calibrating the ANN models, all four NB tumors among the test samples were correctly diagnosed with high confidence. This not only demonstrates the high similarity of NB cell lines to the tumors of origin, but also validates the use of cell lines for ANN calibration. One embodiment of a method of the invention accurately classified all 63 training SRBCTs and showed no evidence of over-training, thereby demonstrating the robustness of this method.

DETAILED DESCRIPTION OF THE PREFERRED EMBODIMENTS

The invention is a method of classifying, diagnosing, prognosticating about, and predicting disease conditions or other biological states using supervised pattern recognition methods to analyze high dimensional data.

Figure 1:
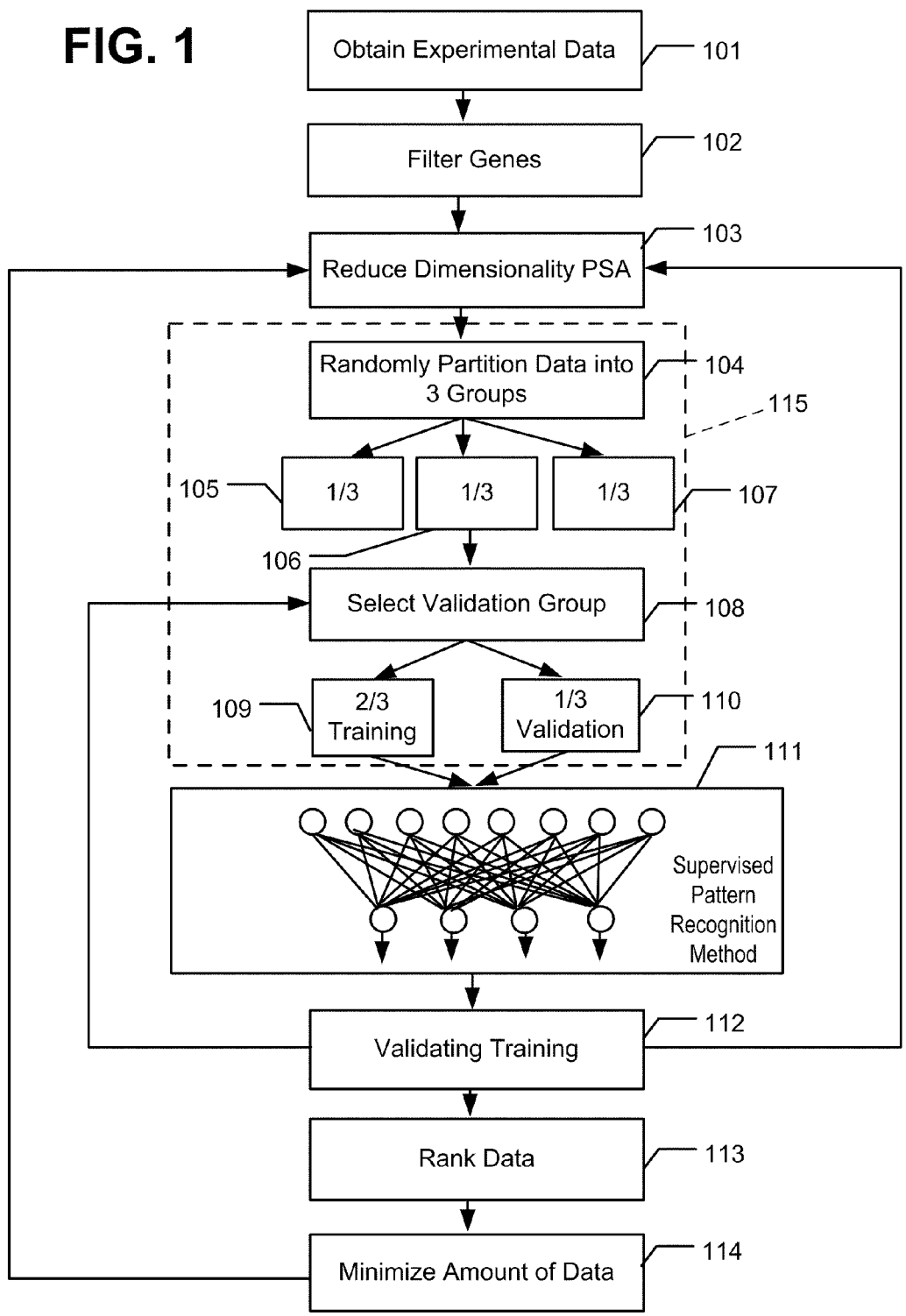
FIG. 1 illustrates a process flow for a method to classify and diagnose diseases using artificial neural networks according to one embodiment of the invention.

One embodiment of the invention is illustrated in FIG. 1. This process flow describes an embodiment of the method that includes obtaining experimental data 101, filtering the data 102, reducing the dimensionality of the data 103, setting up a validation method 115, training a supervised pattern recognition method 111, validating the outcome of the supervised pattern recognition method 112, and once the supervised pattern recognition method is validated, ranking the data based on the outcome of the supervised pattern recognition method 113. Further detail and more specific embodiments of methods of the invention are described below.

Any diagnostic categories can be diagnosed using the technology described here. It includes distinguishing patients with multiple sclerosis, rheumatoid arthritis, and other inflammatory or autoimmune diseases. It may also diagnose other systemic diseases based on gene expression profiles of white cells, including infections with particular organisms, cancer, or myocardial infarctions.

Obtaining Experimental Data

The first step in methods of the invention is to obtain experimental data. Experimental data utilized in methods of the invention is high dimensional data. High dimensional data is data that has at least hundreds of individual pieces of information associated with one sample. An example of high dimensional data useful in methods of the invention is gene expression data. Gene expression data is high dimensional data because each sample or person has a large number of gene expression levels. Generally speaking, gene expression data generally has thousands of gene expression levels for each sample. Other examples of high dimensional data useful in the invention include but are not limited to protein arrays and protein chips, cell array based expression analysis, analysis of patterns of single nucleotide polymorphisms in disease conditions, and comparative genomic hybridization on methaphase, BAC genomic, cDNA and oligonucleotide arrays.

Preferably, the gene expression data is obtained through use of DNA microarray technology. DNA microarrays are preferred as a source of data because they generally offer a more complete picture of the interactions of a large number of genes with a limited number, or even one experiment. An example of a general description of how gene expression data can be obtained by using cDNA microarray technology is given below.

DNA microarrays, although a relatively new technology, have already been saddled with a number of different names, biochip, DNA chip, gene chip, genome chip, cDNA microarray, and gene array. The use of any of these terms herein refers generally to DNA microarrays. The underlying principle of DNA microarrays is base pairing or hybridization i.e., A-T and G-C for DNA, and A-U and G-C for RNA.

DNA microarrays provide a medium for matching known and unknown DNA samples based on the base pairings given above. DNA microarrays can either be fabricated by high-speed robotics or can be fabricated in a laboratory setting. They are generally patterned on glass, but can also be fabricated on nylon substrates. Microarrays generally have sample spot sizes of less than 200 µm diameter, and generally contain thousands of DNA spots on one microarray.

One method of fabricating cDNA microarrays begins by first producing gene-specific DNA by polymerase chain reaction (PCR) amplification of purified template plasmid DNAs from cloned expressed sequence tags (ESTs). The PCR product is then purified, resuspended and printed onto a substrate. cDNA microarrays are also commercially available from a number of sources, including but not limited to Affymetric, Inc. (Santa Clara, Calif.), Agilent Technologies (Palo Alto, Calif.), and Research Genetics (Huntsville, Ala.).

One general procedure for a cDNA microarray experiment begins by preparing DNA samples and arraying them (either with an arraying robot, or by hand), to form a DNA microarray. Next, the RNA samples are extracted from the cells of interest, purified, reverse transcribed into cDNA and differentially fluorescently labeled to create probes. Then, the fluorescently labeled cDNA probes are hybridized to the cDNA microarray. If a probe contains a cDNA whose sequence is complementary to the DNA on a given spot, the cDNA probe will hybridize to that spot. After the cDNA probes are hybridized to the array, and any loose probe has been washed away, the microarray is imaged to determine how much of each probe is hybridized to each spot. This indicates how much of each gene from the microarray is expressed in the two samples.

The experimental high dimensional data, preferably obtained from gene expression experiments, preferably performed using cDNA microarrays, is then further analyzed by a method of the invention.

Filtering the Data

The next step in a method of the invention is filtering the data 102 to remove individual pieces of data that are deemed undesirable. This filtering step functions to eliminate weak and/or problematic data from further use in the method. Accomplishment of the step of filtering depends greatly on the type of high dimensional data utilized. Any method known to those of ordinary skill in the art can be used to eliminate data determined to be undesirable.

One basis for carrying out this filtering, if a DNA microarray is being utilized for obtaining the high dimensional data, is the intensity of the fluorescence from the individual microarray spots. This basis of omitting data is based on failure or error in the imaging of the specific spots. A preferred method of performing initial data filtering on cDNA microarray data to remove those spots where imaging was a problem is to utilize the intensity of the various spots and utilize only those spots that have an intensity over a certain threshold value. Other methods of filtering DNA microarray data include but are not limited to eliminating spots in which the number of pixels represented is less than a threshold defined by the user, eliminating spots in which the standard deviation of the signal on the spots is too large, as defined by the user, eliminating spots in which the background intensity of a single spot is too high, or any combination thereof. In addition quality values based on intensity, can be assigned to each spot, standard deviation of intensity, background and/or size of each spot, then a spot could be eliminated if its quality value falls below a threshold as defined by the user.

Reducing the Dimensionality of the Data

The next step in methods of the invention is reducing the dimensionality of the data 103. The number of samples needed to calibrate a classifier with good predictive ability, depends critically on the number of features used in the design of the classifier. In the case of high-dimensional data, such as microarray data, where the number of samples is much smaller than the number of individual pieces of data there exists a large risk of over-fitting. There are two different solutions to this problem. First, the calibration process can be carefully monitored using a cross-validation scheme to avoid over-fitting (see below). Second, the dimension of the data can be reduced, either by using a dimensional reduction algorithm or by selecting a smaller set of data for input to the supervised pattern recognition method. Dimensionality reduction allows the number of parameters representing each sample to be reduced. This allows for the design of a classifier that has less risk of over-fitting, thereby increasing its predictive ability.

Examples of methods of reducing the dimensionality of the data include but are not limited to principal component analysis (PCA), weighted gene analysis, t-test, rank based Wilcoxon or Mann-Whitney tests, signal-to-noise statistic, Fisher's discriminant analysis, or ANOVA tests.

In a preferred embodiment of the invention, PCA is used to reduce the dimensionality of the data.

In the case of PCA on gene expression data, reduction of the dimensionality is achieved by rotating gene expression space, such that the variance of the expression is dominated by as few linear combinations of genes as possible Even though the formal dimension of the problem is given by the number of individual data points, the effective dimension is just one less than the number of samples. Hence the eigenvalue problem underlying PCA can be solved without diagonalizing 2308×2308 matrices by using singular value decomposition. Thus each sample is represented by 88 numbers, which are the results of projections of the data using the PCA eigenvectors.

A potential risk when using PCA on relatively few samples is that components might be singled out due to strong noise in the data. It could be argued that the outputs (labels) should be included in the dimensional reduction, using e.g. the Partial Least Squares (PLS) algorithm, in order to promote components with strong relevance for the output. However, based on explorations with similar data sets, this is not optimal; bias is introduced and implicitly "over-trains" from the outset by including the outputs in the procedure.

Setting up a Validation Method for the Supervised Pattern Recognition Method

Once the data has been filtered 102 and its dimensionality reduced 103, a validation method is set up for monitoring and validating the training of the supervised pattern recognition method 115. Any method commonly used by those of skill in the art for validating the training of a supervised pattern recognition method can be used.

In one embodiment, the first step in setting us a validation method is to randomly divide the data into three groups of data, 105, 106, and 107. Then, one of those groups is chosen as a validation group 108. The first two of the groups 105 and 106 are combined into a training group 109, which is used to train the supervised pattern recognition method 111 and the third group 107 is used to validate the performance of the supervised pattern recognition method 111, once trained, and is called a validation group 110.

In this specific preferred embodiment, the 3-fold cross validation procedure (steps 104 through 110) is performed on all of the samples. A data group having 63 samples is given as an example. The 63 known (labeled) samples are randomly shuffled 104 and split into 3 equally sized groups (105, 106, and 107). The supervised pattern recognition method 111 is then calibrated as discussed below using the training group 109. The third group, a validation group 110, is reserved for testing predictions. Comparisons with the known answers refer to the results from the validation group 110 (i.e. when using a model, the samples used for training the model are never used in predictions). This procedure is repeated 3 times, each time with a different group used for validation. The random shuffling 104 is done about 100 to 10000 times. For each shuffling, one supervised pattern recognition method 111 model is generated. Thus, in total each sample belongs to a validation group 110, 1250 times and 3750 supervised pattern recognition methods 111 have been calibrated.

Training the Supervised Pattern Recognition Method

The supervised pattern recognition method 111 is then trained. The specific method of training the supervised pattern recognition method 111 is dependent on the specific form that the supervised pattern recognition method 111 takes. The choice of the supervised pattern recognition method 111 and the training thereof is well within one of skill in the art, having read this specification.

One example of a supervised pattern recognition method is an artificial neural network (ANN). ANNs are computer-based algorithms that are modeled on the structure and behavior of neurons in the human brain and can be trained to recognize and categorize complex patterns. Pattern recognition is achieved by adjusting parameters of the ANN by a process of error minimization through learning from experience. They can be calibrated using any type of input data, such as gene-expression levels generated by cDNA microarrays, and the output can be grouped into any given number of categories. ANNs have been recently applied to clinical problems such as diagnosing myocardial infarcts and arrhythmias from electrocardiograms and interpreting radiographs and magnetic resonance images. However, ANNs have not been used to decipher gene-expression signatures of SRBCTs or for diagnostic classification.

In embodiments where an artificial neural network (ANN) is employed as the supervised pattern recognition method 111, calibration is preferably performed using JETNET (C. Peterson, T. Roegnvaldsson and L. Loennblad, "JETNET 3.0—A versatile artificial neural network package," *Computer Physics Communications* 81, 185-220 (1994)). Preferably, the software is used with a learning rate $\eta=0.7$, momentum coefficient $p=0.3$ and the learning rate is decreased with a factor 0.99 after each iteration. Initial weight values are chosen randomly from $[-r, r]$, where $r=0.1/\max_i F_i$ and the "fanin" $F_i$ is the number of nodes connecting to node i. The calibration is performed using a training set and it is monitored both for the training set and a validation set, which is not subject to calibration (see below). The weight values are updated after every 10 samples and the calibration is terminated after 100 passes (epochs) through the entire training set. In one embodiment of a method of the invention, the resulting parameters for the completed training of a supervised pattern recognition method 111 defines a "model".

In preferred embodiments, due to the limited amount of calibration data and the fact that four output nodes are needed (Ewing's sarcoma (EWS), Burkitt's lymphoma (BL), neuroblastoma (NB) and rhabdomyo sarcoma (RMS)), linear perceptrons (LP) with 10 input nodes representing the PCA components described above are utilized. In other words, the supervised pattern recognition method 111 generally contains 44 parameters including four threshold units. Since 10 components could be used without risking "over-training" the optimization of the number of components to a smaller number is generally not necessary.

The possibility of using all the PCA components as inputs followed by a subsequent pruning of weights to avoid "overfitting" is also one alternative. This resulted in the dominant 4-8 PCA components (depending on the composition of the training set 107) being the surviving inputs. Generally, the less dominant PCA components contain variance not related to separating the four cancers, but rather to, for example, experimental conditions (noise) or variance related to sub-groupings within a cancer type.

Verifying the Outcome of the Supervised Pattern Recognition Method

Once the supervised pattern recognition method 111 is trained, the next step is to determine whether the validation of the supervised pattern recognition method 111 is successful 112. This step determines whether the supervised pattern recognition method 111 adequately predicted the results for the validation data set 110 using any number of performance measurements and error measurements.

Any method known to those of ordinary skill in the art can be utilized to evaluate the performance of the training of the supervised pattern recognition method 111. Generally speaking, the performance is evaluated by comparison with some predetermined level of correct predictions that the user has determined is acceptable.

If the performance of the supervised pattern recognition method 111 is sufficiently poor, and a measure of error is greater than an allowable threshold, the processing may return to module 103 where the dimensionality of the data is reduced in a different manner and the entire training and validation process is repeated.

Ranking the Data

Once module 112 determines that the network 111 has been adequately trained, the processing proceeds to rank the output of the supervised pattern recognition method 113.

The outcome of the supervised pattern recognition method 111 can be looked at either independently or in a compiled form. Each supervised pattern recognition method 111 gives a number between 0 (not this disease type) and 1 (this disease type) as an output for each disease type. If the predictions are viewed independently, the maximal output is forced to 1 while the other outputs are forced to 0. Then it is determined how many of the predictions are correct. If the predictions are viewed in a compiled form, all of the predicted outputs are considered in their numerical form, after which all of the numbers are averaged and the resulting average is forced to 0 or 1.

In one embodiment of the method, the predictions, as compiled, are used to classify samples. For validation samples the compilation is based on 1250 models, while for additional unknown samples all 3750 models are used in the compilation.

In one embodiment, each sample is classified as belonging to the disease type corresponding to the largest average in the compilation. In addition, it is desirable to be able to reject the second largest vote as well as test samples that do not belong to any of the disease types. In order to reject those samples that do not belong, a distance $d_c$ from a sample to the ideal vote for each disease type is defined as:

$$d_c = \frac{1}{2}\sum_{i=1}^{4}(o_i - \delta_{i,c})^2 \quad (1)$$

where c is a disease type, $o_i$ is the average from the compilation for disease type i, and $\delta_{i,c}$ is unity if i corresponds to disease type c and zero otherwise. The distance is normalized such that the distance between two ideal samples belonging to different disease categories is unity. Based on the validation group, an empirical probability distribution of its distances is generated for each disease type.

The empirical probability distributions are preferably built using each supervised pattern recognition method 111 independently (not the average from the compilation). Thus, the number of entries in each distribution is given by 1250 multiplied by the number of samples belonging to the disease type. For a given test sample, the possible classifications based on these probability distributions can be rejected. This means that for each disease category a cutoff distance from an ideal sample is defined, within which, based on the validation samples, a sample of this category is expected to be. The distance given by the 95th percentile of the probability distribution is preferably chosen as a cutoff, which means that if a sample is outside of this cutoff distance it cannot be confidently diagnosed. It should be noted that the classification as well as the extraction of important genes (see below) converges using less than 100 supervised pattern recognition method 111 models. 3750 supervised pattern recognition method 111 models are preferred is because sufficient statistics exist for these empirical probability distributions.

For each disease category the sensitivity and specificity of the diagnosis may be calculated (see Table 1 below). Table 1 gives sensitivity, specificity and ROC curve areas for both validation and test samples. Both the sensitivity and the specificity are very high for all categories. It should be noted, that they generally depend on the kind of samples that are used as test samples.

TABLE 1

| Category | Sensitivity | Specificity | ROC curve area |
|----------|-------------|-------------|----------------|
| EWS | 93% | 100% | 1.0 |
| BL | 100% | 100% | 1.0 |
| NB | 100% | 100% | 1.0 |
| RMS | 96% | 100% | 1.0 |

For example, in the case of SRBCT classification, using normal muscle samples as tests makes it harder to separate out RMS samples. If only samples from the four categories were used as blind distance cutoffs, it could easily have been designed such that both the sensitivity and the specificity would have been 100% for all diseases. However, it is preferred that the method is tested using a variety of blind tests. If it is desirable to improve rejection of for example normal muscle samples, one could incorporate them as a fifth category in the training process. However, using more samples of all four categories in the training is initially probably the best way to improve the diagnostic separation.

The Receiver Operator Characteristic (ROC) curve area is identical to another more intuitive and easily computed measure of discrimination: the probability that in a randomly chosen pair of samples, one belonging to and one not belonging to the disease category, the one belonging to the category is the one with the closest distance to the ideal for that particular category. Since the ROC curve areas are unity for all disease categories (see Table 1), it is possible to define cutoff distances such that both the sensitivity and the specificity are 100% for all diseases. However, based on the training and validation groups it is difficult to motivate such cutoff distances.

The next step in a method in accordance with the invention is to actually rank the data. This step can in principle be done in two ways: (1) model-independent and (2) model-dependent analysis respectively. Due to the relative small number of samples, the model-dependent analysis is preferred when using ANN models.

The sensitivity (S) of the outputs (o) with respect to any of the 2308 input variables ($x_k$) is defined as:

$$S_k = \frac{1}{N_s} \frac{1}{N_o} \sum_{s=1}^{N_s} \sum_{i=1}^{N_o} \left| \frac{\delta o_i}{\delta x_k} \right| \quad (2)$$

where $N_s$ is the number of samples (63 or 88) and $N_o$ is the number of outputs (4). The procedure for computing $S_k$ involves a committee of 3750 models. In addition we have defined a sensitivity for each output i ($S_i$), which is analogous to Eq. (2) but without the sum over outputs. Furthermore, a sensitivity can be defined for each sample (or subsets of samples) individually, by only using that sample(s) in the sum over samples in Eq. (2). For all these sensitivities the sign of the sensitivity has also been defined. The sign signals whether the largest contribution to the sensitivity stems from positive or negative terms. A positive sign implies that increasing the expression rate of the gene increases the possibility that the sample belongs to this cancer type, while a negative sign means that decreasing the expression rate of the gene increases the same possibility. In other words, the sign does not tell whether a gene is up- or down-regulated but if it is more or less expressed in this cancer type as compared to the others. This means the genes are ranked not only according to their importance for the total classification, but also according to their importance for the different disease categories separately. The genes are preferably given a total rank as well as a separate rank for each disease category. Based on these ranks each gene is classified according to which disease category it is highly expressed in.

In one embodiment, once ranked, a relevant set of data can be selected module 114 by minimizing the amount of data to be used to classify and identify a particular disease. In one embodiment, a pre-determined amount of data having the highest ranking are selected. Of course, other selection methods may be employed without deviating from the spirit and scope of the present invention as recited in the attached claims.

Implementation of Methods of the Invention

Figure 2:
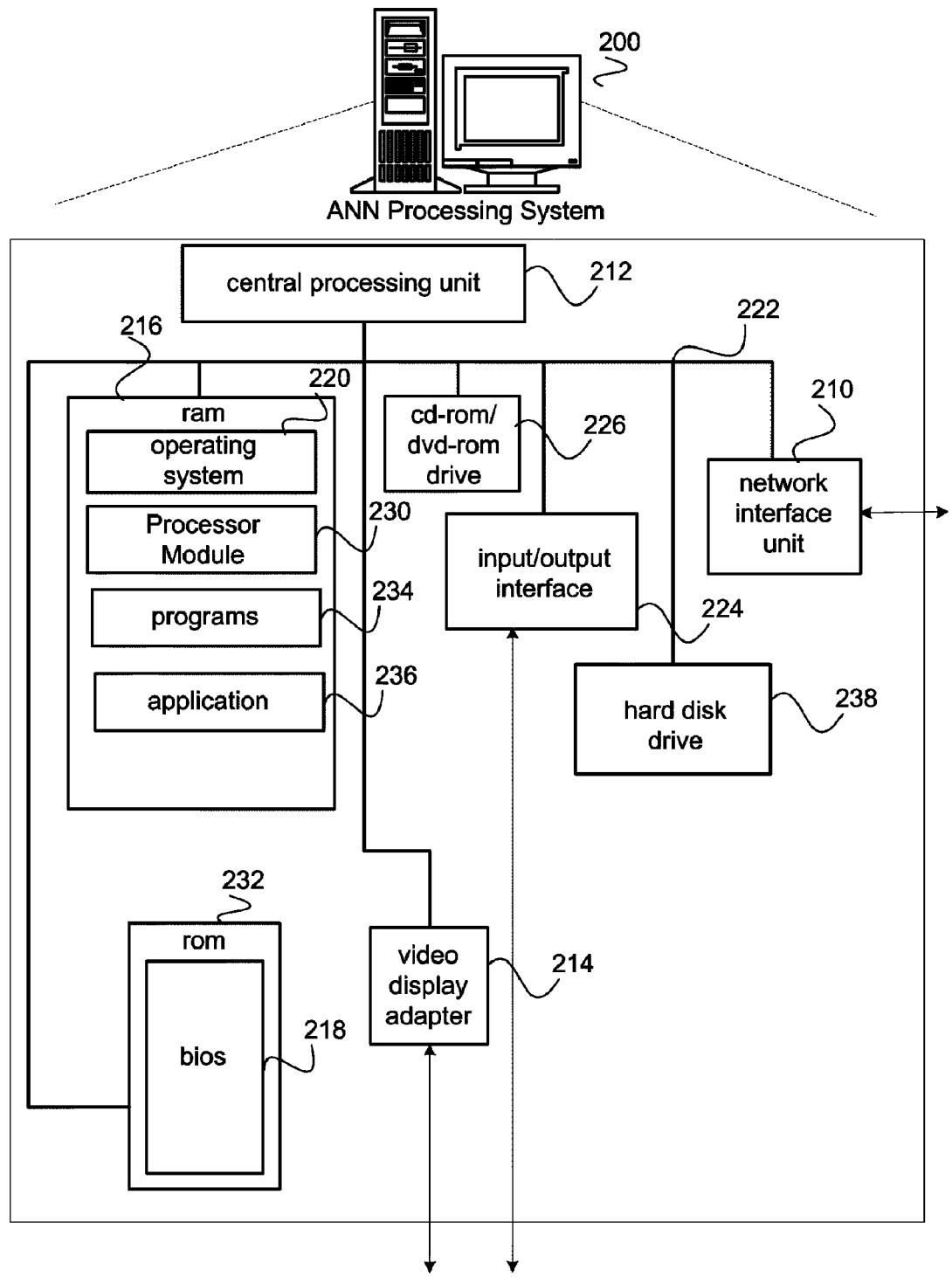
FIG. 2 illustrates a general purpose computing system utilized as part of an artificial neural network according to another embodiment of the invention.

In embodiments of the method in which the supervised pattern recognition method 111 is an artificial neural network, a general purpose computing system as depicted in FIG. 2 can be utilized. An exemplary ANN processing system 200 provides an artificial neural network that also receives experimental data to train the artificial neural network, to verify the output of an artificial neural network, and to identify relevant genes using the neural network.

Those of ordinary skill in the art will appreciate that the ANN processing system 200 may include many more components than those shown in FIG. 2. However, the components shown are sufficient to disclose an illustrative embodiment for practicing the present invention. As shown in FIG. 2, the ANN processing system 200 is connected to a WAN/LAN, or other communications network, via network interface unit 210. Those of ordinary skill in the art will appreciate that network interface unit 210 includes the necessary circuitry for connecting the ANN processing system 200 to a WAN/LAN, and is constructed for use with various communication protocols including the TCP/IP protocol. Typically, network interface unit 210 is a card contained within the ANN processing system 200.

The ANN processing system 200 also includes processing unit 212, video display adapter 214, and a mass memory, all connected via bus 222. The mass memory generally includes RAM 216, ROM 232, and one or more permanent mass storage devices, such as hard disk drive 228, a tape drive, CD-ROM/DVD-ROM drive 226, and/or a floppy disk drive. The mass memory stores operating system 220 for controlling the operation of ANN processing system 200. It will be appreciated that this component may comprise a general purpose server operating system as is known to those of ordinary skill in the art, such as UNIX, LINUX, MAC OS?, or Microsoft WINDOWS NT?. Basic input/output system ("BIOS") 218 is also provided for controlling the low-level operation of ANN processing system 200.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing an ANN processing and network development. More specifically, the mass memory stores applications including ANN processing module 230, programs 234, and other applications 236. ANN processing module 230 includes computer executable instructions which, when executed by ANN processing system 200, performs the logic described above.

The ANN processing system 200 also comprises input/output interface 224 for communicating with external devices, such as a mouse, keyboard, scanner, or other input devices not shown in FIG. 2. Likewise, ANN processing system 200 may further comprise additional mass storage facilities such as CD-ROM/DVD-ROM drive 226 and hard disk drive 228. Hard disk drive 228 is utilized by ANN processing system 200 to store, among other things, application programs, databases, and program data used by ANN processing module 230. For example, customer databases, product databases, image databases, and relational databases may be stored. The operation and implementation of these databases is well known to those skilled in the art.

Figure 3:
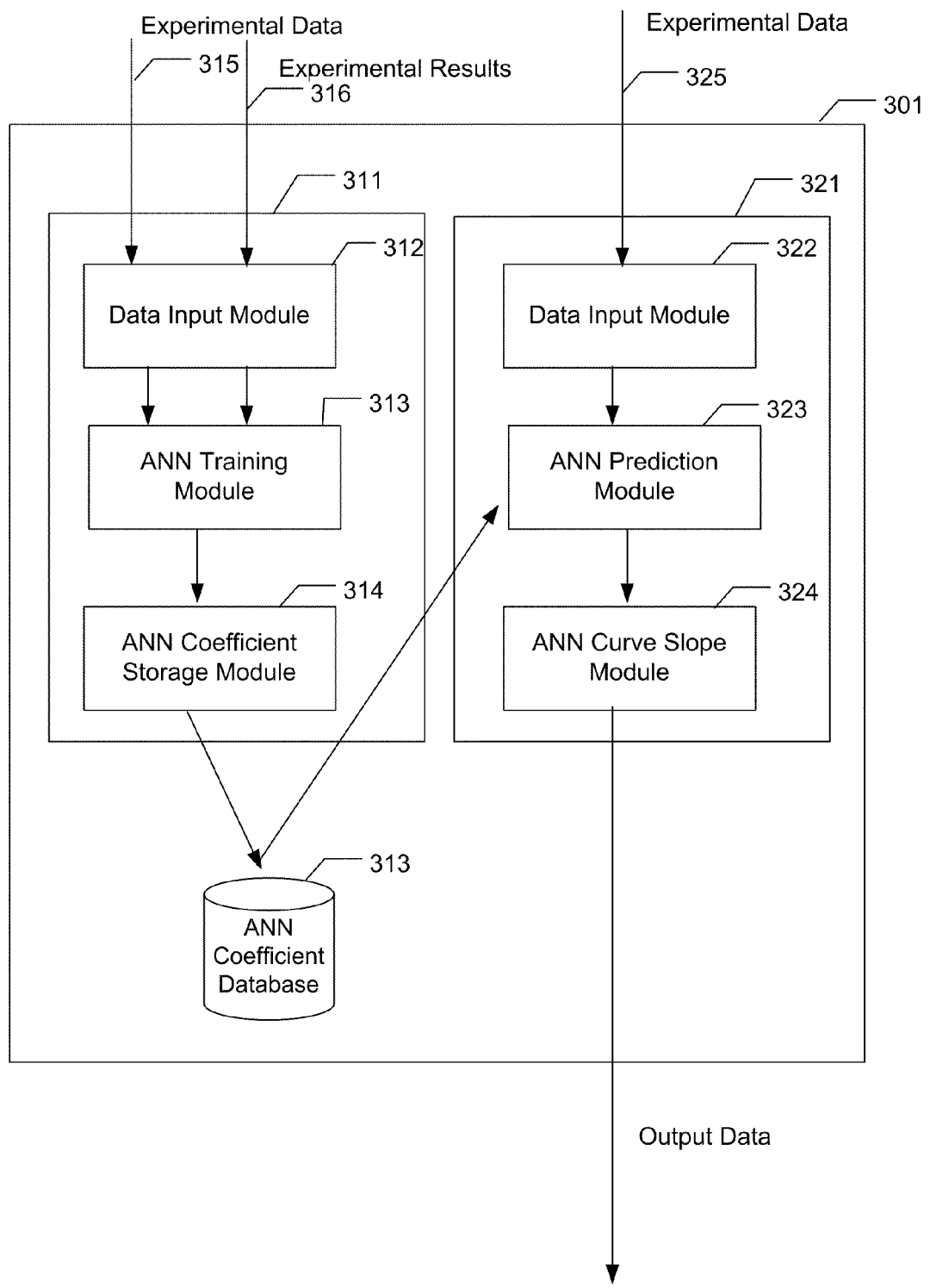
FIG. 3 illustrates a set of processing modules making up an embodiment of an artificial neural network according to the invention.

A set of processing modules making up an embodiment of an artificial neural network according to the invention is illustrated in FIG. 3. The artificial neural network disclosed herein corresponds to a generic neural network of no particular topology for the network of nodes contained therein. The neural network typically utilizes a form of competitive learning for the operation of the nodes within the network. Within competitive learning networks, a large number of data vectors are distributed in a highly dimensional space. These data vectors represent known values for experimental data that typically reflect a probability distribution of the input experimental data. From this probability distribution representation, predictions for unknown values for similar input data may be determined.

In all of these competitive learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the invention as recited within the attached claims. Each of these algorithm architectures represents the same probability distribution relationship; however each of the various algorithm architectures better optimize corresponding processing parameters, which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

Now referring to FIG. 3, an artificial neural network processing system 301 comprises a learning module 311, a prediction module 321, and a database of network node coefficients 313. The learning module 311 is used with a set of experimental data 315 that possesses a corresponding set of experimental results 316 to generate a set of network node coefficients that represent a probability distribution relationship for the experimental data 315-experimental result 316 data set for a particular neural network topology and algorithm architecture. The learning module 311 includes a data learning input module 312 that receives the experimental data 315-experimental result 316 data set generated using the process described above. The learning module 311 also includes an ANN training module 313 that processes the experimental data 315-experimental result 316 data set to generate the coefficients used to specify the probability distribution relationship and an ANN coefficient storage module 314 for storing the coefficients that have been previous generated within the database 313 for later use.

The data processing within the learning module 311 may proceed in a batch processing fashion in which all of the vectors within the experimental data 315-experimental result 316 data set are processed at a single time. In such a process, the experimental data 315-experimental result 316 data set is received by the input module 312, processed by the training module 313, and the generated coefficients are placed within the database 313 by the storage module 314. Alternatively, the experimental data 315-experimental result 316 data set may be processed as a sequence of smaller data sets in which the experimental data 315-experimental result 316 data set data values are generated at different times. In such a process, the training module 313 uses the previously stored coefficients retrieved by the storage module along with a new small data set provided by the input module 312 to generate an updated set of coefficients. These updated coefficients may be once again stored within the database 313 for use at a later time.

Once an artificial neural network 301 has been trained, the prediction module 321 may be used to predict, or classify, a particular test data value 325. The prediction module 321 includes a data prediction input module 322, an ANN prediction module 323, and an ANN curve slope module 324. The data prediction input module 322 receives the input test data generated as described above for use in the prediction module. The ANN prediction module 323 receives and utilizes the network coefficient values for the neural network from the ANN coefficient database 313 to predict the possible result for the probability distribution relationship specified within the neural network. This output value is used by the ANN curve slope module 324 to determine all possible values for a given gene, in the manner discussed above, to determine a curve slope value. This slope value is then output for later use in ranking and classifying the individual genes used to determine the presence, or lack there of, for a disease.

The embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the invention describe the use of an artificial neural network to identify relevant genes associated with diseases and use the identified genes to classify and identify diseases, one skilled in the are will recognize that the use of the processing system discussed above are merely example embodiments of the invention. As long as experimental data is used to self-train a processing system using competitive learning processing, the present invention to would be useable in other data processing systems. It is to be understood that other embodiments may be utilized and operational changes may be made without departing from the scope of the present invention as recited in the attached claims.

WORKING EXAMPLES

The following examples provide a nonlimiting illustration of various embodiments of the invention.

Example 1

Preparation of Microarrays

Preparation of Glass cDNA Microarrays, probe labeling, hybridization and image acquisition were performed according to the protocol given below, which is a standard NHGRI protocol (www.nhgri.nih.gov/DIR/LCG/15K/HTML/protocol.html).

Gene-specific DNA was produced by PCR amplification of purified template plasmid DNAs from cloned ESTs. The PCR product was purified by ethanol precipitation, thoroughly resuspended in 3×SSC, and printed onto a poly-L-lysine coated slide.

The materials, reagents, and solutions used include: 96 well alkaline lysis miniprep kit (Edge BioSystems, Gaithersburg, Md.); LB Broth (Biofluids, Rockville, Md.); Superbroth (Biofluids, Rockville, Md.); dATP, dCTP, dGTP, dTTP, 100 mM each #27-2035-02, store frozen, −20° C. (Pharmacia, Peapack, N.J.); PCR primer AEK M13F (5'-GTTG-TAAAACGACGGCCAGTG-3') (SEQ ID NO: 97) and AEK M13R (5'-CACACAGGAAACAGCTATG-3') (SEQ ID NO: 98) at 1 mM concentration, store frozen, −20° C.; 10×PCR Buffer, # N808-0189, and Ampli-Taq DNA polymerase, # N808-4015 store frozen, −20° C. (Perkin Elmer, Norwalk, CT); Carbenicillin (Gibco-BRL, Rockville, Md.); Ethanol (200 Proof USP Ethyl Alcohol); 1M Tris-HCl (pH 8); 0.5M NaEDTA (pH 8); T Low E; Buffer; 20×SSC; Glycerol (enzyme grade); Sodium Acetate (tri-hydrate); Boric Acid; Sodium Hydroxide (1M); Glacial Acetic Acid; Succinic anhydride, #23969-0 and 1-methyl-2-pyrrolidinone, #32863-4 (Aldrich Chemical Co., St. Louis, Mo.); Diethyl Pyrocarbonate (DEPC) treated $H_2O$; Master set of clone-purified, sequence verified human ESTs (e.g. gf211 release, Research Genetics, Huntsville, Ala.); 96 pin inoculating block (#VP 4088, V&P Scientific, Inc, San Diego, Calif.); Airpore Tape Sheets, (#19571, QIAGEN Inc., Valencia, Calif.); Sterile 96-well plate seals, (e.g. # SEAL-THN-STR (Elkay Products, Inc., Shrewsbury, Mass.); 96-well U-Bottom Microtiter Plates, #3799 and 96-well V-Bottom Microtiter Plates, #3894 (Corning Inc., Corning, N.Y.); Thin wall PCR plate and Cylcleseal PCR plate sealer (e.g. #1038-50-0 and #1044-39-4, Robbins Scientific Corp. Sunnyvale, Calif.); household one-gallon sealable storage bags (e.g. Glad Lock); heat sealable storage bags and heat sealer; 0.2 mm Sterile Filtration unit; Diamond scribe for writing on slides; Pyrex baking dish (~24×34×5 cm); UV transparent plastic wrap (e.g. Glad Cling Wrap); 30 slide rack (stainless steel) #113 and 30 slide glass tank, #122 (Shandon Lipshaw, Pittsburgh, Pa.); 1 L glass tank; 1 L glass beaker; 1 L graduated; cylinder; Stir bar; Slide Box (plastic with no paper or cork liners), (e.g. #60-6306-02, PGC Scientific, Gaithersburg, Md.); PCR heat cycler (e.g. DNA Engine Tetrad, MJ Research, Waltham, Mass.); Centrifuge with a horizontal ("swinging bucket") rotor with a depth capacity of 6.2 cm for spinning microtiter plates and filtration plates (e.g. Sorvall Super T 21, Sorvall Inc., Newtown, Conn.); 37° C. Shaker incubator with holders for deep-well plates; 37° C. Waterbath; 65° C. Incubator; Vortex mixer; Immunowash microtiter plate washer, #1575 (BioRad, Hercules, Calif.); pH Meter; Platform Shaker; UV Stratalinker 2400, (Stratagene La Jolla, Calif.); Stirrer/Hotplate; Robotic slide printer; −80° C. Freezer; −20° C. Freezer; 45% (w/v) Sterile Glycerol; 450 grams enzyme grade glycerol per liter 9 Autoclave and store at room temperature); T low E Buffer; 1M Tris-HCl (pH 8.0) 10 mL; 0.5 M EDTA (pH 8.0) 0.2 mL; DEPC treated $H_2O$ 990 mL (Autoclave and store at room temperature); Carbenicillin stock solution (1 gram of carbenicillin in 10 mls of sterile water, Sterile filter with a 0.2 micron filter, Store frozen at −20° C.); LB with 100 µg/ml carbenicillin (Add 1 ml of carbenicillin stock solution to 1 liter of LB, Make fresh); 3M Sodium Acetate pH=6.0 (408.24 grams sodium acetate (tri-hydrate) per liter, 3M acetic acid (172.4 ml per liter), Titrate the pH of the 3M sodium acetate solution to pH 6.0 with the 3M acetic acid solution, Filter sterilize using a 0.2 micron filter, Store at room temperature); Ethanol/acetate mix (Ethanol (100%) 950 ml, Sodium acetate pH=6.0, 50 ml); 1000 ml 3×SSC; DEPC $H_2O$ 42.5 ml; 20×SSC 7.5 ml; 50 ml 70% Ethanol; Ethanol (100%) 350 ml; DEPC $H_2O$ 150 ml; 500 ml.

The first step was to grow the EST clones. The cDNA clones were obtained from Research Genetics (Huntsville, Ala.) and were their standard microarray set, which consisted of 3789 sequence-verified known genes and 2778 sequence-verified ESTs.

The sealed master plates were incubated over night at 37° C. Most suppliers provide low density bacterial cultures. Replicating directly from these dilute stocks frequently results in non-growth in the secondary culture. If making the template from a plate that had previously been cultured to high density before freezing, this initial growth step should not be used, as it will reduce the viability of the cultures.

A set of standard 96 well round (U) bottom plates were then prepared by labeling all plates and placing 100 µl of LB broth containing 100 ?g/ml carbenicillin in each well. These plates were used as working copies. To preserve the master set of plates, it was useful to make replicate copies of the master plate to serve as working copies when the master plate was first replicated. The EST clones were then checked to insure that they were in a vector conferring ampicillin resistance, as is common with human IMAGE clones.

The master plates were spun briefly (about two minutes) at 1000 rpm in a horizontal microtiter plate rotor to remove condensation and droplets from the seals before opening. Bacterial culture fluid on the sealers can easily be transferred from one well to others, cross-contaminating the stocks.

Then a container was partially filled with 100% alcohol. The 96 pin-replicating tool was dipped in the alcohol, removed and then the pins were flamed.

The inoculation block was allowed to cool briefly, then the replicating tool was dipped in the master plate and then into the daughter plate. This was repeated as necessary for each plate inoculated. It is useful to color the plate corner near the A-1 well of all master and daughter plates with a marker pen before beginning the replication process in order to reduce mistakes in the relative orientation of the plates. The suggested plates have a notch at this corner as well.

The inoculated LB plates, with the lids on, were placed into a one gallon sealable bag containing a moistened paper towel and grow overnight at 37° C. Many 37° C. incubators tend to dry out microtiter plate cultures. Placing the plates in a highly humidified bag avoids this problem.

Next, deep well plates were filled with 1 ml of Superbroth (100 µg/ml carbenicillin) per well. These plates served as the source of culture for template preparation. Using the replicating tool, the deep well plates were then inoculated directly from the freshly grown LB plates. Next, the openings of the deep well plates were covered with Qiagen Airpore Tape Sheets and the plastic lids were placed over the sheet. The plates were then placed in a 37° C. shaker incubator at 200 RPM for twenty-four hours. 50 µl of 45% (w/v) sterile glycerol was added to each well of any working plates that are to be frozen (−80° C.) and subsequently used as culture sources.

After the EXT clones were grown, the plasmid templates have to be isolated. First, the lysis buffer (Edge Biosystems Kit) was warmed to 37° C. to dissolve the SDS. Then the RNAse solution was added to the resuspension buffer (Edge Biosystems Kit), 1 ml/100 ml, and stored at 4° C. The receiving plates were prepared from the Edge Biosystems Kit by adding 350 µl of ethyl alcohol to each well of the receiving plates. The filter plate was then placed on top and secured with tape. The bacterial cultures in the deep well plates were centrifuged at 1500×g for seven minutes in a centrifuge equipped with a horizontal rotor for 96-well plates. They were then briefly inverted and excess media was tapped out on a clean paper towel. The pellets will loosen and may be lost when pouring off excess media if this step is delayed.

The pellet was then resuspended in 100 µl of Resuspension Buffer, and Vortexed until the entire pellet was re-suspended. This step is critical. Poor resuspension of the cells results in clumps of cells that do not lyse in subsequent steps. This reduces the yield and decreases the purity of the product. 100 µl of Lysis Buffer was then added and the solution was mixed gently by rocking the plates from side to side, to avoid shearing the bacterial chromosomal DNA. 100 µl of Precipitation buffer was added to each well and briefly mixed. Then, 100 µl of Neutralization buffer was added to each well and Vortexed.

The contents of the deep wells were then transferred to the waiting filter plates/receiving plate stacks using the wide bore pipette tips provided in the kits. The stacked plates were then centrifuged at 1500×g for twelve minutes in a centrifuge equipped with a horizontal rotor for 96-well plates. The stacked plates were then removed from the centrifuge. The filter plates were removed and discarded. The alcohol and filtrate were decanted from the receiver plate and the excess alcohol was touched off on clean paper towels. 500 µl of 70% ethanol was added to each well and immediately decanted and excess alcohol was touched off with a clean paper towel. Then, the plates were placed in a clean drawer without their lids, covered with a clean paper towel and allowed to dry overnight.

The next day, the DNA was resuspended in 200 µl of T Low E Buffer. The top was sealed with plate sealer and rehydrated at 4° C. for at least two days before using. They were stored at −20° C. in the interim.

After the plasmid templates have been isolated, the EST inserts were amplified. For each 96 well plate to be amplified, a PCR reaction mixture was prepared containing the following ingredients: 1000 µl of 10×PCR Buffer, 20 ?L of dATP (100 mM), 20 ?L of dGTP (100 mM), 20 ?L of dCTP (100 mM), 20 ?L of dTTP (100 mM), 5 ?L of AEK M13F primer (1 mM), 5 µL of AEK M13R primer (1 mM), 100 µL of AmpliTaq polymerase (5 U/µl), and 8800 mL of $H_2O$. The 96-well PCR plates were then labeled and 100 µl of the PCR reaction mixture from above was aliquotted to each well. The plates were then gently tapped to insure that no air bubbles were trapped at the bottom of the wells. 1 µl of purified EST plasmid template from above was then added to each well. The donor and recipient plates were then marked at the corner, near the A1 well to facilitate correct orientation during transfer of the template. It was important to make sure that the pipette tips were all submerged in the PCR reaction mix when delivering the template. Missing the liquid was easier when multi-channel pipettes were used.

The following thermal cycle series was then performed: 1 initial cycle of heating to 96° C. and holding for 30 sec, 25 cycles of denaturing at 94° C. for 30 sec, reannealing at 55° C. for 30 sec, and extending at 72° C. for 150 sec, one final cycle of holding at 72° C. for 5 minutes, then cooling to ambient temperature. After the above cycle, the plates were held at 4° C. while quality controls were performed.

The quality control was done by agarose gel electrophoresis of the ESTs. If this was the first time the template for these ESTs was being amplified, 2 µl of each PCR product was analyzed on a 2% agarose gel. If amplified products from this template had been previously tested, then one row of wells from each plate amplified was analyzed. Gel imaging allowed a rough quantitation of product while giving an excellent characterization of the product. Band size, as well as the number of bands observed in the PCR products, contributed to an understanding of the final results of the hybridization. The use of gel well formats suitable for loading from 96 well plates and programmable pipetters made this form of analysis feasible on a large scale.

The materials, reagents and solutions for the quality control check included: Electrophoresis apparatus with capacity for four 50 well combs, (e.g. #D3, Owl Scientific, Woburn, Mass.); 50× Tris-Acetate Electrophoresis BufferM; Agarose; Dye Solution (Xylene Cyanol/Bromophenol Blue) (e.g. #351-081-030, Quality Biological Inc., Gaithersburg Md.); Glycerol (enzyme grade); Ethidium Bromide solution (10 mg/ml); 100 base-pair ladder size standard; Programmable, 12-channel pipetter (e.g. #2019, Matrix Technologies, Lowell, Mass.); Disposable microtiter mixing trays (e.g. Falcon #353911, Becton Dickinson, Franklin Lake, N.J.); Electrophoresis power supply; 1×TAE Buffer; 50×TAE Buffer 40 ml; Ethidium Bromide (10 mg/ml) 0.1 ml and Water 960 ml; 1000 ml; Loading Buffer; Glycerol (enzyme grade) 4.0 ml, DEPC Water 0.9 ml, and Dye Solution* 0.1 ml for a total of 5.0 ml (*This solution is 0.25% (w/v) Xylene Cyanol and 0.25% (w/v) Bromophenol Blue); 100 bp Size Standards; DNA ladder (1 mg/ml) 50 µL, 1M Tris-HCl (pH 8.0) 5 µl, 0.5 M EDTA (pH 8.0) 5 µl, and Loading Buffer 440 µl for a total of 500 µl The electrophoresis was carried out with a 2% agarose gel (1×TAE) with four combs (50 tooth) that was submerged in an electrophoresis apparatus with sufficient 1×TAE buffer to just cover the surface of the gel. A reservoir of Loading Buffer was prepared, using 12 wells of a microtiter plate. Then a pipetter was programmed to sequentially carry out the following steps: fill with 2 µl, fill with 1 µL, fill with 2 µl, mix a volume of 5 µl five times, expel 5 µl. Twelve (12) disposable tips were then placed on the pipetter. 2 µl of PCR product from wells A1-A12 of the PCR plate were loaded, followed by 1 µl of air, then 2 µl of Loading Buffer from the reservoir. The tips were then placed in clean wells of a disposable mixing tray and the pipette was allowed to mix the sample and loading dye. The pipette tip was then placed in a 50 well row so that the tip containing the PCR product from well A1 is in the second well of the row, and the other tips are in every other succeeding well.

The process was repeated (changing tips each time), to load PCR plate row B starting in the 3rd well, interleaved with the A row, the C row starting at well 26, and the D row at well 27, interleaved with the C row. Then 5 µl of 100 bp Size Standards were placed in wells 1 and 50. This process was repeated, to load samples from rows E, F, G, and H in the second, 50 well row of gel wells, to load samples from two 96 well PCR plates per gel, or single row samples from 16 PCR plates. To reduce diffusion and mixing, a voltage was applied to the gel for a minute between loading each well strip. This caused the DNA to enter the gel, and reduced band spreading and sample loss.

A voltage was then applied to the gel and it was run until the bromophenol blue (faster band) had nearly migrated to the next set of wells. For a gel that is 14 cm in the running dimension, and 3 cm between each row of wells, 200 volts were applied for 15 minutes. Digital photos of the gel were taken and the images stored for future reference. The gels should show bands of fairly uniform brightness distributed in size between 600 to 2000 base-pairs. Further computer analysis of such images can be carried out with image analysis packages to provide a list of the number and size of bands. Ideally this information can be made available during analysis of the data from hybridizations involving these PCR products.

After the quality control checks are run on the plates, the next step involves purifying the PCR products. 96 well V-bottom plates were filled with 200 µl per well of ethanol/acetate mix. The ethanol acetate solution used for precipitation is less acidic (pH 6) than is typically used. In this instance, more acidic solutions produce precipitates which are harder to resuspend without improving yield.

100 μl per well of PCR product was transferred into V-bottom plates and mixed by pipetting a volume of 75 μl per well four times. The plates were then placed in a −80° C. freezer for one hour or stored overnight at −20° C. The plates were stored at −20° C. if they were to be left for more than one hour, because aggressive precipitation produces precipitates which are hard to resuspend. The plates were then thawed to reduce brittleness and melt any ice, which may have formed in the wells.

The plates were loaded into a centrifuge with a horizontal microtiter plate rotor and spun at 2600×g for 40 minutes at 4° C. Next, the supernatant from each well was aspirated using the Immunowash plate washer. Settings for the depth of aspiration by the plate washer needed to be adjusted to suit the microtiter plates used. It is advisable to leave approximately 10-20 ml in the bottom of the well to avoid disturbing the pellet.

200 μl of 70% ethanol was delivered to each well in the plate using the Immunowash plate washer, and the plates were centrifuged at 2600×g for 40 minutes. The supernatant was aspirated from each well using the Immunowash plate washer, and the plates were dried overnight in a closed drawer. They should not be dried in a speed-vac because desiccated PCR products are hard to resuspend.

After the PCR products were purified, they were then resuspended by adding 40 μl of 3×SSC per well. The plates were then sealed with a foil sealer, taking care to achieve a tight seal over each well. The plates were then placed in heat sealable bags with paper towels moistened with 3×SSC and the bag was sealed with a heat sealer. The high external humidity within the sealed bag helped to keep the volumes in the individual wells from varying. The bags were then placed in a 65° C. incubator for 2 hours. The heat in the incubator was then turned off, and the plates were allowed to cool gradually in the incubator to avoid condensation on the sealers. The plates were stored at −20° C.

The yield of the PCR suspension was then checked by fluorometric determination of DNA concentration. 1 μl of resuspended PCR product from one row of wells from each plate on a 2% agarose gel was analyzed as previously described. Adequate precipitation and resuspension produced very intense bands, with no material failing to leave the loading well, and no smear of material from the band towards the loading well.

While it would be ideal to be able to exactingly quantify each EST PCR product and spot each DNA species at equivalent concentrations, it is impractical for most labs to do so when thousands of ESTs must be prepared. Fortunately, it is possible to use a strategy where excess DNA is spotted, so that the exact quantities used do not produce much variation in the observed results. When using this strategy, it is necessary to track the average productivity of the PCR reactions. Fluorometry provides a simple way to obtain an approximate concentration of the double-stranded PCR product in the PCR reaction mix.

Next, the double stranded DNA was quantified. The materials, reagents, and solutions necessary include: reference double-stranded DNA (0.5 mg/ml) (e.g. #15612-013 Gibco/BRL, Bethesda, Md.), 96 well plates for fluorescent detection (e.g. #7105, Dynex, Chantilly, Va.), Fluorometer (e.g. #LS50B, Perkin Elmer, Norwalk, Conn.), FluoReporter Blue dsDNA Quantitation Kit (#F-2962, Molecular Probes, Eugene, Oreg.), TE, 12 channel multi-pipetters, Computer equipped with Microsoft Excel software, Ds-DNA Standards: 50 μg/ml, 100 μg/ml, 250 μg/ml, 500 μg/ml, μl TE 90, 80, 50, 0 μl ds-DNA (0.5 mg/ml) 10, 20, 50, 100, (It is good practice to check both the integrity (agarose gel) and the concentration (absorbance) of the standard before use); Fluor Buffer (Hoechst 33258 solution (contains the dye at an unspecified concentration in a 1:4 mixture of DMSO:$H_2O$) (from kit) 25 μl, TNE Buffer (TNE Buffer is 10 mM Tris-HCl (pH 7.4), 2 M NaCl, 1 mM EDTA) (from kit) 10 ml.

The double stranded DNA was quantified as follows. 96 well plates were labeled for fluorescence assay. 200 μl of Fluor Buffer was added to each well. 1 μl of PCR product from each well in a row of a PCR plate was added to a row of the fluorometry plate. Samples were added to rows A through G of the fluorometry plate. In the final row of the fluorometry plate 1 μl of each of the series of ds-DNA standards 0 μg/ml (TE only), 50, 100, 250 and 500 μg/ml ds-DNA were added. This series was repeated twice in the final row.

The fluorometer was set for excitation at 346 nm and emission at 460 nm, and adjusted as necessary to read the plate. If the fluorometer used did not support automated analysis, the data table was exported to Excel. The response for the standards was tested to see that it was linear and reproducible from the range of 0 to 500 μg/ml of ds-DNA.

Next, the concentration of ds-DNA in the PCR reactions was calculated using the following equation, after subtracting the average 0 μg/ml value from all other sample and control values:

[ds-DNA (μg/ml)]=((PCR sample value)/(average 100 μg/ml value))*100

Constantly tracking the yields of the PCRs makes it possible to rapidly detect many ways in which PCR can fail or perform poorly. This assay can also be applied after precipitation and resuspension of the PCR products to monitor overall recovery of product. 1 μl of amplified products from one row of wells from each amplified plate by fluorometry was analyzed.

Slides were then coated with poly-L-lysine to have a surface that is both hydrophobic and positively charged. The hydrophobic character of the surface minimizes spreading of the printed spots, and the charge appears to help position the DNA on the surface in a way that makes cross-linking more efficient.

Materials, reagents, and solutions for coating the slides includes: Gold Seal Microscope Slides (#3011, Becton Dickinson, Franklin Lake, N.J.), Ethanol (100%), Poly-L-lysine (#P8920, Sigma, St. Louis, Mo.), 50 Slide Stainless Steel Rack, #900401, and 50 Slide Glass Tank, #900401, (Wheaton Science Products, Millville, N.J.), Sodium Hydroxide, Stir Plate, Stir Bar, Platform Shaker, 30 Slide Rack, #196, plastic, and 30 slide Box, #195, plastic, (Shandon Lipshaw, Pittsburgh, Pa.), Sodium Chloride, Potassium Chloride, Sodium Phosphate Dibasic Heptahydrate, Potassium Phosphate Monobasic, Autoclave, 0.2 mm Filter: Nalgene, Centrifuge: Sorvall Super 20, Slide Box (plastic with no paper or cork liners), (e.g. #60-6306-02, PGC Scientific, Gaithersburg, Md.), 1 L Glass Beaker; 1 L Graduated Cylinder, 1M Sodium Borate (pH 8.0) (Dissolve 61.83 g of Boric acid in 900 ml of DEPC $H_2O$. Adjust the pH to 8.0 with 1N NaOH. Bring volume up to one liter. Sterilize with a 0.2 micron filter and store at room temperature), Cleaning Solution ($H_2O$ 400 ml, Ethanol 600 ml, NaOH 100 g -Dissolve NaOH in $H_2O$. Add ethanol and stir until the solution clears. If the solution does not clear, add $H_2O$ until it does), and Poly-L-lysine Solution (poly-L-lysine (0.1% w/v) 35 ml PBS 35 ml $H_2O$ 280 ml 350 ml)

First, the slides are placed into 50 slide racks and the racks are placed in glass tanks with 500 ml of cleaning solution. Gold Seal Slides are highly recommended, as they have been found to have consistently low levels of autofluorescence. It was important to wear powder free gloves when handling the slides to avoid contamination.

The tanks are placed on platform shakers for two hours at 60 rpm. After being shook, the cleaning solution was poured out, and the slides were then washed in $H_2O$ for three minutes. This wash was repeated four times. The slides were then transferred to 30 slide plastic racks and placed into small plastic boxes for coating. The slides were then submerged in 200 ml poly-L-lysine solution per box. The slide boxes were then placed on platform shaker for one hour at 60 rpm. The slides were rinsed three times with $H_2O$, and submerged in $H_2O$ for one minute, and then centrifuged for two minutes at 400×g and the slide boxes used for coating were dried.

The slides were then placed back into the slide box used for coating and allowed to stand overnight before transferring to a new slide box for storage. This allowed the coating to dry before it was handled. The slides were allowed to age for two weeks on the bench, in a new slide box, before they were printing on. The coating dried slowly, becoming more hydrophobic with time.

Slide boxes used for long term storage should be plastic and free of cork lining. The glue used to affix the cork will leach out over time and give slides stored in these types of boxes a greasy film that has a high degree of autofluorescence. All glassware and racks used for slide cleaning and coating should be cleaned with highly purified $H_2O$ only, and detergent should not be used.

Once the slides were coated, they were printed. The variety of printers and pens for transferring PCR products from titer plates to slides precludes highly detailed descriptions of the process. The following steps provide a general description of the processing.

The print pens were pre-cleaned according to the manufacturer's specification. The printer slide deck was then loaded with poly-L-lysine coated slides from above. The plates containing the purified EST PCR products were thawed and centrifuged briefly, (about two minutes) at 1000 rpm in a horizontal microtiter plate rotor to remove condensation and droplets from the seals before being opening. 5 to 10 µl of the purified EST PCR products were transferred to a plate that served as the source of solution for the printer. Printing with quill-type pens usually requires that the volume of fluid in the print source was sufficiently low, so that when the pen was lowered to the bottom of the well, it was submerged in the solution to a depth of less than a millimeter. This keeps the pen from carrying a large amount of fluid on the outside of the pen shaft and producing variable, large spots on the first few slides printed.

A repetitive test print was run on the first slide. In this operation, the pens were loaded with the DNA solution, and then the pens serially deposited this solution on the first slide in the spotting pattern specified for the print. This test was run to check the size and shape of the specified spotting pattern, as well as its placement on the slide. It also served to verify that the pens were loading and spotting, and that a single loading produced as many spots as were required to deliver material to every slide in the printer. If one or more of the pens was not performing at the desired level, it was re-cleaned or substituted with another pen and tested again. If all pens were performing, the full print was carried out.

At the end of the print, the slides were removed from the printer, labeled with the print identifier and the slide number by writing on the edge of the slide with a diamond scribe and placed in a dust free slide box to age for one week. It was useful to etch a line, which outlined the printed area of the slide, onto the first slide. This served as a guide to locate the area after the slides have been processed, and the salt spots were then washed off.

The slides were placed, printed side face up, in a casserole dish and covered with cling wrap. The slides were then exposed to a 450 mJ dose of ultraviolet irradiation in the Stratalinker. Slides should have been and were aged at ambient temperature in a closed slide box for one week prior to blocking The slides were then transferred to a 30 slide stainless steel rack and the rack was placed into a small glass tank. 6.0 g succinic anhydride was dissolved in 325 ml 1-methyl-2-pyrrolidinone in a glass beaker by stirring with a stir bar. Nitrile gloves were worn and the work was carried out in a chemical fume hood while handling 1-methyl-2-pyrrolidinone (a teratogen).

25 ml 1M sodium borate buffer (pH 8.0) was added to the beaker. The solution was allowed to mix for a few seconds, then rapidly poured into a glass tank with slides. Succinic anhydride hydrolyzed quite rapidly once the aqueous buffer solution was added. To obtain quantitative passivation of the poly-L-lysine coating, it was critical that the reactive solution be brought in contact with the slides as quickly as possible. The glass tank was placed on a platform shaker in a fume hood for 20 minutes. Small particulates resulting from precipitation of reaction products may be visible in the fluid.

While the slides were incubating on the shaker a boiling $H_2O$ bath was prepared to denature the DNA on the slides. After the slides were incubated for 20 minutes, they were transferred into the boiling $H_2O$ bath. The heating element was immediately turned off after the slides were submerged in the bath. The slides were allowed to stand in the $H_2O$ bath for 2 minutes. The slides were then transferred into a glass tank filled with 100% ethanol and incubated for 4 minutes. The slides were removed and centrifuged at 400 rpm for 3 minutes in a horizontal microtiter plate rotor to dry the slides. The slides were then transferred to a clean, dust free slide box and allowed to stand overnight before being used for collection of gene expression data.

Example 2

Cell Culture and Tumor Samples

The source and other information for the cell lines and tumor samples used herein are described in TABLE 2 below for both the training set and the test samples.

TABLE 2

Supplement Table: Known Molecular Characteristics of Samples.

| Sample Label | Histological Diagnosis | Molecular Markers | Source Label | Source |
|---|---|---|---|---|
| EWS-C1 | EWS-C | EWS-FLI1, 10-6 | A4573 | NCI |
| EWS-C2 | EWS-C | EWS-FLI1, type I | TC71 | NCI |

TABLE 2-continued

Supplement Table: Known Molecular Characteristics of Samples.

| Sample Label | Histological Diagnosis | Molecular Markers | Source Label | Source |
|---|---|---|---|---|
| EWS-C3 | EWS-C | EWS-FLI1, type I | TC106 | NCI |
| EWS-C4 | EWS-C | EWS-FLI1, type I | 5838 | NCI |
| EWS-C6 | EWS-C | EWS-FLI1, type I | A673 | NCI |
| EWS-C7 | EWS-C | EWS-FLI1, type I | ES-CL1 | MSKCC |
| EWS-C8 | EWS-C | EWS-FLI1, type I | TC32 | NCI |
| EWS-C9 | EWS-C | EWS-FLI1, type II | SK-ES-1 | ATCC |
| EWS-C10 | EWS-C | EWS-FLI1, type II | SK-N-MC | ATCC |
| EWS-C11 | EWS-C | EWS-FLI1, type II | RDES | ATCC |
| EWS-T1 | EWS-T | EWE-FLI1, type I | ES20 | MSKCC |
| EWS-T2 | EWS-T | EWS-FLI1, type II | ES13 | MSKCC |
| EWS-T3 | EWS-T | EWS-FLI1, type I | ES16 | MSKCC |
| EWS-T4 | EWS-T | EWS-FLI1, type I | ES17 | MSKCC |
| EWS-T6 | EWS-T | EWS-FLI1, 7-8 | ES22 | MSKCC |
| EWS-T7 | EWS-T | EWS-ERG, 7-9 | ES25 | MSKCC |
| EWS-T9 | EWS-T | EWS-FLI1, type I | 9602P006 | CHTN |
| EWS-T11 | EWS-T | EWS-FLI1, type I | 9703P152 | CHTN |
| EWS-T12 | EWS-T | EWS-FLI1, type I | 9704P218 | CHTN |
| EWS-T13 | EWS-T | EWS-FLI1, type I | ES23 | MSKCC |
| EWS-T14 | EWS-T | EWS-FLI1, type I | 9605P074 | CHTN |
| EWS-T15 | EWS-T | EWS-FLI1, type I | 9609P027 | CHTN |
| EWS-T19 | EWS-T | EWE-FLI1, type I | SARC75 | CHTN |
| RMS-C2 | ERMS-C | — | RD | ATCC |
| RMS-C3 | ARMS-C | ND | RH4 | NCI |
| RMS-C4 | ARMS-C | PAX3-FKHR | RH3 | NCI |
| RMS-C5 | ARMS-C | PAX3-FKHR | RH5 | NCI |
| RMS-C6 | ARMS-C | PAX3-FKHR | RH28 | NCI |
| RMS-C7 | ARMS-C | ND | RH30 | NCI |
| RMS-C8 | ERMS-C | — | CTR | ATCC |
| RMS-C9 | ARMS-C | PAX3-FKHR | RH4 | NCI |
| RMS-C10 | ARMS-C | PAX3-FKHR | RMS13 | NCI |
| RMS-C11 | ERMS-C | — | TE671 | ATCC |
| RMS.T1 | ARMS-T | PAX3-FKHR | RMS3 | MSKCC |
| RMS.T2 | ARMS-T | PAX3-FKHR | RMS6 | MSKCC |
| RMS.T3 | ERMS-T | — | RMS2 | MSKCC |
| RMS.T4 | ERMS-T | no PAX-FKHR | RMS5 | MSKCC |
| RMS.T5 | ARMS-T | PAX3-FKHR | RMS10 | MSKCC |
| RMS.T6 | RMS-T | ND | RT1 | CHTN |
| RMS.T7 | ERMS-T | — | RT4 | CHTN |
| RMS.T8 | RMS-T | ND | RT5 | CHTN |
| RMS.T10 | RMS-T | ND | RT2 | CHTN |
| RMS.T11 | ERMS-T | — | RHAB2 | CHTN |
| NB-C1 | NB-C | MYCN amp | KCNR | NCI |
| NB-C2 | NB-C | — | GICAN | NCI |
| NB-C3 | NB-C | — | SK-N-AS | ATCC |
| NB-C4 | NB-C | MYCN amp | LAN5 | NCI |
| NB-C5 | NB-C | MYCN amp | SK-N-BE2 | ATCC |
| NB-C6 | NB-C | MYCN amp | SK-N-DZ | ATCC |
| NB-C7 | NB-C | — | GICAN | NCI |
| NB-C8 | NB-C | — | NGP | NCI |
| NB-C9 | NB-C | — | SH-SY5Y | ATCC |
| NB-C10 | NB-C | MYCN amp | SK-N-FI | ATCC |
| NB-C11 | NB-C | Single copy MYCN | SK-N-SH | ATCC |
| NB-C12 | NB-C, | MYCN amp | CHP-134B | NCI |
| BL-C1 | BL-C | — | RAMOS (RAI) | ATCC |
| BL-C2 | BL-C | — | ST486 | ATCC |
| BL-C3 | BL-C | — | CA46 | ATCC |
| BL-C4 | BL-C | — | ST486 | ATCC |
| BL-C5 | BL-C | — | RAJI | ATCC |
| BL-C6 | BL-C | — | MC116 | ATCC |
| BL-C7 | BL-C | — | DAUDI | ATCC |
| BL-C8 | BL-C | — | SULTAN | ATCC |
| Test1 | NB-C | MYCN amp | IMR32 | ATCC |
| Test2 | EWS-C | ND | CHOP1 | NCI |
| Test3 | Osteosarcoma-C | — | OsA-CI | ATCC |
| Test4 | ARMS-T | — | ARMD1 | CHTN |
| Test5 | Sarcoma | — | A204 | ATCC |
| Test 6 | EWS-T | EWS-FLI1, type I | 9608P053 | CHTN |
| Test7 | BL-C | — | EB1 | ATCC |
| Test8 | NB-C | — | SMSSAN | NCI |
| Test9 | Sk. Muscle | — | SkM1 | CHTN |
| Test10 | ERMS-T | — | ERDM1 | CHTN |
| Test11 | Prostate Ca.-C | — | PC3 | ATCC |
| Test12 | EWS-T | — | SARC67 | CHTN |
| Test13 | Sk. Muscle | — | SkM2 | CHTN |
| Test 14 | NB-T | Single copy MYCN | NB3 | DZNSG |

TABLE 2-continued

Supplement Table: Known Molecular Characteristics of Samples.

| Sample Label | Histological Diagnosis | Molecular Markers | Source Label | Source |
|---|---|---|---|---|
| Test 15 | BL-C | — | EB2 | ATCC |
| Test 16 | NB-T | Single copy MYCN | NB1 | DZNSG |
| Test 17 | ARMS-T | — | ARMD2 | CHTN |
| Test 18 | BL-C | — | GA10 | ATCC |
| Test 19 | EWS-T | ND | ET3 | CHTN |
| Test 20 | EWS-T | EWS-FLI1, type I | 9903P1339 | CHTN |
| Test 21 | EWS-T | EWS-FLI1, type II | ES23 | MSKCC |
| Test 22 | ERMS-T | — | ERMD2 | CHTN |
| Test 23 | NB-T | Single copy MYCN | NB2 | DZNSG |
| Test 24 | ERMS-T | no PAX-FKHR | RMS4 | MSKCC |
| Test 25 | NB-T | Single copy MYCN | NB4 | DZNSG |

Supplement Table: Known molecular characteristics of samples.
Table labels and abbreviations are described in Table 1 in the manuscript, EWS and ARMS samples with noted translocations were verified by RT-PCR.
ND; not determined.
Amp.: amplification.

All the original histological diagnoses were made at tertiary hospitals, which have reference diagnostic laboratories with extensive experience in the diagnosis of pediatric cancers. Approximately 20% of all samples in each category were randomly selected, blinded and set aside for testing. To augment this test set, we added 4 neuroblastoma tumors and 5 non-SRBCT samples (also blinded to the authors performing the analysis). The EWSs had a spectrum of the expected translocations, and the RMSs were a mixture of both ARMS containing the PAX3-FKHR translocation and embryonal rhabdomyosarcoma (ERMS). The NBs contained both MYCN amplified and single copy samples. The NHLs were cell lines derived from BL. TABLE 2 gives details of these samples as well.

This protocol details the methods used to extract RNA from cells, purify the RNA by a combination of phase extraction and chromatography, and prepare a labeled cDNA copy of the message fraction of the purified RNA. The protocol also describes the process of making fluorescent cDNA representations of the message pools within the isolated total RNA pools. This is accomplished by using the pure total RNA as a substrate for reverse transcription in the presence of nucleotides derivatized with either a Cy3 or a Cy5 fluorescent tag.

The materials, reagents, and solutions needed include: Trizol Reagent (#15596-018, Life Technologies, Rockville, Md.); RNeasy Maxi Kit (#75162, Qiagen, Valencia, Calif.); Chloroform; Ethanol (200 Proof USP Ethyl Alcohol); DPBS (Dulbecco's phosphate buffered saline); 3M sodium acetate (pH 5.2); dATP, dCTP, dGTP, dTTP, 100 mM each, store frozen, −20° C. (#27-2035-02, Pharmacia, Peapack, N.J.); pd(T)12-18 resuspend at 1 mg/ml, and store frozen −20° C. (#27-7858, Amersham Pharmacia Biotech); Anchored oligo primer (anchored; 5'-TTT TTT TTT TTT TTT TTT TTV N-3') (SEQ ID NO: 99); resuspend at 2 mg/ml, store frozen −20° C. (e.g. #3597-006, Genosys) ; CyTM3-dUTP, 1 mM, and CyTM5-dUTP, 1 mM, store −20° C., light sensitive ; RNasinâ Rnase inhibitor, store −20° C. (#N211A, Promega) ; SUPERSCRIPT™ II Rnase H' Reverse Transcriptase Kit, store −20° C., (#18064-014, Life Technologies, Rockville, Md.); C0t-1 DNA, 1 mg/ml, store frozen −20° C. (#15279-011, Life Technologies, Rockville, Md.); 0.5M EDTA(pH 8.0); 1 N NaOH ; 1M TRIS-HCL; (pH7.5); TE pH 7.4; DEPC water 50 X Tris Acetate Buffer; 15 ml round bottom; polypylene centrifuge tubes; 50 ml conical polypropylene centrifuge tubes; 1.5 ml; Eppendorf tubes ; 0.2 ml thin wall PCR tube; MicroCon 100 (Amicon Cat No. 42412); High speed centrifuge for 15 ml tubes; Clinical centrifuge with horizontal rotor for 50 ml conical tubes; Tissue homogenizer (e.g. Polytron PT1200 with Polytron-Aggregate-Dispergier-und-Mischtechnik 147a Ch6014 #027-30-520-0, Brinkmann Instruments Inc., Westbury, N.Y.); RPE Buffer (Add 4 volumes of ethanol per volume of RPE concentrate supplied in Quiagen Kit0; RW1 Buffer (Supplied in Qiagen Kit) 75% EtOH(Ethanol (100%) 375 ml, and DEPC H2O 125 ml for a total of 500 ml); 10× low T dNTP Mix (25 µL dGTP (100 mM), 25 µL dATP (100 mM), 25 µL dCTP (100 mM), 10 µL dTTP (100 mM), and 415 µL DEPC $H_2O$ for a total of 500 µL); 5× First Strand Buffer (Provided with Superscript II); TAE Buffer (50× Tris Acetate Electrophoresis Buffer 20 ml, and DEPC H2O 980 mL for a total of 1000 ml).

If the cells that were used were harvested from tissue culture, the cell pellet was washed twice in DPBS. If the cells that were used were from tissue culture, 1 ml of Trizol was added per $2 \times 10^7$ cells and mixed by shaking. If tissue was being used, 100 mg of frozen tissue was added directly to 4 ml of Trizol, and dissociate by homogenization with a rotating blade tissue homogenizer.

Whatever the source, 2/10 volume of chloroform was added to the cells and shook for 15 seconds, and then allowed to stand for 3 minutes, followed by centrifugation at 12,000×g for 15 minutes at 4° C. The supernatant was taken off and added to a polypropylene tube, while recording the volume of the supernatant.

Then 0.53 volumes of ethanol were slowly added to the supernatant while vortexing, this produced a final ethanol concentration of 35%. The ethanol was added drop by drop and allowed to mix completely with the supernatant before more ethanol is added. If a high local concentration of ethanol is produced, the RNA in that vicinity will precipitate.

The supernatant from an extraction of $2 \times 10^7$ to $1 \times 10^8$ cells was added to an RNeasy maxi column, which is seated in a 50 ml centrifuge tube. The tube was then centrifuged at 2880×g in a clinical centrifuge with a horizontal rotor at room temperature for 5 minutes. The flow-through was then poured back onto the top of the column and centrifuged again. This step is necessary because a significant amount of RNA is not captured by the column matrix in the first pass of the RNA containing solution through the column.

The flow-through was discarded and 15 ml of RW1 buffer was added to the column, followed by centrifugation at 2880×g for 5 minutes. The flow-through was discarded again and then 10 ml of RPE buffer was added, followed again by centrifugation at 2880×g for 5 minutes. Once again, the flow through was discarded and another 10 ml of RPE buffer was added, and the column was centrifuged at 2880×g for 10 minutes.

Next, the column was placed in a fresh 50 ml tube and add 1 ml of DEPC treated water from the kit was added to the column, and the column was allowed to stand for 1 minute. The column was then centrifuged at 2880×g for 5 minutes, and another 1 ml of water was added to the column. The column was allowed to stand for 1 minute, followed by centrifugation at 2880×g for 10 minutes.

Then, 400 µl portions of the column eluate was aliquotted to 1.5 ml Eppendorf tubes, to which 1/10 volume of 3M sodium acetate (pH 5.2) was added, along with 1 ml of ethanol. The tubes were then allowed to stand for 15 minutes, after which they were centrifuged at 12000×g at 4 C for 15 minutes. The pellet was then washed two times in 75% EtOH and stored at −80° C.

The RNA was resuspended at approximately 1 mg/ml in DEPC $H_2O$. It was then concentrated to greater than 7 mg/ml by centrifugation on a MicroCon 100 filter unit, centrifuged at 500×g, checking as necessary to determine the rate of concentration. This step removes many residual, small to medium sized, molecules that inhibit the reverse transcription reaction in the presence of fluorescently derivatized nucleotides. The concentration of RNA in the concentrated sample was then determined by spectrophotometry, and the sample was stored at −80° C.

If an anchored oligo dT primer was used, the primer was annealed to the RNA in the following 17 µl reaction (a 0.2 ml thin wall PCR tube was used so that incubations could be carried out in a PCR cycler):

| Component | addition for Cy5 labeling | addition for Cy3 labeling |
|---|---|---|
| Total RNA (>7 mg/ml) | 150-200 µg | 50-80 µg |
| Anchored primer (2 µg/µl) | 1 µl | 1 µl |
| DEPC H2O | to 17 µl | to 17 µl |

If an oligo dT(12-18) primer was used, the primer was annealed to the RNA in the following 17 µl reaction:

| Component | addition for Cy5 labeling | addition for Cy3 labeling |
|---|---|---|
| Total RNA (>7 mg/ml) | 150-200 µg | 50-80 µg |
| dT(12-18) primer (1 µg/µl) | 1 µl | 1 µl |
| DEPC H2O | to 17 µl | to 17 µl |

The incorporation rate for Cy5-dUTP is less than that of Cy3-dUTP, so more RNA is labeled to achieve more equivalent signal from each species.

It was then heated to 65° C. for 10 minutes and cooled on ice for 2 minutes. Then, 23 µl (8 µl of 5× first strand buffer, 4 µl of 10× low T dNTPs mix, 4 µl of Cy5 or Cy3 dUTP (1 mM), 4 µl of 0.1 M DTT, 1 µl of Rnasin (30 u/?l), and 2 ?l of Superscript II (200 u/?l)) of reaction mixture containing either Cy5-dUTP or Cy3-dUTP nucleotides was added, mixed well by pipetting and a brief centrifuge spin was used to concentrate it in the bottom of the tube. Superscript polymerase is very sensitive to denaturation at air/liquid interfaces, so we were careful to suppress foaming in all handling of this reaction.

It was then incubated at 42° C. for 30 min., after which 2 µl Superscript II was added, making sure the enzyme was well mixed in the reaction volume and incubated at 42° C. for 30-60 min. Then, 5 µl of 0.5M EDTA was added, making sure the reaction was stopped with EDTA before adding NaOH (the next step), since nucleic acids precipitate in alkaline magnesium solutions.

Then, 10 µl 1N NaOH was added and it was incubated at 65? C for 60 minutes to hydrolyze residual RNA, after which it was cooled to room temperature. The purity of the sodium hydroxide solution used in this step is crucial. Slight contamination or long storage in a glass vessel can produce a solution that will degrade the Cy5 dye molecule, turning the solution yellow. Some researchers achieve better results by reducing the time of hydrolysis to 30 minutes.

It was then neutralized by adding 25 µl of 1M Tris-HCl (pH 7.5). Then, the labeled cDNA was desalted by adding the neutralized reaction, 400 µl of TE pH 7.5 and 20 µg of human C0t-1 DNA to a MicroCon 100 cartridge. It was then pipetted to mix, and spun for 10 minutes at 500×g. 200 µl TE pH 7.5 was added, and the solution was then concentrated to about 20-30 µl (approximately 8-10 min at 500×g). Alternatively, a smaller pore MicroCon 30 was used to speed the concentration step. In this case, the first wash was centrifuged for approximately 4.5 minutes at 16,000×g and the second (200 µl wash) for about 2.5 minutes at 16,000×g.

It was then recovered by inverting the concentrator over a clean collection tube and spinning for 3 min at 500×g. In some cases, the cy5 labeled cDNA formed a gelatinous blue precipitate that was recovered in the concentrated volume. The presence of this material signaled the presence of contaminants. The more extreme the contamination, the greater the fraction of cDNA which will be captured in this gel. Even if heat solubilized, this material tends to produce uniform, non-specific binding to the DNA targets. When concentrating by centrifugal filtration, the times required to achieve the desired final volume were variable. Overly long spins can remove nearly all the water from the solution being filtered. When fluor-tagged nucleic acids are concentrated onto the filter in this fashion, they are very hard to remove, so it is necessary to approach the desired volume by conservative approximations of the required spin times. If control of volumes proves difficult, the final concentration can be achieved by evaporating liquid in the speed-vac. Vacuum evaporation, if not to dryness, does not degrade the performance of the labeled cDNA.

Next, a 2-3 µl aliquot of the Cy5 labeled cDNA was taken for analysis, leaving 18-28 µl for hybridization. This probe was run on a 2% agarose gel (6 cm wide×8.5 cm long, 2 mm wide teeth) in Tris Acetate Electrophoresis Buffer (TAE). For maximal sensitivity when running samples on a gel for fluor analysis, a loading buffer with minimal dye was used and no ethidium bromide was added to the gel or running buffer.

The gel was then scanned on a Molecular Dynamics Storm fluorescence scanner (setting: red fluorescence, 200 micron resolution, 1000 volts on PMT). Successful labeling produces a dense smear of probe from 400 by to >1000 bp, with little pile-up of low molecular weight transcripts. Weak labeling and significant levels of low molecular weight material indicates a poor labeling. A fraction of the observed low molecular weight material is unincorporated fluor nucleotide.

Next, the fluorescent cDNA had to be hybridized to the microarray. The volume of hybridization solution required was first determined. The rule of thumb is to use 0.033 µl for each mm 2 of slide surface area covered by the cover slip used to cover the array. An array covered by a 24 mm by 50 mm cover slip required 40 µl of hybridization solution. The volume of the hybridization solution is critical. When too little solution is used, it is difficult to seat the cover slip without introducing air bubbles over some portion of the arrayed ESTs, and the cover slip will not sit at a uniform distance from the slide. If the cover slip is bowed toward the slide in the center, there will be less labeled cDNA in that area and hybridization will be non-uniform. When too much volume is applied, the cover slip will move easily during handling, leading to misplacement relative to the arrayed ESTs, and non-hybridization in some areas of the array.

For a 40 µl hybridization, the Cy3 and Cy5 labeled cDNAs were pooled into a single 0.2 ml thin wall PCR tube and the volume was adjusted to 30 µl by either adding DEPC $H_2O$, or removing water in a SpeedVac. If a vacuum device was used to remove water, high heat or heat lamps were not used to accelerate evaporation because the fluorescent dyes could be degraded.

For a 40 µl hybridization the following components were combined:

|  | High Sample Blocking | High Array Blocking |
|---|---|---|
| Cy5 + Cy3 probe | 30 µl | 28 µl |
| Poly d(A) (8 mg/ml) | 1 µl | 2 µl |
| Yeast tRNA (4 mg/ml) | 1 µl | 2 µl |
| Human C0t-1 DNA (10 mg/ml) | 1 µl | 0 µl |
| 20x SSC | 6 µl | 6 µl |
| 50x Denhardt's blocking solution | 1 µl (optional) | 2 µl |
| Total volume | 40 ul | 40 ul |

Arrays and samples can vary somewhat, making it necessary to vary the composition of the hybridization cocktail. In cases where there is residual hybridization to control repeat DNA samples on the array, more C0t-1 DNA was used, as in the High Sample Blocking formulation. When there is diffuse background or a general haze on all of the array elements, more of the non-specific blocker components was used, as in the High Array Blocking formulation.

The components were mixed well by pipetting, heated at 98° C. for 2 minutes in a PCR cycler, cooled quickly to 25° C. and 0.6 ul of 10% SDS was added. It was then centrifuged for 5 min at 14,000×g. The fluor labeled cDNAs have a tendency to form small, very fluorescent, aggregates which result in bright, punctate background on the array slide. Hard centrifugation will pellet these aggregates, allowing you to avoid introducing them to the array.

The labeled cDNA was applied to a 24 mm×50 mm glass cover slip and then touched with the inverted microarray. Applying the hybridization mix to the array and cover slipping it is an operation which requires some dexterity to get the positioning of the cover slip and the exclusion of air bubbles just right. It was helpful to practice this operation with buffer and plain slides before attempting actual samples. The hybridization solution was added to the cover slip first, since some aggregates of fluor remain in the solution and will bind to the first surface they touch.

The slide was then placed in a microarray hybridization chamber, 5 µl of 3×SSC was added to the reservoir, if the chamber provided one, or at the scribed end of the slide and the chamber was sealed. The chamber was submerged in a 65° C. water bath and the slide was allowed to hybridize for 16-20 hours. There are a wide variety of commercial hybridization chambers. It was worthwhile to prepare a mock hybridization with a blank slide, load it in the chamber and incubate it to test for leaks, or drying of the hybridization fluid, either of which cause severe fluorescent noise on the array.

Next, the unbound fluorescent cDNA was washed off. The hybridization chamber was removed from the water bath, cooled and carefully dried off. The chamber was unsealed and the slide was removed. As there may be negative pressure in the chamber after cooling, it is necessary to remove water from around the seals so that it was not pulled into the chamber and onto the slide when the seals are loosened.

The slide was placed, with the cover slip still affixed, into a Coplin jar filled with 0.5×SSC/0.01% SDS wash buffer. The cover slip was allowed to fall from the slide and then removed from the jar with a forceps. The slide was allowed to wash for 2-5 minutes. The slide was transferred to a fresh Coplin jar filled with 0.06×SSC, and allowed to wash for 2-5 minutes. The sequence of washes may need to be adjusted to allow for more aggressive noise removal, depending on the source of the sample RNA. Useful variations are to add a first wash which is 0.5×SSC/0.1% SDS or to repeat the normal first wash twice.

The slide was then transferred to a slide rack and centrifuged at low rpm (700-1000) for 3 minutes in a clinical centrifuge equipped with a horizontal rotor for microtiter plates. If the slide is simply air dried, it frequently acquires a fluorescent haze. Centrifuging off the liquids results in a lower fluorescent background. As the rate of drying can be quite rapid, it is suggested that the slide be placed in the centrifuge immediately upon removal from the Coplin jar.

Image analysis was performed using DeArray software (Chen, Y., Dougherty, E. R. and Bittner, M. L. Ratio-based decisions and the quantitative analysis of cDNA microarray images, *Biomedical Optics* 2, 364-374 (1997).

Example 3

Data Analysis

To calibrate ANN models to recognize cancers in each of the four SRBCT categories, gene-expression data from cDNA microarrays as obtained via Examples 1 and 2 above were used. The 63 training samples included both tumor biopsy material (13 EWS and 10 RMS) and cell lines (10 EWS, 10 RMS, 12 NB and 8 Burkitt lymphomas (BL; a subset of NHL). For two samples, ST486 (BL-C2 and C4) and GICAN(NB-C2 and C7), we performed two independent microarray experiments to test the reproducibility of the experiments and these were subsequently treated as separate samples.

Genes were filtered based on the intensity of the fluorescence gathered from the cDNA microarray. This type of filtering was designed to remove spots for which image analysis failed. Genes were filtered by requiring that a gene have a red intensity greater than 20 across all experiments. The number of genes that passed this filter was 2308. Each slide was normalized across all experiments. Therefore the expression level was based on a relative (or normalized) red intensity (RRI) for each gene, RRI=mean intensity of that spot/mean intensity of filtered genes. The natural logarithm (ln) of RRI was used as a measure of the expression levels.

Principal component analysis (PCA) further reduced the dimensionality. To allow for a supervised regression model with no over-training (when we have low number of parameters as compared to the number of samples), the dimensionality of the samples was reduced by PCA using centralized ln(RRI) values as input. Thus each sample was represented by 88 numbers, which are the results of projection of the gene expressions using PCA eigenvectors. We used the 10 dominant PCA components for subsequent analysis. These 10 dominant components contained 63% of the variance in the data matrix. The remaining PCA components contained variance unrelated to separating the four cancers.

Figure 5:
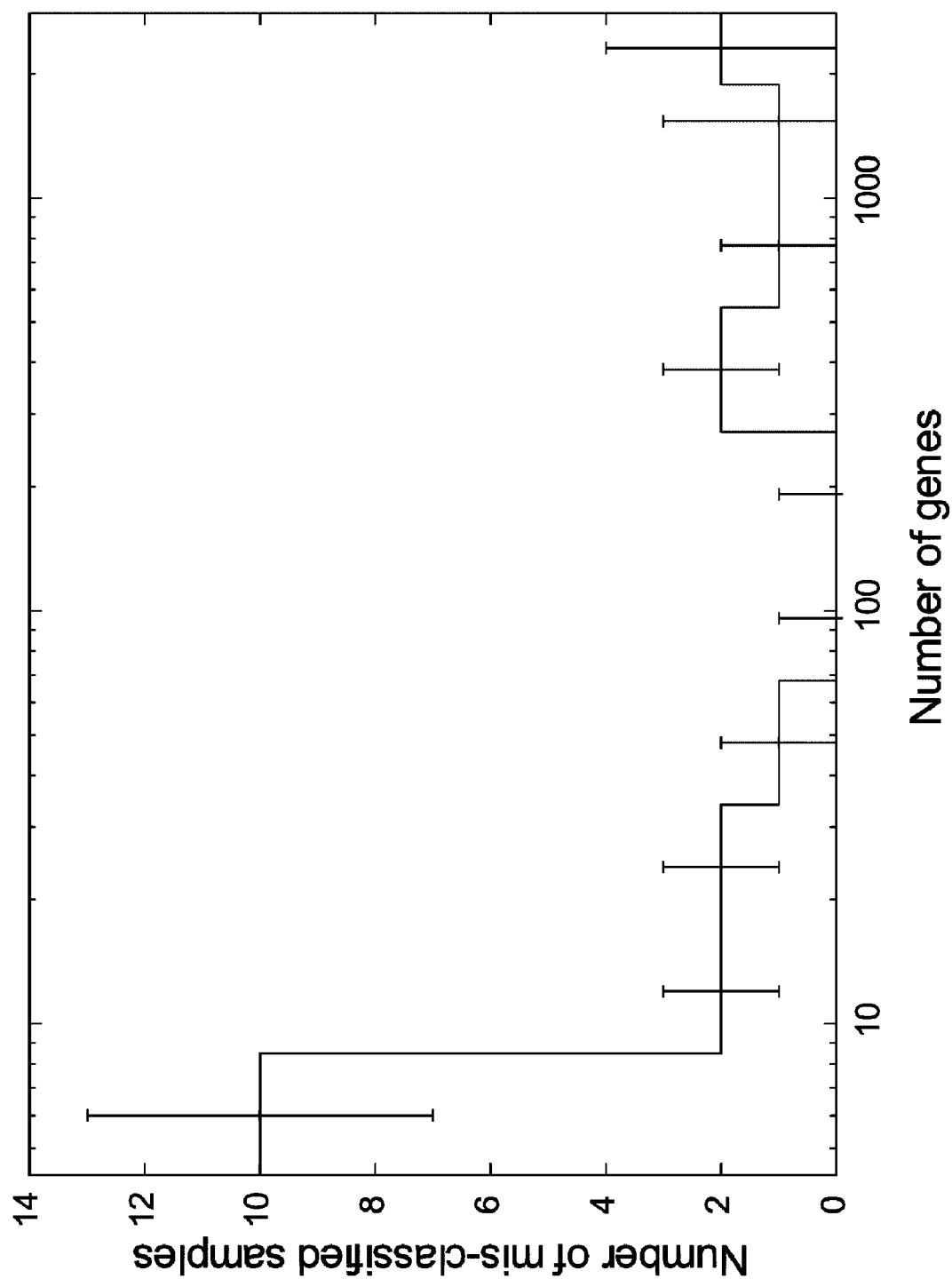
FIG. 5 represents a plot of the average number of misclassified samples for all 3750 models plotted against an increasing number of used genes.

We classified the training samples in the 4 categories using a 3-fold cross validation procedure: the 63 training (labeled) samples were randomly shuffled and split into 3 equally sized groups. Each linear ANN model was then calibrated with the PCA input variables (normalized to centralized z-scores) using 2 of the groups, with the third group reserved for testing predictions (validation). This procedure was repeated 3 times, each time with a different group used for validation. The random shuffling was redone 1250 times and for each shuffling we analyzed 3 ANN models. Thus, in total, each sample belonged to a validation set 1250 times, and 3750 ANN models were calibrated. The three-fold cross-validation procedure produced at total of 3750 ANN models, and the training and validation was successful, see FIG. 5.

Figure 4:
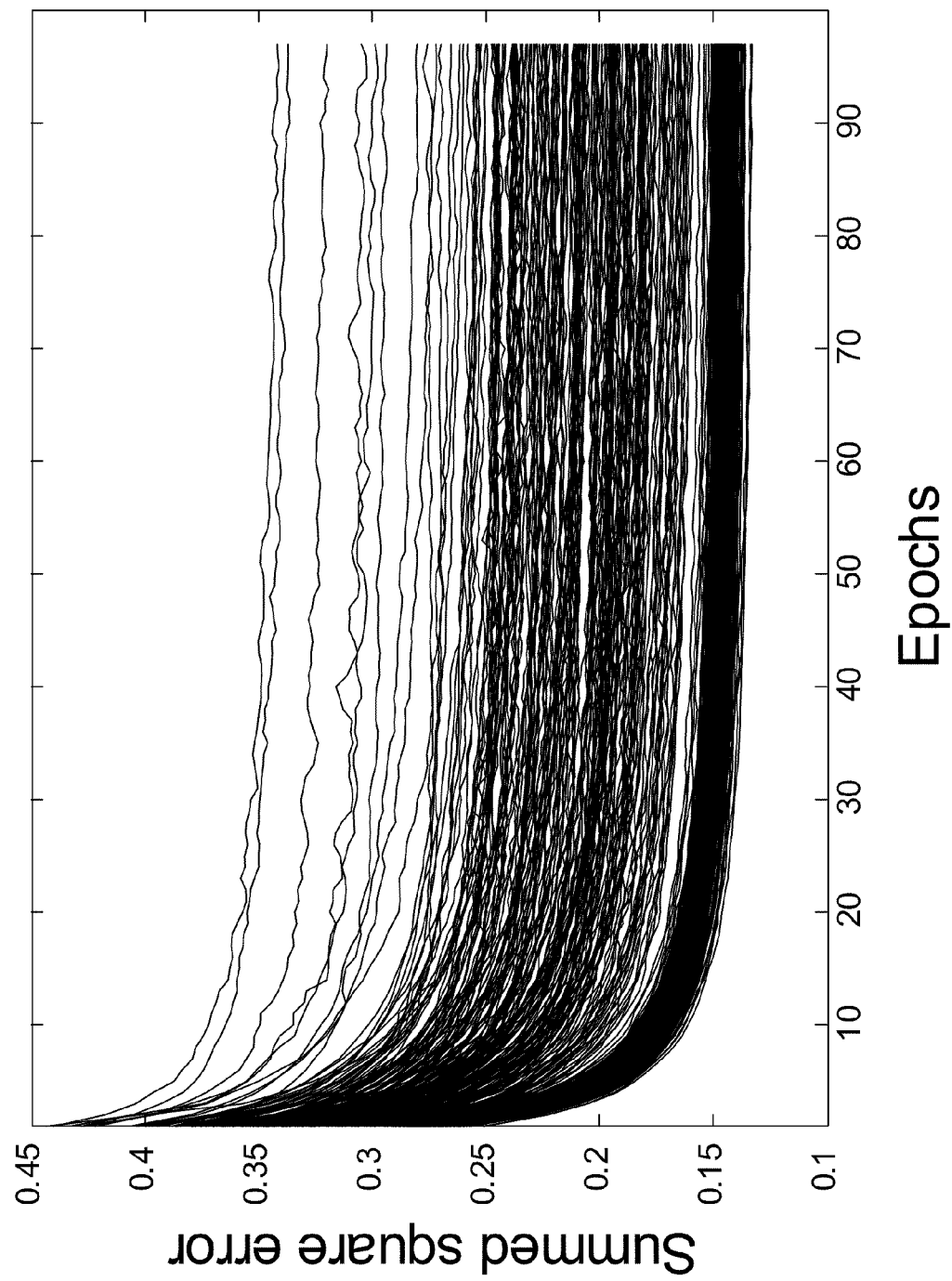
FIG. 4 represents a plot of the average classification error per sample (using a summed square error function) plotted during the training iterations (epochs) for both the training and validation samples.

In addition, there was no sign of 'over-training' of the models, as would be shown by a rise in the summed square error for the validation set with increasing training iterations or 'epochs', see FIG. 4.

For each diagnostic category (EWS, RMS, NB or BL), each ANN model gave an output between 0 (not this category) and 1 (this category). The 1250 outputs for each validation sample were used as a committee as follows. We calculated the average of all the predicted outputs (a committee vote) and then a sample was classified as a particular cancer if it received the highest committee vote for that cancer. In clinical settings, it is important to be able to reject a diagnostic classification including samples not belonging to any of the four diagnoses. Therefore, to be able to reject classification we did as follows. A squared Euclidean distance was computed for each cancer type, between the committee vote for a sample and the 'ideal' output for that cancer type; normalized such that it is unity between cancer types as described above. Using the 1250 ANN models for each validation sample we constructed for each cancer type an empirical probability distribution for the distances. Using these distributions, samples are only diagnosed as a specific cancer if they lie within the 95th percentile. All 3750 models were used to classify the additional 25 test samples.

Using these ANN models, all of the 63 training samples were correctly assigned/classified to their respective categories, having received the highest committee vote (average output) for that category.

Diagnostic results for the 63 training samples can be seen in TABLE 3 below.

TABLE 3

Training sample characteristics

| Sample Label | Source Label | Histological Diagnosis | ANN EWS | Committee Vote RMS | NB | BL | Source |
|---|---|---|---|---|---|---|---|
| EWS-C1 | A4573 | EWS-C | 0.91 | 0.02 | 0.27 | 0.04 | NCI |
| EWS-C2 | TC71 | EWS-C | 0.85 | 0.03 | 0.16 | 0.08 | NCI |
| EWS-C3 | TC106 | EWS-C | 0.89 | 0.04 | 0.10 | 0.08 | NCI |
| EWS-C4 | 5838 | EWS-C | 0.87 | 0.09 | 0.08 | 0.04 | NCI |
| EWS-C6 | A673 | EWS-C | 0.93 | 0.11 | 0.03 | 0.05 | NCI |
| EWS-C7 | ES-CL1 | EWS-C | 0.94 | 0.06 | 0.08 | 0.04 | MSKCC |
| EWS-C8 | TC32 | EWS-C | 0.98 | 0.05 | 0.04 | 0.04 | NCI |
| EWS-C9 | SK-ES-1 | EWS-C | 0.94 | 0.10 | 0.03 | 0.05 | ATCC |
| EWS-C10 | SK-N-MC | EWS-C | 0.81 | 0.22 | 0.03 | 0.06 | ATCC |
| EWS-C11 | RDES | EWS-C | 0.93 | 0.05 | 0.03 | 0.07 | ATCC |
| EWS-T1 | ES20 | EWS-T | 0.99 | 0.04 | 0.03 | 0.06 | MSKCC |
| EWS-T2 | ES13 | EWS-T | 0.95 | 0.08 | 0.06 | 0.04 | MSKCC |
| EWS-T3 | ES16 | EWS-T | 0.97 | 0.10 | 0.05 | 0.03 | MSKCC |
| EWS-T4 | ES17 | EWS-T | 0.93 | 0.14 | 0.11 | 0.02 | MSKCC |
| EWS-T6 | ES22 | EWS-T | 0.97 | 0.12 | 0.04 | 0.04 | MSKCC |
| EWS-T7 | ES25 | EWS-T | 0.99 | 0.04 | 0.03 | 0.04 | MSKCC |
| EWS-T9 | 9602P006 | EWS-T | 0.95 | 0.13 | 0.03 | 0.03 | CHTN |
| EWS-T11 | 9703P152 | EWS-T | 0.99 | 0.03 | 0.06 | 0.03 | CHTN |
| EWS-T12 | 9704P218 | EWS-T | 1.00 | 0.02 | 0.03 | 0.03 | CHTN |
| EWS-T13 | ES23 | EWS-T | 0.67 | 0.28 | 0.16 | 0.04 | MSKCC |
| EWS-T14 | 9605P074 | EWS-T | 0.99 | 0.02 | 0.04 | 0.05 | CHTN |
| EWS-T15 | 9609P027 | EWS-T | 0.99 | 0.03 | 0.06 | 0.03 | CHTN |
| EWS-T19 | SARC75 | EWS-T | 0.93 | 0.06 | 0.09 | 0.04 | CHTN |

TABLE 3-continued

Training sample characteristics

| | | | | | | | |
|---|---|---|---|---|---|---|---|
| RMS-C2 | RD | ERMS-C | 0.06 | 0.81 | 0.11 | 0.03 | ATCC |
| RMS-C3 | RH4 | ARMS-C | 0.04 | 0.84 | 0.05 | 0.03 | NCI |
| RMS-C4 | RH3 | ARMS-C | 0.00 | 0.89 | 0.11 | 0.05 | NCI |
| RMS-C5 | RH5 | ARMS-C | 0.01 | 0.91 | 0.09 | 0.04 | NCI |
| RMS-C6 | RH28 | ARMS-C | 0.00 | 0.87 | 0.07 | 0.07 | NCI |
| RMS-C7 | RH30 | ARMS-C | 0.01 | 0.98 | 0.09 | 0.03 | NCI |
| RMS-C8 | CTR | ERMS-C | 0.03 | 0.86 | 0.07 | 0.03 | ATCC |
| RMS-C9 | RH4 | ARMS-C | 0.05 | 0.86 | 0.03 | 0.05 | NCI |
| RMS-C10 | RMS13 | ARMS-C | 0.01 | 0.90 | 0.14 | 0.03 | NCI |
| RMS-C11 | TE671 | ERMS-C | 0.07 | 0.77 | 0.08 | 0.03 | ATCC |
| RMS-T1 | RMS3 | ARMS-T | 0.02 | 0.93 | 0.03 | 0.06 | MSKCC |
| RMS-T2 | RMS6 | ARMS-T | 0.06 | 0.86 | 0.03 | 0.04 | MSKCC |
| RMS-T3 | RMS2 | ERMS-T | 0.08 | 0.80 | 0.07 | 0.02 | MSKCC |
| RMS-T4 | RMS5 | ERMS-T | 0.07 | 0.93 | 0.03 | 0.03 | MSKCC |
| RMS-T5 | RMS10 | ARMS-T | 0.05 | 0.84 | 0.08 | 0.03 | MSKCC |
| RMS-T6 | RT1 | RMS-T | 0.04 | 0.93 | 0.05 | 0.03 | CHTN |
| RMS-T7 | RT4 | ERMS-T | 0.10 | 0.75 | 0.05 | 0.05 | CHTN |
| RMS-T8 | RT5 | RMS-T | 0.06 | 0.90 | 0.05 | 0.02 | CHTN |
| RMS-T10 | RT2 | RMS-T | 0.02 | 0.92 | 0.06 | 0.03 | CHTN |
| RMS-T11 | RHAB2 | ERMS-T | 0.03 | 0.76 | 0.06 | 0.03 | CHTN |
| NB-C1 | KCNR | NB-C | 0.00 | 0.08 | 0.93 | 0.03 | NCI |
| NB-C2 | GICAN | NB-C | 0.03 | 0.10 | 0.70 | 0.08 | NCI |
| NB-C3 | SK-N-AS | NB-C | 0.01 | 0.26 | 0.64 | 0.04 | ATCC |
| NB-C4 | LAN5 | NB-C | 0.02 | 0.03 | 0.85 | 0.06 | NCI |
| NB-C5 | SK-N-BE2 | NB-C | 0.02 | 0.02 | 0.92 | 0.06 | ATCC |
| NB-C6 | SK-N-DZ | NB-C | 0.02 | 0.02 | 0.89 | 0.09 | ATCC |
| NB-C7 | GICAN | NB-C | 0.07 | 0.05 | 0.80 | 0.08 | NCI |
| NB-C8 | NGP | NB-C | 0.00 | 0.06 | 0.96 | 0.04 | NCI |
| NB-C9 | SH-SYSY | NB-C | 0.06 | 0.04 | 0.85 | 0.04 | CHTN |
| NB-C10 | SK-N-FI | NB-C | 0.00 | 0.12 | 0.91 | 0.03 | CHTN |
| NB-C11 | SK-N-SH | NB-C | 0.06 | 0.01 | 0.95 | 0.05 | CHTN |
| NB-C12 | CHP-134B | NB-C | 0.02 | 0.24 | 0.41 | 0.06 | NCI |
| BL-C1 | RAMOS(RA1) | BL-C | 0.03 | 0.06 | 0.08 | 0.90 | ATCC |
| BL-C2 | ST496 | BL-C | 0.04 | 0.12 | 0.04 | 0.92 | ATCC |
| BL-C3 | CA46 | BL-C | 0.07 | 0.09 | 0.02 | 0.89 | ATCC |
| BL-C4 | ST486 | BL-C | 0.04 | 0.06 | 0.08 | 0.90 | ATCC |
| BL-C5 | RAJI | BL-C | 0.10 | 0.04 | 0.04 | 0.87 | ATCC |
| BL-C6 | MC116 | BL-C | 0.10 | 0.02 | 0.09 | 0.87 | ATCC |
| BL-C7 | DAUDI | BL-C | 0.09 | 0.04 | 0.02 | 0.93 | ATCC |
| BL-C8 | SULTAN | BL-C | 0.20 | 0.03 | 0.03 | 0.89 | ATCC |

Source label refers to the original name of the sample as labeled by the source. Histological diagnosis is defined as cancer type suffixed with -T for a tumor sample and -C for a cell line. Highlighted in gray is the ANN classification of the samples. NCI: National Cancer Institute, National Institutes of Health, ATCC: American Type Culture Collection, MSKCC: Memorial Sloan-Kettering Cancer Center, CHTN: Cooperative Human Tissue Network.

Example 4

Optimization of Genes Utilized for Classification

The contribution of each gene to the classification by the ANN models was determined by measuring the sensitivity of the classification to a change in the expression level of each gene, using the 3750 previously calibrated models.

The sensitivity to the different genes was determined by the absolute value of the partial derivative of the output with respect to the gene expressions, averaged over samples and ANN models. A large sensitivity implied that changing the expression influences the output significantly.

Figure 6:
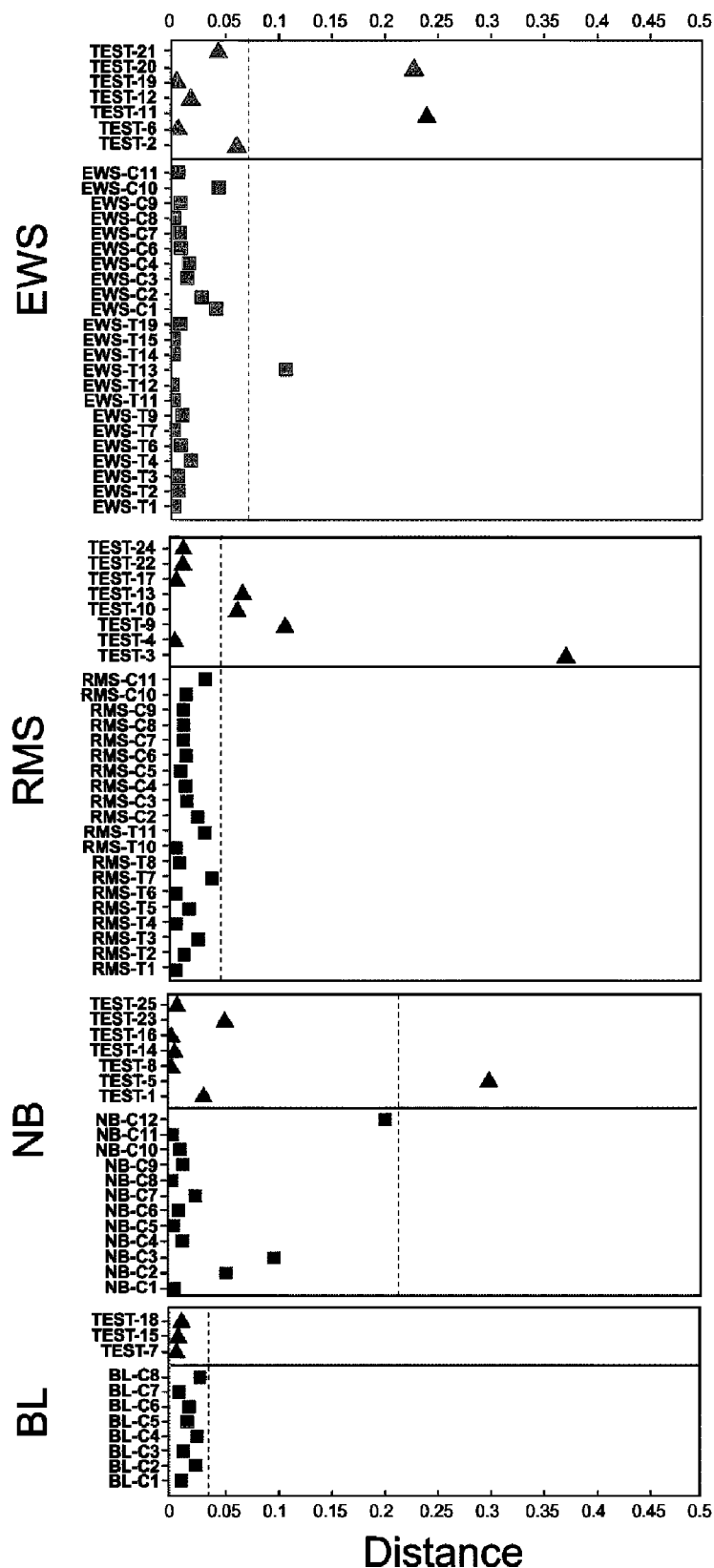
FIG. 6 represents a plot of the distance from the samples committee vote to the ideal vote for that diagnostic category.
Figure 7:
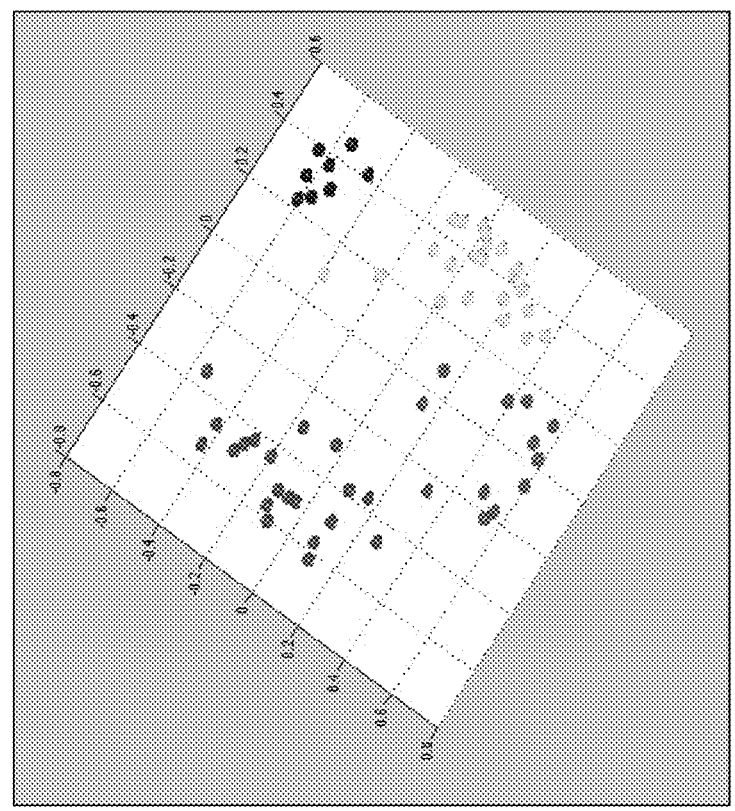
FIG. 7 represents two projections of the MDS plot of the training samples.
Figure 7:
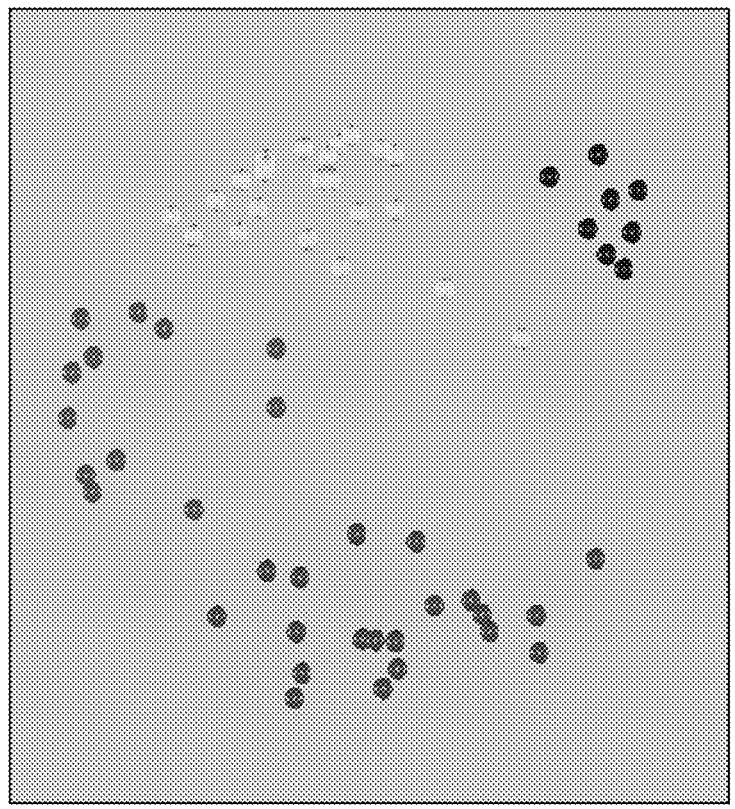
Figure 8:
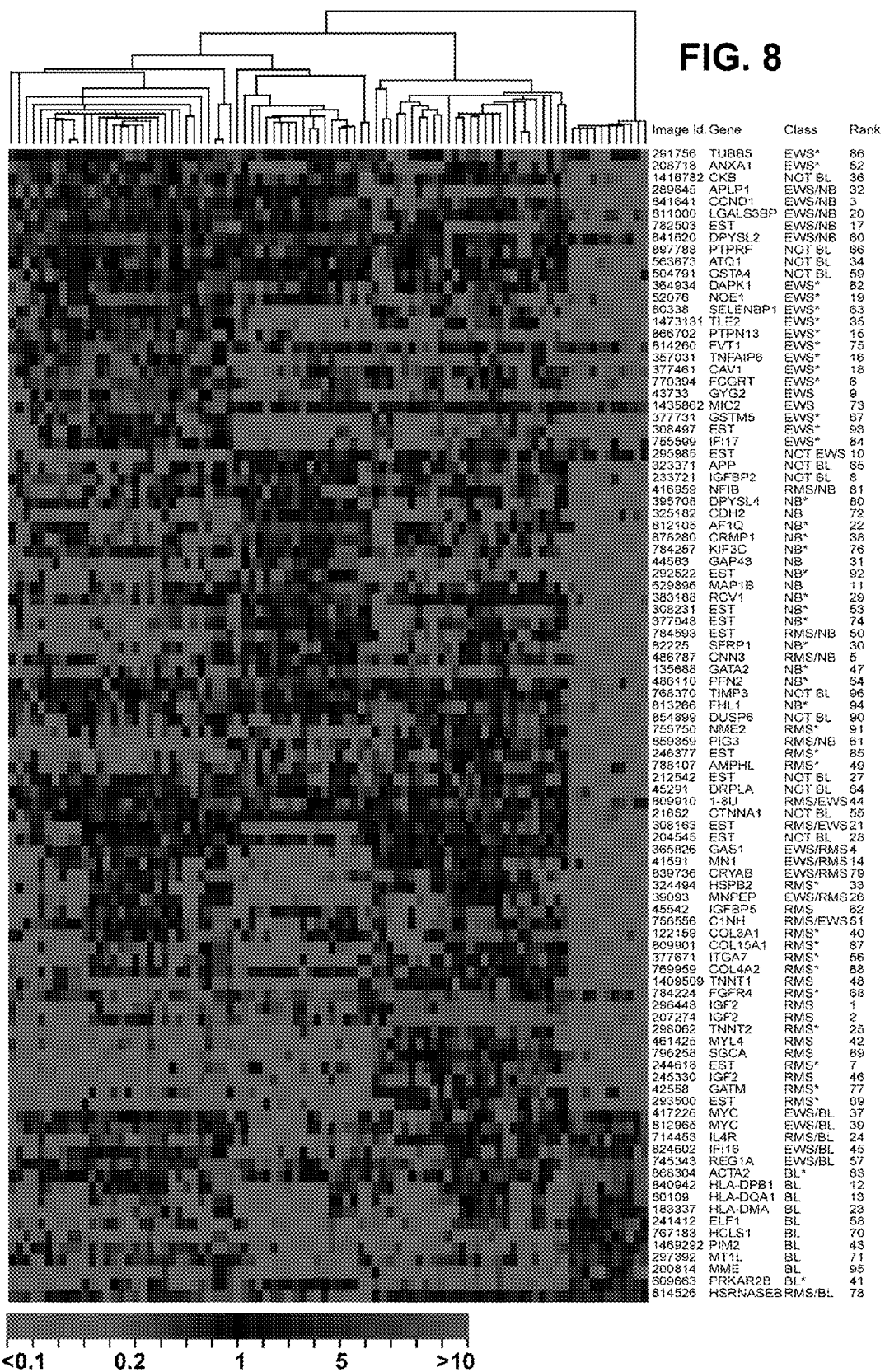
FIG. 8 represents a hierarchical clustering of the samples and genes, where each row represents one of the 96 cDNA clones, and each column represents a separate sample.

In this way the genes were ranked according to their significant for the classification. We then determined the classification error rate using increasing numbers of these ranked genes. The classification error rate minimized to 0% at 96 genes, see FIG. 5. The 10 dominant PCA components for these 96 genes contained 79% of the variance in the data matrix. Using only these 96 genes, we recalibrated the ANN models and again correctly classified all 63 samples, see FIG. 6. Moreover, multidimensional scaling (MDS) analysis using these 96 genes clearly separated the four cancer types, see FIG. 7. The top 96 discriminators represented 93 unique genes, see FIG. 8, as IGF2 was represented by three independent clones and MYC by two.

Of the 96 genes, 13 were anonymous expressed sequence tags (ESTs); 16 genes were specifically expressed in EWS, 20 in RMS, 15 in NB and 10 in BL. Twelve genes were good discriminators on the basis of lack of expression in BL and variable expression in the other three types. One gene (EST; Clone ID 295985) discriminated EWS from other cancer types by its lack of expression in this cancer. The remainder of the genes was expressed in two of the four cancer types. To our knowledge, of the 61 genes that were specifically expressed in cancer type, 41 have not been previously reported as associated with these diseases.

Example 5

Diagnostic Classification and Hierarchical Clustering

The diagnostic classification capabilities of these ANN models were then tested on a set of 25 blinded test samples. Samples were classified to a diagnostic category if they received the highest vote for that category. As this classifier had only four possible outputs, all samples were classified to one of the four categories. We therefore established a diagnostic classification method based on a statistical cutoff to enable us to reject a diagnosis of a sample classified to a given category. If a sample falls outside the 95th percentile of the probability distribution of distances between samples and their ideal output (for example for EWS it is EWS=1, RMS=NB=BL=0), its diagnosis is rejected.

The test samples contained both tumors (5 EWS, 5 RMS and 4 NB) and cell lines (1 EWS, 2 NB and 3 BL). The ability of these models to reject a diagnosis on 5 non-SRBCTs was also tested (consisting of 2 normal muscle tissues (Tests 9 and 13) and 3 cell lines including an undifferentiated sarcoma (Test 5), osteosarcoma (Test 3) and a prostate carcinoma (Test 11)). Using the 3750 ANN models calibrated with the 96 genes, we correctly classified 100% of the 20 SRBCT tests (FIG. 6 and TABLE 4) as well as all 63 training samples, see TABLE 2. Three of these samples, Test 10, Test 20 and EWS-T13 were correctly assigned to their categories (RMS, EWS and EWS respectively), having received the highest vote for their respective categories. However, their distance from a perfect vote was greater than the expected 95th percentile distance (FIG. 6); therefore, we could not confidently diagnose them by this criterion. All of the five non-SRBCT samples were excluded from any of the four diagnostic categories, since they fell outside the 95th percentiles. Using these criteria for all 88 samples, the sensitivity of the ANN models for diagnostic classification was 93% for EWS, 96% for RMS and 100% for both NB and BL. The specificity was 100% for all four diagnostic categories.

Figure 9:
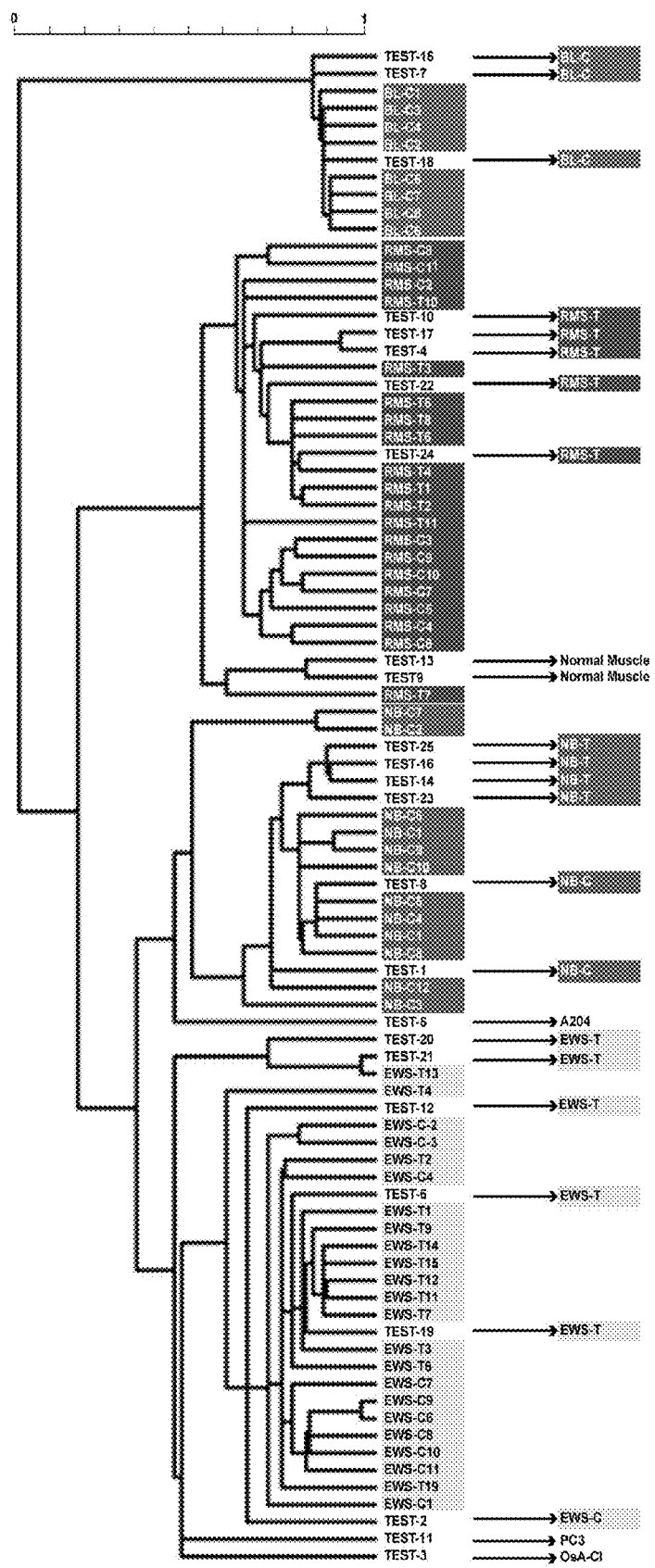
FIG. 9 represents a hierarchical clustering dendrogram of the samples in FIG. 8.

Also, hierarchical clustering using the 96 genes, identified from the ANN models, correctly clustered all 20 of the test samples (FIG. 9). Moreover, the two pairs of samples that were derived from two cell lines, BL-C2 and C4 (ST486) and NB-C2 and C7 (GICAN), were adjacent to one another in the same cluster.

TABLE 4

| Sample label | ANN committee vote | | | | ANN classification | ANN diagnosis | Histological diagnosis | Source label | Source |
|---|---|---|---|---|---|---|---|---|---|
| | EWS | RMS | NB | BL | | | | | |
| Test 1 | 0.01 | 0.07 | 0.76 | 0.06 | NB | NB | NB-C | IMR32 | ATCC |
| Test 2 | 0.67 | 0.06 | 0.08 | 0.09 | EWS | EWS | EWS-C | CHOP1 | NCI |
| Test 3 | 0.11 | 0.17 | 0.16 | 0.11 | RMS | — | Osteosarcoma-C | OsA-CI | ATCC |
| Test 4 | 0.00 | 0.95 | 0.06 | 0.03 | RMS | RMS | ARMS-T | ARMD1 | CHTN |
| Test 5 | 0.11 | 0.11 | 0.25 | 0.10 | NB | — | Sarcoma-C | A204 | ATCC |
| Test 6 | 0.98 | 0.04 | 0.10 | 0.03 | EWS | EWS | EWS-T | 9608P053 | CHTN |
| Test 7 | 0.05 | 0.02 | 0.05 | 0.93 | BL | BL | BL-C | EB1 | ATCC |
| Test 8 | 0.00 | 0.05 | 0.94 | 0.04 | NB | NB | NB-C | SMSSAN | NCI |
| Test 9 | 0.22 | 0.60 | 0.03 | 0.06 | RMS | — | Sk. Muscle | SkM1 | CHTN |
| Test 10 | 0.10 | 0.68 | 0.11 | 0.04 | RMS | — | ERMS-T | ERDM1 | CHTN |
| Test 11 | 0.39 | 0.04 | 0.28 | 0.15 | EWS | — | Prostate Ca.-C | PC3 | ATCC |
| Test 12 | 0.89 | 0.05 | 0.14 | 0.03 | EWS | EWS | EWS-T | SARC67 | CHTN |
| Test 13 | 0.20 | 0.7 | 0.03 | 0.05 | RMS | — | Sk. Muscle | SkM2 | CHTN |
| Test 14 | 0.03 | 0.02 | 0.90 | 0.07 | NB | NB | NB-T | NB3 | DZNSG |
| Test 15 | 0.06 | 0.03 | 0.05 | 0.91 | BL | BL | BL-C | EB2 | ATCC |
| Test 16 | 0.03 | 0.02 | 0.93 | 0.05 | NB | NB | NB-T | NB1 | DZNSG |
| Test 17 | 0.01 | 0.90 | 0.05 | 0.03 | RMS | RMS | ARMS-T | ARMD2 | CHTN |
| Test 18 | 0.06 | 0.04 | 0.04 | 0.88 | BL | BL | BL-C | GA10 | ATCC |
| Test 19 | 0.99 | 0.02 | 0.04 | 0.05 | EWS | EWS | EWS-T | ET3 | CHTN |
| Test 20 | 0.40 | 0.30 | 0.10 | 0.06 | EWS | — | EWS-T | 9903P1339 | CHTN |
| Test 21 | 0.81 | 0.19 | 0.12 | 0.04 | EWS | EWS | EWS-T | ES23 | MSKCC |
| Test 22 | 0.01 | 0.88 | 0.09 | 0.04 | RMS | RMS | ERMS-T | ERMD2 | CHTN |
| Test 23 | 0.07 | 0.08 | 0.70 | 0.06 | NB | NB | NB-T | NB2 | DZNSG |
| Test 24 | 0.05 | 0.87 | 0.06 | 0.03 | RMS | RMS | ERMS-T | RMS4 | MSKCC |
| Test 25 | 0.05 | 0.02 | 0.89 | 0.06 | NB | NB | NB-T | NB4 | DZNSG |

Source label refers to the original name of the sample as designated by the source.
Histological diagnosis is defined as cancer type suffixed with -T for a tumor sample and -C for a cell line.
Normal skeletal muscle (Sk. Muscle) is also included in the test set.
The ANN classification as determined by the committee vote is bolded,
NCI: National Cancer Institute, National Institutes of Health,
ATCC: American Type Culture Collection,
MSKCC: Memorial Sloan-Kettering Cancer Center,
CHTN: Cooperative Human Tissue Network,
DZNSG: German Cancer Research Center, Heidelberg.

Example 6

Expression of FGFR4 on SRBCT Tissue Array

To confirm the effectiveness of the ANN models to identify genes that show preferential high expression in specific cancer types at the protein level, we performed immunohistochemistry on SRBCT tissue arrays for the expression of fibroblast growth factor receptor 4 (FGFR4). This tyrosine kinase receptor is expressed during myogenesis but not in adult muscle, and is of interest because of its potential role in tumor growth and in prevention of terminal differentiation in muscle. Moderate to strong cytoplasmic immunostaining for FGFR4 was seen in all 26 RMSs tested (17 alveolar, 9 embryonal). We also observed generally weaker staining in EWS and NHL in agreement with the microarray results, except for one of anaplastic large cell lymphoma that was strongly positive (data not shown).

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and a computer data product containing a computer program for classifying and diagnosing disease using artificial neural networks.

The above specification, examples and data provide a complete description of the manufacture and use of the composition of the invention. Since many embodiments of the invention can be made without departing from the spirit and scope of the invention, the invention resides in the claims hereinafter appended.

---

The claimed invention is:

1. A method of determining a stage of a disease comprising:
   (a) processing a biological sample from a subject whose stage of the disease is unknown to obtain high dimensional experimental data selected from the group consisting of gene expression levels, protein expression levels, single nucleotide polymorphisms, or comparative genomic analysis;
   (b) detecting the presence of a first set of multiple data points or a second set of multiple data points in the high dimensional experimental data, wherein the first set of multiple data points is predictive for the stage of the disease as determined by a trained supervised pattern recognition method, and a second set of multiple data points is predictive for a different stage of the disease as determined by the trained supervised pattern recognition method; and
   (c) determining whether a subject whose stage of the disease is unknown has the stage of the disease or the different stage of the disease by detecting the presence of said first or second set of multiple data points in data obtained from the biological sample.

2. The method of claim 1, wherein processing the biological sample comprises isolating nucleic acids or proteins from the biological sample and detecting the nucleic acids or proteins from the sample to determine gene expression levels, protein expression levels, single nucleotide polymorphisms, or comparative genomic analysis of each sample.

3. The method of claim 1, wherein said high dimensional data is gene expression data.

4. The method of claim 3, wherein said gene expression data is obtained by using a cDNA or an oligonucleotide microarray.

5. The method of claim 1, wherein said first set of multiple data points comprise at least 96 individual data points.

6. The method of claim 1, wherein said disease is selected from the group consisting of multiple sclerosis, rheumatoid arthritis, and cancer.

7. The method of claim 6, wherein said stage and said different stage are of the same type of cancer.

8. The method of claim 1, wherein the first set of multiple data points and the second set of multiple data points are determined by the method comprising:
   (a) processing a first biological sample known to be of a stage of the disease and a second biological sample known to be of a different stage of the disease to obtain a first set of high dimensional experimental data and a second set of high dimensional experimental data;
   (b) filtering said first and second set of data by removing data that does not meet a predetermined threshold;
   (c) reducing the dimensionality of said first and second set of data;
   (d) training a supervised pattern recognition method using data obtained from the first biological sample and the second biological sample to obtain a probability distribution relationship between the data obtained from the first biological sample and the stage of the disease and between the data obtained from the second biological sample and the different stage of the disease;
   (e) ranking individual data points from said first set of high dimensional data by determining the sensitivity of the data point to the classification of the stage of the disease and ranking individual data points from said second set high dimensional data by determining the sensitivity of the data point to the classification to the different stage of the disease, wherein said ranking is dependent on an outcome of said supervised pattern recognition method; and (f) choosing a first set of multiple data points from said high dimensional data as predictive for the stage of the disease and choosing a second set of multiple data points from said high dimensional data as predictive for the different stage of the disease, wherein said choice is based on said relative ranking of said individual data points.

9. A computer-based method comprising:
(a) obtaining high dimensional experimental data from a biological sample from a subject whose stage of a disease is unknown and providing the high dimensional data to a receiver module;
(b) detecting the presence of a first set of multiple data points or a second set of multiple data points in the high dimensional experimental data, wherein the first set of multiple data points is predictive for the stage of the disease as determined by a trained supervised pattern recognition program, and a second set of multiple data points is predictive for a different stage of the disease as determined by the trained supervised pattern recognition program using a diagnostic module; and
(c) determining whether a subject whose stage of the disease is unknown has the stage of the disease or the different stage of the disease by identifying the presence of said first or second set of multiple data points in data obtained from the biological sample.

10. The method of claim 9, wherein obtaining high dimensional experimental data from the biological sample comprises isolating nucleic acids or proteins from each biological sample and detecting the nucleic acids or proteins from each sample to determine gene expression levels, protein expression levels, single nucleotide polymorphisms, or comparative genomic analysis of each sample.

11. The method of claim 9, wherein the first set of multiple data points and the second set of multiple data points are determined by a method comprising:
(a) obtaining high dimensional experimental data from a first biological sample from a first subject known to have responded to a treatment for the disease and a second biological sample from a second subject known to lack a response to the treatment for the disease and receiving the experimental data representing high dimensional data by a receiver module of the computer;
(b) filtering the experimental data by removing data that does not meet a predetermined threshold by a filter module;
(c) reducing the dimensionality of the experimental data using one or more methods;
(d) dividing the experimental data into a training data set and a validation data set;
(e) generating a first probability distribution relationship between the data obtained from the first biological sample and the stage of the disease and a second probability distribution relationship between the data obtained from the second biological sample and the different stage of the disease using the training data and a training module;
(f) validating the performance of the first and second probability distribution relationship using the validation data set;

(g) choosing a first set of multiple data points from said high dimensional data as predictive for the stage of the disease and choosing a second set of multiple data points from said high dimensional data as predictive for the different stage of the disease, wherein said choice is based on said relative ranking of said individual data points using a ranking module.

12. A computer readable storage medium comprising:
a receiver module for receiving data representing experimental gene expression data obtained from a biological sample from a subject whose stage of a disease is unknown; and
a diagnostic module encoded to diagnose the presence of the stage of the disease and the different stage of the disease in the subject by detecting the presence of a first set of multiple data points or a second set of multiple data points in gene expression data obtained from a biological sample from a subject, wherein the first set of multiple data points is predictive for the stage of the disease, and a second set of multiple data points is predictive for a different stage of the disease.

13. A method of determining a subject's response to a treatment for a disease comprising:
(a) processing a biological sample from a subject whose response to treatment for the disease is unknown to obtain high dimensional experimental data selected from the group consisting of gene expression levels, protein expression levels, single nucleotide polymorphisms, or comparative genomic analysis;
(b) detecting the presence of a first set of multiple data points or a second set of multiple data points in the high dimensional experimental data, wherein the first set of multiple data points is predictive for responsiveness to the treatment for the disease as determined by a trained supervised pattern recognition program, and a second set of multiple data points is predictive for lack of responsiveness to the treatment for the disease as determined by a trained supervised pattern recognition program; and
(c) determining whether a subject whose response to treatment for the disease is unknown is likely to respond to the treatment for the disease or not respond to the treatment for the disease by identifying the presence of said first or said second set of multiple data points in data obtained from the biological sample.

14. The method of claim 13, wherein processing the biological sample comprises isolating nucleic acids or proteins from the biological sample and detecting the nucleic acids or proteins from the sample to determine gene expression levels, protein expression levels, single nucleotide polymorphisms, or comparative genomic analysis of each sample.

15. The method of claim 13, wherein said high dimensional data is gene expression data.

16. The method of claim 15, wherein said gene expression data is obtained by using a cDNA or an oligonucleotide microarray.

17. The method of 16, wherein said step of filtering said gene expression data is based on the intensity of the spots on said microarray.

18. The method of claim 13, wherein said method of reducing the dimensionality of said data is accomplished by principal component analysis.

19. The method of claim 13, wherein said multiple data points chosen from said data comprise at least 96 individual data points.

20. The method of claim 13, wherein said disease is selected from the group consisting of multiple sclerosis, rheumatoid arthritis, and a cancer.

21. The method of claim 20, wherein said disease is the same type of cancer.

22. The method of claim 13, wherein the first and second set of multiple data points are determined by a method comprising:
(a) obtaining high dimensional experimental data from a first subject known to have responded to the treatment for the disease and a second biological sample from a second subject known to lack a response to the treatment for the disease;
(b) filtering said data by removing data that does not meet a predetermined threshold;
(c) reducing the dimensionality of said data;
(d) training a supervised pattern recognition method using data obtained from the first biological sample and the second biological sample to obtain a probability distribution relationship between the data obtained from the first biological sample and the response to the treatment for the disease and between the data obtained from the second biological sample and the lack of response to the treatment for the disease;
(e) ranking individual data points from said high dimensional data by determining the sensitivity of the data point to the classification of the response to the treatment for the disease or the lack of response to the treatment for the disease, wherein said ranking is dependent on an outcome of said supervised pattern recognition method; and
(f) choosing a first set of multiple data points from said high dimensional data as predictive of the response to the treatment for the disease and choosing a second set of multiple data points from said high dimensional data as predictive for the lack of response to the treatment for the disease, wherein said choice is based on said relative ranking of said individual data points.

23. A computer-based method comprising:
(a) obtaining high dimensional experimental data from a biological sample from a subject whose response to treatment for a disease is unknown, and receiving the experimental data representing high dimensional data by a receiver module of the computer;
(b) analyzing the high dimensional data for the presence of a first set of multiple data points or a second set of multiple data points, wherein the first set of multiple data points is predictive for responsiveness to the treatment for the disease, and a second set of multiple data points is predictive for lack of responsiveness to the treatment for the disease using a diagnostic module; and
(c) determining whether a subject whose response to treatment for the disease is unknown is likely to respond to the treatment for the disease or not respond to the treatment for the disease by identifying the presence of said first or said second set of multiple data points in data obtained from the biological sample.

24. The method of claim 23, wherein obtaining high dimensional experimental data from the biological sample comprises isolating nucleic acids or proteins from the biological sample and detecting the nucleic acids or proteins from the sample to determine gene expression levels, protein expression levels, single nucleotide polymorphisms, or comparative genomic analysis of each sample.

25. A computer readable storage medium comprising:
a receiver module for receiving data representing experimental gene expression data obtained from a biological sample from a subject whose response to a treatment for a disease is unknown; and
a diagnostic module encoded to determine whether a subject whose response to a treatment for the disease is unknown is likely to respond to the treatment or lack a response to the treatment for the disease by identifying the presence of said first or second set of multiple data points in data obtained from a biological sample from the subject whose response to the treatment for the disease is unknown, wherein the first set of multiple data points is predictive for the responsiveness to the treatment for the disease, and a second set of multiple data points is predictive for lack of responsiveness to the treatment for the disease.

26. A computer implemented method of determining a first set of multiple data points predictive of the presence of a stage of a disease and a second set of multiple data points predictive of the presence of a different stage of the disease comprising:
(a) obtaining high dimensional experimental data from a first biological sample known to be of a stage of the disease and a second biological sample known to be of a different stage of the disease and providing the high dimensional data to a receiver module;
(b) filtering said data by removing data that does not meet a predetermined threshold;
(c) reducing the dimensionality of said data;
(d) training a supervised pattern recognition method in a training module using data obtained from the first biological sample and the second biological sample to obtain a probability distribution relationship between the data obtained from the first biological sample and the stage of the disease and between the data obtained from the second biological sample and the different stage of the disease;
(e) ranking individual data points from said high dimensional data in a ranking module by determining the sensitivity of the data point to the classification of the stage of the disease or the different stage of the disease, wherein said ranking is dependent on an outcome of said supervised pattern recognition method;
(f) choosing a first set of multiple data points from said high dimensional data as predictive for the stage of the disease and choosing a second set of multiple data points from said high dimensional data as predictive for the different stage of the disease, wherein said choice is based on said relative ranking of said individual data points.

27. A computer implemented method of determining a first set of multiple data points predictive of the responsiveness to a treatment for a disease and a second set of multiple data points predictive of the lack of responsiveness to the treatment of the disease comprising:
(a) obtaining high dimensional experimental data from a biological sample from a first subject known to have responded to the treatment for the disease and a second biological sample from a second subject known to lack a response to the treatment for the disease and providing the high dimensional data to a receiver module;
(b) filtering said data by removing data that does not meet a predetermined threshold;
(c) reducing the dimensionality of said data;
(d) training a supervised pattern recognition method in a training module using data obtained from the first biological sample and the second biological sample to obtain a probability distribution relationship between the data obtained from the first biological sample and the response to the treatment for the disease and between the data obtained from the second biological sample and the lack of response to the treatment for the disease;

(e) ranking individual data points from said high dimensional data in a ranking module by determining the sensitivity of the data point to the classification to the response to the treatment for the disease or the lack of response to the treatment for the disease, wherein said ranking is dependent on an outcome of said supervised pattern recognition method;

(f) choosing a first set of multiple data points from said high dimensional data as predictive of the response to the treatment for the disease and choosing a second set of multiple data points from said high dimensional data as predictive for the lack of response to the treatment for the disease, wherein said choice is based on said relative ranking of said individual data points.

* * * * *

SEQUENCE LISTING

<160> NUMBER OF SEQ ID NOS: 99

<210> SEQ ID NO 1
<211> LENGTH: 2318
<212> TYPE: DNA
<213> ORGANISM: Homo sapiens

<400> SEQUENCE: 1

```
cgcagggacc gtgctccgcc gtctccgccg catcttccac cctcgccgcc gccgcagctc      60
cccgcgctcg tgccaccgcc gccgcgtcca ccctcagcgc caccgccatg cgggagatcg     120
tgcacctgca ggccggccag tgcggcaacc agatcggggc caagttttgg gaggttatca     180
gtgacgaaca tggcatcgac cccacaggca cataccatgg ggacagtgac ctgcaactgg     240
agaggatcaa cgtgtactac aacgaggcca caggaggaaa ttatgtcccc agagcggtgc     300
tggtggacct ggaacccggc accatggact ctgtccgttc tggccccttc ggtcagatct     360
ttcggccgga caacttcgtg tttggccaat ccggagccgg caacaactgg gcaaaggggc     420
actacacgga gggcgcagag ctggtggacg ctgtcctgga cgtagtccgg aaggaggccg     480
agagctgcga ctgccttcag ggcttccagc tgacccactc gctgggggt ggcacggggt     540 ccggaatggg cacgctgctc atcagtaaga tccgcgagga gttcccagac cgcatcatga     600
acaccttcag cgtggtgccc tcgcccaaag tgtcagacac ggtggtggag ccctacaacg     660
ccacgctgtc tgtgcaccag ctggtggaga atacggatga gacctactgc atcgacaacg     720
aggcactcta cgacatctgt ttccgcaccc tcaagctgac cacccccacc tacggggacc     780
tcaaccacct ggtgtcggcc accatgagcg gggtcaccac ctgcctgcgc ttcccgggcc     840
agctgaacgc cgacctgcgc aagctggccg tcaacatggt tcccttcct cgcctgcact     900 tcttcatgcc cggcttcgca ccctgacca gccggggcag ccagcagtac cgggccctga     960
cggtgcccga gctcacccag cagatgttcg atgccaagaa catgatggcg gcgtgcgacc    1020
cgcgccacgg ccgctacctg accgtggccg ccgtgttccg gggccgcatg tccatgaagg    1080
aggtggacga gcagatgctg agcgtgcaga gcaagaacag cagctacttc gtggagtgga    1140
tccccaacaa cgtgaagacg gccgtgtgcg acatcccgcc ccgcggcctg aagatggccg    1200
cgaccttcat cggcaacagc acggccatcc aggagctgtt caagcgcatc tccgagcagt    1260
tcacggccat gttccggcgc aaggccttct gcactgggta cacgggcgag gcatggacg    1320 agatggagtt caccgaggcc gagagcaaca tgaatgacct ggtatctgag taccagcagt    1380
```

| | | | | |
|---|---|---|---|---|
| accaggacgc | cacggccgag | gagggcgagt | tcgaggagga | ggcggaggag gaggtggcct | 1440 |
| aggctgctcc | catcgcttcc | cacctgtccc | ctcgaggctt | ctgacctttg atccgctagg | 1500 |
| ccccccatct | ctgaaccctca | gagccccgct | ttccctccaa | ggctgactcc ccgctgaccc | 1560 |
| taacaatacc | tttggagctc | gctttacctc | tggctactc | atctccgacc ctggctcccc | 1620 |
| tttgagccct | aatttatctt | taaccccctt | gagctcttcc | aaccttgaca ttcccaggag | 1680 |
| gagccccgct | tcacccttc | tgactctgga | aaccgcacct | taactttgc agaccttcct | 1740 |
| tcacccctga | cttctgcttc | acctttgacc | tctgcccccc | atgaatccca ttttacctct | 1800 |
| agacctataa | gttctggttt | atgtttgacc | cctccctctg | agctgcactt caccgctgac | 1860 |
| cttgcctcac | cttttaacccc | ccacctgagc | cccagctcct | acctctgacc ccaacttctc | 1920 |
| tttgatctct | gaatcccctc | tgactccaac | ttctcttttca | ccctctatga gtcccatttt | 1980 |
| acttctacac | ctgcaagtcc | tggtttatat | tggaccccctc | cctccgagct gcagttcacc | 2040 |
| tttgaccttg | cctcaccttt | cacccccccac | ccccacagc | gtcagctcct acctctgacc | 2100 |
| ccagcttctc | tctgattccc | acaggcccca | tgcatcctcc | ctgcctcact cccctcagcc | 2160 |
| cctgccgacc | ttagcttatc | tgggagagaa | acaaggcctg | gtgcctgtga ggaagagagg | 2220 |
| tcacccctac | cctccctccc | cgcttccctg | cctcaccctc | aataaataaa ttaattgttg | 2280 |
| tcatggaaaa | aaaaaaaaaa | aaaaaaaaaa | aaaaaaaa | | 2318 |

```
<210> SEQ ID NO 2
<211> LENGTH: 1399
<212> TYPE: DNA
<213> ORGANISM: Homo sapiens

<400> SEQUENCE: 2
```

| | | | | | |
|---|---|---|---|---|---|
| agtgtgaaat | cttcagagaa | gaatttctct | ttagttcttt | gcaagaaggt agagataaag | 60 |
| acacttttc | aaaaatggca | atggtatcag | aattcctcaa | gcaggcctgg tttattgaaa | 120 |
| atgaagagca | ggaatatgtt | caaactgtga | agtcatccaa | aggtggtccc ggatcagcgg | 180 |
| tgagccccta | tcctaccttc | aatccatcct | cggatgtcgc | tgccttgcat aaggccataa | 240 |
| tggttaaagg | tgtggatgaa | gcaaccatca | ttgacattct | aactaagcga aacaatgcac | 300 |
| agcgtcaaca | gatcaaagca | gcatatctcc | aggaaacagg | aaagcccctg gatgaaacac | 360 |
| ttaagaaagc | ccttacaggt | caccttgagg | aggttgtttt | agctctgcta aaaactccag | 420 |
| cgcaatttga | tgctgatgaa | cttcgtgctg | ccatgaaggg | ccttggaact gatgaagata | 480 |
| ctctaattga | gattttggca | tcaagaacta | acaaagaaat | cagagacatt aacagggtct | 540 |
| acagagagga | actgaagaga | gatctggcca | agacataac | ctcagacaca tctggagatt | 600 |
| ttcggaacgc | tttgctttct | cttgctaagg | gtgaccgatc | tgaggacttt ggtgtgaatg | 660 |
| aagacttggc | tgattcagat | gccagggcct | tgtatgaagc | aggagaaagg agaaagggga | 720 |
| cagacgtaaa | cgtgttcaat | accatcctta | ccaccagaag | ctatccacaa cttcgcagag | 780 |
| tgtttcagaa | atacaccaag | tacagtaagc | atgacatgaa | caagttctg gacctggagt | 840 |
| tgaaaggtga | cattgagaaa | tgcctcacag | ctatcgtgaa | gtgcgccaca agcaaaccag | 900 |
| ctttctttgc | agagaagctt | catcaagcca | tgaaggtgt | tggaactcgc cataaggcat | 960 |
| tgatcaggat | tatggtttcc | cgttctgaaa | ttgactgaa | tgtatcaaa gcattctatc | 1020 |
| agaagatgta | tggtatctcc | ctttgccaag | ccatcctgga | tgaaaccaaa ggagattatg | 1080 |
| agaaaatcct | ggtggctctt | tgtggaggaa | actaaacatt | cccttgatgg tctcaagcta | 1140 |
| tgatcagaag | actttaatta | tatattttca | tcctataagc | ttaaatagga aagtttcttc | 1200 |

-continued

| | |
|---|---|
| aacaggatta cagtgtagct acctacatgc tgaaaaatat agcctttaaa tcatttttat | 1260 |
| attataactc tgtataatag agataagtcc attttttaaa aatgttttcc ccaaaccata | 1320 |
| aaaccctata caagttgttc tagtaacaat acatgagaaa gatgtctatg tagctgaaaa | 1380 |
| taaaatgacg tcacaagac | 1399 |

<210> SEQ ID NO 3
<211> LENGTH: 1432
<212> TYPE: DNA
<213> ORGANISM: Homo sapiens

<400> SEQUENCE: 3

| | |
|---|---|
| gctgttcggc ctgcgtcgct ccgggagctg ccgacggacg gagcgccccc gccccgccc | 60 |
| ggccgcccgc ccgccgccgc catgcccttc tccaacagcc acaacgcact gaagctgcgc | 120 |
| ttcccggccg aggacgagtt ccccgacctg agcgcccaca caaccacat ggccaaggtg | 180 |
| ctgacccccg agctgtacgc ggagctgcgc gccaagagca cgccgagcgg cttcacgctg | 240 |
| gacgacgtca tccagacagg cgtggacaac ccgggccacc cgtacatcat gaccgtgggc | 300 |
| tgcgtggcgg cgacgaggga gtcctacgaa gtgttcaagg atctcttcga ccccatcatc | 360 |
| gaggaccggc acggcggcta caagcccagc gatgagcaca agaccgacct caaccccgac | 420 |
| aacctgcagg gcgcgacga cctggacccc aactacgtgc tgagctcgcg ggtgcgcacg | 480 |
| ggccgcagca tccgtggctt ctgcctcccc ccgcactgca gccgcgggga gcgccgcgcc | 540 |
| atcgagaagc tcgcggtgga agccctgtcc agcctggacg gcgacctggc gggccgatac | 600 |
| tacgcgctca agagcatgac ggaggcggag cagcagcagc tcatcgacga ccacttcctc | 660 |
| ttcgacaagc ccgtgtcgcc cctgctgctg gcctcgggca tggcccgcga ctggccgac | 720 |
| gcccgcggta tctggcacaa tgacaataag accttcctgg tgtgggtcaa cgaggaggac | 780 |
| cacctgcggg tcatctccat gcagaagggg ggcaacatga aggaggtgtt cacccgcttc | 840 |
| tgcaccggcc tcacccagat tgaaactctc ttcaagtcta aggactatga gttcatgtgg | 900 |
| aaccctcacc tgggctacat cctcacctgc ccatccaacc tgggcaccgg gctgcgggca | 960 |
| ggtgtgcata tcaagctgcc caacctgggc aagcatgaga agttctcgga ggtgcttaag | 1020 |
| cggctgcgac ttcagaagcg aggcacaggc ggtgtggaca cggctgcggt gggcggggtc | 1080 |
| ttcgacgtct ccaacgctga ccgcctgggc ttctcagagg tggagctggt gcagatggtg | 1140 |
| gtggacggag tgaagctgct catcgagatg gagcagcggc tggagcaggg ccaggccatc | 1200 |
| gacgacctca tgcctgccca gaaatgaagc ccggcccaca cccgacacca gccctgctgc | 1260 |
| ttcctaactt attgcctggg cagtgcccac catgcacccc tgatgttcgc cgtctggcga | 1320 |
| gcccttagcc ttgctgtaga gacttccgtc acccttggta gagtttattt ttttgatggc | 1380 |
| taagatactg ctgatgctga aataaactag gttttggcc tgcctgcgtc tg | 1432 |

<210> SEQ ID NO 4
<211> LENGTH: 2384
<212> TYPE: DNA
<213> ORGANISM: Homo sapiens

<400> SEQUENCE: 4

| | |
|---|---|
| gagctcctgt caccgctggg gccgggccgg gcgggagtgc aggggacgtg agggcgcaag | 60 |
| ggcgggaca tggggcccgc cagccccgct gctcgcggtc taagtcgccg cccgggccag | 120 |
| ccgccgctgc cgctgctgct gccactattg ctgctgcttc tgcgcgcgca gcccgccatc | 180 |
| gggagcctgg ccggtgggag ccccggccgcg gccgaggccc cggggtcggc ccaggtggct | 240 |

| | | | | |
|---|---|---|---|---|
| ggactatgcg | ggcgcctaac | ccttcaccgg | gacctgcgca | ccggccgctg | ggaaccagac | 300 |
| ccacagcgct | ctcgacgctg | tctccgggac | ccgcagcgcg | tgctggagta | ctgcagacag | 360 |
| atgtacccgg | agctgcagat | tgcacgtgtg | gagcaggcta | cgcaggccat | ccccatggag | 420 |
| cgctggtgcg | ggggttcccg | gagcggcagc | tgcgcccacc | ccaccaccca | ggttgtgccc | 480 |
| ttccgctgcc | tgcctggtga | atttgtgagt | gaggccctgc | tggtgcctga | aggctgccgg | 540 |
| ttcttgcacc | aggagcgcat | ggaccaatgt | gagagttcaa | cccggaggca | tcaggaggca | 600 |
| caggaggcct | gcagctccca | gggcctcatc | ctgcacggct | cgggcatgct | cttaccctgt | 660 |
| ggctcggatc | ggttccgtgg | tgtggagtat | gtgtgctgtc | ccctccagg | gacccccgac | 720 |
| ccatctggga | cagcagttgg | tgaccctcc | acccggtcct | ggccccggg | gagcagagta | 780 |
| gaggggggctg | aggacgagga | agaggaggaa | tccttcccac | agccagtaga | tgattacttc | 840 |
| gtggagcctc | cgcaggctga | agaggaagag | gaaacggtcc | cacccccaag | ctcccataca | 900 |
| cttgcagtgg | tcggcaaagt | cactcccacc | ccgaggccca | cagacggtgt | ggatatttac | 960 |
| tttggcatgc | ctggggaaat | cagtgagcac | gaggggttcc | tgagggccaa | gatggacctg | 1020 |
| gaggagcgta | ggatgcgcca | gattaatgag | gtgatgcgtg | aatgggccat | ggcagacaac | 1080 |
| cagtccaaga | acctgcctaa | agccgacaga | caggccctga | atgagcactt | ccagtccatt | 1140 |
| ctgcagactc | tggaggagca | ggtgtctggt | gagcgacagc | gcctggtgga | aacccacgcc | 1200 |
| acccgcgtca | tcgcccttat | caacgaccag | cgccgggctg | ccttggaggg | cttcctggca | 1260 |
| gccctgcagg | cagatccgcc | tcaggcgag | cgtgtcctgt | tggccctgcg | cgctacctg | 1320 |
| cgtgcggagc | agaaggaaca | gaggcacacg | ctgcgccact | accagcatgt | ggccgccgtg | 1380 |
| gatcccgaga | aggcacagca | gatgcgcttc | caggtgcata | cccaccttca | agtgattgag | 1440 |
| gagagggtga | atcagagcct | gggcctgctt | gaccagaacc | cccacctggc | tcaggagctg | 1500 |
| cggccccaaa | tccaggaact | cctccactct | gaacacctgg | gtcccagtga | attggaagcc | 1560 |
| cctgcccctg | ggggcagcag | cgaggacaag | ggtgggctgc | agcctccaga | ttccaaggat | 1620 |
| gacacccca | tgacccttcc | aaaagggtcc | acagaacaag | atgctgcatc | ccctgagaaa | 1680 |
| gagaagatga | acccgctgga | acagtatgag | cgaaggtga | atgcgtctgt | tccaggggt | 1740 |
| ttcccttccc | actcatcgga | gattcagagg | gatgagctgg | caccagctgg | gacaggggtg | 1800 |
| tcccgtgagg | ctgtgtcggg | tctgctgatc | atgggagcgg | gcggaggctc | cctcatcgtc | 1860 |
| ctctccatgc | tgctcctgcg | caggaagaag | ccctacgggg | ctatcagcca | tggcgtggtg | 1920 |
| gaggtggacc | ccatgctgac | cctggaggag | cagcagctcc | gcgaactgca | gcggcacggc | 1980 |
| tatgagaacc | ccacttaccg | cttcctggag | gaacgaccct | gacccggccc | ccttcacccc | 2040 |
| ttcagccgag | cccagacctc | ccctcttcct | ggagccccag | aacccaact | cccagcctag | 2100 |
| ggcagcaggg | agtcttgaag | tgatcatttc | acacccttt | gtgagacggc | tggaaattct | 2160 |
| tatttcccct | ttccaattcc | aaaattccat | ccctaagaat | tcccagatag | tcccagcagc | 2220 |
| ctccccacgt | ggcacctcct | caccttaatt | tattttttaa | gtttatttat | ggctctttaa | 2280 |
| ggtgaccgcc | accttggtcc | tagtgtctat | tccctggaat | tcaccctctc | atgtttccct | 2340 |
| actaacatcc | caataaagtc | ctcttccta | aaaaaaaaa | aaaa | | 2384 |

<210> SEQ ID NO 5
<211> LENGTH: 1325
<212> TYPE: DNA
<213> ORGANISM: Homo sapiens

<400> SEQUENCE: 5

```
gcagtagcag cgagcagcag agtccgcacg ctccggcgag gggcagaaga gcgcgaggga    60
gcgcggggca gcagaagcga gagccgagcg cggacccagc caggacccac agccctcccc   120
agctgcccag gaagagcccc agccatggaa caccagctcc tgtgctgcga agtggaaacc   180
atccgccgcg cgtaccccga tgccaacctc ctcaacgacc gggtgctgcg ggccatgctg   240
aaggcggagg agacctgcgc gccctcggtg tcctacttca atgtgtgcca aaggaggtc    300 ctgccgtcca tgcggaagat cgtcgccacc tggatgctgg aggtctgcga ggaacagaag   360
tgcgaggagg aggtcttccc gctggccatg aactacctgg accgcttcct gtcgctggag   420
cccgtgaaaa agagccgcct gcagctgctg ggggccactt gcatgttcgt ggcctctaag   480
atgaaggaga ccatccccct gacggccgag aagctgtgca tctacaccga cggctccatc   540
cggcccgagg agctgctgca aatggagctg ctcctggtga caagctcaa gtggaacctg   600 gccgcaatga ccccgcacga tttcattgaa cacttcctct ccaaaatgcc agaggcggag   660
gagaacaaac agatcatccg caaacacgcg cagaccttcg ttgcctcttg tgccacagat   720
gtgaagttca tttccaatcc gccctccatg gtggcagcgg ggagcgtggt ggccgcagtg   780
caaggcctga acctgaggag ccccaacaac ttcctgtcct actaccgcct cacacgcttc   840
ctctccagag tgatcaagtg tgacccagac tgcctccggg cctgccagga gcagatcgaa   900
gccctgctgg agtcaagcct cgccaggcc cagcagaaca tggaccccaa ggccgccgag   960
gaggaggaag aggaggagga ggaggtggac ctggcttgca cacccaccga cgtgcgggac  1020
gtggacatct gagggggcca gcaggcgggg cgccaccgcc accgcagcg agggcggagc  1080 cggccccagg tgctccacat gacagtccct cctctccgga gcattttgat accagaaggg  1140
aaagcttcat tctccttgtt gttggttgtt ttttcctttg ctctttcccc cttccatctc  1200
tgacttaagc aaaagaaaaa gattacccaa aaactgtctt taaagagag agagagaaaa  1260 aaaaaaaaaa aaaaaaaaaa aaaaaaaaaa aaaaaaaaaa aaaaaaaaaa aaaaaaaaaa  1320
aaaaa                                                              1325

<210> SEQ ID NO 6
<211> LENGTH: 2254
<212> TYPE: DNA
<213> ORGANISM: Homo sapiens

<400> SEQUENCE: 6
aatcgaaagt agactctttt ctgaagcatt tcctgggatc agcctgacca cgctccatac    60
tgggagaggc ttctgggtca aaggaccagt ctgcagaggg atcctgtggc tggaagcgag   120
gaggctccac acggccgttg cagctaccgc agccaggatc tgggcatcca ggcacggcca   180 tgaccccctcc gaggctcttc tgggtgtggc tgctggttgc aggaacccaa ggcgtgaacg   240
atggtgacat gcggctggcc gatggggggcg ccaccaacca gggccgcgtg agatcttct   300 acagaggcca gtggggcact gtgtgtgaca acctgtggga cctgactgat gccagcgtcg   360 tctgccggc cctgggcttc gagaacgcca cccaggctct gggcagagct gccttcgggc   420
aaggatcagg cccatcatg ctggacgagg tccagtgcac gggaaccgag gcctcactgg   480
ccgactgcaa gtccctgggc tggctgaaga gcaactgcag gcacgagaga gacgctggtg   540
tggtctgcac caatgaaacc aggagcaccc acacctgga cctctccagg gagctctcgg   600
aggcccttgg ccagatcttt gacagccagc ggggctgcga cctgtccatc agcgtgaatg   660
tgcagggcga ggacgccctg ggcttctgtg gccacgggt catcctgact gccaacctgg   720
aggcccaggc cctgtggaag gagccgggca gcaatgtcac catgagtgtg gatgctgagt   780
```

| | |
|---|---|
| gtgtgcccat ggtcagggac cttctcaggt acttctactc ccgaaggatt gacatcaccc | 840 |
| tgtcgtcagt caagtgcttc cacaagctgg cctctgccta ggggccagg cagctgcagg | 900 |
| gctactgcgc aagcctcttt gccatcctcc tcccccagga cccctcgttc cagatgcccc | 960 |
| tggacctgta tgcctatgca gtggccacag gggacgccct gctggagaag ctctgcctac | 1020 |
| agttcctggc ctggaacttc gaggccttga cgcaggccga ggcctggccc agtgtcccca | 1080 |
| cagacctgct ccaactgctg ctgcccagga gcgacctggc ggtgcccagc gagctggccc | 1140 |
| tactgaaggc cgtggacacc tggagctggg gggagcgtgc ctcccatgag gaggtggagg | 1200 |
| gcttggtgga agatccgc ttccccatga tgctccctga ggagctcttt gagctgcagt | 1260 |
| tcaacctgtc cctgtactgg agccacgagg ccctgttcca gaagaagact ctgcaggccc | 1320 |
| tggaattcca cactgtgccc ttccagttgc tggcccggta caaaggcctg aacctcaccg | 1380 |
| aggataccta caagccccgg atttacacct cgcccacctg gagtgccttt gtgacagaca | 1440 |
| gttcctggag tgcacggaag tcacaactgg tctatcagtc cagacggggg cctttggtca | 1500 |
| aatattcttc tgattacttc caagccccct ctgactacag atactacccc taccagtcct | 1560 |
| tccagactcc acaacacccc agcttcctct tccaggacaa gagggtgtcc tggtccctgg | 1620 |
| tctacctccc caccatccag agctgctgga actacggctt ctcctgctcc tcggacgagc | 1680 |
| tccctgtcct gggcctcacc aagtctggcg gctcagatcg caccattgcc tacgaaaaca | 1740 |
| aagccctgat gctctgcgaa gggctcttcg tggcagacgt caccgatttc gagggctgga | 1800 |
| aggctgcgat tccagtgcc ctggacacca acagctcgaa gagcacctcc tccttcccct | 1860 |
| gcccggcagg gcacttcaac ggcttccgca cggtcatccg cccccttctac ctgaccaact | 1920 |
| cctcaggtgt ggactagacg cgtggccaag ggtggtgaga accggagaac cccaggacgc | 1980 |
| cctcactgca ggctcccctc ctcggcttcc ttcctctctg caatgacctt caacaaccgg | 2040 |
| ccaccagatg tcgccctact cacctgaggc tcagcttcaa gaaattactg gaaggcttcc | 2100 |
| actagggtcc accaggagtt ctcccaccac ctcaccagtt tccaggtggt aagcaccagg | 2160 |
| aggccctcga ggttgctctg gatccccca cagcccctgg tcagtctgcc cttgtcactg | 2220 |
| gtctgaggtc attaaaatta cattgaggtt ccta | 2254 |

<210> SEQ ID NO 7
<211> LENGTH: 4213
<212> TYPE: DNA
<213> ORGANISM: Homo sapiens

<400> SEQUENCE: 7

| | |
|---|---|
| tccactcctg agcccgcgg accccgagca cgcgcctgac agcccctgct ggcccggcgc | 60 |
| gcggcgtcgc caggccagct atggcccccg accggtggc cgccgagacc gcggctcagg | 120 |
| gacctacccc gcgctacttc acctgggacg aggtggccca gcgctcaggg tgcgaggagc | 180 |
| ggtggctagt gatcgaccgt aaggtgtaca acatcagcga gttcacccgc cggcatccag | 240 |
| ggggctcccg ggtcatcagc cactacgccg ggcaggatgc cacggatccc tttgtggcct | 300 |
| tccacatcaa caagggcctt gtgaagaagt atatgaactc tctcctgatt ggagaactgt | 360 |
| ctccagagca gcccagcttt gagcccacca agaataaaga gctgacagat gagttccggg | 420 |
| agctgcgggc cacagtggag cggatggggc tcatgaaggc caaccatgtc ttcttcctgc | 480 |
| tgtacctgct gcacatcttg ctgctggatg gtgcagcctg gctcacccct tgggtctttg | 540 |
| ggacgtcctt tttgcccttc ctcctctgtg cggtgctgct cagtgcagtt caggcccagg | 600 |
| ctggctggct gcagcatgac tttgggcacc tgtcggtctt cagcacctca agtggaacc | 660 |

```
atctgctaca tcattttgtg attggccacc tgaagggggc ccccgccagt tggtggaacc      720
acatgcactt ccagcaccat gccaagccca actgcttccg caaagaccca gacatcaaca      780
tgcatccctt cttctttgcc ttggggaaga tcctctctgt ggagcttggg aaacagaaga      840
aaaaatatat gccgtacaac caccagcaca aatacttctt cctaattggg cccccagcct      900
tgctgcctct ctacttccag tggtatattt tctattttgt tatccagcga aagaagtggg      960
tggacttggc ctggatgatt accttctacg tccgcttctt cctcacttat gtgccactat     1020
tggggctgaa agccttcctg ggccttttct tcatagtcag gttcctggaa agcaactggt     1080
ttgtgtgggt gacacagatg aaccatattc ccatgcacat tgatcatgac cggaacatgg     1140
actgggtttc cacccagctc caggccacat gcaatgtcca caagtctgcc ttcaatgact     1200
ggttcagtgg acacctcaac ttccagattg agcaccatct ttttcccacg atgcctcgac     1260
acaattacca caaagtggct cccctggtgc agtccttgtg tgccaagcat ggcatagagt     1320
accagtccaa gccctgctg tcagccttcg ccgacatcat ccactcacta aaggagtcag      1380
ggcagctctg gctagatgcc tatcttcacc aataacaaca gccaccctgc ccagtctgga     1440
agaagaggag gaagactctg gagccaaggc agagggagc ttagggaca atgccactat       1500 agtttaatac tcagaggggg ttgggtttgg ggacataaag cctctgactc aaactcctcc     1560
cttttatctt ctagccacag ttctaagacc caaagtgggg ggtggacaca gaagtcccta    1620
ggagggaagg agctgttggg gcagggttgt aaattatttc cttttctag tttggcacat      1680 gcaggtagtt ggtgaacaga gagaaccagg agggtaacag aagaggaggg acctactgaa     1740
cccagagtca ggaagagatt taacactaaa attccactca tgccgggcgt ggtggcacgc     1800
gcctgtaatc ccagctaccc aggaggctga ggcaggagaa tcgcttgaac cggggaggtg     1860
gaggttgcag tgagctgaga tcacgccatt gtactccagc ctgggcgaca gagcaagact     1920
ccatttcaaa aaaaaaaaa aaatccactc atataaaagg tgagctcagc tcactggtcc      1980
atttctcagt ggcttctcca tcctcatttg caaacctcag agggataagg cagttgaacc     2040
tgatgagcaa gaattataac agcaaggaaa cattaatgct tagaattctg agatccagca     2100
caactcagtc tgtgggagct cagctcgctg cccagggata ggtatgacct atgtctgcct     2160
taggctgctg ggagatgcca ttctccagtt tcagaagcag gcagggcaaa ggtcaagact     2220
gtggtattgg ggtcttttgg ctctgaagga tcctggaacc actgattttg gtttattccc     2280
tccagggtct aaagagaaca agaggtgcta gctcttacca aaacagatgg tagagagagt     2340
tgctggctat ttaaaaagct cttcatctt ttaattcacc tcttcttttc acctctttaa      2400
ccactcctca ggaacagaac acttctagga ctgggggtct tttagctcca taagcaagtg     2460
agcagatggg acaagttagt ctttttctccc tagaaacaaa ggggatgccc agtggtttcc    2520
ctttgcttcc caacctaaaa tttcaagttt aataaaatag caattagcag aagtgaccaa     2580
attgggagat aattatcagt catgaggaaa gacacagatt tcggtcataa agaatgtaag     2640
ggctataagt agaaactttc tataacctaa atgatgttat agaattattt ttgagcagga     2700
gcagaaagat taaatatgat cacttcatac ttctaaatca gaaataggaa gattaaaacc     2760
acagaacagt ttgtgatttc tattgctgta gctaggtatc ttactctgtc cactcttgtt     2820
caagtatcta actcttctgg aaaccaaata ggctttagaa gagattatcc tatattccta     2880
tcagtataat actaaaatgt aacttttaa tcatctggtt tttaaaagat aaacagttta      2940
gcccatctct ccagagagca acataggaa tatgactcag gagcctccta gggcttatca      3000
tcagccctca cacccgcttc cccctccaac ccacagcctt tgcttccagg tggcaggatt     3060
```

-continued

| | |
|---|---|
| actactttgc ctcttcagca gcatctactc taggcatatt gatcatttta gacactggga | 3120 |
| gaagagaacc tcaaactagg aggaaaagac agagcctcca cttagttttg ggaggggatg | 3180 |
| gcagacagtc aaggagatga gcgtcctaag gcatgttggg atagggtcag atgcaccacc | 3240 |
| catggagagg tttgtcaaca caaagacatg gaaggttaga ggtttgtcaa caaaaagaca | 3300 |
| tggaaggtta ggtttgtcaa cacaaagaca tggaagatta gaggtttgtc aacacaaaga | 3360 |
| cacaggaaga atgggctgca gaagatttag atgttttcca tttgggcaca ttttacttag | 3420 |
| ctggagaact aggtttaaaa cagcctgggt aggaaaatta gaagcaagct ggatgcagtg | 3480 |
| gctcatgcct gtaatcccaa cacttttggg aggtccaggc aggaggatca cttgggccca | 3540 |
| ggaggtcaag cctgcagcga gctgagatca caccactgca ctccagcctg ggtgataga | 3600 |
| acaagaccct gtctcaaaaa aaaaaaaaaa caacaaaaac ttagaattga ggagttgtac | 3660 |
| ctccattggc ttcctcactc caaataggt gctgatcctt cctattccta ttctttgcca | 3720 |
| ccttttgggt gtggtgtcac cagcctgttt agccaagtag ctttgggcat aggctgccca | 3780 |
| atctgagcaa acaccagtga ggctctattg agccaagacc aagtcctcaa agcacctgaa | 3840 |
| ccactgtggc cttctcagcc tacagcagtg tggtctctta catggccaca aagggacaca | 3900 |
| cagtgacaaa aggctcggaa tgttacaatg gtaaaatgag tgatctcaaa tccactgaca | 3960 |
| gatataaaat aggcttagag aggaaaagct gcctctggtc aagtagatca tggcagcatg | 4020 |
| aattccaact cactttttta caactccaac ttctatgttt atctttgtta ctttcacttt | 4080 |
| tttacaaccct ggccagaggc attttttaaa tcaggcccaa tatcagtatt cttttttgtgt | 4140 |
| gtgccaattt tgttatcaca tccctatgaa gttgaaaaat aaagttaatt ttgaccaaaa | 4200 |
| aaaaaaaaaa aag | 4213 |

<210> SEQ ID NO 8
<211> LENGTH: 4459
<212> TYPE: DNA
<213> ORGANISM: Homo sapiens

<400> SEQUENCE: 8

| | |
|---|---|
| gtttctctct ctccttctct ctctctctct ctctctcttt ttttccgcc ctagctgggg | 60 |
| ctgtgttgga ggagaggaag aaagagagac agaggattgc attcatccgt tacgttcttg | 120 |
| aaatttccta atagcaagac cagcgaagcg gttgcaccct tttcaatctt gcaaggaaa | 180 |
| aaaacaaaac aaaacaaaaa aaacccaagt ccccttcccg gcagttttg ccttaaagct | 240 |
| gccctcttga aattaatttt ttcccaggag agagatgtct tatcagggga agaaaaatat | 300 |
| tccacgcatc acgagcgatc gtcttctgat caaaggaggt aaaattgtta atgatgacca | 360 |
| gtcgttctat gcagacatat acatggaaga tgggttgatc aagcaaatag gagaaaatct | 420 |
| gattgtgcca ggaggagtga agaccatcga ggcccactcc cggatggtga tccccggagg | 480 |
| aattgacgtc cacactcgtt ccagatgcc tgatcaggga atgacgtctg ctgatgattt | 540 |
| cttccaagga accaaggcgg ccctggctgg ggaaccact atgatcattg accacgttgt | 600 |
| tcctgagcct gggacaagcc tgctcgctgc ctttgaccag tggagggaat gggccgacag | 660 |
| caagtcctgc tgtgactact ctctgcatgt ggacatcagc gagtggcata agggcatcca | 720 |
| ggaggagatg gaagcgcttg tgaaggatca cggggtaaat tccttcctcg tgtacatggc | 780 |
| tttcaaagat cgcttccagc taacggattg ccagatttat gaagtactga gtgtgatccg | 840 |
| ggatattggc gccatagccc aagtccacgc agaaaatggc gacatcattg cagaggagca | 900 |
| gcagaggatc ctggatctgg gcatcacggg ccccgaggga catgtgctga gccgacctga | 960 |

-continued

| | | | | |
|---|---|---|---|---|
| ggaggtcgag | gccgaagccg | tgaatcgtgc | catcaccatc | gccaaccaga ccaactgccc | 1020 |
| gctgtatatc | accaaggtga | tgagcaaaag | ctctgctgag | gtcatcgccc aggcacggaa | 1080 |
| gaagggaact | gtggtgtatg | gcgagcccat | cactgccagc | ttgggaacgg acggctccca | 1140 |
| ttactggagc | aagaactggg | ccaaggctgc | tgcctttgtc | acctcccac ccttgagccc | 1200 |
| tgatccaacc | actccagact | ttctcaactc | cttgctgtcc | tgtggagacc tccaggtcac | 1260 |
| gggcagtgcc | cattgcacgt | taacactgc | ccagaaggct | gtaggaaagg acaacttcac | 1320 |
| cctgattccg | gagggcacca | atggcactga | ggagcggatg | tccgtcatct gggacaaggc | 1380 |
| tgtggtcact | gggaagatgg | atgagaacca | gtttgtggct | gtgaccagca ccaatgcagc | 1440 |
| caaagtcttc | aacctttacc | cccggaaagg | ccgcattgct | gtgggatccg atgccgacct | 1500 |
| ggtcatctgg | gaccccgaca | gcgttaaaac | catctctgcc | aagacacaca acagctctct | 1560 |
| cgagtacaac | atctttgaag | gcatggagtg | ccgcggctcc | ccactggtgg tcatcagcca | 1620 |
| ggggaagatt | gtcctggagg | acggcaccct | gcatgtcacc | gaaggctctg acgctacat | 1680 |
| tccccggaag | cccttccctg | attttgttta | caagcgtatc | aaggcaagga gcaggctggc | 1740 |
| tgagctgaga | ggggttcctc | gtggcctgta | tgacggacct | gtgtgtgaag tgtctgtgac | 1800 |
| gcccaagaca | gtcactccag | cctcctcggc | caagacgtct | cctgccaagc agcaggcccc | 1860 |
| acctgtccgg | aacctgcacc | agtctggatt | cagtttgtct | ggtgctcaga ttgatgacaa | 1920 |
| cattccccgc | cgcaccaccc | agcgtatcgt | ggcgccccc | ggtggccgtg ccaacatcac | 1980 |
| cagcctgggc | tagagctcct | gggctgtgcg | tccactgggg | actggggatg ggacacctga | 2040 |
| ggacattctg | agacttcttt | cttccttcct | ttttttttt | ttgttttttt ttttaagagc | 2100 |
| ctgtgatagt | tactgtggag | cagccagttc | atggggtccc | ccttggggcc ccacacccg | 2160 |
| tctctcacca | agagttactg | attttgctca | tccacttccc | tacacatcta tgggtatcac | 2220 |
| acccaagact | acccaccaag | ctcatacagg | gaaccacacc | caacacttag acatgcgaac | 2280 |
| aagcagcccc | cagcgagggt | ctccttcgcc | ttcaacctcc | tagtgtctgt tagcatcttc | 2340 |
| cttttcatgg | ggggagggaa | gataaagtga | attgcccaga | gctgccttt tcttttcttt | 2400 |
| ttaaaatttt | taagaagttt | tccttgtggg | gctggggagg | ggccggggtc agggagagtc | 2460 |
| tttttttttt | ttttttttaaa | tactaaattg | gaacatttaa | ttccatatta atacaagggg | 2520 |
| tttgaactgg | acatcctaat | gatgcaatta | cgtcatcacc | cagctgattc cgggtggttg | 2580 |
| gcaaactcat | cgtgtctgtc | ctgagaggct | ccacaatgcc | cacccgcatc gccattctgt | 2640 |
| agtcttcagg | gtcagctgtt | gataaagggg | caggcttgcg | ttattggcct agattttgct | 2700 |
| gcagattaaa | tcctttgagg | attctcttct | cttttaccat | ttttctgcgt gctctcactc | 2760 |
| tctctttctc | tctctagctt | tttaattcat | gaatattttc | gtgtctgtct ctctctctct | 2820 |
| ctgtgtttcc | tccagcccctt | gtctcggaga | cggtgttttc | ctcccttgcc ccattatctt | 2880 |
| ttcacctccc | aggtctacca | tttcatggtg | gtcgttgggt | ccgcctaaag gatttgagcg | 2940 |
| tttgccattg | caagcatagt | gctgtgtcat | cctggtccat | gtaggactgg tgctaaccac | 3000 |
| ctgccatcat | gaggatgtgt | gctagagtgt | gggaccctgg | ccaagtgcag gaatgggcca | 3060 |
| tgccgtctca | cccacagtat | cacacgtgga | accgcagaca | gggcccagaa gctttagagg | 3120 |
| tatgaggctg | cagaaccgga | gagattttcc | tctgtgcagt | gctctctggc taaagtcacg | 3180 |
| gtcaaaccta | acaccgagc | ctcattaacc | caagtgaacc | aaccaaagtc accagttcag | 3240 |
| aagtgctaag | ctaataggag | tctgacccga | gggcctgctg | cttcctggtt aagtatcttt | 3300 |
| tgagattcta | gaacacatgg | gagcttttta | ttttcgggga | aaaaccgtat tttttctttg | 3360 |

| | | | | |
|---|---|---|---|---|
| tccaattatt | tctaaagaca | cactacatag | aaagaggccc | tataaactca | aaaagtcatt | 3420 |
| gggaaactta | aagtctattc | tactttgcaa | gaggagaaat | gtgttttatg | aacgatagat | 3480 |
| cacatcagaa | ctcctgtggg | gaggaaacct | tataaattaa | acacatggcc | cccttagaga | 3540 |
| ccacaggtga | tgtctgtctc | catccttccc | tctccttttc | tgtcacctttc | ccctagct | 3600 |
| ggctcctttg | gacctacccc | tgtccttgct | gacttgtgtt | gcattgtatt | ccaaacgtgt | 3660 |
| ttacaggttc | tcttaagcaa | tgttgtattt | gcaggctttt | ctgaatacca | aatctgcttt | 3720 |
| ttgtaaagcg | taaaaacatc | acaaagtagg | tcattccatc | accacccttg | tctctctaca | 3780 |
| cattttgcct | tgggggatct | ggttggggtt | ttgggtttt | tgttgttgtt | gtttatttgt | 3840 |
| tattttaaag | gtaaattgca | cttttaaaaa | aataattggt | tgacttaata | tatttgcttt | 3900 |
| ttttctcacc | tgcacttaga | ggaaatttga | acaagttgga | aaaaaacaat | ttttgtttca | 3960 |
| attctaagaa | acacttgcag | ctctagtatt | cacttgagtc | ttcctgttttt | tcctgtaccg | 4020 |
| ggtcatggta | atttttggtt | gttttggttg | tttctttaaa | aaacaagtta | aaacctgacg | 4080 |
| atttctgcag | gctgtgtaag | catgtttacc | tgttggcttg | ctttgtgtgt | ctgttaaatg | 4140 |
| aatgtcatat | gtaaatgcta | aaataaatcg | acagtgtctc | agaactgaat | aactgcagtg | 4200 |
| acttgatgct | ctaaaacagt | gtaggattta | agaatagatg | gttttaatc | ctggaaattg | 4260 |
| tgattgtgac | ccatgagtgg | aggaactttc | agttctaaag | ctgataaagt | gtgtagccag | 4320 |
| aagagtactt | ttttttttgt | aaccactgtc | ttgatggcaa | aataattatg | gtaaaaaaca | 4380 |
| agtctcgtgt | ttattattcc | ttaagaactc | tgtgttatat | taccatggaa | cgcctaataa | 4440 |
| agcaaaatgt | ggttgtttc | | | | | 4459 |

<210> SEQ ID NO 9
<211> LENGTH: 7718
<212> TYPE: DNA
<213> ORGANISM: Homo sapiens

<400> SEQUENCE: 9

| | | | | | | |
|---|---|---|---|---|---|---|
| cgggagcggc | gggagcggtg | gcggcggcag | aggcggcggc | tccagcttcg | gctccggctc | 60 |
| gggctcgggc | tccggctccg | gctccggctc | cggctccagc | tcgggtggcg | gtggcggag | 120 |
| cgggaccagg | tggaggcggc | ggcggcagag | gagtgggagc | agcggcccta | gcggcttgcg | 180 |
| gggggacatg | cggaccgacg | gccccctggat | aggcggaagg | agtggaggcc | ctggtgcccg | 240 |
| gcccttggtg | ctgagtatcc | agcaagagtg | accggggtga | agaagcaaag | actcggttga | 300 |
| ttgtcctggg | ctgtggctgg | ctgtggagct | agagccctgg | atggcccctg | agccagcccc | 360 |
| agggaggacg | atggtgcccc | ttgtgcctgc | actggtgatg | cttggttttgg | tggcaggcgc | 420 |
| ccatggtgac | agcaaacctg | tcttcattaa | agtccctgag | gaccagactg | gctgtcagg | 480 |
| aggggtagcc | tccttcgtgt | gccaagctac | aggagaaccc | aagccgcgca | tcacatggat | 540 |
| gaagaagggg | aagaaagtca | gctcccagcg | cttcgaggtc | attgagtttg | atgatgggc | 600 |
| agggtcagtg | cttcggatcc | agccattgcg | ggtgcagcga | gatgaagcca | tctatgagtg | 660 |
| tacagctact | aacagcctgg | gtgagatcaa | cactagtgcc | aagctctcag | tgctcgaaga | 720 |
| ggaacagctg | ccccctgggt | tcccttccat | cgacatgggg | cctcagctga | aggtggtgga | 780 |
| gaaggcacgc | acagccacca | tgctatgtgc | cgcaggcgga | aatccagacc | ctgagatttc | 840 |
| ttggttcaag | gacttcctc | ctgtagaccc | tgccacgagc | aacggccgca | tcaagcagct | 900 |
| gcgttcaggt | gccttgcaga | tagagagcag | tgaggaatcc | gaccaaggca | gtacgagtg | 960 |
| tgtggcgacc | aactcggcag | gcacacgtta | ctcagcccct | gcgaacctgt | atgtgcgagt | 1020 |

```
gcgccgcgtg gctcctcgtt tctccatccc tcccagcagc caggaggtga tgccaggcgg    1080
cagcgtgaac ctgacatgcg tggcagtggg tgcacccatg ccctacgtga agtggatgat    1140
gggggccgag gagctcacca aggaggatga gatgccagtt ggccgcaacg tcctggagct    1200
cagcaatgtc gtacgctctg ccaactacac ctgtgtggcc atctcctcgc tgggcatgat    1260
cgaggccaca gcccaggtca cagtgaaagc tcttccaaag cctccgattg atcttgtggt    1320
gacagagaca actgccacca gtgtcaccct cacctgggac tctgggaact cggagcctgt    1380
aacctactat ggcatccagt accgcgcagc gggcacggag ggccccttc aggaggtgga    1440 tggtgtggcc accacccgct acagcattgg cggcctcagc cctttctcgg aatatgcctt    1500
ccgcgtgctg gcggtgaaca gcatcgggcg agggccgccc agcgaggcag tgcgggcacg    1560
cacgggagaa caggcgccct ccagcccacc gcgccgcgtg caggcacgca tgctgagcgc    1620
cagcaccatg ctggtgcagt gggagcctcc cgaggagccc aacggcctgg tgcggggata    1680
ccgcgtctac tatactccgg actcccgccg ccccccgaac gcctggcaca gcacaacac    1740 cgacgcgggg ctcctcacga ccgtgggcag cctgctgcct ggcatcacct acagcctgcg    1800
cgtgcttgcc ttcaccgccg tgggcgatgg ccctcccagc cccaccatcc aggtcaagac    1860
gcagcaggga gtgcctgccc agcccgcgga cttccaggcc gaggtggagt cggacaccag    1920
gatccagctc tcgtggctgc tgcccccctca ggagcggatc atcatgtatg aactggtgta    1980
ctgggcggca gaggacgaag accaacagca caaggtcacc ttcgacccaa cctcctccta    2040
cacactagag gacctgaagc ctgacacact ctaccgcttc cagctggctg cacgctcgga    2100
tatgggggtg ggcgtcttca ccccaccat tgaggcccgc acagcccagt ccacccctc    2160 cgcccctccc cagaaggtga tgtgtgtgag catgggctcc accacggtcc gggtaagttg    2220
ggtcccgccg cctgccgaca gccgcaacgg cgttatcacc cagtactccg tggcccacga    2280
ggcggtggac ggcgaggacc gcgggcggca tgtggtggat ggcatcagcc gtgagcactc    2340
cagctgggac ctggtgggcc tggagaagtg gacggagtac cgggtgtggg tgcgggcaca    2400
cacagacgtg ggccccggcc ccgagagcag cccggtgctg gtgcgcaccg atgaggacgt    2460
gcccagcggg cctccgcgga aggtggaggt ggagccactg aactccactg ctgtgcatgt    2520
ctactggaag ctgcctgtcc ccagcaagca gcatggccag atccgcggct accaggtcac    2580
ctacgtgcgg ctggagaatg gcgagccccg tggactcccc atcatccaag acgtcatgct    2640
agccgaggcc cagtggcggc cagaggagtc cgaggactat gaaaccacta tcagcggcct    2700
gacccccgag accaccctact ccgttactgt tgctgcctat accaccaagg gggatggtgc    2760
ccgcagcaag cccaaaattg tcactacaac aggtgcagtc ccaggccggc ccaccatgat    2820
gatcagcacc acgccatga acactgcgct gctccagtgg cacccaccca aggaactgcc    2880
tggcgagctg ctgggctacc ggctgcagta ctgccgggcc gacgaggcgc ggcccaacac    2940
catagatttc ggcaaggatg accagcactt cacagtcacc ggcctgcaca aggggaccac    3000
ctacatcttc cggcttgctg ccaagaaccg ggctggcttg ggtgaggagt tcgagaagga    3060
gatcaggacc cccgaggacc tgcccagcgg cttccccca aacctgcatg tgacaggact    3120
gaccacgtct accacagaac tggcctggga cccgccagtg ctggcggaga ggaacgggcg    3180
catcatcagc tacaccgtgg tgttccgaga catcaacagc caacaggagc tgcagaacat    3240
cacgacagac acccgcttta cccttactgg cctcaagcca gacaccactt acgacatcaa    3300
ggtccgcgca tggaccagca aaggctctgg cccactcagc cccagcatcc agtcccggac    3360
catgccggtg gagcaagtgt ttgccaagaa cttccgggtg gcggctgcaa tgaagacgtc    3420
```

```
tgtgctgctc agctgggagg ttcccgactc ctataagtca gctgtgccct ttaagattct    3480
gtacaatggg cagagtgtgg aggtggacgg cactcgatg cggaagctga tcgcagacct     3540
gcagcccaac acagagtact cgtttgtgct gatgaaccgt ggcagcagcg caggggcct     3600 gcagcacctg gtgtccatcc gcacagcccc cgacctcctg cctcacaagc cgctgcctgc    3660
ctctgcctac atagaggacg gccgcttcga tctctccatg ccccatgtgc aagacccctc    3720
gcttgtcagg tggttctaca ttgttgtggt acccattgac cgtgtgggcg ggagcatgct    3780
gacgccaagg tggagcacac ccgaggaact ggagctggac gagcttctag aagccatcga    3840
gcaaggcgga gaggagcagc ggcggcggcg cggcaggca  aacgtctga agccatatgt      3900 ggctgctcaa ctggatgtgc tcccggagac ctttaccttg ggggacaaga agaactaccg    3960
gggcttctac aaccggcccc tgtctccgga cttgagctac cagtgctttg tgcttgcctc    4020
cttgaaggaa cccatggacc agaagcgcta tgcctccagc ccctactcgg atgagatcgt    4080
ggtccaggtg acaccagccc agcagcagga ggagccggag atgctgtggg tgacgggtcc    4140
cgtgctggca gtcatcctca tcatcctcat tgtcatcgcc atcctcttgt tcaaaaggaa    4200
aaggacccac tctccgtcct ctaaggatga gcagtcgatc ggactgaagg actccttgct    4260
ggcccactcc tctgaccctg tggagatgcg gaggctcaac taccagaccc caggtatgcg    4320
agaccaccca cccatcccca tcaccgacct ggcggacaac atcgagcgcc tcaaagccaa    4380
cgatggcctc aagttctccc aggagtatga gtccatcgac cctggacagc agttcacgtg    4440
ggagaattca aacctggagg tgaacaagcc caagaaccgc tatgcgaatg tcatcgccta    4500
cgaccactct cgagtcatcc ttacctctat cgatggcgtc cccgggagtg actacatcaa    4560
tgccaactac atcgatggct accgcaagca gaatgcctac atcgccacgc agggccccct    4620
gcccgagacc atgggcgatt tctggagaat ggtgtgggaa cagcgcacgg ccactgtggt    4680
catgatgaca cggctggagg agaagtcccg ggtaaaatgt gatcagtact ggccagcccg    4740
tggcaccgag acctgtggcc ttattcaggt gaccctgttg gacacagtgg agctggccac    4800
atacactgtg cgcaccttcg cactccacaa gagtggctcc agtgagaagc gtgagctgcg    4860 tcagttttcag ttcatggcct ggccagacca tggagttcct gagtacccaa ctcccatcct    4920
ggccttccta cgacgggtca aggcctgcaa ccccctagac gcagggccca tggtggtgca    4980
ctgcagcgcg ggcgtgggcc gcaccggctg cttcatcgtg attgatgcca tgttggagcg    5040
gatgaagcac gagaagacgg tggacatcta tggccacgtg acctgcatgc gatcacagag    5100
gaactacatg tgcagacgg aggaccagta cgtgttcatc catgaggcgc tgctggaggc    5160
tgccacgtgc ggccacacag aggtgcctgc ccgcaacctg tatgcccaca tccagaagct    5220
gggccaagtg cctccagggg agagtgtgac cgccatggag ctcgagttca gttgctggc    5280 cagctccaag gcccacacgt cccgcttcat cagcgccaac ctgccctgca caagttcaa    5340 gaaccggctg gtgaacatca tgccctacga attgacccgt gtgtgtctgc agcccatccg    5400
tggtgtggag ggctctgact acatcaatgc cagcttcctg gatggttata gacagcagaa    5460
ggcctacata gctacacagg ggcctctggc agagagcacc gaggacttct ggcgcatgct    5520
atgggagcac aattccacca tcatcgtcat gctgaccaag cttcgggaga tgggcaggga    5580
gaaatgccac cagtactggc cagcagacg  ctctgctcgc taccagtact ttgttgttga    5640
cccgatggct gagtacaaca tgcccagta  tatcctgcgt gagttcaagg tcacggatgc    5700
ccgggatggg cagtcaagga caatccggca gttccagttc acagactggc cagagcaggg    5760
cgtgcccaag acaggcgagg gattcattga cttcatcggg caggtgcata agaccaagga    5820
```

| | |
|---|---|
| gcagtttgga caggatgggc ctatcacggt gcactgcagt gctggcgtgg gccgcaccgg | 5880 |
| ggtgttcatc actctgagca tcgtcctgga gcgcatgcgc tatgagggcg tggtcgacat | 5940 |
| gtttcagacc gtgaagaccc tgcgtacaca gcgtcctgcc atggtgcaga cagaggacca | 6000 |
| gtatcagctg tgctaccgtg cggccctgga gtacctcggc agctttgacc actatgcaac | 6060 |
| gtaactaccg ctcccctctc ctccgccacc cccgcgtgg ggctccggag ggacccagc | 6120 |
| tcctctgagc cataccgacc atcgtccagc cctcctacgc agatgctgtc actggcagag | 6180 |
| cacagcccac ggggatcaca gcgtttcagg aacgttgcca caccaatcag agagcctaga | 6240 |
| acatccctgg gcaagtggat ggcccagcag gcaggcactg tggcccttct gtccaccaga | 6300 |
| cccacctgga gcccgcttca agctctctgt tgcgctcccg catttctcat gcttcttctc | 6360 |
| atggggtggg gttggggcaa agcctccttt ttaatacatt aagtgggta gactgaggga | 6420 |
| ttttagcctc ttccctctga ttttccttt cgcgaatccg tatctgcaga atgggccact | 6480 |
| gtaggggttg gggtttattt tgttttgttt ttttttttt tttgtatgac ttctgctgaa | 6540 |
| ggacagaaca ttgccttcct cgtgcagagc tggggctgcc agcctgagcg gaggctcggc | 6600 |
| cgtgggccgg gaggcagtgc tgatccggct gctcctccag cccttcagac gagatcctgt | 6660 |
| ttcagctaaa tgcagggaaa ctcaatgttt ttttaagttt tgttttccct ttaaagcctt | 6720 |
| tttttaggcc acattgacag tggtgggcgg ggagaagata gggaacactc atccctggtc | 6780 |
| gtctatccca gtgtgtgttt aacattcaca gcccagaacc acagatgtgt ctgggagagc | 6840 |
| ctggcaaggc attcctcatc accatcgtgt ttgcaaaggt taaacaaaa acaaaaaacc | 6900 |
| acaaaataa aaacaaaaa aaacaaaaaa cccaaaaaaa aaaaaaaaa gagtcagccc | 6960 |
| ttggcttctg cttcaaaccc tcaagagggg aagcaactcc gtgtgcctgg ggttcccgag | 7020 |
| ggagctgctg gctgacctgg gcccacagag cctggctttg gtccccagca ttgcagtatg | 7080 |
| gtgtggtgtt tgtaggctgt ggggtctggc tgtgtggcca aggtgaatag cacaggttag | 7140 |
| ggtgtgtgcc acaccccatg cacctcaggg ccaagcgggg gcgtggctgg cctttcaggt | 7200 |
| ccaggccagt gggcctggta gcacatgtct gtcctcagag caggggccag atgattttcc | 7260 |
| tccctggttt gcagctgttt tcaaagcccc cgataatcgc tcttttccac tccaagatgc | 7320 |
| cctcataaac caatgtggca agactactgg acttctatca atggtactct aatcagtcct | 7380 |
| tattatccca gcttgctgag gggcagggag agcgcctctt cctctgggca gcgctatcta | 7440 |
| gataggtaag tgggggcggg gaagggtgca tagctgtttt agctgaggga cgtggtgccg | 7500 |
| acgtccccaa acctagctag gctaagtcaa gatcaacatt ccagggttgg taatgttgga | 7560 |
| tgatgaaaca ttcatttta ccttgtggat gctagtgctg tagagttcac tgttgtacac | 7620 |
| agtctgtttt ctatttgtta agaaaaacta cagcatcatt gcataattct tgatggtaat | 7680 |
| aaatttgaat aatcagattt cttacaaaaa aaaaaaaa | 7718 |

<210> SEQ ID NO 10
<211> LENGTH: 1809
<212> TYPE: DNA
<213> ORGANISM: Homo sapiens

<400> SEQUENCE: 10

| | |
|---|---|
| cctgctccaa ggtccagaga gctttctggt ctttgcagca ggcctgccgc cttcatgtcc | 60 |
| actctcctca tcaatcagcc ccagtatgcg tggctgaaag agctggggct ccgcgaggaa | 120 |
| aacgagggcg tgtataatgg aagctgggga ggccggggag aggttattac gacctattgc | 180 |
| cccgctaaca acgagccaat agcaagagtc cgacaggcca gtgtgcagag ctatgaagaa | 240 |

-continued

| | |
|---|---|
| actgtaaaga aagcaagaga agcatggaaa atctgggcag atattcctgc tccaaaacga | 300 |
| ggagaaatag taagacagat tggcgatgcc ttgcgggaga agatccaagt actaggaagc | 360 |
| ttggtgtctt tggagatggg gaaaatctta gtggaaggtg tgggtgaagt tcaggagtat | 420 |
| gtggatatct gtgactatgc tgttggttta tcaaggatga ttggaggacc tatcttgcct | 480 |
| tctgaaagat ctggccatgc actgattgag cagtggaatc ccgtaggcct ggttggaatc | 540 |
| atcacggcat tcaatttccc tgtggcagtg tatggttgga caacgccat cgccatgatc | 600 |
| tgtggaaatg tctgcctctg aaaggagct ccaaccactt ccctcattag tgtggctgtc | 660 |
| acaaagataa tagccaaggt tctggaggac aacaagctgc tggtgcaat ttgttccttg | 720 |
| acttgtggtg gagcagatat tggcacagca atggccaaag atgaacgagt gaacctgctg | 780 |
| tccttcactg ggagcactca ggtgggaaaa caggtgggcc tgatggtgca ggagaggttt | 840 |
| gggagaagtc tgttggaact tggaggaaac aatgccatta ttgcctttga agatgcagac | 900 |
| ctcagcttag ttgttccatc agctctcttc gctgctgtgg aacagctgg ccagaggtgt | 960 |
| accactgcga ggcgactgtt tatacatgaa agcatccatg atgaggttgt aaacagactt | 1020 |
| aaaaaggcct atgcacagat ccgagttggg aacccatggg accctaatgt tctctatggg | 1080 |
| ccactccaca ccaagcaggc agtgagcatg tttcttggag cagtggaaga agcaaagaaa | 1140 |
| gaaggtggca cagtggtcta tgggggcaag gttatggatc gccctggaaa ttatgtagaa | 1200 |
| ccgacaattg tgacaggtct tggccacgat gcgtccattg cacacacaga gactttcgct | 1260 |
| ccgattctct atgtctttaa attcaagaat gaagaagagg tctttgcatg gaataatgaa | 1320 |
| gtaaaacagg gactttcaag tagcatcttt accaaagatc tgggcagaat ctttcgctgg | 1380 |
| cttggaccta aaggatcaga ctgtggcatt gtaaatgtca acattccaac aagtggggct | 1440 |
| gagattggag gtgcctttgg aggagaaaag cacactggtg gtggcaggga gtctggcagt | 1500 |
| gatgcctgga acagtacat gagaaggtct acttgtacta tcaactacag taaagacctt | 1560 |
| cctctggccc aaggaatcaa gtttcagtaa aggtgtttta gatgaacatc ccttaatttg | 1620 |
| aggtgttcca gcagctgttt ttggagaaga caaagaagat taaagttttc cctgaataaa | 1680 |
| tgcattatta tgactgtgac agtgactaat ccccctatga ccccaaagcc ctgattaaat | 1740 |
| caagagattc ctttttttaaa aatcaaaata aaattgttac aacatagcca tagttactaa | 1800 |
| aaaaaaaaa | 1809 |

<210> SEQ ID NO 11
<211> LENGTH: 1317
<212> TYPE: DNA
<213> ORGANISM: Homo sapiens

<400> SEQUENCE: 11

| | |
|---|---|
| agctcccgcg cgctagagcc gcctgctggt ctcacccagc cgggaccgct gacctggcgc | 60 |
| tttgtgcggc tccaggcctc cgagtggact ccagaaagcc tgaaaagcta tcatggcagc | 120 |
| aaggcccaag ctccactatc ccaacggaag aggccggatg gagtccgtga gatgggtttt | 180 |
| agctgccgcc ggagtcgagt ttgatgaaga atttctggaa acaaaagaac agttgtacaa | 240 |
| gttgcaggat ggtaaccacc tgctgttcca acaagtgccc atggttgaaa ttgacgggat | 300 |
| gaagttggta cagacccgaa gcattctcca ctacatagca gacaagcaca atctctttgg | 360 |
| caagaacctc aaggagagaa ccctgattga catgtacgtg gaggggacac tggatctgct | 420 |
| ggaactgctt atcatgcatc ctttcttaaa accagatgat cagcaaaagg aagtggttaa | 480 |
| catggcccag aaggctataa ttagatactt tcctgtgttt gaaaagattt taagggtca | 540 |

-continued

| | |
|---|---|
| cggacaaagc tttcttgttg gtaatcagct gagccttgca gatgtgattt tactccaaac | 600 |
| cattttagct ctagaagaga aaattcctaa tatcctgtct gcatttcctt tcctccagga | 660 |
| atacacagtg aaactaagta atatccctac aattaagaga ttccttgaac ctggcagcaa | 720 |
| gaagaagcct cccccctgatg aaatttatgt gagaaccgtc tacaacatct ttaggccata | 780 |
| aaacaacaca tccatgtgtg agtgacagtg tgttcctaga gatggtattg tctacagtca | 840 |
| tgtcttaatg gatcccagct ctgtcatggt gctatctatg tattaagttg ggtcctaagt | 900 |
| tgggtctttt gtgtcaacga gatcatctct tctagaaata tcaacctttt ttgtccagta | 960 |
| aataattgtt aggggatctt tattggaaaa cttttttgga gaggctggta tttaagttag | 1020 |
| atctgattgg gctactcatg tcctgtagcc agttcatcct cataataaga atgggcagga | 1080 |
| tctcttgttc tctcctgagt gtctttctac tctcctgagc gtcttctgc tctccttatc | 1140 |
| ctgttctctt atccttatcc cctccagtct ctgcctaatt tttagtgttt aataacaacc | 1200 |
| gaatgtctag taaatgactc tcctctgagc tgtaataaat aaaatggtag taatgaatgc | 1260 |
| aatcagtatt agccaaaata aagaatttat gagtcattaa aaaaaaaaa aaaaaa | 1317 |

```
<210> SEQ ID NO 12
<211> LENGTH: 5910
<212> TYPE: DNA
<213> ORGANISM: Homo sapiens

<400> SEQUENCE: 12
```

| | |
|---|---|
| cggaggacag ccggaccgag ccaacgccgg ggactttgtt ccctccacgg aggggactcg | 60 |
| gcaactcgca gcggcagggt ctgggccgg cgcctgggag ggatctgcgc cccccactca | 120 |
| ctccctagct gtgttcccgc cgccgccccg gctagtctcc ggcgctggcg cctatggtcg | 180 |
| gcctccgaca gcgctccgga gggaccgggg gagctcccag gcgcccggga ctggagactg | 240 |
| atgcatgagg ggcctacgga ggcgcaggag cggtggtgat ggtctgggaa gcggagctga | 300 |
| agtcccctgg gctttggtga ggcgtgacag tttatcatga ccgtgttcag gcaggaaaac | 360 |
| gtggatgatt actacgacac cggcgaggaa cttggcagtg gacagtttgc ggttgtgaag | 420 |
| aaaatgccgtg agaaaagtac cggcctccag tatgccgcca aattcatcaa gaaaggagg | 480 |
| actaagtcca gccggcgggg tgtgagccgc gaggacatcg agcgggaggt cagcatcctg | 540 |
| aaggagatcc agcaccccaa tgtcatcacc ctgcacgagg tctatgagaa caagacggac | 600 |
| gtcatcctga tcttggaact cgttgcaggt ggcgagctgt ttgacttctt agctgaaaag | 660 |
| gaatctttaa ctgaagagga agcaactgaa tttctcaaac aaattcttaa tggtgtttac | 720 |
| tacctgcact cccttcaaat cgcccacttt gatcttaagc ctgagaacat aatgctttg | 780 |
| gatagaaatg tccccaaacc tcggatcaag atcattgact ttgggttggc ccataaaatt | 840 |
| gactttggaa atgaatttaa aaacatattt gggactccag agtttgtcgc tcctgagata | 900 |
| gtcaactatg aacctcttgg tcttgaggca gatatgtgga gtatcggggt aataacctat | 960 |
| atcctcctaa gtgggccctc cccatttctt ggagacacta agcaagaaac gttagcaaat | 1020 |
| gtatccgctg tcaactacga atttgaggat gaatacttca gtaataccag tgccctagcc | 1080 |
| aaagatttca taagaagact tctggtcaag gatccaaaga gagaatgac aattcaagat | 1140 |
| agtttgcagc atccctggat caagcctaaa gatacacaac aggcacttag tagaaaagca | 1200 |
| tcagcagtaa acatggagaa attcaagaag tttgcagccc ggaaaaatg gaaacaatcc | 1260 |
| gttcgcttga tatcactgtg ccaaagatta tccaggtcat tcctgtccag aagtaacatg | 1320 |
| agtgttgcca gaagcgatga tactctggat gaggaagact cctttgtgat gaaagccatc | 1380 |

| | |
|---|---|
| atccatgcca tcaacgatga caatgtccca ggcctgcagc accttctggg ctcattatcc | 1440 |
| aactatgatg ttaaccaacc caacaagcac gggacacctc cattactcat tgctgctggc | 1500 |
| tgtgggaata ttcaaatact acagttgctc attaaaagag gctcgagaat cgatgtccag | 1560 |
| gataagggcg ggtccaatgc cgtctactgg gctgctcggc atggccacgt cgataccttg | 1620 |
| aaatttctca gtgagaacaa atgccctttg gatgtgaaag acaagtctgg agagatggcc | 1680 |
| ctccacgtgg cagctcgcta tggccatgct gacgtggctc aagttacttg tgcagcttcg | 1740 |
| gctcaaatcc caatatccag gacaaaggaa gagaaaccc ccctgcactg tgctgcttgg | 1800 |
| cacggctatt actctgtggc caaagccctt tgtgaagccg gctgtaacgt gaacatcaag | 1860 |
| aaccgagaag gagagacgcc cctcctgaca gcctctgcca ggggctacca cgacatcgtg | 1920 |
| gagtgtctgg ccgaacatgg agccgacctt aatgcttgcg acaaggacgg acacattgcc | 1980 |
| cttcatctgg ctgtaagacg gtgtcagatg gaggtaatca agactctcct cagccaaggg | 2040 |
| tgtttcgtcg attatcaaga caggcacggc aatactcccc tccatgtggc atgtaaagat | 2100 |
| ggcaacatgc ctatcgtggt ggccctctgt gaagcaaact gcaatttgga catctccaac | 2160 |
| aagtatgggc gaacgcctct gcaccttgcg gccaacaacg gaatcctaga cgtggtccgg | 2220 |
| tatctctgtc tgatgggagc cagcgttgag gcgctgacca cggacggaaa gacggcagaa | 2280 |
| gatcttgcta gatcggaaca gcacgagcac gtagcaggtc tccttgcaag acttcgaaag | 2340 |
| gatacgcacc gaggactctt catccagcag ctccgaccca cacagaacct gcagccaaga | 2400 |
| attaagctca gctgtttggg ccactcggga tccgggaaaa ccaccccttgt agaatctctc | 2460 |
| aagtgtgggc tgctgaggag cttttttcaga aggcgtcggc ccagactgtc ttccaccaac | 2520 |
| tccagcaggt tcccacccttc accctggct tctaagccca cagtctcagt gagcatcaac | 2580 |
| aacctgtacc caggctgcga gaacgtgagt gtgaggagcc gcagcatgat gttcgagccg | 2640 |
| ggtcttacca aagggatgct ggaggtgttt gtggccccga cccaccaccc gcactgctcg | 2700 |
| gccgatgacc agtccaccaa ggccatcgac atccagaacg cttatttgaa tggagttggc | 2760 |
| gatttcagcg tgtgggagtt ctctggaaat cctgtgtatt tctgctgtta tgactatttt | 2820 |
| gctgcaaatg atcccacgtc aatccatgtt gttgtcttta gtctagaaga gcctatgag | 2880 |
| atccagctga acccagtgat tttctggctc agtttcctga agtcccttgt cccagttgaa | 2940 |
| gaacccatag ccttcggtgg caagctgaag aacccactcc aagttgtcct ggtggccacc | 3000 |
| cacgctgaca tcatgaatgt tcctcgaccg gctggaggcg agtttggata tgacaaagac | 3060 |
| acatcgttgc tgaaagagat taggaacagg tttggaaatg atcttcacat ttcaaataag | 3120 |
| ctgtttgttc tggatgctgg ggcttctggg tcaaaggaca tgaaggtact tcgaaatcat | 3180 |
| ctgcaagaaa tacgaagcca gattgtttcg gtctgtcctc ccatgactca cctgtgtgag | 3240 |
| aaaatcatct ccacgctgcc ttcctggagg aagctcaatg gacccaacca gctgatgtcg | 3300 |
| ctgcagcagt ttgtgtacga cgtgcaggac cagctgaacc cctggccag cgaggaggac | 3360 |
| ctcaggcgca ttgctcagca gctccacagc acaggcgaga tcaacatcat gcaaagtgaa | 3420 |
| acagttcagg acgtgctgct cctggacccc cgctggctct gcacaaacgt cctggggaag | 3480 |
| ttgctgtccg tggagacccc acgggcgctg caccactacc ggggccgcta caccgtggag | 3540 |
| gacatccagc gcctggtgcc cgacagcgac gtggaggagc tgctgcagat cctcgatgcc | 3600 |
| atggacatct gcgcccggga cctgagcagc gggaccatgg tggacgtccc agccctgatc | 3660 |
| aagacagaca acctgcaccg ctcctgggct gatgaggagg acgaggtgat ggtgtatggt | 3720 |
| ggcgtgcgca tcgtgcccgt ggaacacctc acccccttcc catgtggcat ctttcacaag | 3780 |

```
gtccaggtga acctgtgccg gtggatccac cagcaaagca cagagggcga cgcggacatc   3840
cgcctgtggg tgaatggctg caagctggcc aaccgtgggg ccgagctgct ggtgctgctg   3900
gtcaaccacg gccagggcat tgaggtccag gtccgtggcc tggagacgga gaagatcaag   3960
tgctgcctgc tgctggactc ggtgtgcagc accattgaga cgtcatggc caccacgctg   4020 ccagggctcc tgaccgtgaa gcattacctg agccccagc agctgcggga gcaccatgag   4080
cccgtcatga tctaccagcc acgggacttc ttccgggcac agactctgaa ggaaacctca   4140
ctgaccaaca ccatgggggg gtacaaggaa agcttcagca gcatcatgtg cttcgggtgt   4200
cacgacgtct actcacaggc cagcctcggc atggacatcc atgcatcaga cctgaacctc   4260
ctcactcgga ggaaactgag tcgcctgctg acccgcccg accccctggg gaaggactgg   4320
tgccttctcg ccatgaactt aggcctccct gacctcgtgg caaagtacaa caccaataac   4380
ggggctccca aggatttcct ccccagcccc ctccacgccc tgctgcggga tggaccacc   4440 taccctgaga gcacagtggg caccctcatg tccaaactga gggagctggg tcgccgggat   4500
gccgcagacc ttttgctgaa ggcatcctct gtgttcaaaa tcaacctgga tggcaatggc   4560
caggaggcct atgcctcgag ctgcaacagc ggcacctctt acaattccat tagctctgtt   4620
gtatcccggt gagggcagcc tctggcttgg acagggtctg tttggactgc agaaccaagg   4680
gggtgatgta gcccatcctt ccctttggag atgctgaggg tgtttcttcc tgcacccaca   4740
gccaggggga tgccactcct ccctccggct tgacctgttt ctctgccgct acctccctcc   4800
ccgtctcatt ccgttgtctg tggatggtca ttgcagttta agagcagaac agatctttta   4860 cttttggccgc ttgaaaagct agtgtacctc ctctcagtgt tttggactcc atctctcatc   4920
ctccagtacc ttgcttctta ctgataattt tgctggaatt cctaactttt caatgacatt   4980
ttttttaact atcatattga ttgtccttta aaaagaaaa gtgcatattt atccaaaatg   5040
tgtatttctt atacgctttt ctgtgttata ccatttcctc agcttatctc ttttatattt   5100
gtaggagaaa ctcccatgta tggaatccca ctgtatgatt tataaacaga caatatgtga   5160
gtgccttttg cagaagaggg tgtgtttgaa atcatcggag tcagccagga gctgtcacca   5220
aggaaacgct acctctctgt cccttgctgt atgctgatca tcgccagagg tgcttcaccc   5280
tgagttttgt tttgtattgt tttctgacag ttttttctgtt ttgtttggca aggaaagggg   5340
agaagggaat cctcctccag ggtgatttta tgatcagtgt tgttgctcta ggaagacatt   5400
tttccgtttg cttttgttcc aatgtcaatg tgaacgtcca catgaaacct acacactgtc   5460
atgcttcatc attccctctc atctcaggta gaaggttgac acagttgtag ggttacagag   5520
acctatgtaa gaattcagaa gacccctgac tcatcatttg tggcagtccc ttataattgg   5580
tgcatagcag atggtttcca catttagatc ctggtttcat aacttcctgt acttgaagtc   5640
taaaagcaga aaataaagga agcaagtttt cttccatgat tttaaattgt gatcgagttt   5700
taaattgata ggagggaaca tgtcctaatt cttctgtcct gagaagcatg taatgttaat   5760
gttatatcat atgtatatat atatatgcac tatgtatata catatatatt aatactggta   5820
tttttactta atctataaaa tgtcgttaaa aagttgtttg tttttttctt tttttataaa   5880
taaactgttg ctcgttaaaa aaaaaaaaa                                     5910
```

<210> SEQ ID NO 13
<211> LENGTH: 980
<212> TYPE: DNA
<213> ORGANISM: Homo sapiens

<400> SEQUENCE: 13

```
gcgcggggga gccattagga ggcgaggaga gaggagggcg cagctcccgc ccagcccagc      60
cctgcccagc cctgcccgga ggcagacgcg ccggaaccgg gacgcgataa atatgcagag     120
cggaggcttc gcgcagcaga gcccgcgcgc cgcccgctcc gggtgctgaa tccaggcgtg     180
gggacacgag ccaggcgccg ccgcggagc cagcggagcc ggggccagag ccggagcgcg      240
tccgcgtcca cgcagccgcc ggccggccag cacccagggc cctgcatgcc aggtcgttgg     300
aggtggcagc gagacatgca cccggcccgg aagctcctca gcctcctctt cctcatcctg     360
atgggcactg aactcactca aaataaaaga gaaaacaaag cagagaagat gggagggcca     420
gagagcgaga ggaagaccac aggagagaag acactgaacg agcttccctt gttttgcctg     480
gaagcccacg ctggctccct ggctctgccc aggatgtgca gtccaaatcc caatccagca     540
gtggggttat gtcgtcccgc ttaccctcag agcccttctc ctggtgctgc ccagacgatc     600
agccagtccc tcctggagag gttctgcatg gcctctagga gagaagtttt cttggcccca     660
ggaaggcctg tggagggtg tggttgtgc actgttgctg acagatgca ttcattcatg        720 tgcacacaca cacacacaca tgcacacaca ggggagcaga tacctgcaga gaagagccaa     780
ccaggtcctg attagtggca agctgcccca caaagggcta tgcctgtgtc ttattgagac     840
accttggcaa agagatggct gattctgggt ggtcctggac atggccgcac ccaagggccc     900
tccaagcctt aatggcaccc tgaagcctcc atgcccaggc caaaagatgc ttttcctccc     960
taaaaaaaaa aaaaaaaaa                                                  980

<210> SEQ ID NO 14
<211> LENGTH: 1721
<212> TYPE: DNA
<213> ORGANISM: Homo sapiens

<400> SEQUENCE: 14
caccagcaca gcaaacccgc cgggatcaaa gtgtaccagt cggcagcatg gctacgaaat      60
gtgggaattg tggacccggc tactccaccc ctctggaggc catgaaagga cccagggaag     120
agatcgtcta cctgccctgc atttaccgaa acacaggcac tgaggcccca gattatctgg     180
ccactgtgga tgttgacccc aagtctcccc agtattgcca ggtcatccac cggctgccca     240
tgcccaacct gaaggacgag ctgcatcact caggatggaa cacctgcagc agctgcttcg     300
gtgatagcac caagtcgcgc accaagctgg tgctgcccag tctcatctcc tctcgcatct     360
atgtggtgga cgtgggctct gagccccggg ccccaaagct gcacaaggtc attgagccca     420
aggacatcca tgccaagtgc gaactggcct ttctccacac cagccactgc ctggccagcg     480
gggaagtgat gatcagctcc ctgggagacg tcaagggcaa tggcaaaggg ggttttgtgc     540
tgctggatgg ggagacgttc gaggtgaagg ggacatggga gagacctggg ggtgctgcac     600
cgttgggcta tgacttctgg taccagcctc gacacaatgt catgatcagc actgagtggg     660
cagctcccaa tgtcttacga gatggcttca accccgctga tgtggaggct ggactgtacg     720
ggagccactt atatgtatgg gactggcagc gccatgagat tgtgcagacc ctgtctctaa     780
aagatgggct tattcccttg gagatccgct tcctgcacaa cccagacgct gcccaaggct     840
ttgtgggctg cgcactcagc tccaccatcc agcgcttcta caagaacgag ggaggtacat     900
ggtcagtgga gaaggtgatc caggtgcccc ccaagaaagt gaagggctgg ctgctgcccg     960
aaatgccagg cctgatcacc gacatcctgc tctccctgga cgaccgcttc ctctacttca    1020
gcaactggct gcatgggac ctgaggcagt atgacatctc tgacccacag agaccccgcc     1080
tcacaggaca gctcttcctc ggaggcagca ttgttaaggg aggccctgtg caagtgctgg    1140
```

| | |
|---|---|
| aggacgagga actaaagtcc cagccagagc ccctagtggt caagggaaaa cgggtggctg | 1200 |
| gaggccctca gatgatccag ctcagcctgg atgggaagcg cctctacatc accacgtcgc | 1260 |
| tgtacagtgc ctgggacaag cagttttacc ctgatctcat cagggaaggc tctgtgatgc | 1320 |
| tgcaggttga tgtagacaca gtaaaaggag ggctgaagtt gaaccccaac ttcctggtgg | 1380 |
| acttcgggaa ggagccccct tggcccagcc cttgcccatga gctccgctac cctgggggcg | 1440 |
| attgtagctc tgcatctggg atttgaactc caccctcatc acccacactc ctattttgg | 1500 |
| gccctcactt ccttggggac ctggcttcat tctgctctct cttggcaccc gaccctggc | 1560 |
| agcatgtacc acacagccaa gctgagactg tggcaatgtg ttgagtcata tacatttact | 1620 |
| gaccactgtt gcttgttgct cactgtgctg cttttccatg agctcttgga ggcaccaaga | 1680 |
| aataaactcg taaccctgtc cttcaaaaaa aaaaaaaaa a | 1721 |

<210> SEQ ID NO 15
<211> LENGTH: 2588
<212> TYPE: DNA
<213> ORGANISM: Homo sapiens

<400> SEQUENCE: 15

| | |
|---|---|
| ggcacgaggc tctctcctcc ctctttcttc gggcagcctc cccaccaccc cacttcagcc | 60 |
| tcccccactc ttgccgcctc catatcatca agctctggtg gcgcctgggg ggcttttcgg | 120 |
| atcggcagga tgtaccccca gggaaggcac ccgaccccgc tccagtccgg ccagccccttc | 180 |
| aagttctcga tcttggagat ctgcgaccgc atcaaagaag aattccagtt tcttcaggct | 240 |
| caataccaca gcctcaagct agaatgtgag aagctggcca gcgagaagac ggaaatgcag | 300 |
| cgacattatg tcatgtatta tgagatgtcg tacgggctca acattgaaat gcataagcag | 360 |
| gcggagattg tgaagcgtct gagcggtatc tgcgctcaga ttatcccctt cctgacccag | 420 |
| gagcatcagc agcaggtgct ccaggccgta gaacgcgcca gcaggtcac cgtgggggag | 480 |
| ctgaacagcc tcatcgggca gcagctccag ccgctgtccc accacgcacc ccctgtgccc | 540 |
| ctcaccccccc gcccagccgg gctggtgggc ggcagtgcta cggggctgct tgctctgtct | 600 |
| ggagccctgg ctgcccaggc tcagctggcg gcggctgtca aggaggaccg tgcgggcgtg | 660 |
| gaggccgagg ggtccagagt ggagagagcc ccgagcagga gtgcatctcc ctcgcccct | 720 |
| gagagtctcg tggaggagga cgaccgagt ggccctggtg gtggcgggaa gcagagagca | 780 |
| gatgagaagg agccatcagg accttatgaa agcgacgaag acaagagtga ttacaatctg | 840 |
| gtggtggacg aggaccaacc ctcagagccc ccagcccgg ctaccacccc ctgcggaaag | 900 |
| gtacccatct gcattcctgc ccgtcgggac ctggtggaca gtccagcctc cttggcctct | 960 |
| agccttggct caccgctgcc tagagccaag gagctcatcc tgaatgacct tcccgccagc | 1020 |
| actcctgcct ccaaatcctg tgactcctcc ccgccccagg acgcttccac ccccgggccc | 1080 |
| agctcggcca gtcacctctg ccagcttgct gccaagccag caccttccac ggacagcgtc | 1140 |
| gccctgagga gccccctgac tctgtccagt cccttcacca cgtccttcag cctgggctcc | 1200 |
| cacagcactc tcaacggaga cctctccgtg cccagctcct acgtcagcct ccacctgtcc | 1260 |
| ccccaggtca gcagctctgt ggtgtacgga cgctccccg tgatggcatt tgagtctcat | 1320 |
| ccccatctcc gagggtcatc cgtctcttcc tccctaccca gcatccctgg gggaaagccg | 1380 |
| gcctactcct tccacgtgtc tgcggacggg cagatgcagc cggttcccctt cccctcggat | 1440 |
| gcactggtag gcgcgggcat cccgcggcac gccggcagc tgcacacgct ggcccatggc | 1500 |
| gaggtggtct gcgcggtcac catcagcggc tccacacagc atgtgtacac gggcggcaag | 1560 |

| | |
|---|---|
| ggctgtgtga aggtgtggga cgtgggccag cctggggcca agacgcccgt ggcccagctc | 1620 |
| gactgcctga accgagacaa ctacattcgt tcctgcaagt tgctgccgga tggccggagt | 1680 |
| ctgatcgtgg gcggtgaggc cagcaccttg tccatttggg acctggcggc gcccaccccc | 1740 |
| cgtatcaagg ccgagctgac ttcctcagcc ccagcctgct acgccctggc cgtcagcccc | 1800 |
| gacgccaagg tttgcttctc ctgctgcagc gatggcaaca ttgtggtctg ggacctgcag | 1860 |
| aatcagacta tggtcaggca gttccagggc cacacgacg cgccagctg cattgatatt | 1920 |
| tccgattacg gcactcggct ctggacaggg ggcctggaca cacggtgcg ctgctgggac | 1980 |
| ctgcgggagg gccgccagct gcagcagcat gacttcagct cccagatttt ctccctgggc | 2040 |
| cactgcccta accaggactg gctggcggtc ggaatggaga gtagcaacgt ggagatcctg | 2100 |
| cacgtccgca agccggagaa ataccagctg cacctccacg agagctgcgt gctgtccctg | 2160 |
| aagtttgcct cctgcggacg gtggtttgtg agcaccggga aggacaacct gctcaacgcc | 2220 |
| tggaggacgc cgtacggggc cagcattttc cagtccaagg agtcgtcctc agtcctgagt | 2280 |
| tgtgacatct ccagaaataa caaatacatc gtgacaggct cggggacaa gaaggccacc | 2340 |
| gtgtatgagg tggtctactg agacatgacc ccccttcctg tacccgaagt ccagactccc | 2400 |
| aggggaatca gcagccagga cagacatcct agcagccgcc tcccagccct gcctaggaac | 2460 |
| cgtacatccc atctgctctc tggccaacgg cttcacacct tccccctgctg catgtggggg | 2520 |
| ccgatgggca ggggacctcg gtggaaataa aatgtatcta tcacatccgc aaaaaaaaaa | 2580 |
| aaaaaaaa | 2588 |

<210> SEQ ID NO 16
<211> LENGTH: 8133
<212> TYPE: DNA
<213> ORGANISM: Homo sapiens

<400> SEQUENCE: 16

| | |
|---|---|
| cgtccctgca gccctcgccc ggcgctccag tagcaggacc cggtctcggg accagccggt | 60 |
| aatatgcacg tgtcactagc tgaggccctg gaggttcggg gtggaccact tcaggaggaa | 120 |
| gaaatatggg ctgtattaaa tcaaagtgct gaaagtctcc aagaattatt cagaaaagta | 180 |
| agcctagctg atcctgctgc ccttggcttc atcatttctc catggtctct gctgttgctg | 240 |
| ccatctggta gtgtgtcatt tacagatgaa aatatttcca atcaggatct tcgagcattc | 300 |
| actgcaccag aggttcttca aaatcagtca ctaacttctc tctcagatgt tgaaagatc | 360 |
| cacatttatt ctcttggaat gacactgtat tgggggctg attatgaagt gcctcagagc | 420 |
| caacctatta gcttggaga tcatctcaac agcatactgc ttggaatgtg tgaggatgtt | 480 |
| atttacgctc gagtttctgt tcggactgtg ctggatgctt gcagtgccca cattaggaat | 540 |
| agcaattgtg caccctcatt ttcctacgtg aaacacttgg taaaactggt tctgggaaat | 600 |
| ctttctggga cagatcagct ttcctgtaac agtgaacaaa agcctgatcg aagccaggct | 660 |
| attcgagatc gattgcgagg aaaaggatta ccaacaggaa gaagctctac ttctgatgta | 720 |
| ctagacatac aaaagcctcc actctctcat cagacctttc ttaacaaagg gcttagtaaa | 780 |
| tctatgggat ttctgtccat caaagataca caagatgaga attatttcaa ggacattta | 840 |
| tcagataatt ctggacgtga agattctgaa aatacattct ccccttacca gttcaaaact | 900 |
| agtggcccag aaaaaaaacc catccctggc attgatgtgc tttctaagaa gaagatctgg | 960 |
| gcttcatcca tggacttgct ttgtacagct gacagagact tctcttcagg agagactgcc | 1020 |
| acatatcgtc gttgtcaccc tgaggcagta acagtgcgga cttcaactac tcctagaaaa | 1080 |

```
aaggaggcaa gatactcaga tggaagtata gccttggata tctttggccc tcagaaaatg    1140
gatccaatat atcacactcg agaattgccc acctcctcag caatatcaag tgctttggac    1200
cgaatccgag agagacaaaa gaaacttcag gttctgaggg aagccatgaa tgtagaagaa    1260
ccagttcgaa gatacaaaac ttatcatggt gatgtcttta gtacctccag tgaaagtcca    1320
tctattattt cctctgaatc agatttcaga caagtgagaa gaagtgaagc ctcaaagagg    1380
tttgaatcca gcagtggtct cccaggggta gatgaaacct taagtcaagg ccagtcacag    1440
agaccgagca gacaatatga aacacccttt gaaggcaact taattaatca agagatcatg    1500
ctaaaacggc aagaggaaga actgatgcag ctacaagcca aaatggccct tagacagtct    1560
cggttgagcc tatatccagg agacacaatc aaagcgtcca tgcttgacat caccagggat    1620
ccgttaagag aaaattgccc tagaaacagcc atgactcaaa gaaaactgag gaatttcttt    1680
ggccctgagt ttgtgaaaat gacaattgaa ccatttatat ctttggattt gccacggtct    1740
attcttacta agaaagggaa gaatgaggat aaccgaagga aagtaaacat aatgcttctg    1800
aacgggcaaa gactggaact gacctgtgat accaaaacta tatgtaaaga tgtgttttgat    1860 atggttgtgg cacatattgg cttagtagag catcatttgt ttgctttagc tacccctcaaa    1920 gataatgaat atttctttgt tgatcctgac ttaaaattaa ccaaagtggc cccagaggga    1980 tggaagaag aaccaagaa aaagaccaaa gccactgtta attttacttt gttttcaga    2040 attaaatttt ttatggatga tgttagtcta atacaacata ctctgacgtg tcatcagtat    2100
taccttcagc ttcgaaaaga tattttggag gaaaggatgc actgtgatga tgagacttcc    2160
ttattgctgg catccttggc tctccaggct gagtatggag attatcaacc agaggttcat    2220
ggtgtgtctt actttagaat ggagcactat ttgcccgcca gagtgatgga gaaacttgat    2280
ttatcctata tcaagaaga gttacccaaa ttgcataata cctatgtggg agcttctgaa    2340
aaagagacag agttagaatt tttaaaggtc tgccaaagac tgacagaata tggagttcat    2400
tttcaccgag tgcaccctga gaagaagtca caaacaggaa tattgcttgg agtctgttct    2460
aaaggtgtcc ttgtgtttga agttcacaat ggagtgcgca cattggtcct tcgctttcca    2520
tggagggaaa ccaagaaaat atcttttttct aaaaagaaaa tcacattgca aaatacatca    2580
gatggaataa acatggctt ccagacagac aacagtaaga tatgccagta cctgctgcac    2640
ctctgctctt accagcataa gttccagcta cagatgagag caagacagag caaccaagat    2700
gcccaagata ttgagagagc ttcgtttagg agcctgaatc tccaagcaga gtctgttaga    2760
ggatttaata tgggacgagc aatcagcact ggcagtctgg ccagcagcac cctcaacaaa    2820
cttgctgttc gacctttatc agttcaagct gagattctga agaggctatc ctgctcagag    2880
ctgtcgcttt accagccatt gcaaacagt tcaaaagaga agaatgacaa agcttcatgg    2940
gaggaaaagc ctagagagat gagtaaatca taccatgatc tcagtcaggc ctctctctat    3000
ccacatcgga aaaatgtcat tgttaacatg gaaccccac cacaaaccgt tgcagagttg    3060
gtgggaaaac cttctcacca gatgtcaaga tctgatgcag aatctttggc aggagtgaca    3120
aaacttaata attcaaagtc tgttgcgagt ttaaatagaa gtcctgaaag gaggaaaacat    3180 gaatcagact cctcatccat tgaagaccct gggcaagcat atgttctagg aatgactatg    3240
catagttctg gaaactcttc atcccaagta cccttaaaag aaaatgatgt gctacacaaa    3300
agatggagca tagtatcttc accagaaagg gagatcacct tagtgaacct gaaaaagat    3360 gcaaagtatg gctgggatt tcaaattatt ggtggggaga agatgggaag actgaccta    3420 ggcatattta tcagttcagt tgcccctgga ggaccagctg acttggatgg atgcttgaag    3480
```

```
ccaggagacc gtttgatatc tgtgaatagt gtgagtctgg agggagtcag ccaccatgct   3540
gcaattgaaa ttttgcaaaa tgcacctgaa gatgtgacac ttgttatctc tcagccaaaa   3600
gaaaagatat ccaaagtgcc ttctactcct gtgcatctca ccaatgagat gaaaaactac   3660
atgaagaaat cttcctacat gcaagacagt gctatagatt cttcttccaa ggatcaccac   3720
tggtcacgtg gtaccctgag gcacatctcg gagaactcct ttgggccgtc tggggcctg    3780 cgggaaggaa gcctgagttc tcaagattcc aggactgaga gtgccagctt gtctcaaagc   3840
caggtcaatg gtttctttgc cagccattta ggtgaccaaa cctggcagga atcacagcat   3900
ggcagccctt ccccatctgt aatatccaaa gccaccgaga agagactttt cactgatagt   3960
aaccaaagca aaactaaaaa gccaggcatt tctgatgtaa ctgattactc agaccgtgga   4020
gattcagaca tggatgaagc cacttactcc agcagtcagg atcatcaaac accaaaacag   4080
gaatcttcct cttcagtgaa tacatccaac aagatgaatt ttaaaacttt tcttcatca    4140 cctcctaagc ctggagatat cttTgaggtt gaactggcta aaaatgataa cagcttgggg   4200
ataagtgtca cggtactgtt tgacaaggga ggtgtgaata cgagtgtcag acatggtggc   4260
atttatgtga aagctgttat tccccaggga gcagcagagt ctgatggtag aattcacaaa   4320
ggtgatcgcg tcctagctgt caatggagtt agtctagaag gagccaccca taagcaagct   4380
gtggaaacac tgagaaatac aggacaggtg gttcatctgt tattagaaaa gggacaatct   4440
ccaacatcta agaacatgt cccggtaacc ccacagtgta cccttctcaga tcagaatgcc    4500 caaggtcaag gcccagaaaa agtgaagaaa acaactcagg tcaaagacta cagctttgtc   4560
actgaagaaa atacatttga ggtaaaatta tttaaaaata gctcaggtct aggattcagt   4620
ttttctcgag aagataatct tataccggag caaattaatg ccagcatagt aagggttaaa   4680
aagctctttc ctggacagcc agcagcagaa agtggaaaaa ttgatgtagg agatgttatc   4740
ttgaaagtga atggagcctc tttgaaagga ctatctcagc aggaagtcat atctgctctc   4800 agggaactg ctccagaagt attcttgctt ctctgcagac ctccacctgg tgtgctaccg    4860
gaaattgata ctgcgctttt gacccactt cagtctccag cacaagtact tccaaacagc    4920
agtaaagact cttctcagcc atcatgtgtg gagcaaagca ccagctcaga tgaaaatgaa   4980
atgtcagaca aaagcaaaaa acagtgcaag tccccatcca aagagacagt tacagtgac    5040 agcagtggga gtgagaagaa tgacttagtg acagctccag caaacatatc aaattcgacc   5100
tggagttcag ctttgcatca gactctaagc aacatggtat cacaggcaca gagtcatcat   5160
gaagcaccca gagtcaaga agataccatt tgtaccatgt tttactatcc tcagaaaatt    5220
cccaataaac cagagtttga ggacagtaat ccttccctc taccaccgga tatggctcct   5280
gggcagagtt atcaaccca tcagaatct gcttcctcta gttcgatgga taagtatcat    5340
atacatcaca tttctgaacc aactagacaa gaaaactgga cacctttgaa aaatgacttg   5400
gaaaatcacc ttgaagactt tgaactgaa gtagaactcc tcattaccct aattaaatca   5460
gaaaaaggaa gcctgggttt tacagtaacc aaaggcaatc agagaattgg ttgttatgtt   5520
catgatgtca tacaggatcc agccaaaagt gatggaaggc taaaacctgg ggaccggctc   5580
ataaaggtta atgatacaga tgttactaat atgactcata cagatgcagt taatctgctc   5640
cgggctgcat ccaaaacagt cagattagtt attggacgag ttctagaatt acccagaata   5700
ccaatgttgc ctcatttgct accggacata acactaacgt gcaacaaaga ggagttgggt   5760
ttttccttat gtgagggtca tgacagcctt tatcaagtgg tatatattag tgatattaat   5820
ccaaggtccg tcgcagccat tgagggtaat ctccagctat tagatgtcat ccattatgtg   5880
```

```
aacggagtca gcacacaagg aatgaccttg gaggaagtta acagagcatt agacatgtca   5940
cttccttcat tggtattgaa agcaacaaga aatgatcttc cagtggtccc cagctcaaag   6000
aggtctgctg tttcagctcc aaagtcaacc aaaggcaatg gttcctacag tgtggggtct   6060
tgcagccagc ctgccctcac tcctaatgat tcattctcca cggttgctgg ggaagaaata   6120
aatgaaatat cgtaccccaa aggaaaatgt tctacttatc agataaaggg atcaccaaac   6180
ttgactctgc ccaaagaatc ttatatacaa gaagatgaca tttatgatga ttcccaagaa   6240
gctgaagtta tccagtctct gctggatgtt gtggatgagg aagcccagaa tcttttaaac   6300
gaaaataatg cagcaggata ctcctgtggt ccaggtacat aaagatgaa tgggaagtta    6360
tcagaagaga gaacagaaga tacagactgc gatggttcac ctttacctga gtattttact   6420
gaggccacca aatgaatggg ctgtgaagaa tattgtgaag aaaaagtaaa aagtgaaagc   6480
ttaattcaga agccacaaga aaagaagact gatgatgatg aaataacatg gggaaatgat   6540
gagttgccaa tagagagaac aaaccatgaa gattctgata aagatcattc ctttctgaca   6600
aacgatgagc tcgctgtact ccctgtcgtc aaagtgcttc cctctggtaa atacacgggt   6660
gccaacttaa aatcagtcat tcgagtcctg cggggtttgc tagatcaagg aattccttct   6720
aaggagctgg agaatcttca agaattaaaa cctttggatc agtgtctaat tgggcaaact   6780
aaggaaaaca gaaggaagaa cagatataaa aatatacttc cctatgatgc tacaagagtg   6840
cctcttggag atgaaggtgg ctatatcaat gccagcttca ttaagatacc agttgggaaa   6900
gaagagttcg tttacattgc ctgccaagga ccactgccta caactgttgg agacttctgg   6960
cagatgattt gggagcaaaa atccacagtg atagccatga tgactcaaga agtagaagga   7020
gaaaaaatca aatgccagcg ctattggccc aacatcctag gcaaaacaac aatggtcagc   7080
aacagacttc gactggctct tgtgagaatg cagcagctga agggctttgt ggtgagggca   7140
atgaccettg aagatattca gaccagagag gtgcgccata tttctcatct gaatttcact   7200
gcctggccag accatgatac accttctcaa ccagatgatc tgcttacttt tatctcctac   7260
atgagacaca tccacagatc aggcccaatc attacgcact gcagtgctgg cattggacgt   7320
tcagggaccc tgatttgcat agatgtggtt ctgggattaa tcagtcagga tcttgatttt   7380
gacatctctg atttggtgcg ctgcatgaga ctacaaagac acggaatggt tcagacagag   7440
gatcaatata ttttctgcta tcaagtcatc ctttatgtcc tgacacgtct tcaagcagaa   7500
gaagagcaaa aacagcagcc tcagcttctg aagtgacatg aaaagagcct ctggatgcat   7560
ttccatttct ctccttaacc tccagcagac tcctgctctc tatccaaaat aagatcacag   7620
agcagcaagt tcatacaaca tgcatgttct cctctatctt agaggggtat tcttcttgaa   7680
aataaaaaat attgaaatgc tgtatttta cagctacttt aacctatgat aattatttac    7740
aaaattttaa cactaaccaa acaatgcaga tcttagggat gattaaaggc agcatttgat   7800
gatagcagac attgttacaa ggacatggtg agtctatttt taatgcacca atcttgttta   7860
tagcaaaaat gttttccaat attttaataa agtagttatt ttatagggga tacttgaaac   7920
cagtatttaa gctttaaatg acagtaatat tggcatagaa aaaagtagca aatgtttact   7980
gtatcaattt ctaatgttta ctatatagaa tttcctgtaa tatatttata actttttca    8040
tgaaaatgga gttatcagtt atctgtttgt tactgcatca tctgtttgta atcattatct   8100
cactttgtaa ataaaaacac accttaaaac atg                                8133
```

<210> SEQ ID NO 17
<211> LENGTH: 2272
<212> TYPE: DNA

<213> ORGANISM: Homo sapiens

<400> SEQUENCE: 17

```
aggcgcccgc cgccgcgcg tgattctcgc ctcgccgcag cccagccctg cgcgccttgc      60
ccggcggccc ccgcccggcc gctccgggcc cctggccccg cggagcgatg ctgctgctgg    120
ctgccgcctt cctcgtggcc ttcgtgctgc tgctgtacat ggtgtctccg ctcatcagcc    180
ccaagcccct cgcccgccc ggggcgcatg tggtggttac aggaggttcc agtggcatcg    240
ggaagtgcat tgctatcgag tgctataaac aaggagcttt tataactctg gttgcacgaa    300
atgaggataa gctgctgcag gcaaagaaag aaattgaaat gcactctatt aatgacaaac    360
aggtggtgct ttgcatatca gttgatgtat ctcaagacta taaccaagta gagaatgtca    420
taaaacaagc acaggagaaa ctgggtccag tggacatgct ggtaaattgt gcaggaatgg    480
cagtgtcagg aaaatttgaa gatcttgaag ttagtacctt gaaaggtta atgagcatca     540
attacctggg cagcgtgtac cccagccggg ccgtgatcac caccatgaag gagcgccggg    600
tgggcaggat cgtgtttgtg tcctcccagg caggacagtt gggattattc ggtttcacag    660
cctactctgc atccaagttt gccataaggg gattggcaga agctttgcag atggaggtga    720
agccatataa tgtctacatc acagttgctt acccaccaga cacagacaca cctggctttg    780
ccgaagaaaa cagaacaaag cctttggaga ctcgacttat ttcagagacc acatctgtgt    840
gcaaaccaga acaggtggcc aaacaaattg ttaaagatgc catacaagga aatttcaaca    900
gttcccttgg ctcagatggg tacatgctct cggccctgac ctgtgggatg gctccagtaa    960
cttctattac tgagggctc cagcaggtgg tcaccatggg ccttttccgc actattgctt   1020
tgttttacct tggaagtttt gacagcatag ttcgtcgctg catgatgcag agagaaaaat   1080
ctgaaaatgc agacaaaact gcctaatctt cttacccctt ggaagaagac tgtttccaaa   1140
taatttgaac agcttgctgc taaatgggac ccaattttg gcctatagac acttatgtat    1200
tgttttcgaa tacgtcagat tggaccagtg ctcttcagga atgtggctgc aagcaagggg   1260
ctagaagttc acctcctgac agtattatta atactatgca aatatggaat aggagaccat   1320
ttgattttct aggctttgtg gtagagaggt gaaggtatga gaattaatag cgtgtgaaca   1380
aagtaaagaa caggattcca gaatgatcat taaatttgtt tctatttatt cttttttgcc   1440
cccctagaga ttaagtccag aaatgtactt tctggcacat aaagaaatct tgaggacttt   1500
gtttaaacct tccataaaaa aacaatttc ggtttctcgg gttctctctc tctgtctctc    1560
tgtctctctg tctctctgtc tctctgtctc tctctctctc tctcttcctt tctttgtgta   1620
ttttattcaa gatgagttgg acccattgcc agtgagtctg aatgtcactg acagccctgt   1680
gttgtgctca ggactcactc tgctgctggt ggaaactcat ggcttctctc tctcttgat    1740
cccataaagc tacgagggg acgggagagg gcagtgcaat gggaagtaaa gagatatttt   1800
ccagtaggaa aagcaatgct ttcttgtctt tagactcaaa tgcttaggga acgtttcatt   1860
tctcattcat ggggaaaggc agcctcctta aatgttttct gaagagcggt aaaatctaga   1920
agcttaagaa tttacagttc cttcaataac catgatgacc tgaagttcac ctatcccatt   1980
ttagcatcta cttgtttttc ccatctcttc cttttccaatt ttgcttatac tgctgtaata  2040
tttttgtaaa aaaaaaaaa aaggaaaaaa aagaccagct aaaattttcg acttgacttt    2100
ttaacttaac tcatgaatta attaaagcaa atgaaaaaat taaaaagtgt gactttttct   2160
cggagcatat atgtagcttt taggaaaggc tgatgatggt ataagtttg ctcattaaga    2220
aaaaagaca aggctgattt tgaagagagt tgcttttgaa ataaaatgat ca             2272
```

<210> SEQ ID NO 18
<211> LENGTH: 1414
<212> TYPE: DNA
<213> ORGANISM: Homo sapiens

<400> SEQUENCE: 18

| | | | | | |
|---|---|---|---|---|---|
| gaattcgcac | tgctctgaga | atttgtgagc | agcccctaac | aggctgttac | ttcactacaa | 60 |
| ctgacgatat | gatcatctta | atttacttat | ttctcttgct | atgggaagac | actcaaggat | 120 |
| ggggattcaa | ggatggaatt | tttcataact | ccatatggct | tgaacgagca | gccggtgtgt | 180 |
| accacagaga | agcacggtct | ggcaaataca | agctcaccta | cgcagaagct | aaggcggtgt | 240 |
| gtgaatttga | aggcggccat | ctcgcaactt | acaagcagct | agaggcagcc | agaaaaattg | 300 |
| gatttcatgt | ctgtgctgct | ggatggatgg | ctaagggcag | agttggatac | cccattgtga | 360 |
| agccagggcc | caactgatga | tttggaaaaa | ctggcattat | tgattatgga | atccgtctca | 420 |
| ataggagtga | agatgggat | gcctattgct | acaacccaca | cgcaaaggag | tgtggtggcg | 480 |
| tctttacaga | tccaaagcga | atttttaaat | ctccaggctt | cccaaatgag | tacgaagata | 540 |
| accaaatctg | ctactggcac | attagactca | agtatggtca | gcgtattcac | ctgagttttt | 600 |
| tagattttga | ccttgaagat | gacccaggtt | gcttggctga | ttatgttgaa | atatatgaca | 660 |
| gttacgatga | tgtccatggc | tttgtgggaa | gatactgtgg | agatgagctt | ccagatgaca | 720 |
| tcatcagtac | aggaaatgtc | atgaccttga | agtttctaag | tgatgcttca | gtgacagctg | 780 |
| gaggtttcca | aatcaaatat | gttgcaatgg | atcctgtatc | caaatccagt | caaggaaaaa | 840 |
| atacaagtac | tacttctact | ggaaatataa | acttttgc | tggaagattt | agccacttat | 900 |
| aaaaaaaaaa | aaggatgatc | aaaacacaca | gtgtttatgt | tggaatcttt | tggaactcct | 960 |
| ttgatctcac | tgttattatt | aacatttatt | tattattttt | ctaaatgtga | aagaaataca | 1020 |
| taatttaggg | aaaattggaa | aatataggaa | actttaaacg | agaaaatgaa | acctctcata | 1080 |
| atcccactgc | atagaaataa | caagcgttaa | catttcata | tttttttctt | tcagtcattt | 1140 |
| ttgtatttgt | ggtatatgta | tatatgtacc | tatatgtatt | tgcatttgaa | attttggaat | 1200 |
| cctgctctat | gtacagtttt | gtattatact | ttttaaatct | tgaactttat | gaacattttc | 1260 |
| tgaaatcatt | gattattcta | caaaaacatg | attttaaaca | gctgtaaaat | attctatgat | 1320 |
| atgaatgttt | tatgcattat | ttaagcctgt | ctctattgtt | ggaatttcag | gtcattttca | 1380 |
| taaatattgt | tgcaataaat | atccttcgga | attc | | | 1414 |

<210> SEQ ID NO 19
<211> LENGTH: 2704
<212> TYPE: DNA
<213> ORGANISM: Homo sapiens

<400> SEQUENCE: 19

| | | | | | |
|---|---|---|---|---|---|
| gggagaaacg | ttctcactcg | ctctctgctc | gctgcgggcg | ctccccgccc | tctgctgcca | 60 |
| gaaccttggg | gatgtgccta | gacccggcgc | agcacacgtc | cgggccaacc | gcgagcagaa | 120 |
| caaaccttg | gcgggcggcc | aggaggctcc | ctcccagcca | ccgcccccct | ccagcgcctt | 180 |
| tttttccccc | catacaatac | aagatcttcc | ttcctcagtt | cccttaaagc | acagcccagg | 240 |
| gaaacctcct | cacagttttc | atccagccac | gggccagcat | gtctggggc | aaatacgtag | 300 |
| actcggaggg | acatctctac | accgttccca | tccgggaaca | gggcaacatc | tacaagccca | 360 |
| acaacaaggc | catggcagac | gagctgagcg | agaagcaagt | gtacgacgcg | cacaccaagg | 420 |
| agatcgacct | ggtcaaccgc | gaccctaaac | acctcaacga | tgacgtggtc | aagattgact | 480 |

```
ttgaagatgt gattgcagaa ccagaaggga cacacagttt tgacggcatt tggaaggcca    540
gcttcaccac cttcactgtg acgaaatact ggttttaccg cttgctgtct gccctctttg    600
gcatcccgat ggcactcatc tggggcattt acttcgccat tctctctttc ctgcacatct    660
gggcagttgt accatgcatt aagagcttcc tgattgagat tcagtgcatc agccgtgtct    720
attccatcta cgtccacacc gtctgtgacc cactctttga agctgttggg aaaatattca    780
gcaatgtccg catcaacttg cagaaagaaa tataaatgac atttcaagga tagaagtata    840
cctgattttt tttcctttta attttcctgg tgccaatttc aagttccaag ttgctaatac    900
agcaacaatt tatgaattga attatcttgg ttgaaaataa aaagatcact ttctcagttt    960
tcataagtat tatgtctctt ctgagctatt tcatctattt ttggcagtct gaattttaa    1020 aacccattta aattttttc cttaccttt tatttgcatg tggatcaacc atcgctttat    1080
tggctgagat atgaacatat tgttgaaagg taatttgaga gaaatatgaa gaactgagga    1140
ggaaaaaaaa aaaaagaaa agaaccaaca acctcaactg cctactccaa aatgttggtc    1200
attttatgtt aagggaagaa ttccagggta tggccatgga gtgtacaagt atgtgggcag    1260
attttcagca aactcttttc ccactgttta aggagttagt ggattactgc cattcacttc    1320
ataatccagt aggatccagt gatccttaca agttagaaaa cataatcttc tgccttctca    1380
tgatccaact aatgccttac tcttcttgaa attttaacct atgatatttt ctgtgcctga    1440
atatttgtta tgtagataac aagacctcag tgccttcctg ttttttcacat tttccttttc    1500 aaatagggtc taactcagca actcgcttta ggtcagcagc ctccctgaag accaaaatta    1560
gaatatccat gacctagttt tccatgcgtg tttctgactc tgagctacag agtctggtga    1620
agctcacttc tgggcttcat ctggcaacat ctttatccgt agtgggtatg gttgacacta    1680
gcccaatgaa atgaattaaa gtggaccaat agggctgagc tctctgtggg ctggcagtcc    1740
tggaagccag cttttccctgc ctctcatcaa ctgaatgagg tcagcatgtc tattcagctt    1800
cgtttatttt caagaataat cacgctttcc tgaatccaaa ctaatccatc accggggtgg    1860
tttagtggct caacattgtg ttcccatttc agctgatcag tgggcctcca aggaggggct    1920
gtaaaatgga ggccattgtg tgagcctatc agagttgctg caaacctgac ccctgctcag    1980
taaagcactt gcaaccgtct gttatgctgt gacacatggc ccctccccct gccaggagct    2040
ttggacctaa tccaagcatc cctttgccca gaaagaagat gggggaggag gcagtaataa    2100
aaagattgaa gtattttgct ggaataagtt caaattcttc tgaactcaaa ctgaggaatt    2160
tcacctgtaa acctgagtcg tacagaaagc tgcctggtat atccaaaagc ttttattcc    2220 tcctgctcat attgtgattc tgcctttggg gacttttctt aaaccttcag ttatgatttt    2280 ttttcatac acttattgga actctgcttg attttgcct cttccagtct tcctgacact    2340
ttaattacca acctgttacc tactttgact ttttgcattt aaaacagaca ctggcatgga    2400 tatagttta cttttaaact gtgtacataa ctgaaaatgt gctatactgc atactttta    2460 aatgtaaaga tatttttatc tttatatgaa gaaaatcact taggaaatgg ctttgtgatt    2520
caatctgtaa actgtgtatt ccaagacatg tctgttctac atagatgctt agtccctcat    2580
gcaaatcaat tactggtcca aaagattgct gaaatttat atgcttactg atatatttta    2640
caatttttta tcatgcatgt cctgtaaagg ttacaagcct gcacaataaa aatgtttaac    2700
ggtt                                                                 2704
```

<210> SEQ ID NO 20
<211> LENGTH: 1440
<212> TYPE: DNA

<213> ORGANISM: Homo sapiens

<400> SEQUENCE: 20

```
cgggcgcaga agcccctcct cggcgtcctg gtcccggccg tgcccgcggt gtcccgggag      60
gaaggggcgg gccggggtc gggaggagtc acgtgccccc tcccgcccca ggtcgtcctc     120
tcagcatggg ggtcccgcgg cctcagccct gggcgctggg gctcctgctc tttctccttc     180
ctgggagcct gggcgcagaa agccacctct ccctcctgta ccaccttacc gcggtgtcct     240
cgcctgcccc ggggactcct gccttctggg tgtccggctg gctgggcccg cagcagtacc     300
tgagctacaa tagcctgcgg ggcgaggcgg agccctgtgg agcttgggtc tgggaaaacc     360
aggtgtcctg gtattgggag aaagagacca cagatctgag gatcaaggag aagctctttc     420
tggaagcttt caaagctttg gggggaaaag gtccctacac tctgcagggc ctgctgggct     480
gtgaactggg ccctgacaac acctcggtgc ccaccgccaa gttcgccctg aacggcgagg     540
agttcatgaa tttcgacctc aagcaggca cctggggtgg ggactggccc gaggccctgg     600
ctatcagtca gcggtggcag cagcaggaca aggcggccaa caaggagctc accttcctgc     660
tattctcctg cccgcaccgc ctgcgggagc acctggagag gggccgcgga aacctggagt     720
ggaaggagcc cccctccatg cgcctgaagg cccgacccag cagccctggc ttttccgtgc     780
ttacctgcag cgccttctcc ttctaccctc cggagctgca acttcggttc ctgcggaatg     840
ggctggccgc tggcaccggc cagggtgact tcggccccaa cagtgacgga tccttccacg     900
cctcgtcgtc actaacagtc aaaagtggcg atgagcacca ctactgctgc attgtgcagc     960
acgcggggct ggcgcagccc ctcagggtgg agctggaatc tccagccaag tcctccgtgc    1020
tcgtggtggg aatcgtcatc ggtgtcttgc tactcacggc agcggctgta ggaggagctc    1080
tgttgtggag aaggatgagg agtgggctgc cagcccctg gatctcccct cgtggagacg    1140
acaccggggt cctcctgccc accccagggg aggcccagga tgctgatttg aaggatgtaa    1200
atgtgattcc agccaccgcc tgaccatccg ccattccgac tgctaaaagc gaatgtagtc    1260
aggcccttt catgctgtga gacctcctgg aacactggca tctctgagcc tccagaaggg    1320
gttctgggcc tagttgtcct ccctctggag ccccgtcctg tggtctgcct cagtttcccc    1380
tcctaataca tatggctgtt ttccacctcg ataatataac acgagtttgg gcccgaaaaa    1440
```

<210> SEQ ID NO 21
<211> LENGTH: 1634
<212> TYPE: DNA
<213> ORGANISM: Homo sapiens

<400> SEQUENCE: 21

```
ccctaagtga gaggaccaac agttccgaca gcgagcgctc cccagatctg ggccacagca      60
cgcagattcc aagaaaggtg gtgtatgacc agctcaatca gatcctggtg tcagatgcag     120
ccctcccaga aaatgtcatt ctggtgaaca ccactgactg gcaggccag tatgtggctg     180
agctgctcca ggaccagcgg aagcctgtgg tgtgcacctg ctccaccgtg gaggtccagg     240
ccgtgctgtc cgcccctgctc acccggatcc agcgctactg caactgcaac tcttccatgc     300
cgaggccagt gaaggtggct gctgtgggag gccagagcta cctgagctcc atcctcaggt     360
tctttgtcaa gtccctggcc aacatgacct ccgactggct tggctacatg cgcttcctca     420
tcatccccct cggttctcac cctgtggcca aatacttggg gtcagtcgac agtaaataca     480
gtagttcctt cctggattct ggttggagag atcgttcag tcgctcggag ccaccagtgt     540
cagagcaact ggacgtggca gggcgggtga tgcagtacgt caacggggca gccacgacac     600
```

```
accagcttcc cgtggccgaa gccatgctga cttgccggca taagttccct gatgaagact    660
cctatcagaa gtttattccc ttcattggcg tggtgaaggt gggtctggtt gaagactctc    720
cctccacagc aggcgatggg gacgattctc ctgtggtcag ccttactgtg ccctccacat    780
caccaccctc cagctcgggc ctgagccgag acgccacggc cacccctccc tcctccccat    840
ctatgagcag cgccctggcc atcgtgggga ccctaatag cccatatggg gacgtgattg     900
gcctccaggt ggactactgg ctgggccacc cggggagcg gaggagggaa ggcgacaaga     960
gggacgccag ctcgaagaac accctcaaga gtgtcttccg ctcagtgcag gtgtcccgcc   1020
tgccccatag tggggaggcc cagctttctg caccatggc catgactgtg gtcaccaaag    1080
aaaagaacaa gaaagttccc accatcttcc tgagcaagaa accccgagaa aaggaggtgg   1140
attctaagag ccaggtcatt gaaggcatca gccgcctcat ctgttcttcc ccctccttag   1200
gccccagcct gggcccagac ccatcctccc agccaggttt cctccagca ggctccttcc    1260 ctccctgtca cctccctctc accaaccccgg ggtctgagcc cctcattcct gaccgtccgt  1320
gttctcagga gtggttgagg acacagggcc ccagcccagc cctctgcacc cccagcccg    1380 gccatctgcg ccccacagcc ctttggagc ttttctcttg tcctctcact ccttcccaga    1440 agttttttgca cagaacttca ttttgaaagt gttttttctca ttctccatac ctcccccaag  1500
ctctcctcca gccttccca gggctcagcc ctgctgtcct gagcgtctcc tgggccagag    1560
agaggagatg ggggtgggag ggactgagtt gatgttgggt ttttcattca ataaattggt   1620
gatttcttac cgac                                                     1634

<210> SEQ ID NO 22
<211> LENGTH: 1264
<212> TYPE: DNA
<213> ORGANISM: Homo sapiens

<400> SEQUENCE: 22
ggcacgaggg gaggccgggg cggggcgggc gcagccggcg ctgagcttgc agggccgctc     60
ccctcacccg cccccttcga gtccccgggc ttcgccccac ccggcccgtg ggggagtatc    120
tgtcctgccg ccttcgccca cgccctgcac tccgggaccg tccctgcgcg ctctgggcgc    180
accatggccc gcggggctgc gctggcgctg ctgctcttcg gcctgctggg tgttctggtc    240
gccgccccgg atggtggttt cgatttatcc gatgcccttc ctgacaatga aaacaagaaa    300
cccactgcaa tccccaagaa acccagtgct ggggatgact ttgacttagg agatgctgtt    360
gttgatggag aaaatgacga cccacgacca ccgaacccac ccaaaccgat gccaaatcca    420
aaccccaacc accctagttc ctccggtagc ttttcagatg ctgaccttgc ggatggcgtt    480
tcaggtggaa aggaaaaagg aggcagtgat ggtggaggca gccacaggaa agaaggggaa    540
gaggccgacg ccccaggcgt gatccccggg attgtggggg ctgtcgtggt cgccgtggct    600
ggagccatct ctagcttcat tgcttaccag aaaaagaagc tatgcttcaa agaaaatgca    660
gaacaagggg aggtggacat ggagagccac cggaatgcca acgcagagcc agctgttcag    720
cgtactcttt tagagaaata gaagattgtc ggcagaaaca gcccaggcgt tggcagcagg    780
gttagaacag ctgcctgagg ctcctccctg aaggacacct gcctgagagc agagatggag    840
gccttctgtt cacggcggat tctttgtttt aatcttgcga tgtgctttgc ttgttgctgg    900
gcggatgatg tttactaacg atgaattta catccaaagg gggataggca cttggacccc    960
cattctccaa ggcccggggg ggcggttccc catgggatgt gaaaggctgg ccattattaa   1020
gtccctgtaa ctcaaatgtc aaccccaccg aggcaccccc ccgtccccca gaatcttggc   1080
```

```
tgtttacaaa tcacgtgtcc atcgagcacg tctgaaaccc ctggtagccc cgacttcttt    1140
ttaattaaaa taaggtaagc ccttcaattt gtttcttcaa tatttctttc atttgtaggg    1200
atatttgttt ttcatatcag actaataaaa agaaattaga aaccaaaaaa aaaaaaaaaa    1260
aaaa                                                                 1264

<210> SEQ ID NO 23
<211> LENGTH: 1567
<212> TYPE: DNA
<213> ORGANISM: Homo sapiens

<400> SEQUENCE: 23
tcctgggcct ctcaaagtct gagccccgct ccgctgatgc ctgtctgcag aatccgcacc      60
aaccagcacc atgcccatga ctctggggta ctgggacatc cgtgggctgg cccacgccat    120
ccgcttgctc ctggaataca cagactcaag ctatgtggaa aagaagtaca cgctggggga    180
cgctcctgac tatgcagaa gccagtggct gaatgaaaaa ttcaagctgg gcctggactt    240
tcccaatctg ccctacttga ttgatggggc tcacaagatc acccagagca atgccatcct    300
gcgctacatt gcccgcaagc acaacctgtg tggggagaca gaagaggaga agattcgtgt    360
ggacattttg gagaaccagg ttatggataa ccacatggag ctggtcagac tgtgctatga    420
cccagatttt gagaaactga agccaaaata cttggaggaa ctccctgaaa agctaaagct    480
ctactcagag tttctgggga agcggccatg gtttgcagga gacaagatca cctttgtgga    540
tttccttgcc tatgatgtcc ttgacatgaa gcgtatattt gagcccaagt gcttggacgc    600
cttcctaaac ttgaaggact tcatctcccg ctttgagggt ttgaagaaga tctctgccta    660
catgaagtcc agccaattcc tccgaggtct tttgtttgga aagtcagcta catggaacag    720
caaatagggc ccagtgatgc cagaagatgg gagggaggag ccaaccttgc tgcctgcgac    780
cctggaggac agcctgactc cctgacctg ccttcttcct ttttccttct ttctactctc    840
ttctcttccc caaggcctca ttggcttcct ttcttctaac atcatccctc cccgcatcga    900
ggctctttaa agcttcagct ccccactgtc ctccatcaaa gtcccctcc taacgtcttc    960 cttttccctgc actaacgcca acctgactgc ttttcctgtc agtgcttttc tcttctttga   1020
gaagccagac tgatctctga gctccctagc actgtcctca aagaccatct gtatgccctg   1080
ctccctttgc tgggtcccta ccccagctcc gtgtgatgcc cagtaaagcc tgaaccatgc   1140
ctgccatgtc ttgtcttatt ccctgaggct cccttgactc aggactgtgc tcgaattgtg   1200
ggtggttttt tgtcttctgt tgtccacagc cagagcttag tggatgggtg tgtgtgtgtg   1260
tgtgttgggg gtggtgatca ggcaggttca taaatttcct tggtcatttc tgccctctag   1320
ccacatccct ctgttcctca ctgtggggat tactacagaa aggtgctctg tgccaagttc   1380
ctcactcatt cgcgctcctg taggccgtct agaactggca tggttcaaag aggggctagg   1440
ctgatgggga aggggctga gcagctccca ggcagactgc cttctttcac cctgtcctga   1500
tagacttccc tgatctagat atccttcgtc atgacacttc tcaataaaac gtatcccacc   1560
gtattgt                                                             1567

<210> SEQ ID NO 24
<211> LENGTH: 900
<212> TYPE: DNA
<213> ORGANISM: Homo sapiens

<400> SEQUENCE: 24
ggcacgagcg tgcgtgctgg cgtgcgttca ctttcagcct ggtgtggggc ttgtaaacat      60
```

| | |
|---|---|
| ataacataaa aatggcttcc aaaagagctc tggtcatcct ggctaaagga gcagaggaaa | 120 |
| tggagacggt catccctgta gatgtcatga ggcgagctgg gattaaggtc accgttgcag | 180 |
| gcctggctgg aaaagaccca gtacagtgta gccgtgatgt ggtcatttgt cctgatgcca | 240 |
| gccttgaaga tgcaaaaaaa gagggaccat atgatgtggg ggttctacca ggaggtaatc | 300 |
| tgggcgcaca gaatttatct gagtctgctg ctgtgaagga gatactgaag gagcaggaaa | 360 |
| accggaaggg cctgatagcc gccatctgtg caggtcctac tgctctgttg gctcatgaaa | 420 |
| taggttttgg aagtaaagtt acaacacacc ctcttgctaa agacaaaatg atgaatggag | 480 |
| gtcattacac ctactctgag aatcgtgtgg aaaaagacgg cctgattctt acaagccggg | 540 |
| ggcctgggac cagcttcgag tttgcgcttg caattgttga gccctgaat ggcaaggagg | 600 |
| tggcggctca agtgaaggct ccacttgttc ttaaagacta gagcagcgaa ctgcgacgat | 660 |
| cacttagaga acaggccgt taggaatcca ttctcactgt gttcgctcta aacaaaacag | 720 |
| tggtaggtta atgtgttcag aagtcgctgt ccttactact tttgcggaag tatggaagtc | 780 |
| acaactacac agagatttct cagcctacaa attgtgtcta tacatttcta agccttgttt | 840 |
| gcagaataaa cagggcattt agcaaaaaaa aaaaaaaaaa aaaaaaaaaa aaaaaaaaaa | 900 |

<210> SEQ ID NO 25
<211> LENGTH: 647
<212> TYPE: DNA
<213> ORGANISM: Homo sapiens

<400> SEQUENCE: 25

| | |
|---|---|
| gctcactgag caccgtccca gcatccggac accacagcgg cccttcgctc cacgcagaaa | 60 |
| accacacttc tcatacccttc actcaacact tccttcccca agccagaag atgcacaagg | 120 |
| aggaacatga ggtggctgtg ctgggggcac cccccagcac catccttcca aggtccaccg | 180 |
| tgattaacat ccacagcgag acctccgtgc ccgaccatgt cgtctggtcc ctgttcaaca | 240 |
| ccctcttctt gaactggtgc tgtctgggct tcatagcatt cgcctactcc gtaaagtcta | 300 |
| gggacaggaa gatggttggc gacgtgaccg ggcccaggc ctatgcctcc accgccaagt | 360 |
| gcctgaacat ctgggccctg attctgggca tcctcatgac cattggattc atcctgttac | 420 |
| tggtattcgg ctctgtaaca gtctaccata ttatgttaca gataatacag gaaaaacggg | 480 |
| gttactagta gccgcccata gcctgcaacc tttgcactcc actgtgcaat gctggccctg | 540 |
| cacgctgggg ctgttgcccc tgccccttg gtcctgcccc tagatacagc agtttatacc | 600 |
| cacacacctg tctacagtgt cattcaataa agtgcacgtg cttgtga | 647 |

<210> SEQ ID NO 26
<211> LENGTH: 2850
<212> TYPE: DNA
<213> ORGANISM: Homo sapiens

<400> SEQUENCE: 26

| | |
|---|---|
| aaaagaccag gtaattttaa catttgtgga atcacaaatg taaattcata agaagctcta | 60 |
| attaaaaaaa aaagtctga agtatatgag cataacaact taggagtgtg tctacatact | 120 |
| taacttttga agttttttgg caactttata acttttttt aaatttacaa gtctacttaa | 180 |
| agacttctta taccccaaat gattaagtta attttagagg tcacctttct cacagcagtg | 240 |
| tcacttgaaa tttagtaggg aaggatattg cagtattttt cagtttcctt agcacagcac | 300 |
| cacagaaagc agcttattcc ttttgagtgg cagacactcg acggtgcctg ccaactttc | 360 |
| ctcctgagtg gcaagcagat gagtctcagt aattcatact gaaccaaaat gccacataca | 420 |

| | |
|---|---|
| ctaggggcag tcagaaactg gctgagaaat ccccgcctc attcgcccct ctgctcccag | 480 |
| gaactagagt ccagttaaag cccctatgcg aaaggccgaa ttccacccca gggtttgtta | 540 |
| taacagtggc cagtctgaac cccatttgct cgtgctcaaa acttgattcc cacttgaaag | 600 |
| ccttccgggc gcgctgcctc gttgccccgc ccctttggca ggagagaggc agtgggcgag | 660 |
| gccgggctgg ggccccgcct cccactcacc tgccggtgcc tgaaattatg tgcggccccg | 720 |
| cgggctgctt tccgaggtca gagtgccctg ctgctgtctc agaggcatct gttctgcaaa | 780 |
| tcttaggaag aaaaatgtcc ctagtagcaa acgggtgtct tctgtgcata aataagtaca | 840 |
| acacaattct ccgaaagttc gggtaaaaag agatgcggta gcagctgccc tgtgtgaagc | 900 |
| tgtctacccc gcatctctca ggcgctaagc tcagtttttg tttttgtttt tgttttttta | 960 |
| aagaaaagat gtataattgc aggaattttt tttattttt ttattttcca tcattctata | 1020 |
| tatgtgatgg tgaaagatat gcctggaaaa gttttgtttt gaaagtttta ttttctgctt | 1080 |
| cgtcttcagt tggcaaaagc tctcaattct ttagcttcca gtttcttttc tctcttttc | 1140 |
| tttgttaggt aattaaaggt atgtaaacaa attatctcat gtagcagggg attttcatgt | 1200 |
| tgagaggaat cttccgtgtg agttgtttgg tcacacaaat aaccctttct caattttagg | 1260 |
| agtttggatt gtcaaatgta ggttttctc aaaggggca tataactaca tattgactgc | 1320 |
| caagaactat gactgtagca ctaatcagca cacatagagc cacacaatta tttaatttct | 1380 |
| aactctctgt ggtccctaga aaaattccgt tgatgtgctt aggttaaagt tctgaagata | 1440 |
| cccgttgtac ccttacttga agttttctaa tcttaagttt tatgaaatgc aataatatgt | 1500 |
| atcagctagc aatatttctg tgatcaccaa caactctcag tttgatctta aagtctgaat | 1560 |
| aataaaacaa atcccagcag taatacattt cttaaacctc acagtgcatg atatatcttt | 1620 |
| tcattctgat cctgtgtttg caaaaatata cacatgtata tcatagttcc tcactttta | 1680 |
| ttcatttgtt ttcctattac ctgtagtaaa tatattagtt agtacatgga atttatagca | 1740 |
| tcagctaccc ccaggaacag cacctgacag gcggggatt ttttttcaag ttgttctaca | 1800 |
| tttgcataaa ttatttctat tattattcat gtatgttatt tatttctgaa tcacactagt | 1860 |
| cctgtgaaag tacaactgaa ggcagaaagt gttaggattt tgcatctaat gttcattatc | 1920 |
| atggtattga tggacctaag aaaataaaaa ttagactaag cccccaaata agctgcatgc | 1980 |
| atttgtaaca tgattagtag atttgaatat atagatgtag tattttgggt atctaggtgt | 2040 |
| tttatcatta tgtaaaggaa ttaaagtaaa ggactttgta gttgttttta ttaaatatgc | 2100 |
| atatagtaga gtgcaaaaat atagcaaaaa taaaaactaa aggtagaaaa gcattttaga | 2160 |
| tatgccttaa tttagaaact gtgccaggtg gccctcggaa tagatgccag gcagagacca | 2220 |
| gtgcctgggt ggtgcctcct cttgtctgcc ctcatgaaga agcttccctc acgtgatgta | 2280 |
| gtgccctcgt aggtgtcatg tggagtagtg ggaacaggca gtactgttga gaggagagca | 2340 |
| gtgtgagagt ttttctgtag aagcagaact gtcagcttgt gccttgaggc ttccagaacg | 2400 |
| tgtcagatgg agaagtccaa gtttccatgc ttcaggcaac ttagctgtgt acagaagcaa | 2460 |
| tccagtgtgg taataaaaag caaggattgc ctgtataatt tattataaaa taaaagggat | 2520 |
| tttaacaacc aacaattccc aacacctcaa aagcttgttg cattttttgg tatttgaggt | 2580 |
| ttttatctga aggttaaagg gcaagtgttt ggtatagaag agcagtatgt gttaagaaaa | 2640 |
| gaaaaatatt ggttcgcgta gagtgcaaat tagaactaga aagttttata cgattatcat | 2700 |
| tttgagatgt gttaaagtag gttttcactg taaaatgtat tagtgtttct gcattgccat | 2760 |
| agggcctggt taaaacttc tcttaggttt caggaagact gtcacataca gtaagctttt | 2820 |

```
ttccttctga cttataatag aaaatgtttt                                       2850
```

<210> SEQ ID NO 27
<211> LENGTH: 3579
<212> TYPE: DNA
<213> ORGANISM: Homo sapiens

<400> SEQUENCE: 27

```
agtttcctcg gcagcggtag gcgagagcac gcggaggagc gtgcgcgggg gccccgggag        60
acggcggcgg tggcggcgcg ggcagagcaa ggacgcggcg gatcccactc gcacagcagc       120
gcactcggtg ccccgcgcag ggtcgcgatg ctgcccggtt tggcactgct cctgctggcc       180
gcctggacgg ctcgggcgct ggaggtaccc actgatggta atgctggcct gctggctgaa       240
ccccagattg ccatgttctg tggcagactg aacatgcaca tgaatgtcca gaatgggaag       300
tgggattcag atccatcagg gaccaaaacc tgcattgata ccaaggaagg catcctgcag       360
tattgccaag aagtctaccc tgaactgcag atcaccaatg tggtagaagc caaccaacca       420
gtgaccatcc agaactggtg caagcggggc cgcaagcagt gcaagaccca tccccacttt       480
gtgattccct accgctgctt agttggtgag tttgtaagtg atgcccttct cgttcctgac       540
aagtgcaaat tcttacacca ggagaggatg gatgtttgcg aaactcatct tcactggcac       600
accgtcgcca agagacatg cagtgagaag agtaccaact gcatgactac ggcatgttg        660
ctgccctgcg gaattgacaa gttccgaggg gtagagtttg tgtgttgccc actggctgaa       720
gaaagtgaca atgtggattc tgctgatgcg gaggaggatg actcggatgt ctggtggggc       780
ggagcagaca cagactatgc agatgggagt gaagacaaag tagtagaagt agcagaggag       840
gaagaagtgg ctgaggtgga agaagaagaa gccgatgatg acgaggacga tgaggatggt       900
gatgaggtag aggaagaggc tgaggaaccc tacgaagaag ccacagagag aaccaccagc       960
attgccacca ccaccaccac caccacagag tctgtggaag aggtggttcg agaggtgtgc      1020
tctgaacaag ccgagacggg gccgtgccga gcaatgatct cccgctggta ctttgatgtg      1080
actgaaggga gtgtgccccc attcttttac ggcggatgtg gcggcaaccg gaacaacttt      1140
gacacagaag agtactgcat ggccgtgtgt ggcagcgcca tgtcccaaag tttactcaag      1200
actacccagg aacctcttgc ccgagatcct gttaaacttc ctacaacagc agccagtacc      1260
cctgatgccg ttgacaagta tctcgagaca cctgggatg agaatgaaca tgcccatttc      1320
cagaaagcca agagaggct tgaggccaag caccgagaga aatgtccca ggtcatgaga      1380
gaatgggaag aggcagaacg tcaagcaaag aacttgccta aagctgataa gaaggcagtt      1440
atccagcatt tccaggagaa agtggaatct ttggaacagg aagcagccaa cgagagacag      1500
cagctggtgg agacacacat ggccagagtg gaagccatgc tcaatgaccg ccgccgcctg      1560
gccctggaga actacatcac cgctctgcag gctgttcctc ctcggcctcg tcacgtgttc      1620
aatatgctaa agaagtatgt ccgcgcagaa cagaaggaca gcagcacac cctaaagcat      1680
ttcgagcatg tgcgcatggt ggatcccaag aaagccgctc agatccggtc ccaggttatg      1740
acacacctcc gtgtgattta tgagcgcatg aatcagtctc tctcccctgct ctacaacgtg      1800
cctgcagtgg ccgaggagat tcaggatgaa gttgatgagc tgcttcagaa agagcaaaac      1860
tattcagatg acgtcttggc caacatgatt agtgaaccaa ggatcagtta cggaaacgat      1920
gctctcatgc catctttgac cgaaacgaaa accaccgtgg agctccttcc cgtgaatgga      1980
gagttcagcc tggacgatct ccagccgtgg cattctttg gggctgactc tgtgccagcc      2040
aacacagaaa acgaagttga gcctgttgat gcccgccctg ctgccgaccg aggactgacc      2100
```

| | |
|---|---:|
| actcgaccag gttctgggtt gacaaatatc aagacggagg agatctctga agtgaagatg | 2160 |
| gatgcagaat tccgacatga ctcaggatat gaagttcatc atcaaaaatt ggtgttcttt | 2220 |
| gcagaagatg tgggttcaaa caaaggtgca atcattggac tcatggtggg cggtgttgtc | 2280 |
| atagcgcacg tgatcgtcat caccttggtg atgctgaaga agaaacagta cacatccatt | 2340 |
| catcatggtg tggtggaggt tgacgccgct gtcaccccag aggagcgcca cctgtccaag | 2400 |
| atgcagcaga acggctacga aaatccaacc tacaagttct tgagcagat gcagaactag | 2460 |
| accccgcca cagcagcctc tgaagttgga cagcaaaacc attgcttcac tacccatcgg | 2520 |
| tgtccattta tagaataatg tgggaagaaa caaacccgtt ttatgattta ctcattatcg | 2580 |
| ccttttgaca gctgtgctgt aacacaagta gatgcctgaa cttgaattaa tccacacatc | 2640 |
| agtaatgtat tctatctctc tttacatttt ggtctctata ctacattatt aatgggtttt | 2700 |
| gtgtactgta aagaatttag ctgtatcaaa ctagtgcatg aatagattct ctcctgatta | 2760 |
| tttatcacat agcccttag ccagttgtat attattcttg tggtttgtga cccaattaag | 2820 |
| tcctacttta catatgcttt aagaatcgat gggggatgct tcatgtgaac gtgggagttc | 2880 |
| agctgcttct cttgcctaag tattccttc ctgatcacta tgcattttaa agttaaacat | 2940 |
| ttttaagtat ttcagatgct ttagagagat ttttttttcca tgactgcatt ttactgtaca | 3000 |
| gattgctgct tctgctatat ttgtgatata ggaattaaga ggatacacac gtttgtttct | 3060 |
| tcgtgcctgt tttatgtgca cacattaggc attgagactt caagcttttc ttttttgtc | 3120 |
| cacgtatctt tgggtctttg ataaagaaaa gaatccctgt tcattgtaag cacttttacg | 3180 |
| gggcgggtgg ggaggggtgc tctgctggtc ttcaattacc aagaattctc caaaacaatt | 3240 |
| ttctgcagga tgattgtaca gaatcattgc ttatgacatg atcgctttct acactgtatt | 3300 |
| acataaataa attaaataaa ataaccccgg gcaagacttt tctttgaagg atgactacag | 3360 |
| acattaaata tcgaagtaa ttttgggtgg ggagaagagg cagattcaat tttcttaac | 3420 |
| cagtctgaag tttcatttat gatacaaaag aagatgaaaa tggaagtggc aatataaggg | 3480 |
| gatgaggaag gcatgcctgg acaaaccctt cttttaagat gtgtcttcaa tttgtataaa | 3540 |
| atggtgtttt catgtaaaata aatacattct tggaggagc | 3579 |

<210> SEQ ID NO 28
<211> LENGTH: 1433
<212> TYPE: DNA
<213> ORGANISM: Homo sapiens

<400> SEQUENCE: 28

| | |
|---|---:|
| attcggggcg agggaggagg aagaagcgga ggaggcggct cccgctcgca gggccgtgca | 60 |
| cctgcccgcc cgcccgctcg ctcgctcgcc cgccgcgccg cgctgccgac cgccagcatg | 120 |
| ctgccgagag tgggctgccc cgcgctgccg ctgccgccgc cgccgctgct gccgctgctg | 180 |
| ccgctgctgc tgctgctact gggcgcgagt ggcggcggcg gcggggcgcg cgcggaggtg | 240 |
| ctgttccgct gcccgccctg cacacccgag cgcctggccg cctgcgggcc ccgccggtt | 300 |
| gcgccgcccg ccgcggtggc cgcagtggcc ggaggcgccc gcatgccatg cgcggagctc | 360 |
| gtccgggagc cgggctgcgg ctgctgctcg gtgtgcgccc ggctggaggg cgaggcgtgc | 420 |
| ggcgtctaca ccccgcgctg cggccagggg ctgcgctgct atccccaccc gggctccgag | 480 |
| ctgcccctgc aggcgctggt catgggcgag ggcacttgtg agaagcgccg ggacgccgag | 540 |
| tatggcgcca gccggagca ggttgcagac aatggcgatg accactcaga aggaggcctg | 600 |
| gtggagaacc acgtggacag caccatgaac atgttgggcg ggggaggcag tgctggccgg | 660 |

| | |
|---|---|
| aagcccctca agtcgggtat gaaggagctg gccgtgttcc gggagaaggt cactgagcag | 720 |
| caccggcaga tgggcaaggg tggcaagcat caccttggcc tggaggagcc caagaagctg | 780 |
| cgaccacccc ctgccaggac tccctgccaa caggaactgg accaggtcct ggagcggatc | 840 |
| tccaccatgc gccttccgga tgagcggggc cctctggagc acctctactc cctgcacatc | 900 |
| cccaactgtg acaagcatgg cctgtacaac ctcaaacagt gcaagatgtc tctgaacggg | 960 |
| cagcgtgggg agtgctggtg tgtgaacccc aacaccggga agctgatcca gggagccccc | 1020 |
| accatccggg gggaccccga gtgtcatctc ttctacaatg agcagcagga ggcttgcggg | 1080 |
| gtgcacaccc agcggatgca gtagaccgca gccagccggt gcctggcgcc cctgcccccc | 1140 |
| gcccctctcc aaacaccggc agaaaacgga gagtgcttgg gtggtgggtg ctggaggatt | 1200 |
| ttccagttct gacacacgta tttatatttg gaaagagacc agcaccgagc tcggcacctc | 1260 |
| cccggcctct ctcttcccag ctgcagatgc cacacctgct ccttcttgct ttccccgggg | 1320 |
| gaggaagggg gttgtggtcg gggagctggg gtacaggttt ggggaggggg aagagaaatt | 1380 |
| tttattttg aacccctgtg tccctttgc ataagattaa aggaaggaaa agt | 1433 |

<210> SEQ ID NO 29
<211> LENGTH: 2370
<212> TYPE: DNA
<213> ORGANISM: Homo sapiens

<400> SEQUENCE: 29

| | |
|---|---|
| cctggaactc tagcacgccg agtgaacttg aatctttggc tatttaagga ggactgggtt | 60 |
| tgttgtgaag ttgcggtgat ccagcgcaga gccccgtcct gattgatcgc atcgcggggc | 120 |
| tcagatgact gtaaaatgaa tagatgaaat tcttgcttct cgaagatttt cttgggcatc | 180 |
| tcccggaaag tgcgttttaa ggcgaagtca tgatgtattc tcccatctgt ctcactcagg | 240 |
| atgaatttca cccattcatg gaagcacttc ttccacatgt ccgtgcaatt gcctatactt | 300 |
| ggttcaacct gcaggctcga aaacgcaagt acttaaaaa gcatgagaag cgaatgtcaa | 360 |
| aggatgaaga aagagcagtc aaagatgagc ttctcagtga aaagcctgaa atcaaacaga | 420 |
| agtgggcatc caggctcctt gccaaactgc gcaaagatat tcgccaggag tatcgagagg | 480 |
| actttgtgct caccgtgact ggcaagaagc accgtgctg tgtcttatcc aatcccgacc | 540 |
| agaagggtaa gattaggaga atcgactgcc tgcgacaggc agacaaagtc tggcgtctgg | 600 |
| atctagtcat ggtgatcctg ttcaaaggca tccccttgga agtaccgat ggagagcggc | 660 |
| tcatgaaatc cccacattgc acaaaccag cactttgtgt ccagccacat catatcacag | 720 |
| tatcagttaa ggagcttgat ttgttttgg catactacgt gcaggagcaa gattctggac | 780 |
| aatcaggaag tccaagccac aatgatcctg ccaagaatcc tccaggttac cttgaggata | 840 |
| gttttgtaaa atctggagtc ttcaatgtat cagaacttgt aagagtatcc agaacgccca | 900 |
| taacccaggg aactggagtc aacttcccaa ttggagaaat cccaagccaa ccatactatc | 960 |
| atgacatgaa ctcgggggtc aatcttcaga ggtctctgtc ttctccacca agcagcaaaa | 1020 |
| gacccaaaac tatatccata gaygaaaata tggaaccaag tcctacagga acttttacc | 1080 |
| cctctccaag ttcaccagct gctggaagtc gaacatggca cgaaagagat caagatatgt | 1140 |
| cttctccgac tactatgaag aagcctgaaa agccattgtt cagctctgca tctccacagg | 1200 |
| attcttcccc aagactgagc actttcccc agcaccacca tcccggaata cctggagttg | 1260 |
| cacacagtgt catctcaact cgaactccac ctccaccttc accgttgcca tttcaacac | 1320 |
| aagctatcct tcctccagcc ccatcgagct acttttctca tccaacaatc agatatcctc | 1380 |

| | |
|---|---|
| cccacctgaa tcctcaggat actctgaaga actatgtacc ttcttatgac ccatccagtc | 1440 |
| cacaaaccag ccagtcctgg tacctgggct agcttggttc ctttccaagt gtcaaatagg | 1500 |
| acacccatct taccggccaa tgtccaaaat tacggtttga acataattgg agaacctttc | 1560 |
| cttcaagcag aaacaagcaa ctgagggaaa aagaaacaca acaatagttt aagaaatttt | 1620 |
| tttttttaaat aaaaaaaagg aaaagaggaa gactggacaa acaacacaa aggcagaaag | 1680 |
| gaaagaaact gaagaaagaa gataatagac cagcaattgc agcacttaca atcactaatt | 1740 |
| cccttaaggt taaactgtaa tgacataaaa agggtcgatg atatttcact gatggtagat | 1800 |
| cgcagcccct gcaacgtagc ctttgttaca tgaagtccgc tgggaaatag atgttctgtc | 1860 |
| tctatgacaa tatattttaa ctgactttct agatgcctta atatttgcat gataagctag | 1920 |
| ttttattggt ttagtattct tgttgtttac gcatggaatc actattcctg gttatctcac | 1980 |
| caacgaaggc taggaggcgg cgtcagagat gctgggtgac agagccatga gccagccatt | 2040 |
| ttataagcac tctgatttct aaaagttaaa aaaaatatat gaaatctctg tagcctttag | 2100 |
| ttatcagtac agatttatta aatttcggcc cttaacccag cctttttccag tgtgtaaccc | 2160 |
| agtttgaaat cttaaaaaaa gaaaaaatga aaaaaaagg aaaaaagaa aaaggaaaa | 2220 |
| aaacagtttg aacacaaagg ctctatggaa gaaatgcctc tatgtaggtg aagtgttctc | 2280 |
| tctgcatgca acagtaaaaa ttaatataat attttcccca caaagaaac acttaacaga | 2340 |
| gggcaagtgc aatttattaa atttatattc | 2370 |

<210> SEQ ID NO 30
<211> LENGTH: 2699
<212> TYPE: DNA
<213> ORGANISM: Homo sapiens

<400> SEQUENCE: 30

| | |
|---|---|
| gcccagcggg ggcgggactg gaacggagcc gtgcggcccc gcgcgctcgc agtctgtctc | 60 |
| ccgccgtccc cacgcacgcg tcccggctca cgcgtccgcc cgcccgcccc cgcttgtgcc | 120 |
| gcccctacca gagaccccca ggagcaggat gtccttccag ggcaagaaaa gcatcccccg | 180 |
| gatcacgagt gaccgccttc tgatcagagg tgggaggatc gtgaatgacg accagtcctt | 240 |
| ttacgctgat gtgcacgtgg aagatggctt gataaaacaa atcggagaaa acctcatcgt | 300 |
| ccctgggggc atcaagacca ttgacgccca cggcctgatg gtccttcctg gtggcgttga | 360 |
| cgtccacaca aggctgcaga tgcctgtcct gggcatgaca ccggctgacg acttctgtca | 420 |
| gggcaccaag gcagcgctag caggaggaac caccatgatc ttggaccacg tcttccccga | 480 |
| cacgggtgtg agcctgctgg cggcctacga gcggtggcgg gagcgggcgg acagcgcggc | 540 |
| ctgctgcgac tactccctgc acgtggacat cacccgatgg catgagagca tcaaggagga | 600 |
| gctggaggcc ctggtcaagg agaagggtgt gaactccttc ctggtcttca tggcatacaa | 660 |
| ggaccggtgc cagtgcagcg acagccagat gtacagagat ttcagcatca tccgggacct | 720 |
| gggggccttg gcccaggtgc acgctgagaa cggggacatc gtggaggagg agcagaagcg | 780 |
| gttgctggag ctcggcatca ctggccccga gggccacgtg tcagccacc cgaggaggt | 840 |
| ggaggctgag gcggtgtacc gagctgtcac catcgccaag caggcaaact gcccgctgta | 900 |
| cgtcaccaag gtgatgagca aggggcggc cgacgccatc gctcaggcca agcgcagagg | 960 |
| ggtggtcgtg tttggggagc ccatcaccgc cagcctgggc accgacggtt cacactactg | 1020 |
| gagcaagaac tgggccaagg ccgcagcctt cgtcacatca ccccctgtca cccagaccc | 1080 |
| caccacggca gaccacctca cctgcttgct gtccagcggg gacctccagg tgacaggcag | 1140 |

```
cgcccactgc accttcacca ctgcccagaa ggctgtgggc aaggacaact tcgcgctgat    1200
ccccgagggc accaacggca ttgaggagcg catgtcgatg gtctgggaga aatgtgtggc    1260
ctctgggaag atggacgaga atgagttcgt cgcggtgacc agtacaaatg ctgccaaaat    1320 cttcaattt tacccaagga aggggcgagt ggctgtgggc tctgacgctg acctggtcat    1380
atggaacccc aaggccacca agatcatctc tgccaagacc cacaatctga acgtggagta    1440
caacatcttc gagggagtgg agtgccgggg agcgcctgcc gtggtcataa gtcagggccg    1500
agtggcgctg gaggacggga agatgtttgt caccccgggg gcgggccgct tcgtccctcg    1560
gaaaacattc ccggactttg tctacaagag gatcaaagct cgcaacaggc tggcggagat    1620
ccacggtgtg ccccgtgggc tgtatgacgg gcccgtccac gaggtgatgg tgcctgccaa    1680
gccagggagt ggcgctccgg cccgcgcgtc ctgcccagge aagatctccg tgcctcctgt    1740
gcgcaaccta catcagtcgg ggttcagcct atctgggtct caggctgatg accacatcgc    1800
ccgacgcaca gcacagaaga tcatggcacc cctggcggc cgctccaaca tcacctctct    1860
ctcctagacg cccaggaccg gccctgtgag ccgtgctggc ccacccgag gccgcgggggg    1920 ccccagggca ctcgcccccc tccttagcat tttctttttgt agaagtttct cgaaggtgct    1980
tggcggtctt gccttccccc tccccacagg ctctccttgt ggggtcccag gtcctgctgc    2040
caagagcccc tcaagagaag ggctgaacct ggggagatgt cactgccagg gtgaggtgga    2100
gccacatggc agggacaatg ccggcagcct gagcccaggc accccagtgc cgctgggcc    2160 cagcctgggg acagggaacc tgccgggctc acagtgtggg agcagctgga caccaggctt    2220
cttggtgaac cggcgagggg ccgagtcccg cctggtgggc atttgctgcc gcctccccac    2280
caccagtcac tgcctcgcag agccctacac tcccgcagcc gctcctcaga ggcctgtgcc    2340
catcgcaggc ctgggaggaa agtgggcgca gagccctcct gctcacacag ctgctgagac    2400
ttcagggacc catcagaact tggtgcagca cagccccgcc cgtggagggt ccctttttacg    2460 caccccaagg cccacaccta agcttccatg tagccctcat ccaggaagt tttgcgatcc    2520 tttaggaaga cactgtcctc ttattacaga ttgtgtattt ccgtaggctt cttagtagca    2580
gctttgtaca ctgaggacac tgtagccagg aacctgtgca tgccacccac cgcctggaca    2640
ggcagtcatc ctgcctctga tgtgaatcag gcccattaaa gacgtctggg tttgaagcc     2699

<210> SEQ ID NO 31
<211> LENGTH: 4122
<212> TYPE: DNA
<213> ORGANISM: Homo sapiens

<400> SEQUENCE: 31
tttgtcatca gctcgctctc cattggcggg gagcggagag cagcgaagaa ggggtgggg      60 aggggagggg aagggaaggg ggtggaaact gcctggagcc gtttctccgc gccgctgttg    120
gtgctgccgc tgcctcctcc tcctccgccg ccgccgccgc cgccgccgcc tcctccggct    180
cttcgctcgg cccctctccg cctccatgtg ccggatagcg ggagcgctgc ggaccctgct    240
gccgctgctg gcgccctgc ttcaggcgtc tgtagaggct tctggtgaaa tcgcattatg     300
caagactgga tttcctgaag atgtttacag tgcagtctta tcgaaggatg tgcatgaagg    360
acagcctctt ctcaatgtga agtttagcaa ctgcaatgga aaaagaaaag tacaatatga    420
gagcagtgag cctgcagatt ttaaggtgga tgaagatggc atggtgtatg ccgtgagaag    480
ctttccactc tcttctgagc atgccaagtt cctgatatat gcccaagaca aagagaccca    540
ggaaaagtgg caagtggcag taaaattgag cctgaagcca accttaactg aggagtcagt    600
```

-continued

| | |
|---|---|
| gaaggagtca gcagaagttg aagaaatagt gttcccaaga caattcagta agcacagtgg | 660 |
| ccacctacaa aggcagaaga gagactgggt catccctcca atcaacttgc cagaaaactc | 720 |
| caggggacct tttcctcaag agcttgtcag gatcaggtct gatagagata aaaacctttc | 780 |
| actgcggtac agtgtaactg ggccaggagc tgaccagcct ccaactggta tcttcattat | 840 |
| caaccccatc tcgggtcagc tgtcggtgac aaagcccctg gatcgcgagc agatagcccg | 900 |
| gtttcatttg agggcacatg cagtagatat taatggaaat caagtggaga accccattga | 960 |
| cattgtcatc aatgttattg acatgaatga caacagacct gagttcttac accaggtttg | 1020 |
| gaatgggaca gttcctgagg gatcaaagcc tggaacatat gtgatgaccg taacagcaat | 1080 |
| tgatgctgac gatcccaatg ccctcaatgg gatgttgagg tacagaatcg tgtctcaggc | 1140 |
| tccaagcacc ccttcaccca acatgtttac aatcaacaat gagactggtg acatcatcac | 1200 |
| agtggcagct ggacttgatc gagaaaaagt gcaacagtat acgttaataa ttcaagctac | 1260 |
| agacatggaa ggcaatccca catatggcct ttcaaacaca gccacggccg tcatcacagt | 1320 |
| gacagatgtc aatgacaatc ctccagagtt tactgccatg acgttttatg gtgaagttcc | 1380 |
| tgagaacagg gtagacatca tagtagctaa tctaactgtg accgataagg atcaacccca | 1440 |
| tacaccagcc tggaacgcag tgtacagaat cagtggcgga gatcctactg gacggttcgc | 1500 |
| catccagacc gacccaaaca gcaacgacgg gttagtcacc gtggtcaaac caatcgactt | 1560 |
| tgaaacaaat aggatgtttg tccttactgt tgctgcagaa atcaagtgc cattagccaa | 1620 |
| gggaattcag caccogcctc agtcaactgc aaccgtgtct gttacagtta ttgacgtaaa | 1680 |
| tgaaaaccct tattttgccc ccaatcctaa gatcattcgc caagaagaag gcttcatgc | 1740 |
| cggtaccatg ttgacaacat tcactgctca ggacccagat cgatatatgc agcaaaatat | 1800 |
| tagatacact aaaattatctg atcctgccaa ttggctaaaa atagatcctg tgaatggaca | 1860 |
| aataactaca attgctgttt tggaccgaga atcaccaaat gtgaaaaaca atatatataa | 1920 |
| tgctactttc cttgcttctg acaatggaat tcctcctatg agtggaacag gaacgctgca | 1980 |
| gatctattta cttgatatta tgacaatgcc cctcaagtg ttacctcaag aggcagagac | 2040 |
| ttgcgaaact ccagacccca attcaattaa tattacagca cttgattatg acattgatcc | 2100 |
| aaaatgctgga ccatttgctt ttgatcttcc tttatctcca gtgactatta agagaaattg | 2160 |
| gaccatcact cggcttaatg gtgattttgc tcagcttaat ttaaagataa aatttcttga | 2220 |
| agctggtatc tatgaagttc ccatcataat cacagattcg ggtaatcctc ccaaatcaaa | 2280 |
| tatttccatc ctgcgcgtga aggttttgcc agtgtgactcc aacggggact gcacagatgt | 2340 |
| ggacaggatt gtgggtgcgg ggcttggcac cggtgccatc attgccatcc tgctctgcat | 2400 |
| catcatcctg cttatccttg tgctgatgtt tgtggtatgg atgaaacgcc gggataaaga | 2460 |
| acgccaggcc aaacaacttt taattgatcc agaagatgat gtaagagata atattttaaa | 2520 |
| atatgatgaa gaaggtggag gagaagaaga ccaggactat gacttgagcc agctgcagca | 2580 |
| gcctgacact gtggagcctg atgccatcaa gcctgtggga atccgacgaa tggatgaaag | 2640 |
| acccatccac gctgagcccc agtatccggt ccgatctgca gccccacacc ctggagacat | 2700 |
| tggggacttc attaatgagg gccttaaagc ggctgacaat gaccccacag ctccaccata | 2760 |
| tgactcccetg ttagtgtttg actatgaagg cagtggctcc actgctgggt ccttgagctc | 2820 |
| ccttaattcc tcaagtagtg gtggtgagca ggactatgat tacctgaacg actggggccc | 2880 |
| acggttcaag aaacttgctg acatgtatgg tggaggtgat gactgaactt cagggtgaac | 2940 |
| ttggttttttg gacaagtaca aacaatttca actgatattc ccaaaaagca ttcagaagct | 3000 |

-continued

| | |
|---|---|
| aggctttaac tttgtagtct actagcacag tgcttgctgg aggctttggc ataggctgca | 3060 |
| aaccaatttg ggctcagagg gaatatcagt gatccatact gtttggaaaa acactgagct | 3120 |
| cagttacact tgaattttac agtacagaag cactgggatt ttatgtgcct ttttgtacct | 3180 |
| ttttcagatt ggaattagtt ttctgtttaa ggctttaatg gtactgattt ctgaaacgat | 3240 |
| aagtaaaaga caaatatttt tgtggtggga gcagtaagtt aaaccatgat atgcttcaac | 3300 |
| acgcttttgt tacattgcat ttgctttat taaaatacaa aattaaacaa acaaaaaaac | 3360 |
| tcatggagcg attttattat cttggggat gagaccatga gattggaaaa tgtacattac | 3420 |
| ttctagtttt agactttagt ttgtttttt ttttcacta aaatcttaaa acttactcag | 3480 |
| ctggttgcaa ataaagggag ttttcatatc accaatttgt agcaaaattg aattttttca | 3540 |
| taaactagaa tgttagacac attttggtct taatccatgt acactttttt atttctgtat | 3600 |
| ttttccactt cactgtaaaa atagtatgtg tacataatgt tttattggca tagtctatgg | 3660 |
| agaagtgcag aaacttcaga acatgtgtat gtattatttg gactatggat tcaggttttt | 3720 |
| tgcatgttta tatctttcgt tatggataaa gtatttacaa aacagtgaca tttgattcaa | 3780 |
| ttgttgagct gtagttagaa tactcaattt ttaattttt taatttttt atttttatt | 3840 |
| ttcttttgg tttggggagg gagaaaagtt cttagcacaa atgttttaca taatttgtac | 3900 |
| caaaaaaaaa aaaaggaaa ggaagaaag gggtggcctg acactggtgg cactactaag | 3960 |
| tgtgtgtttt ttaaaaaaaa aaatggaaaa aaaaaagctt ttaaactgga gagacttctg | 4020 |
| acaacagctt tgcctctgta ttgtgtacca gaatataaat gatacacctc tgaccccagc | 4080 |
| gttctgaata aaatgctaat tttggaaaaa aaaaaaaaaa aa | 4122 |

<210> SEQ ID NO 32
<211> LENGTH: 1653
<212> TYPE: DNA
<213> ORGANISM: Homo sapiens

<400> SEQUENCE: 32

| | |
|---|---|
| agtcagcacg ggggtgctgg aagagatcgg gaataatagc gcagaccaat gagcctaggg | 60 |
| agatgctttc atcgtctctc cttccctcaa gtgttctgga acctatcatt tgaattagcc | 120 |
| gagtcaggca ggagggggcg gggaatcctt ccgcccttct taggaggggc tgcattgcag | 180 |
| ggggagagtg aactgacaga ctcagtcact gaagagggaa aaggagtgag aagacaaagc | 240 |
| cgtcaaagcc ccaacagctt tgtatttctc cagcccggcg cagaccccgg agctcccgag | 300 |
| gcactccctc catctttgga acacgccagt aattgattga taacaggaag ctatgaggga | 360 |
| ccctgtgagt agccagtaca gttccttct tttctggagg atgcccatcc cagaactgga | 420 |
| tctgtcggag ctggaaggcc tgggtctgtc agatacagcc acctacaagg tcaaagacag | 480 |
| cagcgttggc aaaatgatcg ggcaagcaac tgcagcagac caggagaaaa accctgaagg | 540 |
| tgatggcctc cttgagtaca gcaccttcaa ccttctggaga gctcccattg ccagcatcca | 600 |
| ctccttcgaa ctggacttgc tctaaggcca agacttctct ctcccatcac cttgccctca | 660 |
| ttgtcttccc tctcaagccc cttccttcc actcctttcc cattttaatc ttgttctctc | 720 |
| cctactgtgt tggtggtgct gatgaatctg ccagagttga gttctatgta tttatttatc | 780 |
| tatctgtcta ctccatttct ctcaaaagcc ctcaagtcac aaagtaaatg gttcaagcaa | 840 |
| tggagtactg ggtcacaggg attcctcctt tccccccaa atattaactc cagaaactag | 900 |
| gcctgactgg ggacacctga gagtagtata gtagtgcaaa atggaagact gattttgac | 960 |
| tctattataa tcagcttcag agattcctta aaccttccta atttcctgct ccagggcagt | 1020 |

| | |
|---|---|
| aaacacaaat atttcttcaa ggggtgatga aaacctcgga agttttaatt tgaggttatc | 1080 |
| tgctacgaaa cagtatttct aaaaggctaa agtgataagt ctcttgcttt ttttttgatcc | 1140 |
| tgctcttata ttctttttt tcctcagaga aatcaggagg gtagttagag gtataaaaca | 1200 |
| ggaggaaata ttatggaaaa tgaaaatagg gaaaataatt gaatcatttt agaagtagct | 1260 |
| aatttctttt ctcaaaagag tgtcccttct tcacacctac tcactttaca actttgctcc | 1320 |
| taactgtggg ttgaaaactc tagctaaaga aagttatcaa atcttaacat gcattcctac | 1380 |
| tattatgata gttttttaagg tttcaattca atcttctgaa cggcataagt cctatttttag | 1440 |
| ccttacctcc tgcatttgca atacgtaata ctgatcagtg gcacagttc ttcagctaca | 1500 |
| ttgagaccct gaaatgaaca attatattct gactcgacat cttgtcccca atccttccaa | 1560 |
| aaatattgat ggtgatttgt gctaccattt actcgtttat ttaataaaga cattcaatcc | 1620 |
| cagaaaaaaa aaaaaaaaaa aaaaaaaaaa aaa | 1653 |

<210> SEQ ID NO 33
<211> LENGTH: 2928
<212> TYPE: DNA
<213> ORGANISM: Homo sapiens

<400> SEQUENCE: 33

| | |
|---|---|
| ccgatccggg cggtgctggc agccggagcg gcggcgggcg ggccgagcag ccggggcagc | 60 |
| cgcgcgtggg catccacggg cgccgagcct ccgtccgtgt ctctatccct cccgggcctt | 120 |
| tgtcagcgcg cccgctggga gcggggccga gagcgccggt tccagtcaga cagccccgca | 180 |
| ggtcagcggc cgggccgagg gcgccagagg gggccatgtc gtaccagggc aagaagagca | 240 |
| tcccgcacat cacgagtgac cgactcctca tcaaaggtgg acggatcatc aacgatgacc | 300 |
| aatccctta tgctgacgtc tacctggagg atggacttat caaacaaata ggagagaact | 360 |
| taatcgttcc tggtggagtg aagaccattg aagccaacgg gcggatggtt attcccggag | 420 |
| gtattgatgt caacacgtac ctgcagaagc cctcccaggg gatgactgcg gctgatgact | 480 |
| tcttccaagg gaccagggcg gcactggtgg gcgggaccac gatgatcatt gaccatgttg | 540 |
| ttcctgaacc tgggtccagc ctactgacct cttttcgagaa gtggcacgaa gcagctgaca | 600 |
| ccaaatcctg ctgtgattac tccctccacg tggacatcac aagctggtac gatggcgttc | 660 |
| gggaggagct ggaggtgctg gtgcaggaca aaggcgtcaa ttccttccaa gtctacatgg | 720 |
| cctataagga tgtctaccaa atgtccgaca gccagctcta tgaagccttt accttcctta | 780 |
| agggcctggg agctgtgatc ttggtccatg cagaaaatgg agatttgata gctcaggaac | 840 |
| aaaagcggat cctggagatg ggcatcacgg gtcccgaggg ccatgccctg agcagacctg | 900 |
| aagagctgga ggccgaggcg gtgttccggg ccatcaccat tgcgggccgg atcaactgcc | 960 |
| ctgtgtacat caccaaggtc atgagcaaga gtgcagccga catcatcgct ctggccagga | 1020 |
| agaaagggcc cctagttttt ggagagccca ttgccgccag cctggggacc gatggcaccc | 1080 |
| attactggag caagaactgg gccaaggctg cggcgttcgt gacttcccct cccctgagcc | 1140 |
| cggaccctac cacgccgac tacttgacct ccctactggc ctgtgggac ttgcaggtca | 1200 |
| caggcagcgg ccactgtccc tacagcactg cccagaaggc ggtgggcaag gacaacttta | 1260 |
| ccctgatccc cgagggtgtc aacgggatag aggagcggat gacggtcgtc tgggacaagg | 1320 |
| cggtggctac tggcaaaatg gatgagaacc agtttgtcgc tgtcaccagc accaatgcag | 1380 |
| ccaagatctt taacctgtac ccaaggaaag ggcggattgc cgtgggctcg gatgccgacg | 1440 |
| tggtcatctg ggaccccgac aagttgaaga ccataacagc caaaagtcac aagtcggcgg | 1500 |

```
tggagtacaa catcttcgag ggtatggagt gccacggctc cccactagtg gtcatcagcc    1560
agggcaagat cgtctttgaa gacgaaaaca tcaacgtcaa caagggcatg ggccgcttca    1620
ttccgcggaa ggcgttcccg gagcacctgt accagcgcgt caaaatcagg aataaggttt    1680
ttggattgca aggggtttcc aggggcatgt atgacggtcc tgtgtacgag gtaccagcta    1740
cacccaaata tgcaactccc gctccttcag ccaaatcttc gccttctaaa caccagcccc    1800
cacccatcag aaacctccac cagtccaact tcagcttatc aggtgcccag atagatgaca    1860
acaatcccag gcgcaccggc caccgcatcg tggcgccccc tggtggccgc tccaacatca    1920
ccagcctcgg ttgaacgtgg atgcgcggag gagctagcct gaaggattct gggaatcatg    1980
tccatcccTT ttcctgtcag tgttttTGAA acccacagtt ttagttggtg ctgatggagg    2040
gaggggGAAG tcgaaggatg ctcttTCCCT tttctgttta ggaagaagtg gtactagtgt    2100
ggtgtgtttg cttggaaatt ccttgcccca cagttgtgtt catgctgaat ccacctcgga    2160
gcatggtgtt ttcattcccc cttcctagtg aaccacaggt tttagcattg tcttgttctg    2220
tcccttccac ttctaactcc actggctcca tgattctctg agtggtggtt cctttgcacc    2280
ctgtagatgt tctaggatag ttgatgcatg ttactaaatt acgtatgcaa gtctgtgagt    2340
gcgtctgagg ggacatcgcc aaggactgac tgagacacga tgccgagacc tcaagccctg    2400
aggggcagtc ccaaaaccct tacagtgaag atgtttactc attgcccccca cctctggtcc    2460 acactagaaa gaagctcgcc ccacctccac ctgtgagatc cgtgaattct cggaatggca    2520
ggggaagcct tgcactaggt tgcagagaag catcctccac atcctgtgtc agaaaccctg    2580
gtctccgtgg cacttgtaac tcaccgtgct gtcttctggt ctgtgtgtgt tcttcaagcc    2640
agctctaggc ttcaggccga ccaggttca cactcagaaa gaggtctccc catcccatt    2700 cggggctgac gatgggggc tgatggctgc ccctgcgtgg cctgagtcct ggtccctctg    2760
aggcagttga cggggcagtc agatttttaa agttttgtac aaagttttcc tttgtaatca    2820
ctcccatttt tacttaacaa ccaacttgtt gtggctctta tttctgaatt caaagcttgt    2880
gaaaaaataa agaaaatgaa ctgcccactg aaaaaaaaaa aaaaaaaa                 2928
```

<210> SEQ ID NO 34
<211> LENGTH: 4913
<212> TYPE: DNA
<213> ORGANISM: Homo sapiens

<400> SEQUENCE: 34

```
cctcccagcg tccccaccct aggaggctgc atgcggattg aagacgtgcg cctgggggct      60
gggccggccc cgctgatccc gacctagcga gcaggatagc aggaccgccc aggctgcgga     120
ggggctcggg ggcaggaagg tcagagcagc aagatggcca gtaagaccaa ggccagcgag     180
gccctcaagg tggtggcccg gtgccgcccc ctcagcagga aggaggaggc tgctggtcac     240
gagcagatcc tgaccatgga cgtgaaactg ggccaggtga ccctgcggaa cccccgcgcc     300
gccccggggg agctgcccaa gaccttcacc tttgacgccg tgtatgatgc cagctccaag     360
caggccgacc tgtatgacga aaccgtgagg cccctgatag actccgtgct ccagggtttc     420
aatggcacgg tgtttgccta tggccagacg ggcactggca agacctatac catgcagggg     480
acctgggtgg agcccgagct gcgcgggGTC atcccgaatg cctttgagca catcttcacc     540
cacatctccc gctcccagaa ccaacagtac ctggtccggg cctcctattt ggagatctac     600
caggaagaga ttcgagacct gctctccaag gagccgggca agaggctaga gctgaaagag     660
aaccccgaga ctggcgtcta catcaaggac ctctcctcct tcgtcaccaa gaatgtcaag     720
```

```
gagattgagc atgtgatgaa cctggggaac cagacccggg ctgtgggcag cacccacatg   780
aatgaggtca gctcccgctc ccatgccatc ttcatcatca ctgtggagtg cagcgaacgt   840
ggctctgatg ccaggacca catccgagtg ggcaagctca acctcgtgga cctggctggc   900
agcgagaggc agaacaaggc aggcccaac acagcgggag gggcagccac accatcctcg   960
ggtggcggtg gtggcggtgg aggcagtggt ggtggtgctg gtggagagag gcctaaggaa  1020
gcctccaaaa tcaacctctc attatctgcc ctgggcaacg tgattgctgc cctggcgggc  1080
aacaggagca cccacattcc ctaccgggac tccaagctga cccggctgct ccaggactcc  1140 ctgggggga atgcgaagac catcatggta gccacactgg ggccagcttc tcacagctac  1200
gatgagagcc tctccacctt gcgctttgcc aaccgagcca gaacatcaa gaacaagccc  1260 cgggtgaacg aggaccccaa ggacacactg ctgcgggaat ccaagagga gattgcccgc  1320 ctgaaggccc agctggagaa aggggggatg ctggggaagc ggccccggag aagagcagc   1380 cgcaggaaga aggccgtgtc cgccccgcct gggtaccctg agggcccagt gattgaggct  1440
tgggtggcag aagaggagga tgacaacaac aacaaccacc gcccgcccca gcccatcctg  1500
gagtcagcct tggagaagaa catggagaat tacctgcagg aacagaagga gcggctggag  1560
gaggagaagg cagccatcca ggatgaccgc agcctggtga gcgaggagaa gcagaagctg  1620
ctggaggaga aggagaagat gctggaggac ctgcggcggg aacagcaggc cacagagctg  1680
cttgcggcca agtacaaggc catggagagc aagctcctca tcggggggag gaacatcatg  1740
gatcacacca cgaacagca gaaagatgttg aactgaaga ggcaggagat tgccgagcag   1800
aaacgtcgtg agcgggagat gcagcaggag atgatgctcc gggacgagga gactatggag  1860
ctccggggca cctacacatc cctgcagcag gaggtggagg tcaaaaccaa gaaactcaag  1920
aagctctacg ccaagctgca ggcggtgaag gcggagatcc aggaccagca tgatgagtat  1980
atccgcgtgc ggcaggacct ggaggaggcg cagaacgagc agaccgcgga actcaagctc  2040
aagtacctaa tcatcgagaa cttcatcccg ccggaggaga gaacaagat catgaaccgg  2100 cttttcctgg actgtgagga ggagcagtgg aagttccagc cactggtgcc agccggcgtc  2160
agtagcagcc agatgaagaa gcggccaaca tctgcagtgg gctacaagag gcctatcagc  2220
cagtatgctc gggttgccat ggcaatgggg tccacccca ggtacagggc tgaaaacata  2280
atgtttctgg agttggatgt gtcccctcca gctgtctttg agatggaatt ctctcacgac  2340
caagaacaag accctcgtgc gctacacatg gagaggctca tgcgattgga cagctttctg  2400
gaaagacctt ccacgtctaa agtccgaaag tccagatcct ggtgccagag tcctcagcgg  2460
cctccacctt ccaccacaca tgcctccctg gcctctgctt ctctgcgccc tgcaacagtg  2520
gcggaccatg agtgacaacc atcacgtcag gctgcccatc caatagactc ctgggatggg  2580
gcagccaacc ctggctcatc tcatctgccg cttggtgcgt gtgcgtgtgc gtgcatgtgc  2640
gtgtgcgtgt gtgcagggt gagaatctgg cagatggtgc ctctgcctgc tcttcttcgc  2700
ctcctttatt taattcatgt tatttattcg cggacgtctg ttcgtgttgg ggagatgccc  2760
tcgcctgagc cgtctgggcc taccgtggtc actgcgtacg ctctttttct tctgacttga  2820
gagctccccc agtcagatct caggcttgtc ccctgtcag ctgcctccag aagggaaggt  2880
agccagtgcc tgagaagaca gtcccttttc tacccaccgc actccataac ctccatcttc  2940
tcccacactg atggcgagca gcccctgagc actttctggg actgggagac tgcttggtgt  3000
tccctgagga caagagacat cctgacagtg ttgggcatct gctcccgtg gacacagccc  3060 cactctccac tttctgagcc tcagacaacc tcattcagcc tcttgggctc cttttcaagg  3120
```

| | | | | |
|---|---|---|---|---|
| acattaataa | cctcaccaac | atagctcatg | cccttcagct | ttgacaagaa ctcacggctt | 3180
| cccaaactct | gctttctgcc | caccttggat | gggaactgtg | gaccaagcaa ttaccatcgc | 3240
| cttggaacct | gcaggaaatg | gaacagcaat | tgagacaact | tgaacagtca tcaacggaag | 3300
| tccctccact | ggattccttt | gtttctgtcc | cctccgagga | gtcattttgg tcgacaggct | 3360
| ctcaaggcaa | ctccccattt | tcaagaggct | gctcctgcct | gcttcgatca tttctccctg | 3420
| cagctgccta | gaccccgttc | acagtgggag | gagtcaatgt | cattctaccc ctcgctaaac | 3480
| gaagatatta | acatctattg | cttttttccct | tcatctgtca | caggaaacag aagcccaggc | 3540
| acaatctttt | ccagctttgc | ctgttacccc | tgtttctgaa | ttgcatctttt aaggtattat | 3600
| tttgttgaca | atagatcctt | tattcactag | ttacgcaaat | tggttcctag ggggatactc | 3660
| cttaccttcc | tttgtgatgg | cccaaaatgt | ctctaggtat | ctcaagtgat aagtaaattt | 3720
| ctacaaaaaa | aaaatggtta | atgttcattg | actggctttt | taagtgtata ttttggagga | 3780
| cgggtgaaga | ggtcataacg | aaagcaagcg | agtgaattag | gatttcaaag tgccctaata | 3840
| gtgtgagtct | ccagttccta | gaatatgaag | agtgctgtcg | ttggggtgaa accatgagac | 3900
| tgacagatct | gcctgaaatg | ggggtgtgg | gaggtggtgg | cggggttat tctctttcct | 3960
| tcaggaaatg | aaccccttctt | acatcattca | agttctgctc | tgaggatcaa gcttgggtct | 4020
| gatttaactc | agcgacactg | tcatttctgc | ttcattactg | gactagaggg ttgagccacc | 4080
| cacttgccat | ttgctcctgt | ccttccagga | aatcacaatt | ttcatcagag cccaagagat | 4140
| tatttgagac | tcaggattca | gatcagaggt | tcgactgtgg | ctgggacagg agttgtgtgt | 4200
| agaaattcac | caggtggcct | gagcgcaggg | ggacctccag | gctgcgttga gcagcctctc | 4260
| ccactgacct | ctttctcgtt | tgtgacaaa | gcagcacgta | tcacctcatt catcacttgg | 4320
| acacatcgcc | tttgcattgt | cttgtcacac | ctccctcaca | gtcttatagc acaatatacc | 4380
| caaatcagcc | cccccagtcc | gaggctgggc | ccaaggtatg | tcggaggag gagctcctgc | 4440
| ctgcggtttt | gtgtatgtgt | gtatgtgtgt | gcgtgtttgt | gtgcgtgttt acctccacag | 4500
| gggacactct | acactcagtg | taagatctgc | tgggaacagg | gccaccagga gtgcgtggat | 4560
| ctcagtctct | ctgtctctct | ttctctccttt | ttaattttgg | tgtatcaaat atttgattga | 4620
| caaagtaagg | gccttgatta | ggaccaaatt | ctcgtgtgtt | gctatggtct ttatttagga | 4680
| caacaattaa | caatgcagtg | gcccattctt | gtcactctac | acatatgact atacgggaca | 4740
| tatgtaatat | ataaatatat | atataaaaca | ttcccctctg | tccccttggc ttcggatgga | 4800
| ggaatttctg | ttgagctgaa | atgcacctgc | agctgggtgc | tgccagcagc ttgcaggccc | 4860
| cagccctgtt | ccaatcaatg | cagttgacaa | taaaggaatg | agtatcgtca cgg | 4913

<210> SEQ ID NO 35
<211> LENGTH: 1231
<212> TYPE: DNA
<213> ORGANISM: Homo sapiens

<400> SEQUENCE: 35

| | | | | |
|---|---|---|---|---|
| gaattccaga | aaagaggtgg | agaggggggg | aataagaaag | agagagaagg aaaggagaga | 60
| aggcaggaag | aaggcaaggg | acgagacaac | catgctgtgc | tgtatgagaa gaaccaaaca | 120
| ggttgaaaaa | aatgatgacg | accaaaagat | tgaacaagat | ggtatcaaac cagaagataa | 180
| agctcataag | gccgcaacca | aaattcaggc | tagcttccgt | ggacacataa caaggaaaaa | 240
| gctcaaagga | gagaagaagg | atgatgtcca | agctgctgag | gctgaagcta ataagaagga | 300
| tgaagcccct | gttgccgatg | gggtggagaa | gaagggagaa | ggcaccacta ctgccgaagc | 360

```
agccccagcc actggctcca agcctgatga gcccggcaaa gcaggagaaa ctccttccga      420
ggagaagaag gggagggtg atgctgccac agagcaggca gcccccagg ctcctgcatc        480 ctcagaggag aaggccggct cagctgagac agaaagtgcc actaaagctt ccactgataa      540
ctcgccgtcc tccaaggctg aagatgcccc agccaaggag gagcctaaac aagccgatgt      600
gcctgctgct gtcactgctg ctgctgccac caccctgcc gcagaggatg ctgctgccaa       660
ggcaacagcc cagcctccaa cggagactgg ggagagcagc caagctgaag agaacataga     720
agctgtagat gaaaccaaac ctaaggaaag tgcccggcag gacgagggta agaagagga      780 acctgaggct gaccaagaac atgcctgaac tctaagaaat ggcttccac atccccaccc       840 tccctctcc tgagcctgtc tctccctacc ctcttctcag ctccactctg aagtcccttc        900
ctgtcctgct cacgtctgtg agtctgtcct ttcccaccca ctagccctct ttctctctgt       960
gtggcaaaca tttaaaaaaa aaaaaaaaaa gcaggaaaga tcccaagtca acagtgtgg      1020 cttaaacatt ttttgtttct tggtgttgtt atggcaagtt tttggtaatg atgattcaat      1080
cattttggga aattcttgca ctgtatccaa gttatttgat ctggtgcgtg tggccctgtg      1140
ggagtccact ttcctctctc tctctctctc tgttccaagt gtgtgtgcaa tgttccgttc     1200
atctgaggag tccaaaatat tgagtgaatt c                                    1231

<210> SEQ ID NO 36
<211> LENGTH: 1587
<212> TYPE: DNA
<213> ORGANISM: Homo sapiens

<400> SEQUENCE: 36
ccacgcgtcc gcgttcttgc tacaattgta ccatctggta attcctgaaa atgtcaattt       60
ttttgtgtta atatttttgg tttcaaacaa taacaaatgt ctctagaaag aaattttaag      120
aaagcttaat taatagtaaa aatgcctttc ctgaaataat cttggaaaat ttttttaaatg     180 tcaaaatgat gagtcatgct aatacattga gggtttgttt tttgtttgt ttgtttgttt       240 ttgagacaga gtttcgctct tgttgcccag gctggagtgc aatggcccga tctcagctca     300
ccgcaacctc cacctcccgg attccagcga ttctcctgcc tcagcctaca ttaagggttt      360
tgtcagacaa ttgtcacacg aagaatagtg tcacttatct gctcttgaca cacagaactg     420
gcctggcata tagcttttcca gattttactc aaacttggta ctccagtttg aaaatttaaa    480
ttttgactgc tgattagctg aaagcctag ttttaatgga agaaagttt gcttttaaaa       540 ctgaaagtag tttcttttg ctaacaaatc taacttcata cataattggc catattagta      600
aaacacctca tgatagcagt gtatatatag tcttgtttgt agttggaagt catcttttag     660
gagttattct caaatatata taatagctac ccatgcatca ttattaaaat ccccaaattc     720
aaaaaacctc tgatatatat ataatttt ttttttttt ttttttggc caactgagat         780 tgaaatccaa gtgctggttt ctagttctga acatcaacta aagagttttg gaatgacag      840 caatttataa caagttcata ttgacttcct ctctatggca ggaagacatt ctgtgctgtt     900
ttgaacagat taaagatttg tgtagtttgt gggaaattga cgttttttgtt taaattccac   960 ccgcgtttgt cttttcctac cacctgtggc caggtgctcg ctggccatca cagttgcgat    1020
tccatgagta gctgctttat gactgctttt tgtactatct ggatgtgccc agagttactt    1080
ctgtacaagc tctgtatctg tgtccgttga gaacattatt ttaacaagaa gaacaccaac    1140
agtagcatga aatataatac tgttttataa ttctaaagct gctgttaatt tatgaagtac    1200
ataataatct aatgtaaact gcagaagtca gagcaagtgc ctacattttg ttattttgg    1260
```

| | |
|---|---|
| cattactaca gagccatgta caatagaaag caatgcaaga cttgtaaact ctcaccactt | 1320 |
| cttgtaatat caaatgttcc ccctcaggtt attttgctta tggtacccat gagttgcctc | 1380 |
| tctctgtaca tagataaatt gttccaatat tttcctttga tgtttggaac tacagatagt | 1440 |
| caagggctgg aaattttagt tttcaatata agcttccagc ttagcaatta cctctagtcc | 1500 |
| aagacaatat ttgattccta gttctgtttg gggcaaattt tcatttatct aaataaaatg | 1560 |
| caatctaatt aaaaaaaaaa aaaaaaa | 1587 |

<210> SEQ ID NO 37
<211> LENGTH: 9161
<212> TYPE: DNA
<213> ORGANISM: Homo sapiens

<400> SEQUENCE: 37

| | |
|---|---|
| ctgaaaactg gagagtgtga gagcgggagg agccccccgac cacacaaacc cagcctgggg | 60 |
| aggaacctac tagtggctgc accctctttt ttaatagcac caattgtgtt tcccaagatg | 120 |
| atgtagagaa tttcagtgct gtgtaccacg tcggaggcag aaattcctct gctgtcccag | 180 |
| gagcaggcag ggcagttttt atctggaaaa gctaaaggtc tcctcttttg tttgtgtttt | 240 |
| tgtgcctgca caggacaaaa gatccttcat caccgaagtg acgttttaga aacagtggtc | 300 |
| ctgatcaacc cttctgatga agcagtcagc accgaggtgc gcttaatgat cactgatgct | 360 |
| gcccgacaca agctgctcgt gctgaccggg cagtgctttg aaaataccgg agagctcatt | 420 |
| ctccagtccg gctctttctc cttccagaac ttcatagaga ttttcaccga tcaagagatc | 480 |
| ggggagttac taagcaccac ccatcctgcc aacaaagcca gcttaaccct gttctgtcct | 540 |
| gaagaagggg actggaagaa ctccaatctt gacagacaca atctccaaga cttcatcaat | 600 |
| attaaactca attcagcttc tatcttgcca gaaatggaag gactttctga gtttaccgag | 660 |
| tatctctcag aatcagtgga agtcccatct cccctttgaca tcttggaacc tcccacatcg | 720 |
| ggtggatttc tgaagctctc caagccctgc tgttatattt ttccaggagg gaggggcgat | 780 |
| tctgccttgt ttgcagtgaa tggttttcaat atgctcatca atggcggatc agagagaaaa | 840 |
| tcctgcttct ggaagctcat ccgacactta gaccgagtgg actccatcct gctcacccac | 900 |
| attggggatg acaatttgcc tggaataaac agcatgttac agcggaaaat tgcagagctc | 960 |
| gaggaagaac agtcccaggg ctccaccaca aatagtgact ggatgaaaaa cctcatctcc | 1020 |
| cctgacttag gagttgtatt tctcaatgta cctgaaaatc tcaaaaatcc agagccaaac | 1080 |
| atcaagatga gagaagcat agaagaagcc tgcttcactc tccagtacct aaacaaattg | 1140 |
| tccatgaaac cagaacctct gtttagaagt gtaggcaata ctattgatcc tgtcattctt | 1200 |
| ttccaaaaaa tgggagtagg taaacttgag atgtatgtgc ttaatccagt caagagcagc | 1260 |
| aaggaaatgc agtattttat gcagcagtgg actggtacca caaagacaa ggctgaattc | 1320 |
| attctgccta atggtcaaga agtagatctc ccgatttcct acttaacttc agtctcatct | 1380 |
| ttgattgtgt ggcatccagc aaaccctgcg agaaaatca tccgagtcct gtttcctggg | 1440 |
| aacagcaccc agtacaacat cctggaaggg ttggaaaagc tcaaacatct agactttctg | 1500 |
| aagcagccac tggccacccca aaaggatctc actggccagg tgcccactcc tgtggtgaaa | 1560 |
| caaacaaaac tgaaacagag ggctgatagc cgagaaagtc tgaagccagc cgcaaaacca | 1620 |
| cttcctagca aatccgtgcg caaggagtca aaagaagaaa cccctgaggt cacaaaagtg | 1680 |
| aatcacgtgg aaaagccacc caagttgaa agcaaagaaa aggtaatggt gaaaaaagac | 1740 |
| aagccagtaa aaacagagac caaaccttca gtgactgaaa aggaggttcc cagcaaagaa | 1800 |

```
gagccatctc cagtgaaagc cgaggtggct gagaagcaag ccacagatgt caaacccaaa    1860
gctgccaagg agaagacggt gaaaaggaa  acaaaggtaa agcctgaaga caagaaagag    1920
gagaaagaaa agccaaagaa agaagtggct aaaaggagg  acaaaacacc tatcaagaag    1980
gaggaaaaac caaaaaagga agaggtgaaa aagaagtca  aaaagagat  caagaaagaa    2040 gagaaaaaag aacccaagaa agaggttaag aaagaaacac cgccaaagga agtcaagaag    2100
gaagttaaga aggaagagaa gaaggaagtg aaaaaggaag aaaaggaacc caaaaaagaa    2160
attaagaagc tccctaaaga cgcaaagaaa tcatctactc ctctgtctga agcaaaaaaa    2220
ccagctgctt taaaaccaaa agtacccaag aaggaagagt ctgtcaagaa agattctgtt    2280
gctgccggaa agccaaagga aaggggaaa  ataaaagtca ttaagaagga aggcaaggcc    2340
gcagaggctg tcgctgcagc tgtcggcact ggagccacca cagcagctgt catggcggca    2400
gctggaatag cagccattgg ccctgccaaa gaactcgaag ctgagaggtc ccttatgtca    2460
tctcctgagg atctaaccaa ggactttgaa gagttaaagg ctgaagaggt cgatgtaaca    2520
aaggacatca agcctcagct ggagctaatc gaagacgaag agaaactgaa ggaaactgag    2580
ccagtcgaag cctacgtcat ccagaaggag agagaagtca ccaaaggtcc tgccgagtcc    2640
cctgatgagg gaatcactac cactgaaggg gagggcgaat gtgaacagac acctgaggag    2700
ctggagcccg tcgagaagca gggagtagac gacattgaaa aatttgaaga tgaaggagcc    2760
ggttttgaag aatcttcaga gactggagac tatgaagaga aggcagaaac tgaggaggct    2820
gaggagccag aagaggatgg ggaggaacac gtatgtgtga gcgcctccaa gcacagcccc    2880
actgaggatg aggaaagtgc caaggcggag gctgatgcat acatcaggga gaagagggag    2940
tctgtggcca gtggggatga ccgagccgaa gaagacatgg atgaggccat tgagaaagga    3000
gaggctgaac aatctgaaga ggaggctgat gaggaggaca agctgaagaa tgccagagag    3060
gaggaatatg agccggaaaa aatggaagct gaagactatg tgatggctgt ggtcgacaag    3120
gctgcagagg ctggtggtgc cgaggagcag tatggattcc tcaccacacc aaccaagcaa    3180
ctaggagccc agtctcctgg ccgagaacct gcatcttcaa ttcatgatga ctttacct     3240 ggaggctcag agagcgaggc caccgcttct gatgaggaga atcgagaaga ccagcctgag    3300
gaattcactg ccacctctgg ctacactcag tctactattg agatatccag tgagcccacc    3360
cccatggatg agatgtctac ccctcgagac gtgatgagtg atgagaccaa caatgaagag    3420
acggagtccc cttctcagga attcgtaaat atcaccaaat atgaatcttc attgtattct    3480
caggaatact ctaaacctgc tgatgttaca ccgctcaacg gattttctga aggatcaaaa    3540
acagatgcca ctgatggcaa ggattacaat gcttcagcct ctaccatatc accaccctct    3600
tccatggagg aagacaaatt cagcagatct gctttacgtg atgcttactg ctctgaagtg    3660
aaagccagca ccactttgga catcaaagat agcatctcag ctgtttcaag tgaaaaggtc    3720
agcccatcga gagcccgtcc ctgagtccta tctccaccat cacccttaga aaagaccccc    3780
ctgggtgaac gtagtgtgaa cttctctctg acgcccaatg agattaaagt ctctgcagag    3840
gcagaagtag ccccggtgtc tcctgaggtg acccaagaag tagttgaaga acattgtgct    3900
agtcctgagg acaagactct ggaagtggtg tcaccatctc agtccgtgac tggcagtgct    3960
ggtcacacac cttactatca atctcctact gacgagaaat ccagtcatct ccctacagaa    4020
gtcattgaaa aaccaccagc agttccagtg agttttgaat tcagtgatgc caaagatgag    4080
aatgaaaggg cttcagtaag ccccatggat gagcccgtgc ctgactcaga gtctcctatt    4140
gaaaaagttt tgtctccttt acgcagcccg cccctcattg gatccgagtc tgcttatgaa    4200
```

```
agttttctaa gtgctgatga caaggcttct ggcagaggtg ccgaaagtcc tttgaagaa      4260 aagagtggaa aacaaggctc tccagaccaa gtaagtccag tttctgaaat gacttctact      4320
agtctttacc aagacaaaca ggaagggaaa agcacagact ttgcaccaat aaaagaagac      4380
tttggccaag aaaagaaaac tgatgatgtt gaagccatga gttctcaacc agcactggct      4440
ctggatgaaa ggaaattagg agatgtttct cccacacaaa tagatgtcag tcagtttgga      4500
tcttttaaag aagacactaa gatgtccatt tctgaaggta ctgtctcaga caagtcagct      4560
actcctgttg atgagggcgt agcagaagac acgtactctc atatggaggg tgtggcctca      4620
gtgtccacag cctcagtggc tacgagctca tttccagagc caacaacaga tgatgtgtct      4680
ccatctctgc atgctgaggt tggctcccca cattccacag aagtagatga ctcccttca      4740 gtgtctgttg tgcaaacacc taccacattc caggaaacag aaatgtctcc atctaaagaa      4800
gaatgcccaa gaccgatgtc aatttctcca ccagatttct cccctaaaac tgcaaagtcc      4860
aggacacccg ttcaagatca cagatctgaa cagtcctcaa tgtctattga atttggccaa      4920
gaatctcctg agcaatccct tgctatggac ttcagtcgac agtctccaga tcaccctaca      4980
gtgggtgcag gcgtgcttca catcactgaa aatgggccaa ctgaagtgga ctacagtcct      5040
tctgacatgc aggactccag tttatcacat aagataccac ctatggagga gccgtcctac      5100
acccaagata tgatctttc tgagctcatc tcagtatctc aggtagaggc ctccccgtcc      5160
acctcttctg ctcataccc ttctcagatc gcttctcctc tccaagaaga tactctatcc      5220
gatgttgctc ctcccagaga tatgtcctta tatgcctcac tcacctctga aaaagtgcaa      5280
agtctggaag gagagaagct ctctccaaaa tctgatatct ctccactcac cccacgagag      5340
tcctctcctt tatattcacc tactttttca gattctacct ctgcagtcaa agagaaaaca      5400
gcaacttgcc acagttcctc ttctccacca atagatgcag catccgcaga gccctatggc      5460
ttccgtgcct cagtgttatt cgatacaatg caacaccatc tagccttgaa tagagatttg      5520
tccacacctg gcctggagaa ggacagtgga gggaagacac ctggtgactt tagctatgcc      5580
tatcaaaagc ctgaggaaac aaccaggtcc ccagatgaag aagattatga ctatgagtct      5640
tatgagaaga ccacccggac ctcagatgtg ggtggctatt actatgagaa datagagaga      5700
accacaaaat ctccaagtga cagtggctac tcctatgaga ccattgggaa aactaccaag      5760 accccctgaag atggtgacta ttcctatgaa attattgaga agaccacacg gacccctgaa      5820
gagggtgggt actcatatga cataagtgaa aagaccacca gccccccga agtgagtggt      5880 tacagctatg aaaagactga gaggtctaga aggcttctgg atgacatcag caatggctat      5940
gatgactctg aggatggtgg ccacacactt ggggacccca gctactctta tgaaaccact      6000
gagaaaatta ccagtttccc tgagtctgaa ggttattcct atgagacatc tacaaagaca      6060
acacgaaccc ctgatacttc cacatactgt tacgagactg cagagaaaat cactagaacc      6120
cctcaggcat ccacatattc ctacgagact tcagacctat gctacactgc agaaaagaag      6180 tcccctcag aagcccgtca ggatgtcgat ttatgcctcg tgtcctcttg tgaatacaag      6240 cacccccaaga cagagcttc accctctttc attaatccca atcctcttga gtggtttgcc      6300
agtgaagaac ccactgaaga atctgaaaag ccctcactc aatcagggg agccccaccg      6360 cctccaggag gaaagcaaca gggccgacag tgtgatgaaa ccctcccac ctcagtcagc      6420 gagtcagccc catcccagac cgactctgat gttccccgg agactgaaga gtgcccctcc      6480 atcacgccg atgccaatat cgactctgaa gacgagtcgg aaaccatccc cacagacaaa      6540
actgtcacgt acaaacacat ggacccacct ccagctcccg tgcaagaccg cagcccttcg      6600
```

```
ccacgccacc ctgatgtgtc catggtggac ccagaggcct tggccattga gcagaacctg    6660
ggcaaagctc taaagaaaga tctgaaagag aagaccaaaa ccaaaaagcc aggtacaaag    6720
accaagtcat cttcacctgt caaaaagagt gatgggaagt ctaagcccct ggcagcttca    6780
ccaaaaccag cgggcttgaa agaatcctcg gataaagtgt ccagggtggc ttctcctaag    6840
aagaaagaat ctgtggaaaa ggcagcaaaa cccaccacca ctcctgaggt caaagctgca    6900
cgtggggaag agaaagacaa ggagaccaag aatgctgcca atgcctctgc atccaagtcg    6960
gccaagaccg ccactgcagg accaggaact accaagacga ccaagtcatc tgctgtgccc    7020
ccaggcctcc ctgtgtattt ggacctgtgc tacattccta accacagcaa tagtaagaat    7080
gttgatgtgg aattttttcaa gagagtgcgg tcttcctact acgtggtgag tgggaatgac    7140
cctgctgctg aggagcccag ccgggctgtc ctggacgctt tgttggaagg aaaggctcag    7200
tggggcagca acatgcaggt gacactgatc ccaactcatg actcagaagt gatgagggaa    7260
tggtaccagg agacccatga gaaacagcaa gatctcaaca tcatggtttt agcaagcagc    7320
agcacagtgg ttatgcaaga tgaatccttc cctgcatgca agattgaact gtaaaaacca    7380
aggccagcca caccagga tctgaactttt gtttccagaa attcttcaat ttgaaatcac    7440
cttttctaaa aagtcaattc atctagttaa gtcgctgaac aattacctgc caaatgctat    7500
actgtgtcat ggtgatgcaa gtcactaaat ttctcagttt ttgctgattg ctaagggaaa    7560
taacagtatt tccacaatag ggttcaaatt cctgcaaaat tacctacccc agttcatctc    7620
tgctgaacat ttggaaacca tgcactagcc aacccaactg acttctgcta ggtagaggca    7680
tttgtcttag agagagagag agcgcgggag agagtgagag agagtgagag cacaaagata    7740
acgcaggaga gagagagaga aagaatgaga aagaaaagga atgcaagaga aggagatgta    7800
atgacagaga gttctggtga gatacccaga gagaaaaaga gagagcaggg tggggtaagg    7860
aggagaaaat aaaccaacaa ttaggtctgc attttctcag gcagtaggca ttctttagtc    7920
tacataggca aagttttcca ttttttgtcag tctgagtcat caaaaagagt cttaattttc    7980
taaaacaagt tggctagaag aaagtaaaaa gaacaacact tgttatgagg gcatgtgata    8040
ttttcacatc ttaattaagc tccttcagtt tgaaggctgc acactgacat aatgtagtga    8100
gtgtagactg gccatgcaag tggtttgggc cccattcaga actctcagac tctaaacaca    8160
caagtagatt gatctaaggc atgctcccag catttgtcca cccacttagt ccactctgag    8220
tcgattaacc tgcatgcagc aacacccaag tccaccccaa ttaactgaag caaataccaa    8280
agcagttggg agtacatatg gtagacaatt gccttaggaa gtgacttga atgtacaaag    8340 atacttgatg cacttatttt ttaatgtgag acagcaagtt tataaaacat ccatataggaa    8400 ttatagatac ttaaaggaac acgtgggtga gcgtgtgtgg gggtactaga agctgatctg    8460
attggtccaa cagtttgatg ctgagtcatg cgtgttgaat cccacttcag tgcacctgtg    8520
gcctctcagt caaacaagtt gtgcctttca cagcttcttt actactgcaa gttcaagact    8580
gaaatggctt ctatgatcag aactgggaaa acagtgaatc ttatggtgga agaggttctc    8640
agcaagtgta cagtatttac cttcctttgt cttacattgg ctttttaaat tttccattaa    8700
tttcaacata attatgggaa caagtgtaca gaagaatttt tttttaaga tatgtgagaa    8760 cttttcatag atgaactttt taacaaatgt tttcatttac aggaaattgc aaagaaaatt    8820
ctcaagtgat agtcttttt tttaagtgtt tcgtaagaca aaaattgaat aatgtttttt    8880
gaagttctgg caagattgaa gtctgatatt gcagtaatga tatttattaa aaacccataa    8940
ctaccaggaa taatgatacc tcccaccct tgattcccat aacataaaag tgctacttga    9000
```

```
gagtggggga gaatggcatg gtaggctact tttcagggcc ttgacaagta catcacccag      9060
tggtatccta catacttctt tcaagatctt caaccatgag gtaaaagagc caagttcaaa      9120
gaaccctagc acaaatttgc tttgggattt tcttttctgg a                         9161

<210> SEQ ID NO 38
<211> LENGTH: 1190
<212> TYPE: DNA
<213> ORGANISM: Homo sapiens

<400> SEQUENCE: 38
gccctccaca aagctcctgg gcccctcctc ccttcaagga ttgcgaagaa ctggtcgcaa        60
atcctcctaa gccaccagca tctcggtctt cagctcacac cagccttgag cccagcctgc       120
ggccagggga ccacgcacgt cccacccacc cagcgactcc ccagccgctg cccactcttc       180
ctcactcatg gggaacagca aaagtggggc cctgtccaag gagatcctgg aggagctgca       240
gctgaacacc aagttctcgg aggaggagct gtgctcctgg taccagtcct tcctgaagga       300
ctgtcccacc ggccgcatca cccagcagca gttccagagc atctacgcca agttcttccc       360
cgacaccgac cccaaggcct acgcccagca tgtgttccgc agcttcgatt ccaacctcga       420
cggcaccctg gacttcaagg agtacgtcat cgccctgcac atgaccaccg cgggcaagac       480
caaccagaag ctggagtggg ccttctccct ctacgacgtg gacggtaacg ggaccatcag       540
caagaatgaa gtgctggaga tcgtcatggc tattttcaaa atgatcactc ccgaggacgt       600
gaagctcctt ccagacgatg aaaacacgcc ggaaaagcga gccgagaaga tctggaagta       660
ctttggaaag aatgatgatg ataaacttac agagaaagaa ttcattgagg ggacactggc       720
caataaggaa attctgcgac tgatccagtt gagcctcaa aaagtgaagg aaaagatgaa        780
gaacgcctga tgccaactgt tcagctgtcc tccctccacc taccactcac atgacacccg       840
tgagcgcctg tgcacacaca cacacatgca cacacgcg cgcgcacaca cacacacaca        900
catccacccc agggccaaga gaaaggcctg cacacaagcc cacagcacag ctccctgcca       960
aactgaagca tctgtagtga cccactggtt ccttcttcct gggtcttcag cattccctcc      1020
catcatgccc ggtcccaccc ctccctctgt ccaccagccc atgtccctgt gctaatccca      1080
ggattaggcc ataggagtcc taagtgtcac cccgctgtaa gctcctttgt ggagtgctgg      1140
gtaagcagtt tccaataaac gcaagctgag ctggaaaaaa aaaaaaaaaa                 1190

<210> SEQ ID NO 39
<211> LENGTH: 1880
<212> TYPE: DNA
<213> ORGANISM: Homo sapiens

<400> SEQUENCE: 39
aggatgcaag agtcagagtg agggatctgt ccctggatgg ggacaataag gggtcagttc        60
agggggactt ccttgagctc tgaagtttca cctgagaatg ggagattcag aacttggtga       120
cagagtttgt ggagctcact gtgtctttgc tgatccttca gcaaaggaag tgagattgtt       180
tctagctttt ctgtttgggg tgcttctctg tcaactaaaa gtcttcatcc tttaaatatt       240
gcatcatttg tgtatacttc attcattcac ttactcatga cccactcctc gagtgcctgc       300
aatgggcaag cgtctgtcct aggagccgtg tgctgggcca cagttaaatc tgagagatca       360
tgtgtggcat ttctcatgga ttgagatgtc tgagtgtcat tgttttgaga gagctagtgg       420
catggtttat aaagctgttt ttcattttct ccatacagga caacagcttt gagcagttca       480
ttattaatta ttgtaacgaa aagctgcaac aaatcttcat tgaacttact cttaaagaag       540
```

```
agcaggagga gtatatacgg gaggatatag aatggactca cattgactac ttcaataatg        600
ctatcatttg tgacctaata gaaaataaca caaatggaat cctggccatg ctggatgaag        660
agtgcctcag acctggcaca gtcactgatg agaccttctt agaaaagctg aaccaagtat        720
gtgccaccca ccagcatttt gaaagcagga tgagcaagtg ctctcggttc ctcaatgaca        780
cgtctctgcc tcacagctgc ttcaggatcc agcattatgc tggaaaggtg ctgtaccagg        840
tggaaggatt cgttgacaaa aacaatgacc ttctctatcg agacctgccc caagccatgt        900
ggaaggccag ccatgccctc atcaagtctt tgttccccga agggaatccc gccaagatca        960
acctgaaaag gcctcctaca gcaggctcac agttcaaggc atccgtggcc actctgatga       1020
aaaacctaca gaccaagaac ccaaactata ttaggtattt ttggcacatg aaactttcac       1080
agttcaaatg tgagcacacc ccgaaggaat atcattttc  cctttgcttc aatctgagtg       1140
tagcccaagc agagggtaac taaaatactt acagattaaa taatacctta tctgggattg       1200
gcttaaaaaa tgctccacta tccttccccc taaaataaga agtaaaaaa  gtaaagtgtg       1260 gtggagaaga tagtagatat ttaatgaagc tcagtggttg agacctaggg gttttcaact       1320
ttctgtatgt ttattattat ttttttaacg gcaagttaaa aaacaaaatg caagtgtttt       1380
ttctggtcag tgttttgcag aaaactcttg ttggcttcat ttgggattct tgttctatta       1440
gcttagagca cagcattgaa gcaagtgctt tagttaactg ctctggcact tcttaggaga       1500
catgcacttt tttcttccct gtgagaggtg taggcctgga gaaagtaatg attcctaaag       1560
caatctgaat tttttccaag gcagtagaaa gaccttctta aaaagggctg gcgtggtgg        1620 ctcacaccta taatcccaac acttagggag gcggaggcag gtggatcacc tcaggtcagg       1680
aattcgagac tagcctggcc aacatggcaa aaccctgtct ctactaaaaa tataaaaatt       1740
agctgggcgt ggtggcaggg acctataatc ccaactactt gggaggctga ggcaggagaa       1800
tcgcttggag gcagaggttg cagtgagccg aggtcacgcc actgcactcc agcccgggtg       1860
acaatacaag actccatctc                                                  1880

<210> SEQ ID NO 40
<211> LENGTH: 1880
<212> TYPE: DNA
<213> ORGANISM: Homo sapiens

<400> SEQUENCE: 40
aggatgcaag agtcagagtg agggatctgt ccctggatgg ggacaataag gggtcagttc         60 aggggggactt ccttgagctc tgaagtttca cctgagaatg ggagattcag aacttggtga       120
cagagtttgt ggagctcact gtgtctttgc tgatccttca gcaaaggaag tgagattgtt        180
tctagctttt ctgtttgggg tgcttctctg tcaactaaaa gtcttcatcc tttaaatatt        240
gcatcatttg tgtatacttc attcattcac ttactcatga cccactcctc gagtgcctgc        300
aatgggcaag cgtctgtcct aggagccgtg tgctgggcca cagttaaatc tgagagatca        360
tgtgtggcat ttctcatgga ttgagatgtc tgagtgtcat tgttttgaga gagctagtgg       420
catggtttat aaagctgttt ttcatttct  ccatacagga caacagcttt gagcagttca       480
ttattaatta ttgtaacgaa aagctgcaac aaatcttcat tgaacttact cttaaagaag       540
agcaggagga gtatatacgg gaggatatag aatggactca cattgactac ttcaataatg       600
ctatcatttg tgacctaata gaaaataaca caaatggaat cctggccatg ctggatgaag       660
agtgcctcag acctggcaca gtcactgatg agaccttctt agaaaagctg aaccaagtat       720
gtgccaccca ccagcatttt gaaagcagga tgagcaagtg ctctcggttc ctcaatgaca       780
```

| | |
|---|---|
| cgtctctgcc tcacagctgc ttcaggatcc agcattatgc tggaaaggtg ctgtaccagg | 840 |
| tggaaggatt cgttgacaaa acaatgacc ttctctatcg agacctgccc caagccatgt | 900 |
| ggaaggccag ccatgccctc atcaagtctt tgttccccga agggaatccc gccaagatca | 960 |
| acctgaaaag gcctcctaca gcaggctcac agttcaaggc atccgtggcc actctgatga | 1020 |
| aaaacctaca gaccaagaac ccaaactata ttaggtattt ttggcacatg aaactttcac | 1080 |
| agttcaaatg tgagagcacc ccgaaggaat atcattttc cctttgcttc aatctgagtg | 1140 |
| tagcccaagc agagggtaac taaaatactt acagattaaa taataccta tctgggattg | 1200 |
| gcttaaaaaa tgctccacta tccttccc taaaataaga agtaaaaaa gtaaagtgtg | 1260 |
| gtggagaaga tagtagatat ttaatgaagc tcagtggttg agacctaggg gttttcaact | 1320 |
| ttctgtatgt ttattattat tttttaacg gcaagttaaa aaacaaaatg caagtgtttt | 1380 |
| ttctggtcag tgttttgcag aaaactcttg ttggcttcat ttgggattct tgttctatta | 1440 |
| gcttagagca cagcattgaa gcaagtgctt tagttaactg ctctggcact tcttaggaga | 1500 |
| catgcactt tttcttcct gtgagaggtg taggcctgga gaaagtaatg attcctaaag | 1560 |
| caatctgaat tttttccaag gcagtagaaa gaccttctta aaaagggctg ggcgtggtgg | 1620 |
| ctcacaccta taatcccaac acttagggag gcggaggcag gtggatcacc tcaggtcagg | 1680 |
| aattcgagac tagcctggcc aacatggcaa accctgtct ctactaaaaa tataaaaatt | 1740 |
| agctgggcgt ggtggcaggg acctataatc ccaactactt gggaggctga ggcaggagaa | 1800 |
| tcgcttggag gcagaggttg cagtgagccg aggtcacgcc actgcactcc agcccgggtg | 1860 |
| acaatacaag actccatctc | 1880 |

<210> SEQ ID NO 41
<211> LENGTH: 2685
<212> TYPE: DNA
<213> ORGANISM: Homo sapiens

<400> SEQUENCE: 41

| | |
|---|---|
| ggacttggga ggcgcggtga ggagtcaggc ttaaaacttg ttggagggga gtaaccagcc | 60 |
| tgctcctctc gctctcctcc tcgtctgcgc cgcgtttcag agagaaaatt cctgttccaa | 120 |
| gagaaaataa ggcaacatca atgaaggaga aagagccag ccagaaatta tccagcaaat | 180 |
| ctatcatgga tcctaatcag aacgtgaaat gcaagatagt tgtggtggga gacagtcagt | 240 |
| gtggaaaaac tgcgctgctc catgtcttcg ccaaggactg cttccccgag aattacgttc | 300 |
| ctacagtgtt tgagaattac acggccagtt ttgaaatcga cacacaaaga atagagttga | 360 |
| gcctgtggga cacttcgggt tctccttact atgacaatgt ccgccccctc tcttaccctg | 420 |
| attcggatgc tgtgctgatt tgcttttgaca tcagtagacc agagccctg acagtgtcc | 480 |
| tcaaaaagtg gaaggtgaa atccaggaat tttgtccaaa taccaaaatg ctcttggtcg | 540 |
| gctgcaagtc tgatctgcgg acagatgtta gtacattagt agagctctcc aatcacaggc | 600 |
| agacgccagt gtcctatgac caggggcaa atatggccaa acagattgga gcagctactt | 660 |
| atatcgaatg ctcagcttta cagtcggaaa atagcgtcag agacattttt cacgttgcca | 720 |
| ccttggcatg tgtaaataag acaaataaaa acgttaagcg gaacaaatca cagagagcca | 780 |
| caaagcggat ttcacacatg cctagcgac cagaactctc ggcagttgct acggacttac | 840 |
| gaaaggacaa agcgaagagc tgcactgtga tgtgaatctt tcattatctt taatgaagac | 900 |
| aaaggaatct agtgtaaaaa acaacagcaa acaaaaggt gaagtctaaa tgaagtgcac | 960 |
| agccaaagtc atgtatacca gaggcttagg aggcgtttga gaggatactc atctttttgg | 1020 |

-continued

```
aatcctgacc ttaggttcgg catgtagacc aagtgatgag aagtgaatac atggaagagt    1080
ttttaagtgt gacttgaaaa atatgccaaa aaatgagaga tacaaatgag ctagaggaag    1140
atgagggggg atgcgagtac ctccaagaag aaaaatcaca ctctgaatgg tgcttgcatt    1200
tttgggtttt ttttttttt gttataatct attcatggat ctccactttg atttaatttt    1260
taaatgtttt aatctccttt acaaaagta tacgttaata taccgtcctc aaggggaac     1320 tggcactgtg accttagcat ttagttttct agaggatgtg atctaatttc tttctagctc    1380
atcattaaaa aggaaattgt atcaggaccc atgggatata ccagaggca aactttatga     1440 ggctttgaaa tcttgccttc ctgaagatag ctgagtagga tggttctaag gaaagccttt    1500
gcaatcttgc aagatttgta gaccagcact acaaagatcg catagatcaa ataggaaaaa    1560
aaatgtcgat ttttattcag tctgatggtt ctgttcttca ttgtgattgt cattaaaaag    1620
tggtaaattg ctcaatgtaa tattttttgtg cgctgtttag aagttgtgtg attttttgcc   1680
atcgttgata aaaatgcaaa gtcaaataaa aggtgtcttg gtttgatgtc atagaatgat    1740
ccaaggagag aaaaaaggta gttactgttt tcaccagaaa aggtaatgag tgaaggaaag    1800
aatagtagca gaaagcacag tttgtgagta aagctgtctg gaattaagtt accaaaaata    1860
caaagcaaaa ggactattat tttgggttga agctccaaaa ctgacagcat ctgataatct    1920
gttggtttat ttcactttc attaaatgaa cattgatgag agaagatgcc acttacccaa     1980
gctttagaga atccctagtg gaagattata tgataaactt tcagtcctga cataacacta    2040
gggcatttct agagtgtcat tgctaaaacc tcactgaaca gacgcagcca aggtctgtgt    2100
tcagcacttg gtctctgttg ttacgtaaaa taataagcat ttaaaatagt ttacagatat    2160
ttttgaccag ttccttttag agattctttc agagaagaaa ccagatctga cctgtttatt    2220
gttggcgctt gttgaaaacg agctttcttt cccatgatag tgcttcgttt ttgaagtgtt    2280
gaagctgtgc tccccttaaa tcgtggcagg agagattaag gtaattacaa cactcagttc    2340
tatgtcttac aagcactttg tcttgtctct gcaagaaaat tcgattccag tcatttccca    2400
taaaatacag acattttacc aacataatat gctttgattg atgcagcatt atgctttggg    2460
cagtattaca aaatagctgg cgagtgcttt ctgtatttaa atattgtaaa aagaaaataa    2520
gttataactg ttataaagca gaacttttgt tgcattttttt aaactgttga agtcactgtg   2580
tatgtttgtt tggtcaatgt ttccgcagta tttattaaaa catactttttt ttttttcttca  2640 aataaaaaag taaccatgtc tttgtctaaa aaaaaaaaaa aaaaa                    2685
```

<210> SEQ ID NO 42
<211> LENGTH: 4469
<212> TYPE: DNA
<213> ORGANISM: Homo sapiens

<400> SEQUENCE: 42

```
cctgcagcct ccggagtcag tgccgcgcgc ccgccgcccc gcgccttcct gctcgccgca    60
cctccgggag ccggggcgca cccagcccgc agcgccgcct ccccgcccgc gccgcctccg    120
accgcaggcc gagggccgcc actggccggg gggaccgggc agcagcttgc ggccgcggag    180
ccgggcaacg ctggggactg cgccttttgt ccccggaggt ccctggaagt ttgcggcagg    240
acgcgcgcgg ggaggcggcg gaggcagccc cgacgtcgcg gagaacaggg cgcagagccg    300
gcatgggcat cgggcgcagc gaggggggcc gccgcgggc cctgggcgtg ctgctggcgc     360
tgggcgcggc gcttctggcc gtgggctcgg ccagcgagta cgactacgtg agcttccagt    420
cggacatcgg cccgtaccag agcgggcgct tctacaccaa gccacctcag tgcgtggaca    480
```

```
tccccgcgga cctgcggctg tgccacaacg tgggctacaa aagatggtg ctgcccaacc    540 tgctggagca cgagaccatg gcggaggtga agcagcaggc cagcagctgg gtgccctgc     600 tcaacaagaa ctgccacgcc gggacccagg tcttcctctg ctcgctcttc gcgcccgtct    660
gcctggaccg gcccatctac ccgtgtcgct ggctctgcga ggccgtgcgc gactcgtgcg    720
agccggtcat gcagttcttc ggcttctact ggcccgagat gcttaagtgt gacaagttcc    780
cggaggggga cgtctgcatc gccatgacgc cgcccaatgc caccgaagcc tccaagcccc    840
aaggcacaac ggtgtgtcct ccctgtgaca acgagttgaa atctgaggcc atcattgaac    900
atctctgtgc cagcgagttt gcactgagga tgaaaataaa agaagtgaaa aagaaaatg     960 gcgacaagaa gattgtcccc aagaagaaga agcccctgaa gttggggccc atcaagaaga   1020
aggacctgaa gaagcttgtg ctgtacctga agaatgggc tgactgtccc tgccaccagc    1080
tggacaacct cagccaccac ttcctcatca tgggccgcaa ggtgaagagc cagtacttgc   1140
tgacggccat ccacaagtgg gacaagaaaa acaaggagtt caaaaacttc atgaagaaaa   1200
tgaaaaacca tgagtgcccc acctttcagt ccgtgtttaa gtgattctcc cggggggcagg   1260 gtggggaggg agcctcgggt ggggtgggag cggggggggac agtgcccggg aacccgtggt   1320
cacacacacg cactgccctg tcagtagtgg acattgtaat ccagtcggct tgttcttgca   1380
gcattcccgc tcccttttccc tccatagcca cgctccaaac cccagggtag ccatggccgg   1440
gtaaagcaag ggccatttag attaggaagg tttttaagat ccgcaatgtg gagcagcagc   1500
cactgcacag gaggaggtga caaaccattt ccaacagcaa cacagccact aaaacacaaa   1560 aaggggggatt gggcggaaag tgagagccag cagcaaaaac tacattttgc aacttgttgg   1620
tgtggatcta ttggctgatc tatgcctttc aactagaaaa ttctaatgat tggcaagtca   1680
cgttgttttc aggtccagag tagtttcttt ctgtctgctt taaatggaaa cagactcata   1740
ccacacttac aattaaggtc aagcccagaa agtgataagt gcaggagga aaagtgcaag    1800 tccattatct aatagtgaca gcaaagggac caggggagag gcattgcctt ctctgcccac   1860
agtctttccg tgtgattgtc tttgaatctg aatcagccag tctcagatgc cccaaagttt   1920
cggttcctat gagcccgggg catgatctga tccccaagac atgtggaggg gcagcctgtg   1980
cctgcctttg tgtcagaaaa aggaaaccac agtgagcctg agagagacgg cgattttcgg   2040
gctgagaagg cagtagtttt caaaacacat agttaaaaaa gaaacaaatg aaaaaaattt   2100
tagaacagtc cagcaaattg ctagtcaggg tgaattgtga aattgggtga agagcttagg   2160
attctaatct catgtttttt ccttttcaca tttttaaaag aacaatgaca acacccact    2220 tatttttcaa ggttttaaaa cagtctacat tgagcatttg aaaggtgtgc tagaacaagg   2280
tctcctgatc cgtccgaggc tgcttcccag aggagcagct ctccccaggc atttgccaag   2340
ggaggcggat ttccctggta gtgtagctgt gtggctttcc ttcctgaaga gtccgtggtt   2400
gccctagaac ctaacacccc ctagcaaaac tcacagagct ttccgttttt ttctttcctg   2460
taaagaaaca tttcctttga acttgattgc ctatggatca aagaaattca gaacagcctg   2520
cctgttcccc cgcactttt acatatattt gtttcatttc tgcagatgga agttgacat     2580 gggtggggtg tccccatcca gcgagagagt ttcaaaagca aacatctct gcagtttttc     2640 ccaagtaccc tgagatactt cccaaagccc ttatgtttaa tcagcgatgt atataagcca   2700
gttcacttag acaactttac ccttcttgtc caatgtacag gaagtagttc taaaaaaaat   2760
gcatattaat ttcttccccc aaagccggat tcttaattct ctgcaacact ttgaggacat   2820
ttatgattgt ccctctgggc caatgcttat acccagtgag gatgctgcag tgaggctgta   2880
```

| | |
|---|---|
| aagtggcccc ctgcggccct agcctgaccc ggagaaagga tggtagattc tgttaactct | 2940 |
| tgaagactcc agtatgaaaa tcagcatgcc cgcctagtta cctaccggag agttatcctg | 3000 |
| ataaattaac ctctcacagt tagtgatcct gtccttttaa cacctttttt gtggggttct | 3060 |
| ctctgacctt tcatcgtaaa gtgctgggga ccttaagtga tttgcctgta attttggatg | 3120 |
| attaaaaaat gtgtatatat attagctaat tagaaatatt ctacttctct gttgtcaaac | 3180 |
| tgaaattcag agcaagttcc tgagtgcgtg atctgggtc ttagttctgg ttgattcact | 3240 |
| caagagttca gtgctcatac gtatctgctc attttgacaa agtgcctcat gcaaccgggc | 3300 |
| cctctctctg cggcagagtc cttagtggag gggtttacct ggaacataag tagttaccac | 3360 |
| agaatacgga agagcaggtg actgtgctgt gcagctctct aaatgggaat tctcaggtag | 3420 |
| gaagcaacag cttcagaaag agctcaaaat aaattggaaa tgtgaatcgc agctgtgggt | 3480 |
| tttaccaccg tctgtctcag agtcccagga ccttgagtgt cattagttac tttattgaag | 3540 |
| gttttagacc catagcagct ttgtctctgt cacatcagca atttcagaac caaaagggag | 3600 |
| gctctctgta ggcacagagc tgcactatca cgagcctttg ttttctcca caagtatct | 3660 |
| aacaaaacca atgtgcagac tgattggcct ggtcattggt ctccgagaga ggaggtttgc | 3720 |
| ctgtgatttg cctgtgattt cctaattatc gctagggcca aggtgggatt tgtaaagctt | 3780 |
| tacaataatc attctggata gagtcctggg aggtccttgg cagaactcag ttaaatcttt | 3840 |
| gaagaatatt tgtagttatc ttagaagata gcatgggagg tgaggattcc aaaaacattt | 3900 |
| tatttttaaa atatcctgtg taacacttgg ctcttggtac ctgtgggtta gcatcaagtt | 3960 |
| ctccccaggg tagaattcaa tcagagctcc agtttgcatt tggatgtgta aattacagta | 4020 |
| atcccatttc ccaaacctaa aatctgtttt tctcatcaga ctctgagtaa ctggttgctg | 4080 |
| tgtcataact tcatagatgc aggaggctca ggtgatctgt ttgaggagag caccctaggc | 4140 |
| agcctgcagg gaataacata ctggccgttc tgacctgttg ccagcagata cacaggacat | 4200 |
| ggatgaaatt cccgtttcct ctagtttctt cctgtagtac tcctcttta gatcctaagt | 4260 |
| ctcttacaaa agctttgaat actgtgaaaa tgttttacat tccatttcat ttgtgttgtt | 4320 |
| ttttaactg cattttacca gatgtttga tgttatcgct tatgttaata gtaattcccg | 4380 |
| tacgtgttca ttttatttc atgctttttc agccatgtat caatattcac ttgactaaaa | 4440 |
| tcactcaatt aatcaatgaa aaaaaaaaa | 4469 |

<210> SEQ ID NO 43
<211> LENGTH: 1607
<212> TYPE: DNA
<213> ORGANISM: Homo sapiens

<400> SEQUENCE: 43

| | |
|---|---|
| gctctgtagc acccaggagc ggggaagcga agtgcgagag accccggacc ccagcgctgt | 60 |
| ctcttcccgc cgcccgaacc accatgaccc acttcaacaa gggcccttcc tatgggctct | 120 |
| cggccgaagt caagaacaag attgcttcca gtatgatca tcaggcagaa gaagatcttc | 180 |
| gcaattggat agaagaggtg acaggcatga gcattggccc caacttccag ctgggcttaa | 240 |
| aggatggcat catcctctgc gaacttataa acaagctaca gccaggctca gtgaagaagg | 300 |
| tcaacgagtc ctcactgaac tggcctcagt tggagaatat tggcaacttt attaaagcta | 360 |
| ttcaggctta tggtatgaag ccacatgaca tattcgaagc aaatgatctt tttgagaatg | 420 |
| gaaacatgac ccaggttcag actactctgg tggctctagc aggtctggct aaaacaaaag | 480 |
| gattccatac aaccattgac attggagtta agtatgcaga aaaacaaaca agacgttttg | 540 |

```
atgaaggaaa attaaaagct ggccaaagtg taattggtct gcagatggga accaacaaat      600
gtgccagcca ggcaggtatg acagcttacg ggactaggag gcatctttat gatcccaaaa      660
tgcaaactga caaaccttt  gaccagacca caattagtct gcagatgggc actaataaag      720
gagccagcca ggcagggatg ttagcaccag gtaccagaag agacatctat gatcagaagc      780
taacattaca gccggtggac aactcgacaa tttccctaca gatgggtacc aacaaagttg      840
cttcccagaa aggaatgagt gtgtatgggc ttgggcggca agtatatgat cccaaatact      900
gtgctgctcc tacagaacct gtcattcaca acggaagcca aggaacagga acaaatggtt      960
cggaaatcag tgatagtgat tatcaggcag aataccctga tgagtatcat ggcgagtacc     1020
aggatgacta ccccagagat taccaatata gcgaccaagg cattgattat tagatccaca     1080
cagaaggagc tcagtattta gtcctttgtt tttattcagt gagaaccaag ctagccttga     1140 gtaatttta  tcttgtcttc ctaaaacact attaagctta ttgtacttt  aagaaaaatt     1200 gccttacgta cattcctttt tcctttttct gcctcttccc tcaatagttg cctttagtg      1260 ctgtaatagg ttaaatccta cagcataatc aataactcgc atatgaagta aaaggaata      1320 ctgtgaaagg ggagtactct tgtacagcca gttcttttat gcaaaaatct atgcatttt      1380 acaatcttat attaaactgg tatttcaaa  caataggaaa cttttttttt tttttttac      1440 agtttagtgt atctggtttc tacatggaag actaaactca tgcttattgc taaatgtggt     1500
ctttgccaac taaatttaag atgcagcatt ttagaaattt acatatcaat gtttctacag     1560
tattgtttgc taattttaa  ataaagtcat gatcagtgtg aaaaaaa                   1607
```

<210> SEQ ID NO 44
<211> LENGTH: 3144
<212> TYPE: DNA
<213> ORGANISM: Homo sapiens

<400> SEQUENCE: 44

```
ggcacgaggg tccgcccggg ggcgccgccc accgcgcctc gctcgggccg ttgccgtctg       60
cacccagacc ctgagccgcc gccgccggcc atggaggtgg cgccggagca gccgcgctgg      120
atggcgcacc cggccgtgct gaatgcgcag caccccgact cacaccaccc gggcctggcg      180
cacaactaca tggaacccgc gcagctgctg cctccagacg aggtggacgt cttcttcaat      240
cacctcgact cgcagggcaa ccctactat  gccaaccccg ctcacgcgcg ggcgcgcgtc      300
tcctacagcc ccgcgcacgc ccgcctgacc ggaggccaga tgtgccgccc acacttgttg      360
cacagcccgg gtttgccctg gctggacggg ggcaaagcag ccctctctgc cgctgcggcc      420
caccaccaca  accctggac cgtgagcccc ttctccaaga cgccactgca ccctcagct       480 gctggaggcc ctggaggccc actctctgtg tacccagggg ctgggggtgg gagcggggga      540
ggcagcggga gctcagtggc ctccctcacc cctacagcag cccactctgg ctcccacctt      600
ttcggcttcc cacccacgcc acccaaagaa gtgtctcctg accctagcac cacgggggct      660
gcgtctccag cctcatcttc cgcggggggt agtgcagccc gaggagagga caaggacggc      720
gtcaagtacc aggtgtcact gacggagagc atgaagatgg aaagtggcag tccctgcgc      780 ccaggcctag ctactatggg cacccagcct gctacacacc ccccatccc  cacctacccc      840 tcctatgtgc cggcggctgc ccacgactac agcagcggac tcttccaccc cggaggcttc      900 ctgggggggac cggcctccag cttcacccct aagcagcgca gcaaggctcg ttcctgttca      960
gaaggccggg agtgtgtcaa ctgtggggcc acagccaccc ctctctggcg gcgggacggc     1020
accggccact acctgtgcaa tgcctgtggc ctctaccaca gatgaatgg  gcagaaccga     1080
```

```
ccactcatca agcccaagcg aagactgtcg gccgccagaa gagccggcac ctgttgtgca   1140
aattgtcaga cgacaaccac caccttatga cgccgaaacg ccaacgggga ccctgtctgc   1200
aacgcctgtg gcctctacta caagctgcac aatgttaaca ggccactgac catgaagaag   1260
gaagggatcc agactcggaa ccggaagatg tccaacaagt ccaagaagag caagaaaggg   1320
gcggagtgct tcgaggagct gtcaaagtgc atgcaggaga agtcatcccc cttcagtgca   1380
gctgccctgg ctggacacat ggacctgtg ggccacctcc cgcccttcag ccactccgga   1440
cacatcctgc ccactccgac gcccatccac ccctcctcca gcctctcctt cggccacccc   1500
cacccgtcca gcatggtgac cgccatgggc tagggaacag atggacgtcg aggaccgggc   1560
actcccggga tgggtggacc aaacccttag cagcccagca tttcccgaag gccgacacca   1620
ctcctgccag cccggctcgg cccagcaccc cctctcctgg agggcgccca gcagcctgcc   1680
agcagttact gtgaatgttc cccaccgctg agaggctgcc tccgcacctg actgctgccc   1740
aggtggggtt tcctgcatgg acagttgttt ggagaacaac aaggacaact ttatgtagag   1800
aaaaggaggg gacgggacag acgaaggcaa ccatttttag aaggaaaaag gattaggcaa   1860 aaataaattta ttttgctctt gtttctaaca aggacttgga gacttggtgg tctgagctgt   1920
cccaagtcct ccggttcttc ctcgggattg gcgggtccac ttgccagggc tctgggggca   1980
gatttgtggg gacctcagcc tgcaccctct tctcttctgg cttccctctc tgaaatagcc   2040
gaactccagg ctgggctgag ccaaagccag agtggccacg gccagggag ggtgagctgg   2100 tgcctgcttt gacgggccag gccctggagg gcagagacaa tcacgggcgg tcctgcacag   2160
attcccaggc cagggctggg tcacaggaag gaaacaacat tttcttgaaa ggggaaacgt   2220
ctcccagatc gctcccttgg ctttgaggcc gaagctgctg tgactgtgtc cccttactga   2280
gcgcaagcca cagcctgtct tgtcaggtgg accctgtaaa tacatccttt ttctgctaac   2340
ccttcaaccc cctcgcctcc tactctgaga caaaagaaaa aatattaaaa aaatgcatag   2400
gcttaactcg ctgatgagtt aattgtttta ttttaaaact ctttttgggt ccagttgatt   2460
gtacgtagcc acaggagccc tgctatgaaa ggaataaaac ctacacacaa ggttggagct   2520
ttgcaattct ttttggaaaa gagctgggat cccacagccc tagtatgaaa gctggggtg   2580 gggaggggcc tttgctgccc ttggtttctg ggggctggtt ggcatttgct ggcctggcag   2640
ggggtgaagg caggagttgg gggcaggtca ggaccaggac ccaggagag gctgtgtccc   2700 tgctggggtc tcaggtccag ctttactgtg gctgtctgga tccttcccaa ggtacagctg   2760
tatataaacg tgtcccgagc ttagattctg tatgcggtga cggcggggtg tggtggcctg   2820 tgagggccc ctggcccagg aggaggattg tgctgatgta gtgaccaagt gcaatatggg   2880
cgggcagtcg ctgcagggag caccacgcc agaagtaact tattttgtac tagtgtccgc   2940
ataagaaaaa gaatcggcag tatttcctgt ttttatgttt tatttggctt gttttatttt   3000
ggattagtga actaagttat tgttaattat gtacaacatt tatatattgt ctgtaaaaaa   3060
tgtatgctat cctcttattc ctttaaagtg agtactgtta agaataataa aatactttt   3120 gtgaaaaaaa aaaaaaaaaa aaaa                                          3144

<210> SEQ ID NO 45
<211> LENGTH: 2038
<212> TYPE: DNA
<213> ORGANISM: Homo sapiens

<400> SEQUENCE: 45
cgaagggctc gaagatggcc ggttggcaga gctacgtgga taacctgatg tgcgatggct     60
```

-continued

```
gctgccagga ggccgccatt gtcggctact gcgacgccaa atacgtctgg gcagccacgg    120
ccgggggcgt ctttcagagc attacgccaa tagaaataga tatgattgta ggaaaagacc    180
gggaaggttt ctttaccaac ggtttgactc ttggcgcgaa gaaatgctca gtgatcagag    240
atagtctata cgtcgatggt gactgcacaa tggacatccg gacaaagagt caaggtgggg    300
agccaacata caatgtggct gtcggcagag ctggtagagt cttggtcttt gtaatgggaa    360
aagaaggggg ccatggaggc ggattgaata agaaggcata ctcaatggca aaatacttga    420
gagactctgg gttctagctg ctaggcagac tgttaagtat taggggaaaa ttgctcttaa    480
actttcctag ctataagctt aagtcttaat tctggaaatt ttattagcaa tgcagggtga    540
tggggtatga acctgtgtct cctttgtatc cctctgttgg tggggaaagg tgtctttctt    600
tctgccctcc cccccaaaa taattctgtt cacttttgtt ttgtttcctt gtgtactcca    660
gcattggtta tagtcatggg aaaggaaggt gtccacggag gcacacttaa caagaaagca    720
tatgaactcg ctttatacct gaggaggtct gatgtgtaag cagcctctcc ccatctacct    780
agcaactgtc ttcatcaaca accctaatta tggtcacaat gctaccaaac tgtagatggt    840
agctaatttt tctttaccta ttttctaatg tcatgattcc tgtttgccca atggatcatt    900
tgtatgttaa ccactgtatg taaccaaccc ttatctggca acataattgc agcacaataa    960
tgatttgcat gataccttga aattgggggg aggggggcatg ccaagtttggg catcactttg   1020 tcttagcaat taatgggata ttgattacta aaataagtta atattaagca aggtgccggt   1080
tgtacaatct ctgatcagtg tcttttcagc actttgagca tttacttggc tcatttagtc   1140
ttccttttgt agcgcatggt tgggaggaaa aagtgcatgc atcattcctt cactcttctc   1200
tttttcccgc ccccccctcc cttcgcacat aggcatttgg tttgcttcca tctttttta   1260 tgcagtgcct gtttttttt aaccaattaa aatccctttt gttgatgagc tattgagagc    1320
tgcagtagtt tgcttttagt attgttgttg cacttgagca gagacaaacc tttattcata   1380
gtgtctacag gacatatgaa gagtgcaatg gcaaacaag agcaaaaagc acttcctccc    1440
atgaccttac agtaaccata ctgattgaat ccccagggac attccatcat gcaatagct    1500 cagatttttc ttccttttc tttgcacacc agctctactc tttagtaaaa ttgtaaaagg    1560
ctgccattat ggacattagg tatcccaaca taaccatctg gagtgtgtcc agtttgttct    1620
tcataggacc aatttttatt tgcagcttga gttttatat gaagttgcat tattgtggac    1680
ttggctgtct tgtgatgaat ttttttcata tgtattctgt gccatactat tgttaaaatg    1740
aactgttgct attgtgagat ggattttaac tgacctatta agggtttctt tcgaatggca    1800
ctactttagg gacattctag tatttgcttc tattgtttgg gccttgtgga taatgtacag    1860
atttaaaaac aaatcttgtt gctgatttgt ccatttcttt ccctgcactt tgttacatct    1920
gggatacagt ctaactcatc tgatttaata tgcatttaaa aaaatgccat aactattaaa    1980
caccttgttt acagacagat gaaataaatt tattccaacc aaaaaaaaaa aaaaaaa     2038
```

<210> SEQ ID NO 46
<211> LENGTH: 5487
<212> TYPE: DNA
<213> ORGANISM: Homo sapiens

<400> SEQUENCE: 46

```
tctgtcgact tgccccagag ctgatccttg tctttgtcca cttctcagcg aggatggcac     60
ttcagggagc ccttccctta ctatcgcaga gagagcaggc cctccccagt catgtccaac    120
ccagaactct gttttgtttt cttcatagcc ctagcatcac agaaaatcac cctgtgcatt    180
```

```
catgdatgtc cacgggggca agggctttgt gttgcttaac ccagcatcct gaaccgtgtt    240
tgttgaatga atacagaacc ccgtttgctc tgggagagca cagaaaacag tcttctatca    300
tatatcatag ccagctgcaa acagcagatg gcttcccata tcccagagag taagaaccag    360
agagagagag aaagagagag agtttgggtc tttctcctct gtgcctgctc tctccagaga    420
aactggaggg gtagcagtta gcattccccc gctggttcca ccaagcacag tcaaggtctc    480
taggacatgc ccacccctca cctgtggaag cggtcctgct ggggtgggtg ggtgttagtt    540
ggttctggtt tgggtcagag acacccagtg gcccaggtgg gcgtggggcc agggcgcaga    600
cgagaagggg cacgagggct ccgctccgag gacccagcgg caagcaccgg tcccgggcgc    660
gccccagccc acccactcgc gtgcccacgg cggcattatt ccctataagg atctgaacga    720
tccgggggcg gccccgcccc gttacccctt gccccggcc ccgcccctt tttgagggc     780 cgatgaggta atgcggctct gccattggtc tgagggggcg ggcccaaca gcccgaggcg    840 gggtccccgg gggcccagcg ctatatcact cggccgccca ggcagcggcg cagagcgggc    900
agcaggcagg cggcgggcgc tcagacggct tctcctcctc ctcttgctcc tccagctcct    960
gctccttcgc cgggaggccg cccgccgagt cctgcgccag cgccgaggca gcctcgctgc   1020
gccccatccc gtcccgccgg gcactcggag ggcagcgcgc cggaggccaa ggttgccccg   1080
cacggcccgg cgggcgagcg agctcgggct gcagcagccc cgccggcggc gcgcacggca   1140
actttggaga ggcgagcagc agccccggca gcggcggcag cagcggcaat gacccctttgg  1200 ctcgggctca tcgtgctcct gggcagctgg agcctggggg actggggcgc cgaggcgtgc   1260
acatgctcgc ccagccaccc ccaggacgcc ttctgcaact ccgacatcgt gatccgggcc   1320
aaggtggtgg ggaagaagct ggtaaaggag gggccctttcg gcacgctggt ctacaccatc   1380
aagcagatga agatgtaccg aggcttcacc aagatgcccc atgtgcagta catccacacg   1440
gaagcttccg agagtctctg tggccttaag ctggaggtca acaagtacca gtacctgctg   1500
acaggtcgcg tctatgatgg caagatgtac acggggctgt gcaacttcgt ggagaggtgg   1560
gaccagctca ccctctccca gcgcaagggg ctgaactatc ggtatcacct gggttgtaac   1620
tgcaagatca agtcctgcta ctacctgcct tgctttgtga cttccaagaa cgagtgtctc   1680
tggaccgaca tgctctccaa tttcggttac cctggctacc agtccaaaca ctacgcctgc   1740
atccggcaga agggcggcta ctgcagctgg taccgaggat gggcccccccc ggataaaagc   1800 atcatcaatg ccacagaccc ctgagcgcca gacctgccc cacctcactt ccctcccttc    1860
ccgctgagct tccttggac actaactctt cccagatgat gacaatgaaa ttagtgcctg   1920
ttttcttgca aatttagcac ttggaacatt taaagaaagg tctatgctgt catatggggt   1980
ttattgggaa ctatcctcct ggccccaccc tgccccttct ttttggtttt gacatcattc   2040
atttccacct gggaatttct ggtgccatgc cagaaagaat gaggaacctg tattcctctt   2100
cttcgtgata atataatctc tattttttta ggaaaacaaa aatgaaaaac tactccatt    2160 gaggattgta attcccaccc ctcttgcttc ttccccacct caccatctcc cagaccctct   2220
tccctttgcc cttctcctcc aatacataaa ggacacagac aaggaacttg ctgaaaggcc   2280
aaccatttca ggatcagtca aaggcagcaa gcagatagac tcaaggtgtg tgaaagatgt   2340
tatacaccag gagctgccac tgcatgtccc aaccagactg tgtctgtctg tgtctgcatg   2400
taagagtgag ggagggaagg aaggaactac aagagagtcg gagatgatgc agcacacaca   2460
caattcccca gcccagtgat gcttgtgttg accagatgtt cctgagtctg gagcaagcac   2520
ccaggccaga ataacagagc tttcttagtt ggtgaagact taaacatctg cctgaggtca   2580
```

```
ggaggcaatt tgcctgcctt gtacaaaagc tcaggtgaaa gactgagatg aatgtctttc    2640
ctctccctgc ctcccaccag acttcctcct ggaaaacgct ttggtagatt tggccaggag    2700
cttctcttta tgtaaattgg ataaatacac acaccataca ctatccacag atatagccaa    2760
gtagatttgg gtagaggata ctatttccag aatagtgttt agctcaccta gggggatatg    2820
tttgtataca catttgcata tacccacatg gggacataag ctaatttttt tacaggacac    2880
agaattctgt tcaatgctgt taaatatgcc aatagtttaa tctcttctat tttgttgtcg    2940
ttgcttgttt gaagaaaatc atgacattcc aagttgacat ttttttttca ttttaattaa    3000
aatttgaaat tctgaacacc gtcagcaccc tctcttccct atcatgggtc atctgacccc    3060
tgtccgtctc cttgtccctg cttcatgttt gggggccttt ctttaactgc cttcctggct    3120
tagctcagat ggcagatgag agtgtagtca agggcctggg cacaggaggg agagctgcag    3180
agtgtcctgc ctgccttggc tggagggaca cctctcctgg gtgtggagac agcttggttc    3240
cctttcccta gctccctggt gggtgaatgc cacctcctga gatcctcacc tcttggaatt    3300
aaaattgttg gtcactgggg aaagcctgag tttgcaacca gttgtagggt ttctgttgtg    3360 ttttttttt ttttttgaa ataaaactat aatataaatt ctcctattaa ataaaattat    3420
tttaagtttt agtgtcaaaa gtgagatgct gagagtaggt gataatgtat attttacaga    3480 gtggggttg gcaggatggt gacattgaac atgattgctc tctgtctctt ttttcagctt    3540
atgggtattt atcttctatt agtatttgta tcttcagttc attccacttt aggaaacaga    3600
gctgccaatt gaaacagaag aagaaaaaaa aaaaagcag cagacaacac actgtagagt    3660
cttgcacaca cacaagtgcc caggcaaggt gcttggcaga accgcagagt gggaagagag    3720
taccggcatc gggtttcctt gggatcaatt tcattaccgt gtacctttcc cattgtggtc    3780
atgccatttg gcaggggag aatgggaggc ttggccttct ttgtgaggca gtgtgagcag    3840
aagctgatgc cagcatgtca ctggttttga agggatgagc ccagacttga tgttttggga    3900
ttgtccttat tttaacctca aggtctcgca tggtggggcc cctgaccaac ctacacaagt    3960
tccctcccac aagtggacat cagtgtcttc tctgtgaggc atctggccat tcgcactccc    4020
tggtgtggtc agcctctctc acacaaggag gaacttgggt gaaggctgag tgtgaggcac    4080
ctgaagtttc cctgcggagt cgataaatta gcagaaccac atcccatct gttaggcctt    4140 ggtgaggagg ccctgggcaa agaagggtct ttcgcaaagc gatgtcagag gcggttttg    4200 agctttctat aagctatagc tttgtttatt tcacccgttc acttactgta taatttaaaa    4260
tcatttatgt agctgagaca cttctgtatt tcaatcatat catgaacatt ttattttgct    4320
aaatcttgtg tcatgtgtag gctgtaatat gtgtacattg tgtttaagag aaaaatgaaa    4380
cccacatgcc gccattttcc tgaatcaaat tctgcagtgg aatggagagg aaaatacttc    4440
taggcaagca gctagactgg tgaattgggg gaaatagaag gaactagtaa ctgagactcc    4500
tccagcctcc tccctattgg aatcccaatg gctcctggag taggaaaaaa gtttaaacta    4560
cattcatgtt cttgttctgt gtcactcggc cctgggtagt ctaccattta cttcacccca    4620
agtcctgctg cccatccagt tgggaagcca tgattttcct aagaatccag ggccatggga    4680
gatacaattc caagttctcg cttcctcctt tgggcatctc ttctgcctcc caatcaagga    4740
agctccatgc tcaggctctc agctctcggg ccagtgctct gctctgtcca gggtaggtaa    4800
tactgggaga ctcctgtctt ttaccctccc ctcgttccag acctgcctca tggtggcaac    4860
atggttcttg aacaattaaa gaaacaaatg acttttggga atagcccgt ctagggcaaa    4920 ctgtggcccc caggagacac taccctcca tgccccagac ctctgtcttg catgtgacaa    4980
```

-continued

```
ttgacaatct ggactacccc aagatggcac ccaagtgttt ggcttctggc tacctaaggt      5040
taacatgtca ctagagtatt tttatgagag acaaacatta taaaaatctg atggcaaaag      5100
caaaacaaaa tggaaagtag gggaggtgga tgtgacaaca acttccaaat tggctctttg      5160
gaggcgagag gaaggggaga acttggagaa tagtttttgc tttgggggta gaggcttctt      5220
agattctccc agcatccgcc tttcccttta gccagtctgc tgtcctgaaa cccagaagtg      5280
atggagagaa accaacaaga gatctcgaac cctgtctaga aggaatgtat tgttgctaa       5340 atttcgtagc actgtttaca gttttcctcc atgttattta tgaatttat attccgtgaa      5400 tgtatattgt cttgtaatgt tgcataatgt tcacttttta tagtgtgtcc tttattctaa     5460
acagtaaagt ggttttattt ctatcac                                         5487
```

<210> SEQ ID NO 47
<211> LENGTH: 2407
<212> TYPE: DNA
<213> ORGANISM: Homo sapiens

<400> SEQUENCE: 47

```
ggcacgaggc ggaggggggct cagtccgcag ccgccgccgc caccgccgcg cctcggcctc       60
ggtgcaggca gcggccgccg ccgccgagac agctgcgcgg gcgagcatcc ccacgcagca      120
ccttggaagt tgttttcaac catatccagc ctttgccgaa tacatcctat ctgccacaca      180
tccagcgtga ggtccctcca gctacaaggt gggcaccatg gcggagaagt tgactgcca       240 ctactgcagg gatcccttgc aggggaagaa gtatgtgcaa aaggatggcc accactgctg      300
cctgaaatgc tttgacaagt tctgtgccaa cacctgtgtg gaatgccgca agcccatcgg      360
tgcggactcc aaggaggtgc actataagaa ccgcttctgg catgacacct gcttccgctg      420
tgccaagtgc cttcacccct ggccaatga cctttgtg gccaaggaca caagatcct        480 gtgcaacaag tgcaccactc gggaggactc ccccaagtgc aagggtgct tcaaggccat      540 tgtggcagga gatcaaaacg tggagtacaa ggggaccgtc tggcacaaag actgcttcac      600
ctgtagtaac tgcaagcaag tcatcgggac tggaagcttc ttccctaaag gggaggactt      660
ctactgcgtg acttgccatg agaccaagtt tgccaagcat tgcgtgaagt gcaacaaggc      720
catcacatct ggaggaatca cttaccagga tcagccctgg catgccgatt gctttgtgtg      780
tgttacctgc tctaagaagc tggctgggca gcgtttcacc gctgtggagg accagtatta      840
ctgcgtggat tgctacaaga actttgtggc caagaagtgt gctggatgca agaaccccat      900
cactgggttt ggtaaaggct ccagtgtggt ggcctatgaa ggacaatcct ggcacgacta      960
ctgcttccac tgcaaaaaat gctccgtgaa tctggccaac aagcgctttg ttttccacca     1020
ggagcaagtg tattgtcccg actgtgccaa aaagctgtaa actgacaggg gctcctgtcc     1080
tgtaaaatgg catttgaatc tcgttctttg tgtccttact ttctgcccta taccatcaat     1140
aggggaagag tggtccttcc cttctttaaa gttctcctttc cgtctttttct cccattttac    1200 agtattactc aaataagggc acacagtgat catattagca tttagcaaaa agcaaccctg     1260
cagcaaagtg aatttctgtc cggctgcaat ttaaaaatga aaacttaggt agattgactc     1320
ttctgcatgt ttctcataga gcagaaaagt gctaatcatt tagccactta gtgatgtaag     1380
caagaagcat aggagataaa accccccactg agatgcctct catgcctcag ctgggaccca    1440
ccgtgtagac acacgacatg caagagttgc agcggctgct ccaactcact gctcaccctc     1500
ttctgtgagc aggaaaagaa ccctactgac atgcatggtt taacttcctc atcagaactc     1560
tgcccttcct tctgttcttt tgtgctttca ataactaac acgaacttcc agaaaattaa      1620
```

```
catttgaact tagctgtaat tctaaactga cctttccccg tactaacgtt tggtttcccc    1680
gtgtggcatg ttttctgagc gttcctactt taaagcatgg aacatgcagg tgatttggga    1740
agtgtagaaa gacctgagaa aacgagcctg tttcagagga acatcgtcac aacgaatact    1800
tctggaagct taacaaaact aaccctgctg tccttttat tgtttttaat taatattttt     1860
gttttaattg atagcaaaat agtttatggg tttggaaact tgcatgaaaa tattttagcc    1920
ccctcagatg ttcctgcagt gctgaaattc atcctacgga agtaaccgca aaactctaga    1980
gggggagttg agcaggcgcc agggctgtca tcaacatgga tatgacattt cacaacagtg    2040
actagttgaa tcccttgtaa cgtagtagtt gtctgctctt tgtccatgtg ttaatgagga    2100
ctgcaaagtc ccttctgttg tgattcctag gacttttcct caagaggaaa tctggatttc    2160
cacctaccgc ttacctgaaa tgcaggatca cctacttact gtattctaca ttattatatg    2220
acatagtata atgagacaat atcaaaagta aacatgtaat gacaatacat actaacattc    2280
ttgtaggagt ggttagagaa gctgatgcct catttctaca ttctgtcatt agctattatc    2340
atctaacgtt tcagtgtatc cttacagaaa taaagcagca tatgaaaaaa aaaaaaaaaa    2400
aaaaaaa                                                              2407

<210> SEQ ID NO 48
<211> LENGTH: 2649
<212> TYPE: DNA
<213> ORGANISM: Homo sapiens

<400> SEQUENCE: 48
tccgaattaa ttggatttca ttcactgggg aggaacaaaa actatctggg cagcttcatt      60
gagagagatt cattgacact aagagccagc ggctgcagct gggtgcagag agaacctccg     120
gctttacttc tgtctcgtct gccccaaccg ctagcctcgg cttgggtaag gcgaggcgga     180
attaaacccc gctccgagag cggcagcttc gcgcgcggtg cgctcggcct atgcctgccc     240 cgagggggcgt ctggtaggca ccccgccctc tcccgcagct cgaccccat gatagatacg      300 ctcagacccg tgcccttcgc gtcggaaatg gcgatcagca agacggtggc gtggctcaac     360
gagcagctgg agctgggcaa cgagcggctg ctgctgatgg actgccggcc gcaggagcta     420
tacgagtcgt cgcacatcga gtcggccatc aacgtggcca tcccgggcat catgctgcgg     480
cgcctgcaga agggtaacct gccggtgcgc gcgctcttca cgcgcggcga ggaccgggac     540
cgcttcaccc ggcgctgtgg caccgacaca gtggtgctct acgacgagag cagcagcgac     600
tggaacgaga atacgggcgg cgagtcgttg ctcgggctgc tgctcaagaa gctcaaggac     660
gagggctgcc gggcgttcta cctggaaggt ggcttcagta agttccaagc cgagttctcc     720
ctgcattgcg agaccaatct agacggctcg tgtagcagca gctcgccgcc gttgccagtg     780
ctggggctcg ggggcctgcg gatcagctct gactcttcct cggacatcga gtctgacctt     840
gaccgagacc ccaatagtgc aacagactcg gatggtagtc cgctgtccaa cagccagcct     900
tccttcccag tggagatctt gccccttcctc tacttgggct gtgccaaaga ctccaccaac     960
ttggacgtgt tggaggaatt cggcatcaag tacatcttga acgtcacccc caatttgccg    1020
aatctctttg agaacgcagg agagtttaaa tacaagcaaa tccccatctc ggatcactgg    1080
agccaaaacc tgtcccagtt ttttccctgag gccatttctt tcatagatga agcccggggc    1140
aagaactgtg tgtcttggt acattgcttg gctggcatta gccgctcagt cactgtgact    1200
gtggcttacc ttatgcagaa gctcaatctg tcgatgaacg atgcctatga cattgtcaaa    1260
atgaaaaaat ccaacatatc ccctaacttc aacttcatgg gtcagctgct ggacttcgag    1320
```

| | |
|---|---|
| aggacgctgg gactcagcag cccatgtgac aacagggttc cagcacagca gctgtatttt | 1380 |
| accacccctt ccaaccagaa tgtataccag gtggactctc tgcaatctac gtgaaagacc | 1440 |
| ccacatccct ccttgctgga atgtgtctgg cccttcagca gtttctcttg cagcatcag | 1500 |
| ctgggctgct ttctttgtgt gtggcccag gtgtcaaaat gacaccagct gtctgtacta | 1560 |
| gacaaggtta ccaagtgcgg aattggttaa tactaacaga gagatttgct ccattctctt | 1620 |
| tggaataaca ggacatgctg tatagataca ggcagtaggt tgctctgta cccatgtgta | 1680 |
| cagcctaccc atgcagggac tgggattcga ggacttccag gcgcataggg tagaaccaaa | 1740 |
| tgatagggta ggagcatgtg ttctttaggg ccttgtaagg ctgtttcctt ttgcatctgg | 1800 |
| aactgactat ataattgtct tcaatgaaga ctaattcaat tttgcatata gaggagccaa | 1860 |
| agagagattt cagctctgta tttgtggtat cagtttggaa aaaaaaatct gatactccat | 1920 |
| ttgattattg taaatatttg atcttgaatc acttgacagt gtttgtttga attgtgtttg | 1980 |
| ttttttcctt tgatgggctt aaaagaaatt atccaaaggg agaaagagca gtatgccact | 2040 |
| tcttaaaaca gaacaaaaca aaaaagaaa attgtgctct tttctaatcc aaagggtata | 2100 |
| tttgcagcat gcttgacttt accaattctg atgacatctt tacggacact attatcacta | 2160 |
| agaccttgtt atggcgaagt ctttagtctt tttcatgtat tttcctcatg attttttctc | 2220 |
| tttatgtagt ttgactatgc cttacctttg taaatatttt tgcttgtgtt gtcgcaaagg | 2280 |
| ggataatctg ggaaagacac caaatcatgg gctcacttta aaaaagaaa gaataaaaaa | 2340 |
| accttcagct gtgctaaaca gtatattacc tctgtataaa attcttcagg gagtgtcacc | 2400 |
| tcaaatgcaa tactttgggt tggtttcttt cctttaaaaa aatttgtata aaactggaag | 2460 |
| tgtgtgtgtg tgagcatggg tacccatttg ataagagaaa tgcatttgat tgtgaagaag | 2520 |
| ggagagttaa attctccatt atgttcgtgg tgtaaagttt agagctggaa tttattataa | 2580 |
| gaatgtaaaa ccttaaatta ttaataaata actattttgg ctattgaaaa aaaaaaaaaa | 2640 |
| aaaaaaaaa | 2649 |

```
<210> SEQ ID NO 49
<211> LENGTH: 670
<212> TYPE: DNA
<213> ORGANISM: Homo sapiens

<400> SEQUENCE: 49
```

| | |
|---|---|
| cggccacgag gcggaatccc ttctgctctc ccagcgcagc gccgccgccc ggcccctcca | 60 |
| gcttcccgga ccatggccaa cctggagcgc accttcatcg ccatcaagcc ggacggcgtg | 120 |
| cagcgcggcc tggtgggcga gatcatcaag cgcttcgagc agaagggatt ccgcctcgtg | 180 |
| gccatgaagt tcctccgggc ctctgaagaa cacctgaagc agcactacat tgacctgaaa | 240 |
| gaccgaccat tcttccctgg gctggtgaag tacatgaact cagggccggt tgtggccatg | 300 |
| gtctgggagg ggctgaacgt ggtgaagaca ggccgagtga tgcttgggga gaccaatcca | 360 |
| gcagattcaa agccaggcac cattcgtggg gacttctgca ttcaggttgg caggaacatc | 420 |
| attcatggca gtgattcagt aaaaagtgct gaaaaagaaa tcagcctatg gtttaagcct | 480 |
| gaagaactgg ttgactacaa gtcttgtgct catgactggg tctatgaata agaggtggac | 540 |
| acaacagcag tctccttcag cacggcgtgg tgtgtccctg gacacagctc ttcattccat | 600 |
| tgacttagag gcaacaggat tgatcattct tttatagagc atatttgcca ataaagcttt | 660 |
| tggaagccgg | 670 |

```
<210> SEQ ID NO 50
```

<211> LENGTH: 1675
<212> TYPE: DNA
<213> ORGANISM: Homo sapiens

<400> SEQUENCE: 50

```
ccagccgtcc attccggtgg aggcagaggc agtcctgggg ctctggggct cgggctttgt      60
caccgggacc cgcaggagcc agaaccactc ggcgccgcct ggtgcatggg aggggagccg     120
ggccaggagt aagtaactca tacgggcgcc ggggacccgg gtcgggctgg gggcttccaa     180
ctcagaggga gtgtgatttg cctgatcctc ttcggcgttg tcctgctctg ccgcatccag     240
ccctgtaccg ccatcccact tcccgccgtt cccatctgtg ttccgggtgg gatcggtctg     300
gaggcggccg aggacttccc aggcaggagc tcgggcgga ggccgggtcc gcggcagacc      360
agggcagcga ggcgctggcc ggcaggggc gctgcggtgc cagcctgagg ctgggctgct      420
ccgcgaggat acagcggccc ctgccctgtc ctgtcctgcc ctgccctgtc ctgtcctgcc     480
ctgccctgcc ctgtcctgtc ctgccctgcc ctgccctgtg tcctcagaca atatgttagc     540
cgtgcacttt gacaagccgg aggaccggaa aaacctctac gtgaaggagg tggccaagcc     600
gagcccgggg gagggtgaag tcctcctgaa ggtggcggcc agcgccctga ccgggcgga      660
cttaatgcag agacaaggcc agtatgaccc acctccagga gccagcaaca ttttgggact     720
tgaggcatct ggacatgtgg cagagctggg gcctggctgc cagggacact ggaagatcgg     780
ggacacagcc atggctctgc tccccggtgg gggccaggct cagtacgtca ctgtccccga     840
agggctcctc atgcctatcc agagggatt gaccctgacc caggctgcag ccatcccaga      900
ggcctggctc accgccttcc agctgttaca tcttgtggga aatgttcagg ctggagacta     960
tgtgctaatc catgcaggac tgagtggtgt gggcacagct gctatccaac tcacccggat    1020
ggctggagct attcctctgg tcacagctgg ctcccagaag aagcttcaaa tggcagaaaa    1080
gcttggagca gctgctggat tcaattacaa aaagaggat ttctctgaag caacgctgaa     1140
attcaccaaa ggtgctggag ttaatcttat tctagactgc ataggcggat cctactggga    1200
gaagaacgtc aactgcctgg ctcttgatgg tcgatgggtt ctctatggtc tgatgggagg    1260
aggtgacatc aatgggcccc tgttttcaaa gctactttt aagcgaggaa gtctgatcac     1320
cagtttgctg aggtctaggg acaataagta caagcaaatg ctggtgaatg ctttcacgga    1380
gcaaattctg cctcacttct ccacggaggg cccccaacgt ctgctgccgg ttctggacag    1440
aatctaccca gtgaccgaaa tccaggaggc ccataagtac atggaggcca acaagaacat    1500
aggcaagatc gtcctggaac tgccccagtg aaggaggatg gggcaggaca ggacgcggcc    1560
accccaggcc tttccagagc aaacctggag aagattcaca atagacaggc caagaaaccc    1620
ggtgcttcct ccagagccgt ttaaagctga tatgaggaaa taaagagtga actgg         1675
```

<210> SEQ ID NO 51
<211> LENGTH: 4099
<212> TYPE: DNA
<213> ORGANISM: Homo sapiens

<400> SEQUENCE: 51

```
cagctgccag ccgaggaggc gcggcggaga ggggactgcg gtcagctgcg tccacttggg      60
gctgtgcggc ggtcccgcgc ccggcgatgt tcccgggcac tccctgagta gcggcagctt     120
atccccgcc cgctagcccg ccctggtccc cggctcgctc gctggctggc gcggccccgg      180
ccccgctctg cgtcgccccc gcgcggtgg aggcgcgcga gggggacgcg gccggggatg      240
agcggattgc gggtgaactc gccgcccggg ggccccgcga agccgtgagc cgctgctttt     300
```

```
ctccgagtcg ccgccctgcc cttggatttg agatcatgtc catccacatc gtggcgctgg    360
ggaacgaggg ggacacattc caccaggaca accggccgtc ggggcttatc cgcacttacc    420
tggggagaag ccctctggtc tccggggacg agagcagctt gttgctgaac gcggccagca    480
cggtcgcgcg tccggtgttc accgagtatc aggccagtgc gtttgggaat gtcaagctgg    540
tggtccacga ctgtcccgtc tgggacatat ttgacagtga ttggtacact tctcgaaatc    600
taattggggg cgctgacatc attgtgatca aatacaacgt taatgacaag ttttcattcc    660
atgaagtaaa ggataattat attccagtga taaaagagc attaaattca gttccagtaa    720
ttattgctgc tgttggtacc agacaaaatg aagagttacc ttgtacatgc ccactatgta    780
cctcagacag agggagctgt gttagtacaa ctgaagggat ccaacttgca aaagaactag    840
gagcaaccta tcttgaactc cacagccttg atgacttcta cataggaaag tattttggag    900
gagtgttgga gtatttttatg attcaagcct taaatcagaa gacaagtgaa aaaatgaaga    960
aaagaaaaat gagcaactcc tttcatggaa ttagaccacc tcaacttgaa caaccagaaa   1020
aaatgcctgt cttaaaggct gaagcgtcac attataactc tgacttaaat aacttgctgt   1080
tctgctgcca gtgtgtggac gtggtatttt ataaccccga tttaaagaaa gttgtagagg   1140
cccacaagat cgttctctgc gctgtaagcc atgtttttcat gctgcttttc aatgtgaaga   1200
gtcccactga cattcaggat tccagtatca tccgaactac ccaggatctt tttgctataa   1260
acagagatac tgcatttcca ggtgctagcc atgaatcttc aggcaaccca ccattacgag   1320
tcattgttaa agacgccctc ttctgttctt gtttatcaga catccttcgc ttcatttatt   1380
caggtgcttt tcagtgggaa gaattggaag aagatatcag gaagaagttg aaagattctg   1440
gggatgtttc aaatgtaatc gagaaagtta atgcattttt aaaaacacca ggaaagatta   1500
attgcctaag gaattgcaaa acctatcaag ccagaaaacc tttgtggttt tataacactt   1560
ccctcaagtt tttccttaat aagccgatgc ttgccgatgt tgtcttcgaa attcaaggta   1620
cgacagtgcc agcccacagg gccatcctgg tggcccgttg tgaagtgatg gcagccatgt   1680
ttaatggtaa ttacatggaa gcaaagagtg tcctgattcc cgtttatggt gtttccaaag   1740
agactttctt gtcattttta gaatacctgt acacagactc ctgctgccca gctggcatat   1800
tccaggccat gtgtctcctg atctgtgccg agatgtacca agtgtccaga ctgcagcaca   1860
tctgtgagct gttcatcatt acccagctgc agagcatgcc aagcagggaa ctggcatcca   1920
tgaaccttga tatagttgac ctgcttaaaa aggccaagtt tcaccactct gattgccttt   1980
caacctggct acttcatttc attgctacta actacctcat cttcagtcaa aagcctgaat   2040
ttcaggatct ttcagtggaa gaacgcagtt ttgttgaaaa gcacagatgg ccgtcgaata   2100
tgtacttgaa gcagcttgcg gaatacagga agtatattca ctcccggaaa tgtcgttgct   2160
tagtaatgta acctggagct tttatacact acatttcttt tttattatta tgaagaatgg   2220
gatacctcca ggttccagta aaattcttct gaccgaaacc aatgtgggtg ttagaaaaat   2280
taccatatag cttaatatgt ttattagttc tctttggaaa aaaactacca ctgtggtctt   2340
aaaagggaac aaaatatacc ataggctaaa actaaggctt tcactctaga atgcaaagct   2400
gttttgcagc tgtttttccct taaagatgtc ctgttgcttt agtgatattt agaccctct   2460 cagttaagaa atgcttagat taaaaaaaaa aaattacgta ggattaatac agaaatttaa   2520
tcatgtctga ttaattgctc tattaaaata agggcatttt aaagacccag cataaccatt   2580
tgtataatga gaaatctagg ggaaaaccaa tcagtccaac atgagatttt aggaatagaa   2640
atttgccggc catttggaaa gtgaaatgcc acttagttct caattgatga cagtgtttga   2700
```

-continued

| | |
|---|---|
| atcatcataa aaaaaatacc tgcttttcat ctggacaacc caattgagcc actttatctc | 2760 |
| cttttggcaa tctgagtagg cggggaacct aggcagggct ggctttctta gcgtgtaact | 2820 |
| tgtgtagcag cacagggccc acacttagaa ggaccccaca cttggttcaa ggctctgcta | 2880 |
| tagcggaaat tcttaataat gtttgaagaa gggcccatg atttcatttt gtgctgagcc | 2940 |
| ctcaaaatta tgtctgtttc gtggtgggaa atatcctatg ttttcttgct caaacacctt | 3000 |
| tctctctgaa agcagaaaaa ggcactgata taaaggaag agaaggaggc tcaccggagg | 3060 |
| gaagagaaca tagtgaagat tcccgccttt ggggaggtct ggaccaccca gggcctccac | 3120 |
| tgccaccttg gctggcaagg gagaaatgtg ttgtgttgtc ttagctttaa aacagtcaca | 3180 |
| gttcttgctc tatcatagat gaacaaatac tttcttgatc attctgtaag accaggaggt | 3240 |
| tggtaagagt gactaaccag cctaacttta atacacatgt ataaagatgt tcacagagaa | 3300 |
| agatgctctg tagagaattt gctaccgaag ttggctcaag aatttgtttt tagtgttatt | 3360 |
| taccaagatt aggacgtcag tggcttaaat tctttgaatt cttttcaagg actgcaagat | 3420 |
| tatttgataa agagtagcat gaatcttgtg ctctaatatt acacagtaag ttcaaagaaa | 3480 |
| ggatgtaagt caaagacttg ttacatagag ggaaaatgga ctgggataga ggacagactg | 3540 |
| atagtttctt tctttcatat cacatgtata gagaaataat tatatcagaa actcacaaac | 3600 |
| ctagacatgg aaaaacagat tactgtctat tgtcagcatc attttcatct gtaagtcact | 3660 |
| actggaatat atttttcttt taatttccag tgactttaga atacacacag tttttccgac | 3720 |
| ttttcaaaaa tttgattaaa tggttttata gtataatatt gggacccat accgttagcc | 3780 |
| cttgtatgta taccaacact gccaaagtaa aacattaggt caggcatggt ggctcaggcc | 3840 |
| tgtaatccca gcattttggg aggctgaggc aagtggataa cttgaggtca tgagttcgaa | 3900 |
| accagcctgg ccaaaacagt gaaacccgt ctctactaaa aatacaaaat tagccagatg | 3960 |
| tggtggcgca cacctgtaat cccagctact caggaagctg aggcaggaaa atcgcttgaa | 4020 |
| cctgggaggt ggaagttgca gtgagccgag atcgcaccac tgcactccag cctgggtgac | 4080 |
| aagagcgaaa ctccatctc | 4099 |

<210> SEQ ID NO 52
<211> LENGTH: 2508
<212> TYPE: DNA
<213> ORGANISM: Homo sapiens

<400> SEQUENCE: 52

| | |
|---|---|
| cgcgcccctc cctcctcgcg gacctggcgg tgccggcgcc cggagtggcc ctttaaaagg | 60 |
| cagcttattg tccggagggg gcgggcgggg ggcgccgacc gcggcctgag gcccggcccc | 120 |
| tcccctctcc ctccctctgt ccccgcgtcg ctcgctggct agctcgctgg ctcgctcgcc | 180 |
| cgtccggcgc acgctccgcc tccgtcagtt ggctccgctg tcgggtgcgc ggcgtggagc | 240 |
| ggcagccggt ctgacgcgc ggccggggct ggggctggg agcgcggcgc gcaagatctc | 300 |
| cccgcgcgag agcggcccct gccaccgggc gaggcctgcg ccgcgatggc agagatgggc | 360 |
| agtaaagggg tgacgcggg aaagatcgcc agcaacgtgc agaagaagct cacccgcgcg | 420 |
| caggagaagg ttctccagaa gctggggaag gcagatgaga ccaaggatga gcagtttgag | 480 |
| cagtgcgtcc agaatttcaa caagcagctg acgagggca cccggctgca gaaggatctc | 540 |
| cggacctacc tggcctccgt caaagccatg cacgaggctt ccaagaagct gaatgagtgt | 600 |
| ctgcaggagg tgtatgagcc cgattggccc ggcaggatg aggcaaacaa gatcgcagag | 660 |
| aacaacgacc tgctgtggat ggattaccac cagaagctgg tggaccaggc gctgctgacc | 720 |

| | |
|---|---|
| atggacacgt acctgggcca gttccccgac atcaagtcac gcattgccaa gcggggggcgc | 780 |
| aagctggtgg actacgacag tgcccggcac cactacgagt cccttcaaac tgccaaaaag | 840 |
| aaggatgaag ccaaaattgc caagcctgtc tcgctgcttg agaaagccgc cccccagtgg | 900 |
| tgccaaggca aactgcaggc tcatctcgta gctcaaacta acctgctccg aaatcaggcc | 960 |
| gaggaggagc tcatcaaagc ccagaaggtg tttgaggaga tgaatgtgga tctgcaggag | 1020 |
| gagctgccgt ccctgtggaa cagccgcgta ggtttctacg tcaacacgtt ccagagcatc | 1080 |
| gcgggcctgg aggaaaactt ccacaaggag atgagcaagc tcaaccagaa cctcaatgat | 1140 |
| gtgctggtcg gcctggagaa gcaacacggg agcaacacct tcacggtcaa ggcccagccc | 1200 |
| agtgacaacg cgcctgcaaa agggaacaag agcccttcgc ctccagatgg ctcccctgcc | 1260 |
| gccaccccg agatcagagt caaccacgag ccagagccgg ccggcggggc cacgcccggg | 1320 |
| gccaccctcc ccaagtcccc atctcagttt gaggccccgg ggccttttctc ggagcaggcc | 1380 |
| agtctgctgg acctggactt tgaccccctc ccgcccgtga cgagccctgt gaaggcaccc | 1440 |
| acgccctctg gtcagtcaat tccatgggac ctctgggagc ccacagagag tccagccggc | 1500 |
| agcctgcctt ccggggagcc cagcgctgcc gagggcacct ttgctgtgtc ctggcccagc | 1560 |
| cagacggccg agccggggcc tgcccaacca gcagaggcct cggaggtggc gggtgggacc | 1620 |
| caacctgcgg ctggagccca ggagccaggg gagacggcgg caagtgaagc agcctccagc | 1680 |
| tctcttcctg ctgtcgtggt ggagaccttc ccagcaactg tgaatggcac cgtggagggc | 1740 |
| ggcagtgggg ccgggcgctt ggacctgccc ccaggtttca tgttcaaggt acaggcccag | 1800 |
| cacgactaca cggccactga cacagacgag ctgcagctca aggctggtga tgtggtgctg | 1860 |
| gtgatcccct tccagaaccc tgaagagcag gatgaaggct ggctcatggg cgtgaaggag | 1920 |
| agcgactgga accagcacaa ggagctggag aagtgccgtg gcgtcttccc cgagaacttc | 1980 |
| actgagaggg tcccatgacg gcggggccca ggcagcctcc gggcgtgtga agaacacctc | 2040 |
| ctcccgaaaa atgtgtggtt cttttttttg ttttgttttc gtttttcatc ttttgaagag | 2100 |
| caaagggaaa tcaagaggag acccccaggc agagggggcgt tctcccaaag attaggtcgt | 2160 |
| tttccaaaga gccgcgtccc ggcaagtccg gcggaattca ccagtgttcc tgaagctgct | 2220 |
| gtgtcctcta gttgagtttc tggcgcccct gcctgtgccc gcatgtgtgc ctggccgcag | 2280 |
| ggcggggctg ggggctgccg agccaccatg cttgcctgaa gcttcggccg cgccacccgg | 2340 |
| gcaagggtcc tcttttcctg gcagctgctg tgggtggggc ccagacacca gcctagcctg | 2400 |
| gctctgcccc gcagacggtc tgtgtgctgt ttgaaaataa atcttagtgt tcaaaacaaa | 2460 |
| atgaaacaaa aaaaaaatga taaaaactct caaaaaaaaa aaaaaaa | 2508 |

```
<210> SEQ ID NO 53
<211> LENGTH: 2278
<212> TYPE: DNA
<213> ORGANISM: Homo sapiens

<400> SEQUENCE: 53
```

| | |
|---|---|
| ggggagtgct ccattttccc cgacagcgaa tttcccctga gaaacgatac tagaccctgg | 60 |
| gtttgcccac cttgtaactc ttccttatct cctccttttc atccctaatt catcctccct | 120 |
| ctggcatgga attgacgccc gtgcagtaca tttgccaagt ggcaccttct ttcaatttat | 180 |
| gttttatttt gctatggtgg tgattcttta tttgctggtt gtcttttctc acacatcttt | 240 |
| ctctctgtct ctctctttcc tgctctttgt ttttctgccc agaaaaacct gacttcgata | 300 |
| ccaaaaaaga tgaaactaca gaaactcaaa tttaaaaaaa actttaaaag aaacaaaaaa | 360 |

```
atactcaacg attctttcag ctttattaac attttccatt gtttcttgcg acttgtgtct      420
cgttctttgt agtattgatg atgaacattt gataatgaat gttcttgtat attcagataa      480
agaaaaaaaa aaccaaaaaa gcggtctgaa tttaatagtg tttataataa aaattttaaa      540
aatgaccctc atagcacgca aaacaggatg gggaatttcc cctcttcttt ctgtgacaat      600
gcgcatcatt cctgcattag tttttaacac cagactacct acattcatca tttccctcat      660
ttttctttta ttttcttgca tttgtgaatt agttcaagaa tgctagaaaa gtgtcgagtt      720
gtgcacatcc atttcttgtt tcacaatgtt taaaagtgac agtaattcat tttgtaaact      780
aaaaaaaaaa aaaaaaaggt tggaatagtg agcataatag gtacaaccta acacattatt      840
atgtttatta actttgagac ccagaaataa attcttttct tttcttgatt cttgctctta      900
aaaatacaaa aaaaaaaatg ttttgttttg tgttattttt ggtttgttta ttgggggget      960 ttttttaatt gtcaggatta tgatcttgct gttttttcttc aatatgtata caaggtgatg     1020
tgaaaagatg acttgggcag aggagtaaga acaagtaggc ttgttcttct actttgcttc     1080
agaattcagt taatgccaaa agcgaagatc aagcccatgt tgatgtctcg ttgctcacct     1140
gcatttccag agagtgtgac actcatgcag tccctgagaa aaataaaatc agggacatac     1200
ttctcctttt agccttttaa aaattcaaaa acgtttagtc caagggaact ttttatgcta     1260
tcaggaaagg tttttgctgt ttttgattct gattatcaca gccaagtact ttgttttatt     1320
tctccctaat taataactac attccatgag gcctcttcca accaagagg  cctttcttc      1380 caggagagtc ccgcaggaga tgctggtatg atgggcacca ttggttaagt aaactacatg     1440
caggaagaag tccttggggc cagtctgcca gctgagtcct ggttttggat gaagagttaa     1500
tgagatattg ggccaggctc aatgctgtag ttttaatgct aagaggttac gtttacttca     1560
cagagtacac ctcttagtaa cctctgactt aggcagctgc ttaaagcaaa ttgcaaaact     1620
ggcttgattt ggaatgtttt tattagagga aaaagaaag  ccatattatc tggaaaaaaa     1680
ttcattttaa ataccatcat tcaacaaatt atgttcagaa agtggtcaga acttaagcaa     1740
gaaaagtaaa gaaagaatgc agaattgtgg agcaatgctt taggaaatat ttctacctga     1800
acacttgtac tcttgaagtc acaacaaaat aatgatgagc ttttcacatc acctttatgg     1860
tttcaatccc tagctcaaag cttcctggaa tcttttattt tttgtaaact ttttttttcttc    1920 ttgttaaaat aaataaaaca ttcaatgttt ttctcctttt ctctcttatt acttctttcc     1980
tttggcattt tcaatttgaa atgctttcct ttggttgttg gttttattct ccccctaccc     2040 ctccccttt  cttattattc agaatataaa cctgcaaagc tctgctctgt tttggttttg     2100
aaagtttaag cttttctgct tctgtgagag cacaggcttc tgtcccttt  gattccaact     2160 gaactttgt  gttctctaat gatactaaca cggtgtaggt tttacagtct cctaatttgt     2220
actggtaatg catattccaa ataaatagtt tcttttgttg caaaaaaaaa aaaaaaa       2278
```

<210> SEQ ID NO 54  
<211> LENGTH: 4322  
<212> TYPE: DNA  
<213> ORGANISM: Homo sapiens

<400> SEQUENCE: 54

```
cccccagagg cgccggagcc cggaatcccg ctcggagcca gccagccgtc ccgagctacc       60
agcaggtttc attgaaaaca gatcctgcaa aagttccagg tgcccacact ggaaacttgg      120
agatcctgct tcccagacca cagctgtggg gaacttgggg tggagcagag aagtttctgt      180
attcagctgc ccaggcagag gagaatgggg tctccacagc ctgaagaatg aagacacgac      240
```

```
agaataaaga ctcgatgtca atgaggagtg gacggaagaa agaggcccct gggccccggg      300
aagaactgag atcgagggc cgggcctccc ctggaggggt cagcacgtcc agcagtgatg      360
gcaaagctga gaagtccagg cagacagcca agaaggcccg agtagaggaa gcctccaccc      420
caaaggtcaa caagcagggt cggagtgagg agatctcaga gagtgaaagt gaggagacca      480
atgcaccaaa aaagaccaaa actgaggaac tccctcggcc acagtctccc tccgatctgg      540
atagcttgga cgggcggagc cttaatgatg atggcagcag cgaccctagg gatatcgacc      600
aggacaaccg aagcacgtcc cccagtatct acagccctgg aagtgtggag aatgactctg      660
actcatcttc tggcctgtcc cagggccag cccgccccta ccacccacct ccactctttc       720
ctccttcccc tcaaccgcca gacagcaccc ctcgacagcc agaggctagc tttgaacccc      780
atccttctgt gacacccact ggatatcatg ctcccatgga gccccccaca tctcgaatgt      840
tccaggctcc tcctggggcc cctcccctc acccacagct ctatcccggg ggcactggtg       900
gagttttgtc tggaccccca atgggtccca aggggggagg ggctgcctca tcagtggggg      960
gccctaatgg gggtaagcag caccccccac ccactactcc catttcagta tcaagctctg     1020
gggctagtgg tgctccccca acaaagccgc ctaccactcc agtgggtggt gggaacctac     1080
cttctgctcc accaccagcc aacttccccc atgtgacacc gaacctgcct ccccacctg      1140 ccctgagacc cctcaacaat gcatcagcct ctcccctgg cctggggggcc caaccactac     1200 ctggtcatct gccctctccc cacgccatgg gacagggtat cggtggactt cctcctggcc     1260
cagagaaggg cccaactctg gctccttcac cccactctct gctcctgct tcctcttctg      1320 ctccagcgcc ccccatgagg tttccttatt catcctctag tagtagctct gcagcagcct     1380
cctcttccag ttcttcctcc tcttcctctg cctcccccttt cccagcttcc caggcattgc    1440
ccagctaccc ccactctttc cctcccccaa caagcctctc tgtctccaat cagcccccca    1500
agtatactca gccttctctc ccatcccagg ctgtgtggag ccagggtccc ccaccacctc     1560
ctccctatgg ccgcctctta gccaacagca atgcccatcc aggccccttc cctccctcta    1620
ctggggccca gtccaccgcc cacccaccag tctcaacaca tcaccatcac caccagcaac     1680
agcaacagca gcagcagcag cagcagcagc agcagcatca cggaaactct gggccccctc    1740
ctcctggagc atttccccac ccactggagg gcggtagctc ccaccacgca cacccttacg     1800
ccatgtctcc ctccctgggg tctctgaggc cctaccacc agggcagca cacctgcccc      1860 cacctcacag ccaggtgtcc tacagccaag caggccccaa tggccctcca gtctcttcct    1920
cttccaactc ttcctcttcc acttctcaag ggtcctaccc atgttcacac ccctcccctt    1980
cccagggccc tcaaggggcg ccctaccctt tccaccggt gcctacggtc accacctctt     2040 cggctacct tccacggtc attgccaccg tggcttcctc gccagcaggc tacaaaacgg      2100
cctccccacc tgggccccca ccgtacggaa agagagcccc gtcccgggg gcctacaaga     2160 cagccacccc acccggatac aaacccgggt cgcctccctc cttccgaacg gggacccca     2220 cgggctatcg aggaacctcg ccacctgcag gcccagggac cttcaagccg ggctcgccca    2280
ccgtgggacc tgggccctg ccacctgcgg ggccctcagg cctgccatcg ctgccaccac     2340
cacctgcggc ccctgcctca gggccgcccc tgagcgccac gcagatcaaa caggagccgg    2400
ctgaggagta tgagaccccc gagagccgg tgccccagc ccgcagcccc tcgcccctc      2460 ccaaggtggt agatgtaccc agccatgcca gtcagtctgc caggttcaac aaacacctgg    2520
atcgcggctt caactcgtgc gcgcgcagcg acctgtactt cgtgccactg gagggctcca    2580
agctggccaa gaagcgggcc gacctggtgg agaaggtgcg gcgcgaggcc gagcagcgcg    2640
```

-continued

| | |
|---|---|
| cgcgcgaaga aaaggagcgc gagcgcgagc gggaacgcga gaaagagcgc gagcgcgaga | 2700 |
| aggagcgcga gcttgaacgc agcgtgaagt tggctcagga gggccgtgct ccggtggaat | 2760 |
| gcccatctct gggcccagtg ccccatcgcc ctccatttga accgggcagt gcggtggcta | 2820 |
| cagtgccccc ctacctgggt cctgacactc cagccttgcg cactctcagt gaatatgccc | 2880 |
| ggcctcatgt catgtctcct ggcaatcgca accatccatt ctacgtgccc ctgggggcag | 2940 |
| tggacccggg gctcctgggt tacaatgtcc cggccctgta cagcagtgat ccagctgccc | 3000 |
| gggagaggga acgggaagcc cgtgaacgag acctccgtga ccgcctcaag cctggctttg | 3060 |
| aggtgaagcc tagtgagctg aaccccctac atggggtccc tgggccgggc ttggatccct | 3120 |
| ttccccgaca tgggggcctg gctctgcagc ctggcccacc tggcctgcac cctttcccct | 3180 |
| ttcatccgag cctggggccc ctggagcgag aacgtctagc gctggcagct gggccagccc | 3240 |
| tgcggcctga catgtcctat gctgagcggc tggcagctga gaggcagcac gcagaaaggg | 3300 |
| tggcggccct gggcaatgac ccactggccc ggctgcagat gctcaatgtg actccccatc | 3360 |
| accaccagca ctcccacatc cactcgcacc tgcacctgca ccagcaagat gctatccatg | 3420 |
| cagcctctgc ctcggtgcac cctctcattg accccctggc ctcagggtct caccttaccc | 3480 |
| ggatcccta cccagctgga actctcccta accccctgct tcctcaccct ctgcacgaga | 3540 |
| acgaagttct tcgtcaccag ctctttgctg ccccttaccg ggacctgccg gcctcccttt | 3600 |
| ctgccccgat gtcagcagct catcagctgc aggccatgca cgcacagtca gctgagctgc | 3660 |
| agcgcttggc gctggaacag cagcagtggc tgcatgccca tcaccgctg cacagtgtgc | 3720 |
| cgctgcctgc ccaggaggac tactacagtc acctgaagaa ggaaagcgac aagccactgt | 3780 |
| agaacctgcg atcaagagag caccatggct cctacattgg accttggagc accccccaccc | 3840 |
| tccccccacc gtgcccttgg cctgccaccc agagccaaga gggtgctgct cagttgcagg | 3900 |
| gcctccgcag ctggacagag agtgggggag ggagggacag acagaaggcc aaggcccgat | 3960 |
| gtggtgtgca gaggtgggga ggtggcgagg atggggacag aaagcgcaca gaatcttgga | 4020 |
| ccaggtctct cttccttgtc cccctgctt ttctcctccc ccatgcccaa cccctgtggc | 4080 |
| cgccgccct cccctgcccc gttggtgtga ttatttcatc tgttagatgt ggctgttttg | 4140 |
| cgtagcatcg tgtgccaccc ctgcccctcc ccgatccctg tgtgcgcgcc ccctctgcaa | 4200 |
| tgtatgcccc ttgccccttc cccacactaa taatttatat atataaatat ctatatgacg | 4260 |
| ctcttaaaaa aacatcccaa ccaaaaccaa ccaaacaaaa acatcctcac aactccccag | 4320 |
| ga | 4322 |

<210> SEQ ID NO 55
<211> LENGTH: 808
<212> TYPE: DNA
<213> ORGANISM: Homo sapiens

<400> SEQUENCE: 55

| | |
|---|---|
| tgctcccttg ggctctagag aggaggcccc tcttagccct cagcccctcc ttcctctcta | 60 |
| tcttaaagta atttgatcct caggaatttg ttccgccctc atctggcccg gccaaatccc | 120 |
| gatttgacaa atgccaggaa aaggaaactg ttgagaaacc gaaactactg gggaagggga | 180 |
| gggctcactg agtaaccatc ccagtaaccc gaccgccgct ggtcttcgct ggacaccatg | 240 |
| agtcacactg tccaaacctt cttctctcct gtcaacagtg gccagccccc caactatgag | 300 |
| atgctcaagg aggagcacga ggtggctgtg ctggggggc cccacaaccc tgctcccccg | 360 |
| acgtccaccg tgatccacat ccgcagcgag acctccgtgc ccgaccatgt cgtctggtcc | 420 |

| | |
|---|---|
| ctgttcaaca ccctcttcat gaacccctgc tgcctgggct tcatagcatt cgcctactcc | 480 |
| gtgaagtcta gggacaggaa gatggttggc gacgtgaccg gggcccaggc ctatgcctcc | 540 |
| accgccaagt gcctgaacat ctgggccctg attctgggca tcctcatgac cattctgctc | 600 |
| atcgtcatcc cagtgctgat cttccaggcc tatggataga tcaggaggca tcactgaggc | 660 |
| caggagctct gcccatgacc tgtatcccac gtactccaac ttccattcct cgccctgccc | 720 |
| ccggagccga gtcctgtatc agccctttat cctcacacgc ttttctacaa tggcattcaa | 780 |
| taaagtgcac gtgtttctgg tgctgctg | 808 |

<210> SEQ ID NO 56
<211> LENGTH: 3454
<212> TYPE: DNA
<213> ORGANISM: Homo sapiens

<400> SEQUENCE: 56

| | |
|---|---|
| ggaaatgact gctgtccatg caggcaacat aaacttcaag tgggatccta aaagtctaga | 60 |
| gatcaggact ctggcagttg agagactgtt ggagcctctt gttacacagg ttacaaccct | 120 |
| tgtaaacacc aatagtaaag ggccctctaa taagaagaga ggtcgttcta agaaggccca | 180 |
| tgttttggct gcatctgttg aacaagcaac tgagaatttc ttggagaagg gggataaaat | 240 |
| tgcaaaagag agccagtttc tcaaggagga gcttgtggtt gctgtagaag atgttcgaaa | 300 |
| acaaggtgat ttgatgaagg ctgctgctgg agagttcgca gatgatccct gctcttctgt | 360 |
| gaagcgaggc aacatggttc gggcagctcg agctttgctc tctgctgtta cccggttgct | 420 |
| cattttggct gacatggcag atgtctacaa attacttgtt cagctgaaag ttgtggaaga | 480 |
| tggtatattg aaactgagga atgctggcaa tgaacaagac ttagggaatc agtataaagc | 540 |
| cctaaaacct gaagtggata gctgaacat tatggcagca aaaagacaac aggaattgaa | 600 |
| agatgttggg catcgtgatc agatggctgc ggctagagga atcctgcaga gcaacgttcc | 660 |
| gatcctctat actgcatccc aggcatgcct acagcaccct gatgtcgcag cctataaggc | 720 |
| caacagggac ctgatataca agcagctgca gcaggcggtc acagggattt ccaatgcagc | 780 |
| ccaggccact gcctcagacg atgcctcaca gcaccagggt ggaggaggag gagaactggc | 840 |
| atatgcactc aataactttg acaaacaaat cattgtggac cccttgagct tcagcgagga | 900 |
| gcgctttagg ccttccctgg aggagcgtct ggaaagcatc attagtgggg ctgccttgat | 960 |
| ggccgactcg tcctgcacgc gtgatgaccg tcgtgagcga attgtggcag agtgtaatgc | 1020 |
| tgtccgccag gcctgcagga cctgcgtttc ggagtacatg ggcaatgctg gacgtaaaga | 1080 |
| aagaagtgat gcactcaatt ctgcaataga taaaatgacc aagaagacca gggacttgcg | 1140 |
| tagacagctt cgcaaagctg tcatggacca cgtttcagat tctttcctgg aaaccaatgt | 1200 |
| tccacttttg gtattgattg aagctgcaaa gaatggaaat gagaaagaag ttaaggaata | 1260 |
| tgcccaagtt ttccgtgaac atgccaacaa attgattgag gttgccaact tggcctgttc | 1320 |
| catctcaaat aatgaagaag gtgtaaagct tgttcgaatg tctgcaagcc agttagaagc | 1380 |
| cggttgtcct caggttatta atgctgcaac ctgggcttta gcaccaaaac cacagagtaa | 1440 |
| actggcccaa gagaacatgg atcttttaa agaacaatgg gaaaaacaag tccgtgttct | 1500 |
| cacagatgct gtcgatgaca ttacttccat tgatgacttc ttggctgtct cagagaatca | 1560 |
| cattttggaa gatgtgaaca atgtgtcat tgctctccaa gagaaggatg tggatggcct | 1620 |
| ggaccgcaca gctggtgcaa ttcgaggccg ggcagcccgg gtcattcacg tagtcacctc | 1680 |
| agagatggac aactatgagc caggagtcta cacagagaag gttctggaag ccactaagct | 1740 |

-continued

| | |
|---|---|
| gctctccaac acagtcatgc cacgttttac tgagcaagta gaagcagccg tggaagccct | 1800 |
| cagctcggac cctgcccagc ccatggatga gaatgagttt atcgatgctt cccgcctggt | 1860 |
| atatgatggc atccgggaca tcaggaaagc agtgctgatg ataaggaccc ctgaggagtt | 1920 |
| ggatgactct gactttgaga cagaggattt tgatgtcaga agcgagacga gcgtccagac | 1980 |
| agaagacgat cagctgatag ctggccagag tgcccgggcg atcatggctc agcttcccca | 2040 |
| ggagcaaaaa gcgaagattc gggaacaggt ggccagcttc caggaagaaa agagcaagct | 2100 |
| ggatgctgaa gtgtccaaat gggacgacag tggcaatgac atcattgtgc tggccaagca | 2160 |
| gatgtgcatg attatgatgg agatgacaga ctttacccga ggtaaaggac cactcaaaaa | 2220 |
| tacatcggat gtcatcagtg ctgccaagaa aattgctgag gcaggatcca ggatggacaa | 2280 |
| gcttggccgg accattcgag accattgccc cgactcggct tgcaagcagg acctgctggc | 2340 |
| ctacctgcaa cgcatcgccc tctactgcca ccagctgaac atctgcagca aggtcaaggc | 2400 |
| cgaggtgcag aatctcggcg gggagcttgt tgtctctggg gtggacagcg ccatgtccct | 2460 |
| gatccaggca gccaagaact tgatgaatgc tgtggtgcag acagtgaagg catcctacgt | 2520 |
| cgcctctacc aaataccaaa agtcacaggg tatggcttcc ctcaaccttc ctgctgtgtc | 2580 |
| aatgaagatg aaggcaccag agaaaaagcc attggtgaag agagagaaac aggatgagac | 2640 |
| acagaccaag attaaacggg catctcagaa gaagcacgtg aacccagtgc aggccctcag | 2700 |
| cgagttcaaa gctatggaca gcatctaagt ctgcccaggc cggccgcccc caccccttct g | 2760 |
| gctcctgaat atcagtcact gttcgtcact caaatgaatt tgctaaatac aacactgata | 2820 |
| ctagattcca cagggaaatg gcagactga accagtccag gtggtgaatt ttccaagaac | 2880 |
| atagtttaag ttgattaaaa atgcttttag aatgcaggag cctacttcta gctgtatttt | 2940 |
| ttgtatgctt aaataaaata aaattcataa ccaagagatc cacattagct tgttagtaat | 3000 |
| gctctgacca gccgagatg ccattctctt agtgatggcg gcgttaggtt tgagagaagg | 3060 |
| aattggctca acttcagttg agagggtgca gtccagacag cttgactgct tttaaatgac | 3120 |
| caaagatgac ctgtggtaag caacctggca tcttaggaag cagtccttga gaaggcatgt | 3180 |
| tccagaaagg tctctgagga caaactcact cagtaaaaca taatgtatca tgaagaaaac | 3240 |
| tgattctcta tgacatgaaa tgaaaatttt aatgcattgt tataattact aatgtacgct | 3300 |
| gctgcaggac attaataaag ttgctttttt aggctacagt gtctcgatgc cataatcaga | 3360 |
| acacactttt tttcctcttt ctcccagctt caaatgcaca attcatcatt gggctcactt | 3420 |
| ctaataactg cagtgtttcc gccttgcgtt gcag | 3454 |

<210> SEQ ID NO 57
<211> LENGTH: 5128
<212> TYPE: DNA
<213> ORGANISM: Homo sapiens

<400> SEQUENCE: 57

| | |
|---|---|
| ccgagtgcct cgcagcccct cccgaggcgc agccgccaga ccagtggagc cggggcgcag | 60 |
| ggcgggggcg gaggcgccgg ggcggggat gcggggccgc ggcgcagccc cccgccctg | 120 |
| agagcgagga cagcgccgcc cggcccgcag ccgtcgccgc ttctccacct cggcccgtgg | 180 |
| agccggggcg tccgggcgta gccctcgctc gcctgggtca gggggtgcgc gtcggggag | 240 |
| gcagaagcca tggatcccgg gcagcagccg ccgcctcaac cggcccccca gggccaaggg | 300 |
| cagccgcctt cgcagccccc gcaggggcag ggccgccgt ccggaccggg caaccggca | 360 |
| cccgcggcga cccaggcggc gccgcaggca ccccccgccg ggcatcagat cgtgcacgtc | 420 |

-continued

| | |
|---|---|
| cgcggggact cggagaccga cctggaggcg ctcttcaacg ccgtcatgaa ccccaagacg | 480 |
| gccaacgtgc cccagaccgt gcccatgagg ctccggaagc tgcccgactc cttcttcaag | 540 |
| ccgccggagc ccaaatccca ctcccgacag gccagtactg atgcaggcac tgcaggagcc | 600 |
| ctgactccac agcatgttcg agctcattcc tctccagctt ctctgcagtt gggagctgtt | 660 |
| tctcctggga cactgacccc cactggagta gtctctggcc cagcagctac acccacagct | 720 |
| cagcatcttc gacagtcttc ttttgagata cctgatgatg tacctctgcc agcaggttgg | 780 |
| gagatggcaa agacatcttc tggtcagaga tacttcttaa atcacatcga tcagacaaca | 840 |
| acatggcagg accccaggaa ggccatgctg tcccagatga acgtcacagc ccccaccagt | 900 |
| ccaccagtgc agcagaatat gatgaactcg gcttcagcca tgaaccagag aatcagtcag | 960 |
| agtgctccag tgaaacagcc accaccctg gctccccaga gcccacaggg aggcgtcatg | 1020 |
| ggtggcagca actccaacca gcagcaacag atgcgactgc agcaactgca gatggagaag | 1080 |
| gagaggctgc ggctgaaaca gcaagaactg cttcggcagg tgaggccaca ggagttagcc | 1140 |
| ctgcgtagcc agttaccaac actggagcag gatggtggga ctcaaaatcc agtgtcttct | 1200 |
| cccgggatgt ctcaggaatt gagaacaatg acgaccaata gctcagatcc tttccttaac | 1260 |
| agtggcacct atcactctcg agatgagagt acagacagtg gactaagcat gagcagctac | 1320 |
| agtgtccctc gaaccccaga tgacttcctg aacagtgtgg atgagatgga tacaggtgat | 1380 |
| actatcaacc aaagcaccct gccctcacag cagaaccgtt tcccagacta ccttgaagcc | 1440 |
| attcctggga caaatgtgga ccttggaaca ctggaaggag atggaatgaa catagaagga | 1500 |
| gaggagctga tgccaagtct gcaggaagct ttgagttctg acatccttaa tgacatggag | 1560 |
| tctgtttttgg ctgccaccaa gctagataaa gaaagctttc ttacatggtt atagagccct | 1620 |
| caggcagact gaattctaaa tctgtgaagg atctaaggag acacatgcac cggaaatttc | 1680 |
| cataagccag ttgcagtttt caggctaata cagaaaaaga tgaacaaacg tccagcaaga | 1740 |
| tactttaatc ctctattttg ctcttccttg tccattgctg ctgttaatgt attgctgacc | 1800 |
| tctttcacag ttggctctaa agaatcaaaa gaaaaaaact ttttatttct tttgctatta | 1860 |
| aaactactgt tcattttggg ggctggggga agtgagcctg tttggatgat ggatgccatt | 1920 |
| cctttttgccc agttaaatgt tcaccaatca ttttaactaa atactcagac ttagaagtca | 1980 |
| gatgcttcat gtcacagcat ttagtttgtt caacagttgt ttcttcagct tcctttgtcc | 2040 |
| agtggaaaaa catgatttac tggtctgaca agccaaaaat gttatatctg atattaaata | 2100 |
| cttaatgctg atttgaagag atagctgaaa ccaaggctga agactgtttt actttcagta | 2160 |
| ttttcttttc ctcctagtgc tatcattagt cacataatga ccttgatttt attttaggag | 2220 |
| cttataaggc atgagacaat ttccatataa atatattaat tattgccaca tactctaata | 2280 |
| tagattttgg tggataattt tgtgggtgtg cattttgttc tgttttgttg ggttttttgt | 2340 |
| ttttttgtt tttggcaggg tcggtggggg ggttggttgg ttggttggtt ttgtcggaac | 2400 |
| ctaggcaaat gaccatatta gtgaatctgt taatagttgt agcttgggat ggttattgta | 2460 |
| gttgttttgg taaaatcttc atttcctggt tttttttacc accttattta aatctcgatt | 2520 |
| atctgctctc tcttttatat acatacacac acccaaacat aacatttata atagtgtggt | 2580 |
| agtggaatgc atcctttttt aggtttccct gctttccagt taattttaa aatggtagcg | 2640 |
| ctttgtatgc atttagaata catgactagt agtttatatt tcactggtag tttaaatctg | 2700 |
| gttggggcag tctgcagatg tttgaagtag tttagtgttc tagaaagagc tattactgtg | 2760 |
| gatagtgcct aggggagtgc tccacgccct ctgggcatac ggtagatatt atctgatgaa | 2820 |

```
ttggaaagga gcaaaccaga aatggcttta ttttctccct tggactaatt tttaagtctc  2880
gattggaatt cagtgagtag gttcataatg tgcatgacag aaataagctt tatagtggtt  2940
taccttcatt tagctttgga agttttcttt gccttagttt tggaagtaaa ttctagtttg  3000
tagttctcat ttgtaatgaa cacattaacg actagattaa atatattgcct tcaagattgt  3060
tcttacttac aagacttgct cctacttcta tgctgaaaat tgaccctgga tagaatacta  3120
taaggttttg agttagctgg aaaagtgatc agattaataa atgtatattg gtagttgaat  3180
ttagcaaaga aatagagata atcatgatta tacctttatt tttacaggaa gagatgatgt  3240
aactagagta tgtgtctaca ggagtaataa tggtttccaa agagtatttt ttaaaggaac  3300
aaaacgagca tgaattaact cttcaatata agctatgaag taatagttgg ttgtgaatta  3360
aagtggcacc agctagcacc tctgtgtttt aagggtcttt caatgtttct agaataagcc  3420
cttattttca agggttcata acaggcataa aatctcttct cctggcaaaa gctgctatga  3480
aaagcctcag cttgggaaga tagatttttt tccccccaat tacaaaatct aagtattttg  3540
gcccttcaat ttggaggagg gcaaaagttg gaagtaagaa gttttatttt aagtactttc  3600
agtgctcaaa aaaatgcaat cactgtgttg tatataatag ttcataggtt gatcactcat  3660
aataattgac tctaaggctt ttattaagaa aacagcagaa agattaaatc ttgaattaag  3720
tctgggggga aatggccact gcagatggag ttttagagta gtaatgaaat tctacctaga  3780
atgcaaaatt gggtatatga attacatagc atgttgttgg gattttttt aatgtgcaga  3840
agatcaaagc tacttggaag gagtgcctat aatttgccag tagccacaga ttaagattat  3900
atcttatata tcagcagatt agcttagct taggggagg gtgggaaagt ttggggggg    3960
ggttgtgaag atttaggggg accttgatag agaactttat aaacttcttt ctctttaata  4020
aagacttgtc ttacaccgtg ctgccattaa aggcagctgt tctagagttt cagtcaccta  4080
agtacaccca caaacaata tgaatatgga gatcttcctt tacccctcaa ctttaatttg   4140
cccagttata cctcagtgtt gtagcagtac tgtgatacct ggcacagtgc tttgatctta  4200
cgatgccctc tgtactgacc tgaaggagac ctaagagtcc tttcccttttt tgagtttgaa  4260
tcatagcctt gatgtggtct cttgttttat gtccttgttc ctaatgtaaa agtgcttaac  4320
tgcttcttgg ttgtattggg tagcattggg ataagatttt aactgggtat tcttgaattg  4380
cttttacaat aaaccaattt tataatcttt aaatttatca acttttttaca tttgtgttat  4440
tttcagtcag ggcttcttag atctacttat ggttgatgga gcacattgat ttggagtttc  4500
agatcttcca aagcactatt tgttgtaata acttttctaa atgtagtgcc tttaaaggaa  4560
aaatgaacac agggaagtga ctttgctaca aataatgttg ctgtgttaag tattcatatt  4620
aaatacatgc cttctatatg gaacatggca gaaagactga aaaataacag taattaattg  4680
tgtaattcag aattcatacc aatcagtgtt gaaactcaaa cattgcaaaa gtgggtggca  4740
atattcagtg cttaacactt ttctagcgtt ggtacatctg agaaatgagt gctcaggtgg  4800
attttatcct cgcaagcatg ttgttataag aattgtgggt gtgcctatca taacaattgt  4860
tttctgtatc ttgaaaaagt attctccaca ttttaaatgt tttatattag agaattcttt  4920
aatgcacact tgtcaaatat atatatatag taccaatgtt accttttat tttttgtttt   4980
agatgtaaga gcatgctcat atgttaggta cttacataaa ttgttacatt attttttctt  5040
atgtaatacc ttttttgtttg tttatgtggt tcaaatatat tctttcctta aaaaaaaaa   5100
aaaaaaaaa aaaaaaaaa aaaaaaa                                        5128
```

<210> SEQ ID NO 58

```
<211> LENGTH: 1454
<212> TYPE: DNA
<213> ORGANISM: Homo sapiens

<400> SEQUENCE: 58
aattgcttcc ggggagttgc gagggagcga gggggaataa aggacccgcg aggaagggcc      60
cgcggatggc gcgtccctga gggtcgtggc gagttcgcgg agcgtgggaa ggagcggacc     120
ctgctctccc cgggctgcgg gccatggcca cggcggagcg gagagccctc ggcatcggct     180
tccagtggct ctctttggcc actctggtgc tcatctgcgc cgggcaaggg ggacgcaggg     240
aggatggggg tccagcctgc tacggcggat ttgacctgta cttcattttg acaaatcag     300 gaagtgtgct gcaccactgg aatgaaatct attactttgt ggaacagttg gctcacaaat     360
tcatcagccc acagttgaga atgtccttta ttgttttctc cacccgagga caaccttaa     420 tgaaactgac agaagacaga gaacaaatcc gtcaaggcct agaagaactc cagaaagttc     480
tgccaggagg agacacttac atgcatgaag gatttgaaag ggccagtgag cagatttatt     540
atgaaaacag acaagggtac aggacagcca gcgtcatcat tgctttgact gatggagaac     600
tccatgaaga tctctttttc tattcagaga gggaggctaa taggtctcga gatcttggtg     660
caattgttta ctgtgttggt gtgaaagatt tcaatgagac acagctggcc cggattgcgg     720
acagtaagga tcatgtgttt cccgtgaatg acggctttca ggctctgcaa ggcatcatcc     780
actcaatttt gaagaagtcc tgcatcgaaa ttctagcagc tgaaccatcc accatatgtg     840
caggagagtc atttcaagtt gtcgtgagag gaaacggctt ccgacatgcc cgcaacgtgg     900
acagggtcct ctgcagcttc aagatcaatg actcggtcac actcaatgag aagccctttt     960
ctgtggaaga cacttattta ctgtgtccag cgcctatctt aaaagaagtt ggcatgaaag    1020
ctgcactcca ggtcagcatg aacgatggcc tctctttat ctccagttct gtcatcatca    1080
ccaccacaca ctgttctgac ggttccatcc tggccatcgc cctgctgatc ctgttcctgc    1140
tcctagccct ggctctcctc tggtggttct ggccctctg ctgcactgtg attatcaagg    1200
aggtccctcc accccctgcc gaggagagtg aggaaaataa aataaataa caagaagaag    1260 aaagaaagaa atcccacaga aacagataac ctaacacagc ccgtgcaacg tattttatac    1320
aatgctctga aaatcatagt ctcaatctag acagtctttt cctctagttc cctgtattca    1380
aatcccagtg tctaacattc aataaatagc tatatgaaat caaaaaaaaa aaaaaaaaaa    1440
aaaaaaaaaa aaaa                                                     1454

<210> SEQ ID NO 59
<211> LENGTH: 2828
<212> TYPE: DNA
<213> ORGANISM: Homo sapiens

<400> SEQUENCE: 59
agcagccggc acgggacag ccggccgcac aacggatctg caggcgcgga gcaaaatgca      60
cccgccgcgc cgcgcggtcc tgcagccccg ccacggcccc gcggcccgca cccccccggg     120
gcgacagtga gcctctcccg ccaccaccgg gggccgagcg gagggctctc gggtgggaga     180
gcgggaccag atctcgacag ctgttcattt ccaggaagcc accgcagcca gagcgaaagg     240
ggaccttctg ccaccagcgg ggcatcagcc agcggcgcgc atggatttat gaagacactc     300
atgcaagaag tgggcaggac ttggacaaac ttttccaccg gctccgcgtc cgccgctccc     360
cgcgcctcgt ctcctttccc ctcctctccc ggcggccgcc gctgcccgcg atggtggccg     420
cgctgctggg cggcggcggc gaggcccgcg ggggacagt gccggcgcc tggctgtgcc     480
```

-continued

```
tgatggcgct gctgcagctg ctgggctcgg cgccgcgggg atcggggctg gcgcacggcc    540
gccgcctcat ctgctggcag gcgctgctgc agtgccaggg ggagccggag tgcagctacg    600
cctacaacca gtacgccgag gcgtgcgcgc cggtgctggc gcagcacggc ggggcgacg     660 cgcccggggc cgccgccgcc gctttcccgg cctcggccgc ctcttctcg tcgcgctggc     720 gctgcccgag tcactgcatc tcggccctca ttcagctcaa ccacacgcgc cgcgggcccg    780
ccctggagga ctgtgactgc gcgcaggacg agaactgcaa gtccaccaag cgcgccattg    840
agccgtgcct gccccggacg agcggcggcg gcgcgggcgg ccccggcgcg ggcggggtca    900
tgggctgcac cgaggcccgg cggcgctgcg accgcgacag ccgctgcaac ctggcgctga    960
gccgctacct gacctactgc ggcaaagtct tcaacgggct gcgctgcacg gacgaatgcc   1020
gcaccgtcat tgaggacatg ctggctatgc ccaaggtggc gctgctcaac gactgcgtgt   1080
gcgacggcct cgagcggccc atctgcgagt cggtcaagga gaacatggcc cgcctgtgct   1140
tcggcgccga gctgggcaac ggccccggca gcagcggctc ggacggggc ctggacgact   1200 actacgatga ggactacgat gacgagcagc gcaccggggg cgcgggtggt gagcagccgc   1260
tggacgacga cgacggcgtc ccgcacccac cgcgcccggg cagcggcgct gctgcatcgg   1320
gcggccgcgg ggacctgccc tatgggcctg gcgcaggag cagcggcggc ggcggccgct   1380
tggcgccccg gggcgcctgg accccactcg cctccatctt gctgctgctg cttgggccgc   1440
tcttttagcc ctcgcgcccc ccgccgttgg ctgcgggaga gcccgcgtcc cactcccgtg   1500
ctcgcctcga ccccgcgccg ggcacctgtg gcttgggaca gatagaaggg atggttgggg   1560
atacttccca aaactttttc caagtcaact tggtgtagcc ggttccccgg ccacgactct   1620
gggcacttcc cctgaagctc ctctccggag cttgacttct tggacctcct cccccgcccc   1680
aattccaagc tccagaaact cccaactcgt ctgccgtcca gaaagctagc tgcagtgttc   1740
aggacgtccg ggaggaagca agcatgtggg ggacagaaca gtagtcctgg actcgaaagg   1800
gaaggtgctg accagtgggg ccttagcaat ttgaagggtt gggaaggagg aattatattt   1860
gcaaaggggc tgtctattag catatttcct ttgaggggc aaaaaaaagt gccagtatcg    1920
acttttacag attgtggcca gtgaggatat tataatccta tgtaaacaga aaagtcccac   1980
ttaccgattc attctttcac tgtttgtatc tgcgcccaga attctcagtg acgtgggggt   2040
gagggtgggg ggcgattgcc ttagagggaa cccctaaatt ggttttggat aagtttgagc   2100
ccttgacctt aatttcattg ctaccactct gatctcttag cacatttctt aggattaagg   2160
gtccaaaaat gctgatctaa ggggttgcca tggtgttgaa caatgcaact tttattttaa   2220
aaaagctctg cactgccatg tatgaaagtc tctttatgat gtttgttttt ttgtcatttt   2280
tgttctttac atcaagaaat tttatgttta aatatgcgga gaatgtatat tgcctctgct   2340
cctatcaggg ttgctaaacc ctggtacatc gtatataaaa tgtattaaaa ctggggtttg   2400
ttaccagttg ctgtactttg tatatagaat ttttataaat tgtatgcttc agaaataatt   2460 tattttaaa aagaaattaa agttttaaa ctcacatcca tattacacct ttcccccctg     2520
aaatgtatag aatccatttg tcatcaggaa tcaaaaccca cagtccattg tgaagtgtgc   2580
tatatttaga acagtcttaa aatgtacagt gtattttata gaattgaagt taacattctt   2640
attttcaaga gaatttatgg acgttgtaga aatgtacaaa tgcatttcca aactgcctta   2700
aacgttgtat ttttatagac atgtttttt aaaaatccta agttttaaa taactatgga    2760 tttgtgtatt ttttttggtt atttgtttta ttaaaacatg tacatcagta aagagtttta   2820
aacaatga                                                           2828
```

<210> SEQ ID NO 60
<211> LENGTH: 7568
<212> TYPE: DNA
<213> ORGANISM: Homo sapiens

<400> SEQUENCE: 60

| | | | | | | |
|---|---|---|---|---|---|---|
| gcgcggaggc | agggaaccgg | agccttggag | cgacccaacc | cctcgtctcg | ctgccctccc | 60 |
| gcgcctgcaa | cggtgcgcgg | agactccggc | gaactcagac | acccaacggc | ggagaacaga | 120 |
| agcggcaggc | ggcggacgtg | gcccggaagc | tgcgcgccga | acgcagcgca | cccgctgccg | 180 |
| agcagaggag | ccgcgccttt | ccccgaccct | cggctccagc | ccccggcgcc | tgccgcctcg | 240 |
| cagcccctct | gcgtcctcgg | ctcggggggcc | ggcaccggcg | atgccgagcg | gacgctccag | 300 |
| tcctccgacc | cgctgaagaa | gcagcagccg | ctcgcccgga | gcctacgggg | attgtgcgag | 360 |
| cggatcgtgc | tcggtggagg | ctcgggctgc | ggggcgcggg | gactccgggg | ggcgggggga | 420 |
| gggaccgctc | tgtcggtgcc | cggcgccagc | cgcggctttg | aagggtctcc | ctcccctgcc | 480 |
| cttagcagct | ctgccacgga | ctccgggagg | ctgcgggcgg | cgtcctgagg | gctccccagc | 540 |
| agacccaatc | ggacttgaga | aggtgatcgc | tctgctctcc | caacccccctt | ccctccccat | 600 |
| tccccccact | taacttttttg | tctccgttca | tccgcggctt | cgtcccctcc | ccggcagacc | 660 |
| cacccgcggc | tgtgacaacc | gcccggggca | tgggccccccc | aacacggctc | ctagaggccc | 720 |
| cgcggcctcg | caagatgtga | gaggccctcc | ccgggcagaa | tcggagcttc | aggagaggag | 780 |
| ctaatacccc | gcccccgtc | cctcacatca | ggcggggtgg | aggtgcgcgc | tgagcccccg | 840 |
| cggtgctgag | cgtcccggag | cgcccaatcc | tgggctggaa | cgagtagctg | gccggaggcg | 900 |
| cgccgcggag | agccggctgt | catgcccctat | tgatcccccct | ctgccccccg | ccaagtatgt | 960 |
| ttgggctgga | ccaattcgag | ccccaggtca | acagcaggaa | cgctggccag | ggcgagagga | 1020 |
| actttaacga | gaccggactg | agcatgaaca | cccactttaa | ggccccggct | ttccacactg | 1080 |
| gggggccccc | tggccctgtg | gatcctgcta | tgagcgcgct | ggggcaaccc | ccgatcttgg | 1140 |
| gcatgaacat | ggagccctac | ggcttccacg | cgcgcggcca | ctcggagttg | cacgcagggg | 1200 |
| ggctgcaagc | gcagcctgtg | cacggcttct | ttggcggcca | gcagcctcac | cacggccacc | 1260 |
| cgggaagtca | tcatccccac | cagcatcacc | cccactttgg | gggcaacttc | ggtggcccgg | 1320 |
| accccgggggc | ctcgtgcctg | cacggggggtc | gcctgctcgg | ctacggcggc | gcagccggag | 1380 |
| gcctgggcag | ccagccgccc | ttcgccgagg | gctatgagca | catggcggag | agccaggggc | 1440 |
| ctgagagctt | cggcccgcag | cgaccggggga | acctcccgga | cttccacagt | tcaggtgcct | 1500 |
| ccagccaccg | cgtgccggcc | ccatgcctgc | cgctggacca | gagccctaac | cgagccgcct | 1560 |
| ccttccacgg | cctgccgtcc | tccagcgcct | ccgattccca | cagtctggag | ccacggaggg | 1620 |
| tgacgaacca | aggagccgtc | gactcgctgg | aatacaatta | ccgggcgagg | cgccctcggg | 1680 |
| acattttgac | atgttttcgc | cctctgactc | cgaagggcag | ctgcctcatt | atgcagcggg | 1740 |
| tcgccaggtt | cctggggggc | ggctttcccg | gggcgccctc | ggccatgccc | agagctgcgg | 1800 |
| gcatggtggg | cttgtccaaa | atgcacgccc | agccaccgca | gcagcagccc | cagcagcagc | 1860 |
| agcagcccca | gcagcagcag | cagcatggtg | tgttctttga | gaggttcagt | ggggccagaa | 1920 |
| agatgcctgt | gggtctggag | ccctcagtgg | gctccaggca | cccgttaatg | cagcctcccc | 1980 |
| agcaggcccc | gccacccccct | cagcagcagc | cccgcagca | gccgccacag | cagcagccgc | 2040 |
| cgccgccacc | cggggcttcta | gtccgacaaa | attcgttgcc | cgcctgcgct | ccctcggccc | 2100 |
| cagcagggcg | aggcgggcac | gcccagccggc | ggcctgcagg | acggaggccc | catgctgccc | 2160 |

```
agccagcacg cgcaattcga gtatcccatc caccggctgg agaaccggag catgcaccct   2220
tattccgagc ctgttttcag catgcagcat cctcctccgc agcaggcgcc caaccagcgg   2280
ctgcagcatt tcgacgcgcc ccctacatg aacgtggcca agaggcgcgc ttcgactttc    2340
cgggcagcgc gggagtggac cgctgcgctt cgtggaacgg cagcatgcac aacggcgctc   2400
tggataatca cctctcccct tccgcctacc caggcctacc cggcgagttc acaccgcctg   2460
tgcccgacag cttcccttcg gggccgcccc tgcagcatcc ggccccggac caccagtccc   2520
tgcaacagca gcagcagcag cagcagcagc agcaacagca gcagcagcag cagcaacagc   2580
aacagcaaca gcagcagcag cagcagcgcc aaaacgcggc cctcatgatt aagcagatgg   2640
cgtcgcggaa tcagcagcag cggctgcgcc agcccaacct ggctcagcta ggccaccccg   2700
gggacgtggg ccaggcggc ctggtgcatg gcggcccggt gggcggcttg cccagccga     2760 actttgagcg cgaaggcggc agcacgggcg ccgggcgtct gggcaccttc gagcagcagg   2820
cgccgcactt ggcgcaagag agcgcgtggt tctcaggtcc gcatccgccg cccggagacc   2880
tgctgccccg taggatgggc ggctcgggtc tgcccgctga ctgtggcccg cacgacccca   2940
gcctggcgcc ccctcctccg cctggtggct cgggggtgct gttccggggc cctctgcagg   3000
agccgatgag gatgcccgga gaggccacgt gccgcgctgc cttcaccggc ctgcagttcg   3060
ggggcagtct gggaggcctg ggtcagctgc agtcgcccgg ggcgggcgtg gggctcccca   3120
gcgctgcttc ggagcgccgg ccccgccgc cggactttgc tacgtctgcg ctcggggcc    3180 agccgggctt tccgtttggt gcagccggcc ggcagtccac gccgcacagc ggtccaggcg   3240
tgaactcgcc cccagcgcg ggaggggcg gtggcagctc tggtggcggc ggtggcgggg    3300
gtgcctaccc gccgcagcct gatttccagc ccagccagcg cacctcggcc agtaaattgg   3360
gcgcgctctc gctgggctcc ttcaacaagc ccagctccaa ggacaacctg ttcggccaga   3420
gctgcctggc tgcgctctcc accgcttgcc agaacatgat cgccagcctc ggggccccca   3480
acctcaacgt gaccttcaac aagaagaacc cgccagaggg caagaggaaa ctgagccaga   3540
acgagaccga cggcgcggca gtggccggca cccgggctc ggattacttc ccaggaggga   3600
ctgctcctgg gggccccagg acccggaggc cgtccgggac cagtagcagc ggctccaaag   3660
cctcggggcc gcccaaccct ccagcccagg gggacggcac cagcctctcc cccaactaca   3720
ccctggaatc cacgtcgggg aatgacgca agccggtctc cggggcggc ggccggggac     3780 ggggtcgcag aaaaagggac agtggtcacg tgagccctgg caccttcttt gacaagtact   3840
cggcggctcc ggacagcggg ggcgcacctg gggtgagccc agggcagcag caagcgtcag   3900
gcgcagccgt cggggaagc tccgcaggcg agacgcgcgg ggcaccgacg ccccacgaaa    3960
aggcgctcac gtcgccatcc tgggggaagg gggctgagtt gctcctgggg gatcagccgg   4020
acctcattgg gtccctggac ggcgggggcca agtcggacag tagttcgcca aacgtgggtg   4080
agttcgcctc ggacgaggtg agcacgagct acgccaatga ggacgaggtg tcgtccagct   4140
ctgacaaccc ccaggcacta gttaaagcga gcaggagtcc cctggtgacc ggctcgccca   4200
aactccctcc ccgtgggta ggcgccgggg aacacggacc gaaggcgccc ccgcccgccc    4260
tcggcctggg catcatgtct aactctacct cgaccctga cagctacggc ggcggtgggg    4320
gcccgggcca tccgggcact ccgggcctgg agcaggtccg caccccgacg agcagcagcg   4380
gcgccccgcc acccgacgag atccacccc tggagatcct tcaggcgcag atccagctac   4440
agaggcagca gttcagcatc tccgaggacc agctctgggg gctgaagggt ggcaagaagg   4500
gtgagtgcgc cgtcggggcc tcaggggcgc agaatggcga cagcgagctg ggcagctgct   4560
```

```
gctccgaggc ggtcaagagc gccatgagca ccattgacct ggactcgctg atggcagagc    4620
acagcgctgc ctggtacatg cccgctgaca aggccctggt ggacagcgcg gacgacgaca    4680
agacgttggc gccctgggag aaggccaaac cccagaaccc caacagcaaa gaagcccacg    4740
acctccctgc aaacaaggcc tcagcatccc agcctggcag ccacttgcag tgcctgtctg    4800
tccactgcac agacgacgtg ggtgacgcca aggctcgagc ctccgtgccc acctggcggt    4860
ccctgcattc tgacatctcc aacagatttg ggacattcgt ggctgcccta acttgaatga    4920
caagaaagat cccctcctct accaggccct tcctctcccc ctgtctgttt ccttcccct    4980 caaccttacc ccaccctct gttaatttga aagggccact attgctgagt ggatgagttt    5040 ttttttttc ctctaggttg gtacctgctt agtggcatat ggaccggaaa gggttaattt    5100 aaagggggg aacctcaaaa gttttttaa aaagaaact tgtctgccac agtatgttac    5160
cagtgttaac ccttctgcag ttagcaaact tttgcttaag ccttttcct ctagatactc    5220 cccatgtttc ggtaatcttg gcatacattt tttagatgac ctctttcctt gttttgtttt    5280
catgctgctg tatgtccaag tattgttatt tcataataag acaagagttg ctttcttttt    5340
tattcttttt ccttttctta ccccctcccc ttttatttc ttttgcttt gttcactgct    5400 tattaaaatg gaaatcctgg agaatagtag ttctggaata ttgccgggtg aaagtccaat    5460
tgtcatcaca atgttatata ttgacacccc agtgtcatca gtcaggcagg agccaaacaa    5520
tgaatgcccc tcttaggtat tccgcctggg attttgtttt gtctgttccc taagaaaata    5580
tattttcatt cctgcaaaca cagtgctcag ccttcagttc ccttccactt gagttctctc    5640
ttctcctgct ggaagccgcc cctctctgcg atggacgtga ggacgtgtcc agctctgctc    5700
tgtgggaagg agttggaatg ttcgacagca gtgttttctc tccttttctg ggcctcctcg    5760
caaatgccca ggccctgcat tttcacgctg tgctaagcag ccttggtct gcatgggga    5820 tggtgtgctc ccagcctgca gtcttggag caaggctgct gcccgtgcct tgggtgctgg    5880
agttggagga ggctgttctc agccctttcc ctttctgaa agctgttcct ggccgggcat    5940
cccagggaag aaggagggga ctgcgtgtat ctcctccacc tctcccattc catcccagt    6000 ccagcctggg caacccace cctgggaggg atgaggcacc ctcttgctca gcctgctcag    6060
ccttctctga gcctttgcag ggatctgcag actcctgagg gctagaggac agagaaagag    6120
aatagaatga aatgactttg attcctgcgc cttttagttt tgaactctgg aattcctctg    6180 cccctcccc aacatttttt tggaatctca ccctgttgca aaactagagc catgtcccaa    6240
gcatctcaca aaggaataac tgctctgagc agagatgagt ggtggttggc aggggcaggc    6300
aactttgggt gctgctgatg cctgcaaaag ccatttatgg cttgtggtgg gggcacata    6360 gattccccgg tgggttagac aggaagtaac tgatatcact tcacccaaat atataaccgt    6420
gatggttatc tatttaattt cagttttgt taacgagcgt gtcttactaa aacgctccac    6480
tttgagctcc cccaccccct ccaggtcctc agagtttgca gatctgggct ttctaaagca    6540
agtgacctga aggctctggg ctcaccatac aacacccacg ttgtttattt caagaacttt    6600
ttcagcgaag ggagaggagc tttcagaaaa acctcactct ttcccctccc ttctcccctc    6660
tttccttctg ccggtccttt tggctggggt ctgagtctgc ggttctcgcc tgggcagtct    6720
tgacgaggag caaaccccgc cttcagaggg cagacaaagc aggtggcatg aattgatcag    6780
cgagaaaggt gtgagccgag gcagttcctg cgttctgcta caaaaggaat ggaaagggaa    6840
gggaatttcc ccccaccatg ggctgtggga gagttgaccg tattctgggc aagactccat    6900 gaccctctg attctgcagt gtacagctgt ttgagagcct catcattta cttttgaaac    6960
```

```
aggaatgatt tctccttaat tgcttaaggc cggggagcaa agtgtcttaa cttctgtctt    7020
tgactttccc agcgttgagt catcaacact ttgccaatta gctcatggtc ctggcaacct    7080
cagaaacccc tgaagtttta aaaactttct cgctccccac gaccccagaa tgaaacagct    7140
ttaaaaatag ccttaagcaa aaggatgtta tttcattaaa tttggtttaa tggaaagaat    7200
aaaagtaaat gaaaacaca ccctacacac tagactccga acactggtaa tcagtactgc    7260
atagcaaact ctttgggaaa gaaaacgaaa atgttattgc acatgtaaaa tatgaaaact    7320
taactctgct gtgtgttagg caatcctgta atcttttttg actcttaaaa gaaattcatt    7380
tctgaaatgc ttggttggaa gactgtgaca atagctcatg aaattgagtg ttattttttt    7440
cttctttttt taaaaaaata tgtaaagtgc agtcttctgt attcctgcat attgtatata    7500
cctgtatatg ttttcctgag cagttaaata acaataaata tgacgttaat ggtgaaaaaa    7560
aaaaaaaa                                                             7568

<210> SEQ ID NO 61
<211> LENGTH: 691
<212> TYPE: DNA
<213> ORGANISM: Homo sapiens

<400> SEQUENCE: 61
gacccctcac actcacctag ccaccatgga catcgccatc caccacccct ggatccgccg      60 cccccttcttt cctttccact cccccagccg cctctttgac cagttcttcg gagagcacct   120
gttggagtct gatcttttcc cgacgtctac ttccctgagt cccttctacc ttcggccacc    180
ctccttcctg cgggcaccca gctggtttga cactggactc tcagagatgc gcctggagaa    240
ggacaggttc tctgtcaacc tggatgtgaa gcacttctcc ccagaggaac tcaaagttaa    300
ggtgttggga gatgtgattg aggtgcatgg aaaacatgaa gagcgccagg atgaacatgg    360
tttcatctcc agggagttcc acaggaaata ccggatccca gctgatgtag accctctcac    420
cattacttca tccctgtcat ctgatggggt cctcactgtg aatggaccaa ggaaacaggt    480
ctctggccct gagcgcacca ttcccatcac ccgtgaagag aagcctgctg tcaccgcagc    540
ccccaagaaa tagatgccct ttcttgaatt gcatttttta aaacaagaaa gtttccccac    600
cagtgaatga aagtcttgtg actagtgctg aagcttatta atgctaaggg caggcccaaa    660
ttatcaagct aataaaatat cattcagcaa c                                  691

<210> SEQ ID NO 62
<211> LENGTH: 874
<212> TYPE: DNA
<213> ORGANISM: Homo sapiens

<400> SEQUENCE: 62
gcggccgcgt cgaccgctgc gcctgttggg gctgcacctc ggaccagggc ttctgctgca     60
tctgcagcca tgtcgggccg ctcagtgcca catgcccacc cggccaccgc cgagtacgaa    120
tttgccaacc cgagccgcct gggtgagcag cgcttcggag aaggcctcct gccagaagag    180
atcctgaccc ccacactcta ccatggctac tatgtccggc ctcgggccgc cccagctggg    240
gagggcagca gggcaggggc ctccgagctt aggctcagtg agggcaagtt ccaggcattt    300
ctggatgtga gccactttac cccagacgag gtgactgtga ggactgtgga taacctgctg    360
gaggtgtctg cccggcaccc ccagcgcctg gaccgccacg gcttcgtgtc ccgagagttc    420
tgccgcacct atgtcctgcc tgctgatgtc gaccccctggc gagtccgagc tgctctctcc    480
catgatggca tcttaaaccct ggaagcacct cggggtggcc gacatttgga cacagaggtc    540
```

| aatgaggtct acatctccct gctccctgcg cctcctgatc cagaggaaga ggaggaggca | 600 |
| gccatagttg agccctgatt gccacagacc cagcacccag caaatccctc tctacctccc | 660 |
| aaggtgatat gggcagctgc ccaccactcc agaggtagca gcatccttgg gggaagggaa | 720 |
| aggtgcatgg tccacaatgt atggtttggt cccatgggac atgtcatagc cttggtttag | 780 |
| ttttgggtgg agctgaataa acccaaattt cagggcaaaa aaaaaaaaa aaaagaaaaa | 840 |
| aaaaaaaaaa aaaaaaaaaa gtcgacgcgg ccgc | 874 |

<210> SEQ ID NO 63
<211> LENGTH: 2569
<212> TYPE: DNA
<213> ORGANISM: Homo sapiens

<400> SEQUENCE: 63

| tccctcgtct ctctcgggca acatggcggg cgtggaggag gtagcggcct ccgggagcca | 60 |
| cctgaatggc gacctggatc cagacgacag ggaagaagga gctgcctcta cggctgagga | 120 |
| agcagccaag aaaaaaagac gaaagaagaa gaagagcaaa gggccttctg cagcagggga | 180 |
| acaggaacct gataaagaat caggagcctc agtggatgaa gtagcaagac agttggaaag | 240 |
| atcagcattg gaagataaag aaagagatga agatgatgaa gatggagatg gcgatggaga | 300 |
| tggagcaact ggaaagaaga gaaaaagaa gaagaagaa agaggaccaa aagttcaaac | 360 |
| agaccctccc tcagttccaa tatgtgacct gtatcctaat ggtgtatttc ccaaaggaca | 420 |
| agaatgcgaa tacccaccca cacaagatgg gcgaacagct gcttggagaa ctacaagtga | 480 |
| agaaaagaaa gcattagatc aggcaagtga agagatttgg aatgattttc gagaagctgc | 540 |
| agaagcacat cgacaagtta gaaaatacgt aatgagctgg atcaagcctg ggatgacaat | 600 |
| gatagaaatc tgtgaaaagt tggaagactg ttcacgcaag ttaataaaag agaatggatt | 660 |
| aaatgcaggc ctggcatttc ctactggatg ttctctcaat aattgtgctg cccattatac | 720 |
| tcccaatgcc ggtgacacaa cagtattaca gtatgatgac atctgtaaaa tagactttgg | 780 |
| aacacatata agtggtagga ttattgactg tgctttttact gtcactttta atcccaaata | 840 |
| tgatacgtta ttaaaagctg taaaagatgc tactaacact ggaataaagt gtgctggaat | 900 |
| tgatgttcgt ctgtgtgatg ttggtgaggc catccaagaa gttatggagt cctatgaagt | 960 |
| tgaaatagat gggaagacat atcaagtgaa accaatccgt aatctaaatg acattcaat | 1020 |
| tgggcaatat agaatacatg ctggaaaaac agtgccgatt gtgaaaggag gggaggcaac | 1080 |
| aagaatggag gaaggagaag tatatgcaat tgaaaccttt ggtagtacag aaaaggtgt | 1140 |
| tgttcatgat gatatggaat gttcacatta catgaaaaat tttgatgttg acatgtgcc | 1200 |
| aataaggctt ccaagaacaa aacacttgtt aaatgtcatc aatgaaaact ttggaaccct | 1260 |
| tgccttctgc cgcagatggc tggatcgctt gggagaaagt aaatacttga tggctctgaa | 1320 |
| gaatctgtgt gacttgggca ttgtagatcc atatccacca ttatgtgaca ttaaaggatc | 1380 |
| atatacagcg caatttgaac ataccatcct gttgcgtcca acatgtaaag aagttgtcag | 1440 |
| cagaggagat gactattaaa cttagtccaa agccacctca acaccttttat tttctgagct | 1500 |
| ttgttggaaa acatgatacc agaattaatt tgccacatgt tgtctgtttt aacagtggac | 1560 |
| ccatgtaata cttttatcca tgtttaaaaa agaaggaatt tggacaaagg caaaccgtct | 1620 |
| aatgtaatta accaacgaaa aagctttccg gactttaaaa tgctaactgt ttttcccctt | 1680 |
| cctgtctagg aaaatgctat aaagctcaaa ttagttagga atgacttata cgttttgttt | 1740 |
| tgaataccta agagatactt tttggatatt tatattgcca tattcttact tgaatgcttt | 1800 |

```
gaatgactac atccagttct gcacctatac cctctggtgt tgcttttttaa ccttcctgga   1860 atccattttc taaaaaataa agacacattc ttctcagcac cacacaacac ctattccaaa   1920
atcgaccaca tatttggaag taaagctctc ctcagcaaat gtaaagaac agaaattata    1980 acaaactgtc tctcagacca cagtataacc aaactagaac tcaggattaa gaaactcact   2040
caaaaccaca caactacatg gaaactgaac aacctgctcc tgaatgacta ctggatacat   2100
aacaaaatga aggcagaaat aaagatgttc tttaaaacca atgagaacaa agacacaaca   2160
taccagaatc tctgggacac attcaaagca gtgtgtagag ggaaatttat agcactaaat   2220
gcccacaaga gaaagcagga aatatctaaa attgacaccc taacatcaca attaaaagaa   2280
ctagagaagc aagagcaaac acattgaaaa gctaagagaa ggcaagaaat aactaagatc   2340
agagcagaac tgaaggaaat agagacacaa aaaactcttc aaaaaatcaa tgaatccagg   2400
agctggtttt ttgaaacgat caacaaaatt gatagacact agcaagacta ataaagaaga   2460
aaggagagaa gaatcaaata gaagcaataa aaaatgataa aggggatatc accaccaatc   2520
ccacagaaat aaaccaccat cagagaatac tacaaacacc tctacgcaa               2569

<210> SEQ ID NO 64
<211> LENGTH: 3672
<212> TYPE: DNA
<213> ORGANISM: Homo sapiens

<400> SEQUENCE: 64
acatgtgcat atttcattcc ccaggcagac attttttaga aatcaataca tgccccaata    60
ttggaaagac ttgttcttcc acggtgacta cagtacatgc tgaagcgtgc cgtttcagcc   120
ctcatttaat tcaatttgta agtagcgcac gagcctctgt gggggaggat aggctgaaaa   180
aaaaaagtgg gctcgtattt atctacagga ctccatatag tcatatatag gcatataaat   240
ctatgctttt tctttgtttt tttctttctt cctttcttc aaggtttgc attaactttt     300 caaagtagtt cctatagggg cattgaggag cttcctcatt ctgggaaaac tgagaaaacc   360
catattctcc taatacaacc cgtaatagca tttttgcctg cctcgaggca gagtttcccg   420
tgagcaataa actcagcttt tttgtggggc acagtactgg atttgacagt gattccccac   480
gtgtgttcat ctgcacccac cgagccaggc agaggccagc cctccgtggt gcacacagca   540
cgcgcctcag tccatcccat tttagtcttt aaaccctcag gaagtcacag tctccggaca   600
ccacaccaca ttgagcccaa caggtccacg atggatccac ctagtccac cccagccttt    660 ttctttcatc tgaacagaat gtgcattttt ggaagcctcc ctcactctcc atgctggcag   720
agcaggaggg agactgaagt aagagatggc agagggagat ggtggcaaaa aggtttagat   780
gcaggagaac agtaagatgg atggttccgg ccagagtcga tgtggggagg aacagagggc   840
tgaagggaga gggggctgac tgttccattc tagctttggc acaaagcagc agaaagggg    900 aaaagccaat agaaatttcc ttagcttccc caccatatgt attttcatgg atttgagagg   960
aaagagagga aaatggggga atgggttgca aaatagaaat gagcttaatc caggccgcag   1020
agccagggaa ggtgagtaac cttaggaggg tgctagactt tagaagccag ataggaagaa   1080
tcagtctaaa ctggccatgc tttggaaggg acaagactat gtgctccgct gcccaccttc   1140
agcctgcaat gagggactga ggcccacgag tctttccagc tcttcctcca ttctggccag   1200
tccctgcatc ctccctgggg tggaggatgg aaggaaagct gggacaagca gggaacgcat   1260
gattcaggga tgctgtcact cggcagccag attccgaaac tcccattctc caatgacttc   1320
ctcaaccaat gggtggcctt gtgactgttc tttaaggctg aagatatcca ggaaaggggg   1380
```

| | |
|---|---|
| cttggacact ggccaaggag acccottcgt gctgtggaca cagctctctt cactctttgc | 1440 |
| tcatggcatg acacagcgga gaccgcctcc aacaacgaat tggggctac gaagaggaat | 1500 |
| agcgaaaaag caaatctgtt tcaactgatg ggaaccctat agctatagaa cttggggct | 1560 |
| atctcctatg cccctggaca ggacagttgg ctggggacag gagaagtgct caatcttcat | 1620 |
| gagacaaagg ggcccgatca aggcagccac aaggccttga cctgccgagt cagcatgccc | 1680 |
| catctctctc gacagctgtc ccctaaaccc aactcacgtt tctgtatgtc ttaggccagt | 1740 |
| atcccaaacc tcttccacgt cactgttctt tccacccatt ctccctttgc atcttgagca | 1800 |
| gttatccaac taggatctgc caagtggata ctggggtgcc actcccctga gaaaagactg | 1860 |
| agccaggaac tacaagctcc ccccacattc ctcccagcct ggacctaatt cttgagaggg | 1920 |
| gctctctctt cacggactgt gtctggactt tgagcaggct tctgccccctt gcgttggctc | 1980 |
| tttgctgcca gccatcaggt gggggattag agcctggtgt aagtgcgcca gactcttccg | 2040 |
| gtttccaaag ttcgtgcctg cgaacccaaa cctgtgagtc tcttctgcat gcaggagttt | 2100 |
| ctcctgggca gctggtcact ccccagagaa gctgggcctt catggacaca tggaactaag | 2160 |
| cctcccaaat gggagttctg gctgagccca ggtggggag atcctgggaa gggaggcact | 2220 |
| ggaggaagac ggcacctctt cccccatggc agggtgtgag ggaggcaggt ttggaatggt | 2280 |
| gcgagtatgg caatctaagc aggggtctgg tctctttgac tccaggctcg ctttggccga | 2340 |
| ctgtctgctc acccagagac cttggactcc ggactatcca tggctccgaa tctaagtgct | 2400 |
| gcccactccc atgctcacac ccacagaagg tcttcccatc cccttagat tcgtgcctca | 2460 |
| ctccaccagt gaggaagatg cctctgtctt tcccacgact gccaggagat agggaagccc | 2520 |
| agccaggact gaccctcctt cctccagcct gccctgaccc acctggcaaa gcagggcaca | 2580 |
| tggggaggaa gagactggaa cctttctttg acagccaggc ctagacagac aggcctgggg | 2640 |
| acactggccc atgaggggag gaaggcaggc gcacgaggtc cagggaggcc ctttctgat | 2700 |
| catgcccctt ctctcccacc ccatctcccc accaccacct ctgtggcctc catggtaccc | 2760 |
| ccacagggct ggcctcccct agagggtggg cctcaaccac ctcgtcccgc cacgcaccgg | 2820 |
| ttagtgagac agggctgcca cgcaaccgcc aagccccct caaggtggga cagtaccccg | 2880 |
| gacccatcca ctcactcctg agaggctccg gcccagaatg ggaacctcag agaagagctc | 2940 |
| taaggagaag aaaccccata gcgtcagaga ggatatgtct ggcttccaag agaaaggagg | 3000 |
| ctccgttttg caaagtggag gagggacgag ggacaggggt ttcaccagcc agcaacctgg | 3060 |
| gccttgtact gtctgtgttt ttaaaaccac taaagtgcaa gaattacatt gcactgtttc | 3120 |
| tccacttttt attttctctt aggcttttgt ttctatttca aacatacttt cttggttttc | 3180 |
| taatggagta tatagtttag tcatttcaca gactctggcc tcctctcctg aaatcctttt | 3240 |
| ggatggggaa agggaaggtg gggagggtcc gaggggaagg ggaccccagc ttccctgtgc | 3300 |
| ccgctcaccc cactccacca gtccccggtc gccagccgga gtctcctctc taccgccact | 3360 |
| gtcacaccgt agcccacatg gatagcacag ttgtcagaca agattccttc agattccgag | 3420 |
| ttgctaccgg ttgttttcgt tgttgttgtt gttgttttc ttttttcttt ttttttgaa | 3480 |
| gacagcaata accacagtac atattactgt agttctctat agttttacat acattcatac | 3540 |
| cataactctg ttctctcctc tttttgtttt tcaacttta aaacaaaaat aaacgatgat | 3600 |
| aatctttact ggtgaaaagg atggaaaat aaatcaacaa atgcaaccag tttgtgagaa | 3660 |
| aaaaaaaaaa aa | 3672 |

<210> SEQ ID NO 65

<211> LENGTH: 1826
<212> TYPE: DNA
<213> ORGANISM: Homo sapiens

<400> SEQUENCE: 65

```
agtctgcact ggagctgcct ggtgaccaga agtttggagt ccgctgacgt cgccgcccag      60
atggcctcca ggctgaccct gctgaccctc ctgctgctgc tgctggctgg ggatagagcc     120
tcctcaaatc caaatgctac cagctccagc tcccaggatc cagagagttt gcaagacaga     180
ggcgaaggga aggtcgcaac aacagttatc tccaagatgc tattcgttga acccatcctg     240
gaggtttcca gcttgccgac aaccaactca acaaccaatt cagccaccaa ataacagct     300
aataccactg atgaacccac cacacaaccc accacagagc ccaccaccca acccaccatc     360
caacccaccc aaccaactac ccagctccca acagattctc ctacccagcc cactactggg     420
tccttctgcc caggacctgt tactctctgc tctgacttgg agagtcattc aacagaggcc     480
gtgttggggg atgctttggt agatttctcc ctgaagctct accacgcctt ctcagcaatg     540
aagaaggtgg agaccaacat ggccttttcc ccattcagca tcgccagcct ccttacccag     600
gtcctgctcg ggctgggca gaacaccaaa acaaacctgg agagcatcct ctcttacccc     660
aaggacttca cctgtgtcca ccaggccctg aagggcttca cgaccaaagg tgtcacctca     720
gtctctcaga tcttccacag cccagacctg gccataaggg acacctttgt gaatgcctct     780
cggaccctgt acagcagcag ccccagagtc ctaagcaaca acagtgacgc caacttggag     840
ctcatcaaca cctgggtggc caagaacacc aacaacaaga tcagccggct gctagacagt     900
ctgccctccg ataccccgcct tgtcctcctc aatgctatct acctgagtgc caagtggaag     960
acaacatttg atcccaagaa aaccagaatg gaaccctttc acttcaaaaa ctcagttata    1020
aaagtgccca tgatgaatag caagaagtac cctgtggccc atttcattga ccaaactttg    1080
aaagccaagg tggggcagct gcagctctcc cacaatctga gtttggtgat cctggtaccc    1140
cagaacctga acatcgtct tgaagacatg aacaggctc tcagcccttc tgttttcaag    1200
gccatcatgg agaaactgga gatgtccaag ttccagccca ctctcctaac actacccgc    1260
atcaaagtga cgaccagcca ggatatgctc tcaatcatgg agaaattgga attcttcgat    1320
ttttcttatg accttaacct gtgtgggctg acagaggacc cagatcttca ggtttctgcg    1380
atgcagcacc agacagtgct ggaactgaca gagactgggg tggaggcggc tgcagcctcc    1440
gccatctctg tggcccgcac cctgctggtc tttgaagtgc agcagccctt cctcttcgtg    1500
ctctgggacc agcagcacaa gttccctgtc ttcatgggc gagtatatga ccccagggcc    1560
tgagacctgc aggatcaggt tagggcgagc gctacctctc cagcctcagc tctcagttgc    1620
agccctgctg ctgcctgcct ggacttgccc ctgccacctc ctgcctcagg tgtccgctat    1680
ccaccaaaag ggctcctgag ggtctgggca agggacctgc ttctattagc ccttctccat    1740
ggccctgcca tgctctccaa accactttt gcagctttct ctagttcaag ttcaccagac    1800
tctataaata aaacctgaca gaccat                                         1826
```

<210> SEQ ID NO 66
<211> LENGTH: 5489
<212> TYPE: DNA
<213> ORGANISM: Homo sapiens

<400> SEQUENCE: 66

```
ggctgagttt tatgacgggc ccggtgctga agggcaggga acaacttgat ggtgctactt      60
tgaactgctt ttcttttctc cttttgcac aaagagtctc atgtctgata tttagacatg     120
```

```
atgagctttg tgcaaaaggg gagctggcta cttctcgctc tgcttcatcc cactattatt    180
ttggcacaac aggaagctgt tgaaggagga tgttcccatc ttggtcagtc ctatgcggat    240
agagatgtct ggaagccaga accatgccaa atatgtgtct gtgactcagg atccgttctc    300
tgcgatgaca taatatgtga cgatcaagaa ttagactgcc ccaacccaga aattccattt    360
ggagaatgtt gtgcagtttg cccacagcct ccaactgctc ctactcgccc tcctaatggt    420
caaggacctc aaggccccaa gggagatcca ggccctcctg gtattcctgg agaaatggt    480 gaccctggta ttccaggaca accagggtcc cctggttctc ctggccccc tggaatctgt    540 gaatcatgcc ctactggtcc tcagaactat tctccccagt atgattcata tgatgtcaag    600
tctggagtag cagtaggagg actcgcaggc tatcctggac cagctggccc cccaggccct    660
cccggtcccc ctggtacatc tggtcatcct ggttcccctg gatctccagg ataccaagga    720 cccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa gtccagctg gatacctgg attccctggt    900 atgaaaggac acagaggctt cgatggacga aatggagaaa agggtgaaac aggtgctcct    960
ggattaaagg gtgaaaatgg tcttccaggc gaaaatggag ctcctggacc catgggtcca   1020 agagggctc ctggtgagcg aggacggcca ggacttcctg gggctgcagg tgctcggggt   1080
aatgacggtg ctcgaggcag tgatggtcaa ccaggccctc ctggtcctcc tggaactgcc   1140
ggattccctg gatcccctgg tgctaagggt gaagttggac ctgcagggtc tcctggttca   1200
aatggtgccc ctggacaaag aggagaacct ggacctcagg gacacgctgg tgctcaaggt   1260
cctcctggcc ctcctgggat taatggtagt cctggtggta aggcgaaat gggtcccgct   1320 ggcattcctg gagctcctgg actgatggga gcccggggtc ctccaggacc agccggtgct   1380
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg accaaatgg catcccagga   1620 gaaaagggtc ctgctggaga gcgtggtgct ccaggccctg cagggcccag aggagctgct   1680
ggagaacctg gcagagatgg cgtccctgga ggtccaggaa tgagggggcat gcccggaagt   1740 ccaggaggac caggaagtga tgggaaacca gggcctcccg gaagtcaagg agaaagtggt   1800
cgaccaggtc ctcctgggcc atctggtccc gaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaagg accccaggg   1980 cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcagggccc caggactta gggtggagc tggtcccct   2220 ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg cccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
```

-continued

```
gaaactggcc ctccaggacc tgctggtttc cctggtgctc ctggacagaa tggtgaacct    2580
ggtggtaaag gagaaagagg ggctccgggt gagaaaggtg aaggaggccc tcctggagtt    2640
gcaggacccc ctggaggttc tggacctgct ggtcctcctg gtccccaagg tgtcaaaggt    2700
gaacgtggca gtcctggtgg acctggtgct gctggcttcc ctggtgctcg tggtcttcct    2760
ggtcctcctg gtagtaatgg taacccagga ccccccaggtc ccagcggttc tccaggcaag    2820
gatgggcccc caggtcctgc gggtaacact ggtgctcctg gcagccctgg agtgtctgga    2880
ccaaaaggtg atgctggcca accaggagag aaggatcgc ctggtgccca gggcccacca    2940
ggagctccag gcccacttgg gattgctggg atcactggag cacggggtct tgcaggacca    3000
ccaggcatgc caggtcctag gggaagccct ggccctcagg gtgtcaaggg tgaaagtggg    3060
aaaccaggag ctaacggtct cagtggagaa cgtggtcccc ctggaccccca gggtcttcct    3120 ggtctggctg gtacagctgg tgaacctgga agagatggaa accctggatc agatggtctt    3180
ccaggccgag atggatctcc tggtggcaag ggtgatcgtg gtgaaaatgg ctctcctggt    3240 gccccctggcg ctcctggtca tccaggccca cctggtcctg tcggtccagc tggaaagagt    3300
ggtgacagag gagaaagtgg ccctgctggc cctgctggtg ctcccggtcc tgctggttcc    3360
cgaggtgctc ctggtcctca aggcccacgt ggtgacaaag gtgaaacagg tgaacgtgga    3420
gctgctggca tcaaaggaca tcgaggattc cctggtaatc caggtgcccc aggttctcca    3480
ggccctgctg gtcagcaggg tgcaatcggc agtccaggac ctgcaggccc cagaggacct    3540
gttggaccca gtggacctcc tggcaaagat ggaaccagtg gacatccagg tcccattgga    3600
ccaccagggc ctcgaggtaa cagaggtgaa agaggatctg agggctcccc aggccaccca    3660
gggcaaccag gccctcctgg acctcctggt gcccctggtc cttgctgtgg tggtgttgga    3720
gccgctgcca ttgctgggat tggaggtgaa aaagctggcg gttttgcccc gtattatgga    3780
gatgaaccaa tggatttcaa aatcaacacc gatgagatta tgacttcact caagtctgtt    3840
aatggacaaa tagaaagcct cattagtcct gatggttctc gtaaaaaccc cgctagaaac    3900
tgcagagacc tgaaattctg ccatcctgaa ctcaagagtg gagaatactg ggttgaccct    3960
aaccaaggat gcaaattgga tgctatcaag gtattctgta aatggaaac tggggaaaca    4020 tgcataagtg ccaatccttt gaatgttcca cggaaacact ggtggacaga ttctagtgct    4080
gagaagaaac acgtttggtt tggagagtcc atggatggtg gttttcagtt tagctacggc    4140
aatcctgaac ttcctgaaga tgtccttgat gtgcagctgg cattccttcg acttctctcc    4200
agccgagctt cccagaacat cacatatcac tgcaaaaata gcattgcata catggatcag    4260
gccagtggaa atgtaaagaa ggccctgaag ctgatggggt caaatgaagg tgaattcaag    4320
gctgaaggaa atagcaaatt cacctacaca gttctggagg atggttgcac gaaacacact    4380
ggggaatgga gcaaaacagt ctttgaatat cgaacacgca aggctgtgag actacctatt    4440
gtagatattg caccctatga cattggtggt cctgatcaag aatttggtgt ggacgttggc    4500
cctgtttgct ttttataaac caaactctat ctgaaatccc aacaaaaaaa atttaactcc    4560
atatgtgttc ctcttgttct aatccttgtca accagtgcaa gtgaccgaca aaattccagt    4620
tatttatttc caaaatgttt ggaaacagta aatttgaca aagaaaatg atacttctct    4680 ttttttgctg ttccaccaaa tacaattcaa atgctttttg ttttatttt ttaccaattc    4740 caatttcaaa atgtctcaat ggtgctataa taaataaact tcaacactct ttatgataac    4800
aacactgtgt tatattcttt gaatcctagc ccatctgcag agcaatgact gtgctcacca    4860
gtaaaagata acctttcttt ctgaaatagt caaatacgaa attagaaaag ccctccctat    4920
```

```
tttaactacc tcaactggtc agaaacacag attgtattct atgagtccca gaagatgaaa    4980
aaaattttat acgttgataa aacttataaa tttcattgat taatctcctg gaagattggt    5040 ttaaaagaa aagtgtaatg caagaattta agaaatatt tttaaagcca caattatttt     5100
aatattggat atcaactgct tgtaaaggtg ctcctctttt ttcttgtcat tgctggtcaa    5160
gattactaat atttgggaag ctttaaaga cgcatgttat ggtgctaatg tactttcact    5220
tttaaactct agatcagaat tgttgacttg cattcagaac ataaatgcac aaaatctgta    5280
catgtctccc atcagaaaga ttcattggca tgccacaggg attctcctcc ttcatcctgt    5340
aaaggtcaac aataaaaacc aaattatggg gctgcttttg tcacactagc atagagaatg    5400
tgttgaaatt taactttgta agcttgtatg tggttgttga tcttttttt ccttacagac     5460 acccataata aaatatcata ttaaaattc                                      5489

<210> SEQ ID NO 67
<211> LENGTH: 5222
<212> TYPE: DNA
<213> ORGANISM: Homo sapiens

<400> SEQUENCE: 67
ttctgcccgc cgccgccgct gccgagcgcc gcctttgttc cctgcaggaa gggcgagcgc      60
gcgggccagc gctcagccag cgcctcacga cccttcgtcc tccgctaagc tccaacgctc     120
tgctcgacta gccgcgcgcc ttccggggct ccgcagaccc gcgagatggc accaaggagg     180
aacaacgggc agtgctggtg tctgctgatg ctgctctcgg tctccacgcc ctccctgct      240 gtcacccaga cccgcggtgc gacagagact gcttcccagg gtcacctgga cctcacgcag     300
ctcatcggtg tcccgctgcc ctcgtccgta tcctttgtca caggctatgg tggcttcccg     360
gcctacagtt tcgggcctgg tgccaatgtt ggccgcccag ccaggactct catcccatcc     420
accttcttca gggacttcgc catcagggtc gtggtgaagc ccagcagcac ccgtggtggc     480
gtgctcttcg ccatcactga cgccttccag aaggtcatct acctgggcct gcggctctca     540
ggtgtggagg acggccacca gcggatcatc ctctactaca cggagccagg ctcccatgtg     600
tcccaagaag ctgctgcctt ctcggtgcct gtgatgaccc acaggtggaa ccgcttcgcc     660
atgattgtcc agggtgagga agtgaccctc ctcgtgaact gtgaggagca cagccgcatc     720
cccttccagc ggtcctccca ggcttttgct tttgagtcca cgctggaat cttcatgggc      780 aatgcaggag ctacagggct cgagagattc actggctccc tccagcagct caccgtgcac     840
cccgacccca ggactcccga ggagctgtgt gaccctgaag agtcctcggc atctggagag     900
accagtgggc tgcaggaggc agacggagta gctgagatct tagaagccgt cacctacact     960
caagcctcgc ccaaagaagc aaaagttgaa cccataaaca cacctccaac tccatcctcc    1020 cccttgaag acatggaact ttctggtgaa cctgtacccg aggggacccc tgggaaccacc    1080 aacatgagca tcatccagca cagcagcccc aaacaagggt ctggtgagat cctgaatgac    1140
acactggagg gggttcattc tgtggatggt gaccccatta ctgacagcgg ctcagggct    1200 ggggccttcc ttgacattgc tgaagaaag aatttagcag caacagcagc ggggctggcc    1260
gaggtgccca tcagcactgc tggagaagca gaggccagca gtgtgcccac cggggacca    1320 accctctcta tgtccacgga acccagag gaagggtca ctccaggtcc agataatgaa      1380
gagcgtttac gagcaacagc agcaggggag gccgaggcac tcgccagcat gcctgggaa    1440 gtggaggcca gtggtgtggc ccccggggag ctggacctct ccatgtccgc ccagagcctc    1500
ggggaagagg ccactgtggg tccaagcagt gaagacagtt aacaacagc tgcagctgca    1560
```

```
accgaagtgt ccctcagtac ttttgaggat gaggaagcca gtggggtccc cacagatggc    1620
ctggctcccc tcacagccac catggcccct gagcgggcag tcacttctgg tcctggtgat    1680
gaagaagact tggcagcagc acaacagag gagcccctca tcacagctgg gggtgaagag     1740
tccggcagcc ctcccctga tgggccaccg ctgcccctgc ccacagtggc tcctgaaaga     1800
tggatcactc cagctcaaag agaacatgtg ggaatgaaag gacaggctgg gcccaaagga    1860
gaaaagggtg atgctgggga ggagcttcct ggccctcctg aaccttctgg gcctgttgga    1920
cccacggcag gagcagaagc agagggctct ggcctaggct ggggctcgga cgtcggctct    1980
ggctctggtg acctggtggg cagtgagcag ctgctgagag gtcctccagg acccccaggg    2040
ccacctggct tacctgggat tccaggaaaa ccaggaactg atgttttcat ggggacccct    2100
ggatctcctg gagaggatgg acctgctggt gaacctgggc cccgggccc tgagggacag     2160 cctggagttg atggagccac cggccttccc gggatgaaag gggagaaggg agcaagaggg    2220
cctaatggct cagttggtga aaaggtgac cctggcaaca gaggcttacc tggacccccg     2280
gggaaaaagg gacaagctgg ccctcctggg gtcatgggac cccagggcc tcctggaccc    2340 cctgggcccc caggccctgg atgcacaatg ggacttggat tcgaggatac cgaaggctct    2400
ggaagcaccc agctattgaa tgaacccaaa ctctccagac caacggctgc aattggtctc    2460
aaaggagaga aaggagaccg gggacccaag ggagaaaggg ggatggatgg agccagtatt    2520
gtgggacccc ctgggccgag agggccacct gggcacatca aggtcttgtc taattccttg    2580
atcaatatca cccatggatt catgaatttc tcggacattc ctgagctggt ggggcctccg    2640
gggccggacg ggttgcctgg gctgccagga tttccaggtc ctagaggacc aaaaggtgac    2700
actggtttac ctggctttcc aggactaaaa ggagaacagg gcgagaaggg agagccgggt    2760
gccatcctga cagaggacat tcctctggaa aggctgatgg ggaaaagg tgaacctgga     2820 atgcatggag ccccaggacc aatggggccc aaaggaccac caggacataa aggagaattt    2880
ggccttcccg ggcgacctgg tcgcccagga ctgaatggcc tcaagggtac caaaggagat    2940
ccaggggtca ttatgcaggg cccacctggc ttacctggcc ctccaggccc cctgggcca    3000 cctggagctg tgattaacat caaaggagcc attttcccaa tacccgtccg accacactgc    3060
aaaatgccag ttgatactgc tcatcctggg agtccagagc tcatcacttt tcacggtgtt    3120
aaaggagaga aaggatcctg gggtcttcct ggctcaaagg gagaaaaagg cgaccaggga    3180
gcccagggac caccaggtcc tccacttgat ctagcttacc tgagacactt tctgaacaac    3240
ttgaaggggg agaatggaga caaggggttc aaaggtgaaa aaggagaaaa aggagacatt    3300
aatggcagct tccttatgtc tgggcctcca ggcctgcccg gaaatccagg cccggctggc    3360
caaaaagggg agacagtcgt tgggcccaa ggaccccag gtgctcctgg tctgcctggg    3420
ccacctggct ttgaagacc tggtgatcct gggccaccgg gcccccggg gccaccagga     3480 cctccagcta tcctgggagc agctgtggcc cttccaggtc ccctggccc tccaggacag    3540 ccagggcttc ccggatccag aaacctggtc acagcattca gcaacatgga tgacatgctg    3600
cagaaagcgc atttggttat agaaggaaca ttcatctacc tgagggacag cactgagttt    3660
ttcattcgtg ttagagatgg ctggaaaaaa ttacagctgg gagaactgat ccccattcct    3720
gccgacagcc ctcacccccc tgcgctttcc agcaacccac atcagcttct gcctccacca    3780
aaccctattt caagtgccaa ttatgagaag cctgctctgc atttggctgc tctgaacatg    3840 ccatttctg gggacattcg agctgatttt cagtgcttca gcaggccag agctgcagga     3900 ctgttgtcca cctaccgagc attcttatct tcccatttgc aagatctgtc caccattgtg    3960
```

-continued

| | | | | | |
|---|---|---|---|---|---|
| aggaaagcag | agagatacag | ccttcccata | gtgaacctca | agggccaagt | acttttaat | 4020 |
| aatgggact | caatttttc | tggccacgga | ggtcagttca | atatgcatat | tccaatatac | 4080 |
| tcctttgatg | gtcgagacat | aatgacagat | ccttcttggc | cccagaaagt | catttggcat | 4140 |
| ggctccagcc | cccatggcgt | ccgccttgtg | gataactact | gtgaagcatg | gcgaaccgcg | 4200 |
| gacacagcgg | tcacgggact | tgcctccccg | ctgagcacgg | ggaagattct | ggaccagaaa | 4260 |
| gcatacagct | gtgctaatcg | gctaattgtc | ctatgtatcg | aaaacagttt | catgacagac | 4320 |
| gctaggaagt | aatggccttc | tgatgattct | taaagagttt | tcaattttt | cttatgtgaa | 4380 |
| gagttgacac | tgaaatctaa | aatgtttaat | tgttgtaaat | attacagttt | ttttttttt | 4440 |
| actacatatt | ctttacaaca | gcaaccaaag | aaaacatacc | tcaatacact | caaaactgaa | 4500 |
| gacatagagg | actcagatca | aagacaaaat | ctgatccata | tattggtgct | agattctgca | 4560 |
| ggaaacccca | gcagtgtgaa | cgcatcccaa | cataggttaa | gagcaagttg | aaaacaaagg | 4620 |
| ccagattctg | ccactgcatc | cttcagacag | ttatatcctc | cttttaaacc | attgttgttg | 4680 |
| agtgtaagat | gtccttcatg | ttttcttata | aagtcagtgt | ttagaaatgt | tacccttct | 4740 |
| aagttatata | cagatcaaat | gctttttct | ttcacgtaca | tccatcattt | gcaactgctg | 4800 |
| ttcgtacaca | gaaacaggac | tgctcaaatg | atcctatttg | tattttctga | tgctatcaga | 4860 |
| ctctaatgtt | ttttcccta | aaatattatt | gccatcatgc | tttaggaatt | tttatattt | 4920 |
| tacacaatca | tattttagta | tggtgtctgt | ttatgtaact | ctgacttgct | ggaaaagttg | 4980 |
| aaactccaaa | taatctgaaa | ctagaaaaga | aatagcacat | aattactacc | ttccccttgg | 5040 |
| cggctctcct | ccccccaaccc | ccaccccaca | atttatgac | ttccatttgg | caattgttga | 5100 |
| attataactg | cgactgaaac | aaacaggttc | atagagatga | attttctgag | aaacatatat | 5160 |
| ctacatgttg | tataattgga | ttttttttcc | atgtaagtga | acataaaaac | atcttttccg | 5220 |
| gg | | | | | | 5222 |

<210> SEQ ID NO 68
<211> LENGTH: 4079
<212> TYPE: DNA
<213> ORGANISM: Homo sapiens

<400> SEQUENCE: 68

| | | | | | |
|---|---|---|---|---|---|
| ggagcggcgg | gcgggcggga | gggctggcgg | ggcgaacgtc | tgggagacgt | ctgaaagacc | 60 |
| aacgagactt | tggagaccag | agacgcgcct | ggggggacct | ggggcttggg | gcgtgcgaga | 120 |
| tttcccttgc | attcgctggg | agctcgcgca | gggatcgtcc | catggccggg | gctcggagcc | 180 |
| gcgacccttg | gggggcctcc | gggatttgct | accttttgg | ctccctgctc | gtcgaactgc | 240 |
| tcttctcacg | ggctgtcgcc | ttcaatctgg | acgtgatggg | tgccttgcgc | aaggagggcg | 300 |
| agccaggcag | cctcttcggc | ttctctgtgg | ccctgcaccg | gcagttgcag | cccgacccc | 360 |
| agagctggct | gctggtgggt | gctccccagg | ccctggctct | tcctgggcag | caggcgaatc | 420 |
| gcactggagg | cctcttcgct | tgcccgttga | gcctggagga | gactgactgc | tacagagtgg | 480 |
| acatcgacca | gggagctgat | atgcaaaagg | aaagcaagga | gaaccagtgg | ttgggagtca | 540 |
| gtgttcggag | ccaggggcct | gggggcaaga | ttgttacctg | tgcacaccga | tatgaggcaa | 600 |
| ggcagcgagt | ggaccagatc | ctggagacgc | gggatatgat | tggtcgctgc | tttgtgctca | 660 |
| gccaggacct | ggccatccgg | gatgagttgg | atggtgggga | atggaagttc | tgtgagggac | 720 |
| gccccaagg | cctgaacaa | tttgggttct | gccagcaggg | cacagctgcc | gccttctccc | 780 |
| ctgatagcca | ctacctcctc | tttgggggcc | caggaaccta | taattggaag | gggttgcttt | 840 |

-continued

```
ttgtgaccaa cattgatagc tcagaccccg accagctggt gtataaaact ttggaccctg     900
ctgaccggct cccaggacca gccggagact tggccctcaa tagctactta ggcttctcta     960
ttgactcggg gaaaggtctg gtgcgtgcag aagagctgag ctttgtggct ggagccccccc   1020 gcgccaacca caagggtgct gtggttatcc tgcgcaagga cagcgccagt cgcctggtgc    1080
ccgaggttat gctgtctggg gagcgcctga cctccggctt tggctactca ctggctgtgg    1140
ctgacctcaa cagtgatggc tggccagacc tgatagtggg tgcccccctac ttctttgagc   1200 gccaagaaga gctgggggg gctgtgtatg tgtacttgaa ccagggggt cactgggctg       1260 ggatctcccc tctccggctc tgcggctccc ctgactccat gttcgggatc agcctggctg    1320
tcctggggga cctcaaccaa gatggctttc agatattgc agtgggtgcc cccttttgatg    1380 gtgatgggaa agtcttcatc taccatggga gcagcctggg ggttgtcgcc aaaccttcac    1440
aggtgctgga gggcgaggct gtgggcatca agagcttcgg ctactccctg tcaggcagct    1500
tggatatgga tgggaaccaa taccctgacc tgctggtggg ctccctggct gacaccgcag    1560
tgctcttcag ggccagaccc atcctccatg tctcccatga ggtctctatt gctccacgaa    1620
gcatcgacct ggagcagccc aactgtgctg gcggccactc ggtctgtgtg gacctaaggg    1680
tctgtttcag ctacattgca gtccccagca gctatagccc tactgtggcc ctggactatg    1740
tgttagatgc ggacacagac cggaggctcc ggggccaggt tccccgtgtg acgttcctga    1800
gccgtaacct ggaagaaccc aagcaccagg cctcgggcac cgtgtggctg aagcaccagc    1860
atgaccgagt ctgtgtgagac gccatgttcc agctccagga aaatgtcaaa gacaagcttc   1920
gggccattgt agtgaccttg tcctacagtc tccagacccc tcggctccgg cgacaggctc    1980
ctggccaggg gctgcctcca gtggccccca tcctcaatgc ccaccagccc agcacccagc    2040
gggcagagat ccacttcctg aagcaaggct gtggtgaaga caagatctgc cagagcaatc    2100
tgcagctggt ccacgcccgc ttctgtaccc gggtcagcga cacggaattc caacctctgc    2160
ccatggatgt ggatggaaca acagccctgt ttgcactgag tgggcagcca gtcattggcc    2220
tggagctgat ggtcaccaac ctgccatcgg acccagccca gccccaggct gatggggatg    2280
atgcccatga agcccagctc ctggtcatgc ttcctgactc actgcactac tcaggggtcc    2340
gggccctgga ccctgcggag aagccactct gcctgtccaa tgagaatgcc tcccatgttg    2400
agtgtgagct ggggaacccc atgaagagag gtgcccaggt caccttctac ctcatccttta    2460 gcacctccgg gatcagcatt gagaccacgg aactggaggt agagctgctg ttggccacga    2520
tcagtgagca ggagctgcat ccagtctctg cacgagcccg tgtcttcatt gagctgccac    2580
tgtccattgc aggaatggcc attccccagc aactcttctt ctctggtgtg gtgaggggcg    2640
agagagccat gcagtctgag cgggatgtgg gcagcaaggt caagtatgag gtcacggttt    2700
ccaaccaagg ccagtcgctc agaaccctgg gctctgcctt cctcaacatc atgtggcctc    2760
atgagattgc caatgggaag tggttgctgt acccaatgca ggttgagctg gagggcgggc    2820 agggcctgg gcagaaaggg cttgctctc ccaggcccaa catcctccac ctggatgtgg       2880
acagtaggga taggaggcgg cgggagctgg agccacctga gcagcaggag cctggtgagc    2940
ggcaggagcc cagcatgtcc tggtggccag tgtcctctgc tgagaagaag aaaaacatca    3000
ccctggactg cgcccggggc acggccaact gtgtggtgtt cagctgccca ctctacagct    3060
ttgaccgcgc ggctgtgctg catgtctggg gccgtctctg gaacagcacc tttctggagg    3120
agtactcagc tgtgaagtcc ctggaagtga ttgtccgggc caacatcaca gtgaagtcct    3180
ccataaagaa cttgatgctc cgagatgcct ccacagtgat cccagtgatg gtatacttgg    3240
```

-continued

| | |
|---|---|
| acccccatggc tgtggtggca aaggagtgc cctggtgggt catcctcctg gctgtactgg | 3300 |
| ctgggctgct ggtgctagca ctgctggtgc tgctcctgtg aagatggga ttcttcaaac | 3360 |
| gggcgaagca ccccgaggcc accgtgcccc agtaccatgc ggtgaagatt cctcgggaag | 3420 |
| accgacagca gttcaaggag gagaagacgg gcaccatcct gaggaacaac tggggcagcc | 3480 |
| cccggcggga gggcccggat gcacacccca tcctggctgc tgacgggcat cccgagctgg | 3540 |
| gccccgatgg gcatccaggg ccaggcaccg cctaggttcc catgtcccag cctggcctgt | 3600 |
| ggctgccctc catcccttcc ccagagatgg ctccttggga tgaagagggt agagtgggct | 3660 |
| gctggtgtcg catcaagatt tggcaggatc ggcttcctca ggggcacaga cctctcccac | 3720 |
| ccacaagaac tcctcccacc caacttcccc ttagagtgct gtgagatgag agtgggtaaa | 3780 |
| tcagggacag ggccatgggg tagggtgaga agggcagggg tgtcctgatg caaaggtggg | 3840 |
| gagaagggat cctaatccct tcctctccca ttcaccctgt gtaacaggac cccaaggacc | 3900 |
| tgcctccccg gaagtgcctt aacctagagg gtcgggagg aggttgtgtc actgactcag | 3960 |
| gctgctcctt ctctagtttc ccctctcatc tgaccttagt ttgctgccat cagtctagtg | 4020 |
| gtttcgtggt ttcgtctatt tattaaaaaa tatttgagaa caaaaaaaaa aaaaaaaaa | 4079 |

<210> SEQ ID NO 69
<211> LENGTH: 6276
<212> TYPE: DNA
<213> ORGANISM: Homo sapiens

<400> SEQUENCE: 69

| | |
|---|---|
| gagtgtggct gcagtgcgcc gggacaccag ggctccgcgc tccgcactca agaggctccc | 60 |
| gcgtcccaac ccctcgcgcc cgcgcgttcg cggatccagg ccgaggaccg aaaggggccg | 120 |
| cccgagcccc cggggccggc gcccagagag cccagcaagg ccggccgccc tgccggtgtg | 180 |
| ccgccggcgg gtgcttctgg aagggccaat gcgttcgggc agcagccctg aagccgagcc | 240 |
| cgaggctaag tgggactgac cggggcccag agtggacgaa ccgccagcat ggggagagac | 300 |
| cagcgcgcgg tggccggccc tgccctacgg cggtggctgc tgctggggac agtgaccgtg | 360 |
| gggttcctcg cccagagcgt cttggcgggt gtgaagaagt tgatgtgcc gtgtggagga | 420 |
| agagattgca gtggggctg ccagtgctac cctgagaaag gtggacgtgg tcagcctggg | 480 |
| ccagtgggcc cccaggggta caatgggcca ccaggattac aaggattccc cgggctgcag | 540 |
| ggacgtaaag gagacaaggg tgaaagggga gccccggag taacaggacc caagggcgac | 600 |
| gtgggagcaa gaggcgtttc tggattccct ggtgccgatg gaattcctgg acacccgggg | 660 |
| caaggtgggc ccagggaag gccgggctac gatggctgca acggaaccca gggagactca | 720 |
| ggtccacagg ggccccccgg ctctgagggg ttcaccgggc ctcccgggcc caaggacca | 780 |
| aaagggcaga aggtgagcc ttatgcactg cctaaagagg agcgcgacag atatcggggt | 840 |
| gaacctggag agcctggatt ggtcggtttc cagggacctc ccggccgccc tgggcatgtg | 900 |
| ggacagatgg gtccagttgg agctccaggg agaccaggac cacctggacc cctggacca | 960 |
| aaaggacagc aaggcaacag aggacttggt ttctacggag ttaagggtga aaagggtgac | 1020 |
| gtagggcagc cggacccaa cgggattcca tcagacaccc tccacccccat catcgcgccc | 1080 |
| acaggagtca ccttccaccc agatcagtac aaggggtgaaa aaggcagtga ggggaacca | 1140 |
| ggaataagag gcatttcctt gaagggagaa gaaggaatca tgggctttcc tggacttagg | 1200 |
| ggttaccctg gcttgagtgg tgaaaaagga tcaccaggac agaagggaag ccgaggcctg | 1260 |
| gatggctatc aagggcctga tggaccccgg ggacctaagg gagaagccgg agacccaggg | 1320 |

```
cccccctggac tacctgccta ctcccctcac ccttccctag caaaaggtgc cagaggtgac    1380
ccaggattcc caggggccca aggggagcca ggaagccagg gtgagccagg agacccgggc    1440
ctcccaggtc ccccctggcct ctccattgga gatggagatc agaggagagg cctgccgggt   1500
gagatgggac ccaagggctt catcggagac cccggcatcc ctgcgctcta cgggggccca    1560
cctggacctg atggaaagcg agggcctcca ggaccccccg ggctccctgg accacctgga    1620
cctgatggct tcctgtttgg gctgaaagga gcaaaggaa gagcaggctt ccctgggctt     1680
cccggctccc ctggagcccc cggaccaaag gggtggaaag gtgacgctgg ggaatgcaga    1740
tgtacagaag cgacgaagc tatcaaaggt cttccaggac tgccaggacc caagggcttc     1800
gcaggcatca cgggagcc ggggaggaaa ggggacaaag gagacccgg ccaacacggc       1860 ctccctgggt tcccagggct caaggggagtg cctggcaaca ttggtgctcc cggacccaaa  1920
ggagcaaaag gagattccag aacaatcaca accaaggtg agcggggaca gcccggcgtc    1980
ccaggtgtgc ccgggatgaa aggtgacgat ggcagcccag gccgcgatgg gctcgatgga   2040
ttccccggcc tcccaggccc tcccggtgat ggcatcaagg gcctccagg ggacccaggt    2100 tatccaggaa tacctggaac gaagggtact ccaggagaaa tgggcccccc aggactgggc   2160
cttcccggcc tcaaaggcca acgtggttc cctggagacg ccggcttacc tggaccacca    2220
ggcttcctgg gccctcctgg ccccgcaggg acccaggac aaatagattg tgacacagat    2280 gtgaaaggg ccgttggagg tgacagacag gaggccatcc agccaggttg cataggaggg    2340
cccaagggat tgccaggcct gccaggaccc caggcccca caggtgccaa aggcctccga    2400
ggaatcccag gcttcgcagg agctgatgga ggaccagggc ccaggggctt gccaggagac   2460
gcaggtcgtg aagggttccc aggaccccca gggttcatag accccgagg atccaaaggt   2520 gcagtgggcc tccctggccc agatggatcc ccaggtccca tcggcctgcc agggccagat   2580 gggcccctg gggaaagggg cctcctgga gaagtcctgg gagctcagcc cgggccacgg    2640
ggagatgctg gtgtgcctgg acagcctggg cttaaaggcc ttcccggaga cagaggcccc   2700
cctggattca gaggaagcca agggatgcct gggatgccag ggctgaaggg ccagccaggc   2760
ctcccaggac cttccggcca gccaggcctg tatgggcctc caggactgca tggattccca   2820
ggagctcctg gccaagaggg gcccttgggg ctgccaggaa tcccaggccg tgaaggtctg   2880
cctggtgata gagggaccc tggggacaca ggcgctcctg gccctgtggg catgaaaggt   2940
ctctctggtg acagaggaga tgctggcttc acagggagc aaggccatcc aggaagccct    3000
ggatttaaag gaattgatgg aatgcctggg accccgggc taaaggaga tagggctca     3060 cctgggatgg atggttttcca aggcatgcct ggactcaaag ggagacccgg gtttccaggg  3120
agcaaaggcg aggctggatt tttcggaata cccggtctga agggtctggc tggtgagcca   3180
ggttttaaag gcagccgagg ggaccctggg ccccaggac cacctcctgt catcctgcca    3240
ggaatgaaag acattaaagg agagaaagga gatgaagggc ctatgggct gaaaggatac    3300 ctgggcgcaa aaggtatcca aggaatgcca ggcatcccag gctgtcagg aatccctggg   3360 ctgcctggga ggcccggcca catcaaagga gtcaagggag acatcggagt ccccggcatc   3420
cccggtttgc caggattccc tggggtggct ggccccctg gaattacggg attcccagga    3480
ttcataggaa gccggggtga caaaggtgcc ccagggagac caggcctgta tggcgagatt   3540
ggcgcgactg gtgatttcgg tgacatcggg gacactataa atttaccagg aagaccaggc   3600 ctgaagggg agcggggcac cactggaata ccaggtctga agggattctt tggagagaag   3660
ggaacagaag gtgacatcgg cttccctggg ataacaggcg tgactggagt ccaaggccct   3720
```

```
cctggactta aaggacaaac aggctttcca gggctgactg ggcctccagg gtcgcaggga      3780
gagctggggc ggattggact gcctggtggc aaaggagatg atggctgcc gggagctccg       3840 ggcttaccag gttttccggg actccgtggg atccgcggct tacacggctt gccaggcacc      3900
aagggctttc caggatcccc aggttctgac atccacggag acccaggctt ccaggccct      3960 cctggggaaa gaggtgaccc aggagaggcc aacacccttc caggccctgt gggagtccca     4020
ggacagaaag gagaccaagg agctccaggg aacagaggcc cacctgggag cccaggactt     4080
caggggttcc caggcatcac accccttcc aacatctctg gggcacctgg tgacaaaggg      4140
gcgccaggga tatttggcct gaaaggttat cggggcccac cagggccacc aggttctgct     4200
gctcttcctg gaagcaaagg tgacacaggg aacccaggag ctccaggaac cccagggacc     4260
aaaggatggg ccggggactc cgggcccag ggcaggcctg gtgtgtttgg tctcccagga      4320 gaaaagggc caggggtga caaggcttc atggggaaca ctggacccac cggggcggtg        4380
ggcgacagag gccccaaggg acccaaggga gacccaggat tccctggtgc ccccgggact     4440
gtgggagccc ccgggattgc aggaatcccc cagaagattg ccgtccaacc agggacagtg     4500 ggtcccagg ggaggcgagg ccccctggg gcaccggggg agatggggcc cagggcccc        4560 cccggagaac caggttttcg tggggctcca gggaaagctg gccccaagg aagaggtggt      4620 gtgtctgctg ttcccggctt ccggggagat gaaggaccca taggccacca ggggccgatt    4680
ggccaagaag gtgcaccagg ccgtccaggg agcccgggcc tgccgggtat gccaggccgc     4740
agcgtcagca tcggctacct cctggtgaag cacagccaga cggaccagga gcccatgtgc     4800
ccggtgggca tgaacaaact ctggagtgga tacagcctgc tgtacttcga gggccaggag    4860
aaggcgcaca accaggacct gggggctggcg ggctcctgcc tggcgcggtt cagcaccatg    4920
cccttcctgt actgcaaccc tggtgatgtc tgctactatg ccagccggaa cgacaagtcc     4980
tactggctct ctaccactgc gccgctgccc atgatgcccg tggccgagga cgagatcaag     5040
ccctacatca gccgctgttc tgtgtgtgag gcccccggcca tcgccatcgc ggtccacagt    5100
caggatgtct ccatcccaca ctgcccagct gggtggcgga gtttgtggat cggatattcc     5160
ttcctcatgc acacggcggc gggagacgaa ggcggtggcc aatcactggt gtcaccgggc     5220
agctgtctag aggacttccg cgccacacca ttcatcgaat gcaatggagg ccgcggcacc     5280
tgccactact acgccaacaa gtacagcttc tggctgacca ccattcccga gcagagcttc     5340
cagggctcgc cctccgccga cacgctcaag gccggcctca tccgcacaca catcagccgc    5400
tgccaggtgt gcatgaagaa cctgtgagcc ggcgcgtgcc aggaagggcc attttggtgc     5460
ttattcttaa cttattacct caggtgccaa cccaaaaatt ggctttattt ttttcttaaa    5520
aaaaaaaaag tctaccaaag gaatttgcat ccagcagcag cacttagacc tgccagccac     5580
tgtcaccgag cgggtgcaag cactcggggt ccctggaggg caagccctgc ccacagaaag     5640
ccaggagcag ccctggcccc catcagccct gctagacgca ccgcctgaag gcacagctaa     5700
ccacttcgca cacacccatg taaccactgc actttccaat gccacagaca actcacattg     5760
ttcaactccc ttctcggggt gggacagacg agacaacagc acacaggcag ccagccgtgg     5820
ccagaggctc gaggggctca ggggctcagg cacccgtccc cacacgaggg ccccgtgggt    5880
gggcctggcc ctgctttcta cgccaatgtt atgccagctc catgttctcc caaataccgt     5940
tgatgtgaat tattttaaag gcaaaaccgt gctctttatt ttagaaaaca ctgataatca     6000
cactgcggta ggtcattctt ttgccacatc cctatagacc actgggttgg caaaactca     6060 ggcagaagtg gagacccttc tagacatcac tgtcagcctt gctacttgaa ggtacacccc    6120
```

-continued

| | |
|---|---|
| ataggg tcgg aggtgctgtc cccactgccc cacgttgtcc ctgagattta acccctccac | 6180 |
| tgctggggt gagctgtact cttctgactg cccectcctg tgtaacgact acaaaataaa | 6240 |
| acttggttct gaatatttt aaaaaaaaaa aaaaaa | 6276 |

<210> SEQ ID NO 70
<211> LENGTH: 1018
<212> TYPE: DNA
<213> ORGANISM: Homo sapiens

<400> SEQUENCE: 70

| | |
|---|---|
| ggcacgaggc tcaagattca cagcatctca gacgcagcct aggttcccat ggacttgtca | 60 |
| taagacaaaa gaggacagct gtgctgaggg ggcagggtct gcagcctcct ggctgtgcca | 120 |
| ggaccacacc taccaaggcc gcaccaggat gtcggacacc gaggagcagg aatatgagga | 180 |
| ggagcagccg gaagaggagg ctgcggagga ggaggaggaa gaagaggaac gccccaaacc | 240 |
| aagccgcccc gtggtgcctc ctttgatccc gccaaagatc ccagaagggg agcgcgttga | 300 |
| cttcgatgac atccaccgca gcgcatgga gaaagacctg ctggagctgc agacactcat | 360 |
| cgatgtacat ttcgagcagc ggaagaagga ggaagaggag ctggttgcct tgaaggagcg | 420 |
| cattgagcgg cgccggtcag agagagccga gcaacagcgc ttcagaactg agaaggaacg | 480 |
| cgaacgtcag gctaagctgg cggaggagaa gatgaggaag gaagaggaag aggccaagaa | 540 |
| gcgggcagag gatgatgcca agaaaaagaa ggtgctgtcc aacatggggg cccatttggg | 600 |
| cggctacctg gtcaaggcag aacagaagcg tggtaagcgg cagacggggc gggagatgaa | 660 |
| ggtgcgcatc ctctccgagc gtaagaagcc tctggacatt gactacatgg gggaggaaca | 720 |
| gctccgggag aaagcccagg agctgtcgga ctggatccac cagctggagt ctgagaagtt | 780 |
| cgacctgatg gcgaagctga acagcagaa atatgagatc aacgtgctgt acaaccgcat | 840 |
| cagccacgcc cagaagttcc ggaaggggc agggaagggc cgcgttggag gccgctggaa | 900 |
| gtgaggatgc cgccccggac agtggcacct gggaagcctg ggagtgtttg tcccatcggt | 960 |
| agcttgaaat aaacgctccc ctcagacact caaaaaaaaa aaaaaaaaa aaaaaaa | 1018 |

<210> SEQ ID NO 71
<211> LENGTH: 2895
<212> TYPE: DNA
<213> ORGANISM: Homo sapiens

<400> SEQUENCE: 71

| | |
|---|---|
| ccgaggagcg ctcgggctgt ctgcggaccc tgccgcgtgc aggggtcgcg gccggctgga | 60 |
| gctgggagtg aggcggcgga ggagccaggt gaggaggagc caggaaggca gttggtggga | 120 |
| agtccagctt gggtccctga gagctgtgag aaggagatgc ggctgctgct ggccctgttg | 180 |
| ggggtcctgc tgagtgtgcc tgggcctcca gtcttgtccc tggaggcctc tgaggaagtg | 240 |
| gagcttgagc cctgcctggc tcccagcctg gagcagcaag agcaggagct gacagtagcc | 300 |
| cttgggcagc ctgtgcggct gtgctgtggg cgggctgagc gtggtggcca ctggtacaag | 360 |
| gagggcagtc gcctggcacc tgctggccgt gtacgggct ggaggggccg cctagagatt | 420 |
| gccagcttcc tacctgagga tgctggccgc tacctctgcc tggcacgagg ctccatgatc | 480 |
| gtcctgcaga atctcaccct tgattacagg tgactccttga cctccagcaa cgatgatgag | 540 |
| gaccccaagt cccataggga cctctcgaat aggcacagtt accccagca agcaccctac | 600 |
| tggacacacc cccagcgcat ggagaagaaa ctgcatgcag tacctgcggg gaacaccgtc | 660 |
| aagttccgct gtccagctgc aggcaacccc acgcccacca tccgctggct taaggatgga | 720 |

```
caggcctttc atggggagaa ccgcattgga ggcattcggc tgcgccatca gcactggagt    780
ctcgtgatgg agagcgtggt gccctcggac cgcggcacat acacctgcct ggtagagaac    840
gctgtgggca gcatccgcta taactacctg ctagatgtgc tggagcggtc cccgcaccgg    900
cccatcctgc aggccgggct cccggccaac accacagccg tggtgggcag cgacgtggag    960
ctgctgtgca aggtgtacag cgatgcccag ccccacatcc agtggctgaa gcacatcgtc   1020
atcaacggca gcagcttcgg agccgacggt ttccccctatg tgcaagtcct aaagactgca   1080
gacatcaata gctcagaggt ggaggtcctg tacctgcgga acgtgtcagc cgaggacgca   1140
ggcgagtaca cctgcctcgc aggcaattcc atcggcctct cctaccagtc tgcctggctc   1200
acggtgctgc aggtactggg gcgcatcccc cacctcacat gtgacagcct gactccagca   1260
ggcagaacca agtctcccac tttgcagttc tccctggagt caggctcttc cggcaagtca   1320
agctcatccc tggtacgagg cgtgcgtctc tcctccagcg gccccgcctt gctcgccggc   1380
ctcgtgagtc tagatctacc tctcgaccca ctatgggagt tcccccggga caggctggtg   1440
cttgggaagc ccctaggcga gggctgcttt ggccaggtag tacgtgcaga ggcctttggc   1500
atggaccctg cccggcctga ccaagccagc actgtggccg tcaagatgct caaagacaac   1560
gcctctgaca aggacctggc cgacctggtc tcggagatgg aggtgatgaa gctgatcggc   1620
cgacacaaga acatcatcaa cctgcttggt gtctgcaccc aggaagggcc cctgtacgtg   1680
atcgtggagt gcgccgccaa gggaaacctg cgggagttcc tgcgggcccg cgcccccca   1740
ggccccgacc tcagcccga cggtcctcgg agcagtgagg ggccgctctc cttcccagtc   1800
ctggtctcct gcgcctacca ggtggcccga ggcatgcagt atctggagtc ccggaagtgt   1860
atccaccggg acctggctgc ccgcaatgtg ctggtgactg aggacaatgt gatgaagatt   1920
gctgactttg gctggcccg cggcgtccac cacattgact actataagaa aaccagcaac   1980
ggccgcctgc ctgtgaagtg gatggcgccc gaggccttgt ttgaccgggt gtacacacac   2040
cagagtgacg tgtggtcttt tgggatcctg ctatgggaga tcttcaccct cggggctcc   2100
ccgtatcctg gcatcccggt ggaggagctg ttctcgctgc tgcgggaggg acatcggatg   2160
gaccgacccc cacactgccc cccagagctg tacgggctga tgcgtgagtg ctggcacgca   2220
gcgcccctcc agaggcctac cttcaagcag ctggtggagg cgctggacaa ggtcctgctg   2280
gccgtctctg aggagtacct cgacctccgc ctgaccttcg accctatc cccctctggt   2340
ggggacgcca gcagcacctg ctcctccagc gattctgtct tcagccacga cccctgcca   2400
ttgggatcca gctccttccc cttcgggtct ggggtgcaga catgagcaag gctcaaggct   2460
gtgcaggcac ataggctggt ggccttgggc cttgggctc agccacagcc tgacacagtg   2520
ctcgaccttg atagcatggg gcccctgcc cagagttgct gtgccgtgtc caagggccgt   2580
gcccttgccc ttggagctgc cgtgcctgtg tcctgatggc ccaaatgtca gggttctgct   2640
cggcttcttg gaccatggcg cttagtcccc atcccgggtt tggctgagcc tggctggaga   2700
gctgctatgc taaacctcct gcctcccaat accagcagga ggttctgggc ctctgaaccc   2760
cctttcccca cacctccccc tgctgctgct gcccagcgt cttgacggga gcattggccc   2820
ctgagcccag agaagctgga agcctgccga aaacaggagc aaatggcgtt ttataaatta   2880
ttttttgaa ataaa                                                     2895

<210> SEQ ID NO 72
<211> LENGTH: 1356
<212> TYPE: DNA
<213> ORGANISM: Homo sapiens
```

<400> SEQUENCE: 72

```
ttctcccgca accttcccctt cgctccctcc cgtcccccc  agctcctagc ctccgactcc      60
ctccccccct cacgcccgcc ctctcgcctt cgccgaacca aagtggatta attacacgct     120
ttctgtttct ctccgtgctg ttctctcccg ctgtgcgcct gcccgcctct cgctgtcctc     180
tctcccctc  gccctctctt cggccccccc cttcacgtt  cactctgtct ctcccactat     240
ctctgccccc ctctatcctt gatacaacag ctgacctcat ttcccgatac cttttcccc      300
ccgaaaagta caacatctgg cccgccccag cccgaagaca gcccgtcctc cctggacaat     360
cagacgaatt ctccccccc  cccaaaaaa  aaaagccatc ccccgctct  gcccgtcgc      420
acattcggcc cccgcgactc ggccagagcg gcgctggcag aggagtgtcc ggcaggaggg     480
ccaacgcccg ctgttcggtt tgcgacacgc agcaggagg  tgggcggcag cgtcgccggc     540
ttccagacac caatgggaat cccaatgggg aagtcgatgc tggtgcttct caccttcttg     600
gccttcgcct cgtgctgcat tgctgcttac cgccccagtg agaccctgtg cggcggggag     660
ctggtggaca ccctccagtt cgtctgtggg gaccgcggct tctacttcag caggcccgca     720
agccgtgtga gccgtcgcag ccgtggcatc gttgaggagt gctgtttccg cagctgtgac     780
ctggccctcc tggagacgta ctgtgctacc cccgccaagt ccgagaggga cgtgtcgacc     840
cctccgaccg tgcttccgga caacttcccc agataccccg tgggcaagtt cttccaatat     900
gacacctgga agcagtccac ccagcgcctg cgcaggggcc tgcctgccct cctgcgtgcc     960
cgccggggtc acgtgctcgc caaggagctc gaggcgttca gggaggccaa acgtcaccgt    1020
cccctgattg ctctacccac ccaagacccc gcccacgggg gcgcccccc  agagatggcc    1080
agcaatcgga agtgagcaaa actgccgcaa gtctgcagcc cggcgccacc atcctgcagc    1140
ctcctcctga ccacggacgt ttccatcagg ttccatcccg aaaatctctc ggttccacgt    1200
ccccctgggg cttctcctga cccagtcccc gtgcccgcc  tccccgaaac aggctactct    1260
cctcggcccc ctccatcggg ctgaggaagc acagcagcat cttcaaacat gtacaaaatc    1320
gattggcttt aaacacccctt cacataccct ccccc                             1356
```

<210> SEQ ID NO 73
<211> LENGTH: 2281
<212> TYPE: DNA
<213> ORGANISM: Homo sapiens

<400> SEQUENCE: 73

```
aaacaataag catatctaag caactacgat atctgtatgg atcaggccaa agtcccgcta      60
agattctcca atgttttcat ggtctgagcc ccctcctgt  tcccatctcc actgcccctc     120
ggccctgtct gtgccctgcc tctcagagga gggggctcag atggtgcggc ctgagtgtgc     180
ggccggcggc atttgggata cacccgtagg gtgggcgggg tgtgtcccag gcctaattcc     240
atctttccac catgacagag atgcccttgt gaggctggcc tccttggcgc ctgtccccac     300
ggcccccgca gcgtgagcca cgatgctccc catacccccac ccattcccga tacaccttac    360
ttactgtgtg ttggcccagc cagagtgagg aaggagtttg gccacattgg agatggcggt     420
agctgagcag acatgccccc acgagtagcc tgactccctg gtgtgctcct ggaaggaaga     480
tcttggggac cccccaccg  gagcacacct agggatcatc tttgcccgtc tcctggggac     540
cccccaagaa atgtggagtc ctcggggggcc gtgcactgat gcggggagtg tgggaagtct    600
ggcggttgga ggggtgggtg gggggcagtg ggggctgggc gggggagtc  ctggggtagg    660
aagtggtccc gggagatttt ggatggaaaa gtcaggagga ttgacagcag acttgcagaa    720
```

```
ttacatagag aaattaggaa cccccaaatt tcatgtcaat tgatctattc ccctctttg      780
tttcttgggg catttttcct ttttttttt tttgttttt ttttacccct ccttagcttt       840
atgcgctcag aaaccaaatt aaacccccc cccatgtaac agggggcag tgacaaaagc        900
aagaacgcac gaagccagcc tggagaccac cacgtcctgc ccccgccat ttatcgccct       960
gattggattt tgttttcat ctgtccctgt tgcttgggtt gagttgaggg tggagcctcc     1020
tggggggcac tggccactga gccccttgg agaagtcaga ggggagtgga gaaggccact     1080
gtccggcctg gcttctgggg acagtggctg gtccccagaa gtcctgaggg cggagggggg    1140
ggttgggcag ggtctcctca ggtgtcagga gggtgctcgg aggccacagg aggggctcc     1200
tggctggcct gaggctggcc ggaggggaag gggctagcag gtgtgtaaac agagggttcc    1260
atcaggctgg ggcagggtgg ccgccttccg cacacttgag gaaccctccc ctctccctcg    1320
gtgacatctt gcccgcccct cagcaccctg ccttgtctcc aggaggtccg aagctctgtg    1380
ggacctcttg ggggcaaggt ggggtgaggc cgggagtag ggaggtcagg cgggtctgag     1440
cccacagagc aggagagctg ccaggtctgc ccatcgacca ggttgcttgg gccccggagc    1500
ccacgggtct ggtgatgcca tagcagccac caccgcggcg cctagggctg cggcagggac    1560
tcggcctctg ggaggtttac ctcgccccca cttgtgcccc cagctcagcc ccctgcacg     1620
cagcccgact agcagtctag aggcctgagg cttctgggtc ctggtgacgg ggctggcatg   1680
accccggggg tcgtccatgc cagtccgcct cagtcgcaga gggtccctcg gcaagcgccc   1740
tgtgagtggg ccattcggaa cattggacag aagcccaaag agccaaattg tcacaattgt  1800
ggaacccaca ttggcctgag atccaaaacg cttcgaggca ccccaaatta cctgcccatt   1860
cgtcaggaca cccaccccacc cagtgttata ttctgcctcg ccggagtggg tgttcccggg  1920
ggcacttgcc gaccagcccc ttgcgtcccc aggtttgcag ctctcccctg ggccactaac   1980
catcctggcc cgggctgcct gtctgacctc cgtgcctagt cgtggctctc catcttgtct   2040
cctccccgtg tccccaatgt cttcagtggg gggcccctc ttgggtcccc tcctctgcca    2100
tcacctgaag accccacgc caaacactga atgtcacctg tgcctgccgc ctcggtccac   2160
cttgcggccc gtgtttgact caactcagct cctttaacgc taatatttcc ggcaaaatcc   2220
catgcttggg ttttgtcttt aaccttgtaa cgcttgcaat cccaataaag cattaaaagt  2280
c                                                                   2281

<210> SEQ ID NO 74
<211> LENGTH: 1124
<212> TYPE: DNA
<213> ORGANISM: Homo sapiens

<400> SEQUENCE: 74
cgggaaacct gcactgactt ttttctcctt ttggagggag agcagagacc atgtctgaca      60
tagaagaggt ggtggaagag tacgaggagg aggagcagga agaagcagct gttgaagagc    120
aggaggaggc agcggaagag gatgctgaag cagaggctga gaccgaggag accagggcag    180
aagaagatga agaagaagag gaagcaaagg aggctgaaga tggcccaatg gaggagtcca    240
aaccaaagcc caggtcgttc atgcccaact tggtgcctcc caagatcccc gatggagaga    300
gagtggactt tgatgacatc caccggaagc gcatggagaa ggacctgaat gagttgcagg    360
cgctgattga ggctcacttt gagaacagga gaaagagga ggaggagctc gtttctctca    420
aagacaggat cgagacgtc cgggcagagc gggccgagca gcagcgcatc cggaatgagc    480
gggagaagga gcggcagaac cgcctggctg aagagaggc tcgacgagag gaggaggaga   540
```

```
acaggaggaa ggctgaggat gaggcccgga agaagaaggc tttgtccaac atgatgcatt     600
ttgggggtta catccagaag caggcccaga cagagcggaa aagtgggaag aggcagactg     660
agcgggaaaa gaagaagaag attctggctg agaggaggaa ggtgctggcc attgaccacc     720
tgaatgaaga tcagctgagg gagaaggcca aggagctgtg gcagagcatc tataacttgg     780
aggcagagaa gttcgacctg caggagaagt tcaagcagca gaaatatgag atcaatgttc     840
tccgaaacag gatcaacgat aaccagaaag tctccaagac ccgcgggaag gctaaagtca     900
ccgggcgctg gaaatagagc ctggcctcct tcaccaaaga tctgctcctc gctcgcacct     960
gcctccggcc tgcactcccc cagttccggg gccctcctgg gcaccccagg cagctcctgt    1020
ttggaaatgg ggagctggcc taggtgggag ccaccactcc tgcctgcccc cacacccact    1080
ccacaccagt aataaaaagc caccacacac tgaaaaaaaa aaaa                     1124

<210> SEQ ID NO 75
<211> LENGTH: 855
<212> TYPE: DNA
<213> ORGANISM: Homo sapiens

<400> SEQUENCE: 75
atctcatctc ccagacgcca cgtctctcgg tttcttctta gatcactcct ctgccaaaga      60
tcccaacaag acaacatggc tcccaagaag cctgagccta agaaggaggc agccaagcca     120
gctccagctc cagctccagc ccctgcacca gcccctgccc cagctcctga ggctcccaag     180
gaacctgcct ttgaccccaa gagtgtaaag atagacttca ctgccgacca gattgaagag     240
ttcaaagagg cctttttcatt gtttgaccgg accccgactg agagatgaa gatcacctac     300 ggccagtgcg gggatgtact gcgggccctg ggccagaacc ctaccaatgc cgaggtgctg     360
cgtgtgctgg gcaagcccaa gcctgaagag atgaatgtca gatgctgga ctttgagacg     420 ttcttgccca tcctgcagca catttcccgc aacaaggagc agggcaccta tgaggacttc     480
gtggagggcc tgcgtgtctt tgacaaggag agcaatggca cggtcatggg tgctgagctt     540
cggcacgtcc ttgccaccct gggagagaag atgactgagg ctgaagtgga gcagctgtta     600
gctgggcaag aggatgccaa tggctgcatc aattatgaag cctttgtcaa gcacatcatg     660
tcagggtgaa gcagagtctt ccaggtgcct ggcccttggc tttagccata ccagggtgag     720
ttaaagagag gccccggctg ggtgagctga gatgagtcc tcgacttatc accacaccac     780
tgccccaagg accttacagg ccctcctgt taataaacag ctctaacacg gccaggctgg     840
gctctgggat tctga                                                      855

<210> SEQ ID NO 76
<211> LENGTH: 1404
<212> TYPE: DNA
<213> ORGANISM: Homo sapiens

<400> SEQUENCE: 76
gccgggcagc catggctgag acactcttct ggactcctct cctcgtggtt ctcctggcag      60
ggctggggga caccgaggcc cagcagacca cgctacaccc acttgtgggc cgtgtctttg     120
tgcacacctt ggaccatgag acgtttctga gccttcctga gcatgtcgct gtcccacccg     180
ctgtccacat cacctaccac gcccacctcc agggacaccc agacctgccc cggtggctcc     240
gctacaccca gcgcagcccc caccaccctg gcttcctcta cggctctgcc accccagaag     300
atcgtgggct ccaggtcatt gaggtcacag cctacaatcg gacagctttt gataccactc     360
ggcagaggct ggtgctggag attggggacc cagaaggccc cctgctgcca taccaagccg     420
```

| | | |
|---|---|---|
| agttcctggt gcgcagccac gatgcggagg aggtgctgcc ctcaacacct gccagccgct | 480 | |
| tcctctcagc cttggggga ctctgggagc ccggagagct tcagctgctc aacgtcacct | 540 | |
| ctgccttgga ccgtgggggc cgtgtccccc ttcccattga gggccgaaaa aaggggtat | 600 | |
| acattaaggt gggttctgcc tcaccttttt ctacttgcct gaagatggtg gcatcccccg | 660 | |
| atagccacgc ccgctgtgcc cagggccagc ctccacttct gtcttgctac gacaccttgg | 720 | |
| caccccactt ccgcgttgac tggtgcaatg tgacccctggt ggataagtca gtgccggagc | 780 | |
| ctgcagatga ggtgcccacc ccaggtgatg ggatcctgga gcatgacccg ttcttctgcc | 840 | |
| cacccactga ggccccagac cgtgacttct tggtggatgc tctggtcacc ctcctggtgc | 900 | |
| ccctgctggt ggccctgctt ctcaccttgc tgctggccta tgtcatgtgc tgccggcggg | 960 | |
| agggaaggct gaagagagac ctggctacct ccgacatcca gatggtccac cactgcacca | 1020 | |
| tccacgggaa cacagaggag ctgcggcaga tggcggccag ccgcgaggtg ccccggccac | 1080 | |
| tctccaccct gccccatgttc aatgtgcaca caggtgagcg gctgcctccc cgcgtggaca | 1140 | |
| gcgcccaggt gcccctcatt ctggaccagc actgacagcc cagccagtgg ttccaggtcc | 1200 | |
| agccctgact tcatcctccc ttctctgtcc acaccacgag tggcacatcc cacctgctga | 1260 | |
| ttccagctcc tggccctcct ggaacccagg ctctaaacaa gcagggagag ggggtggggt | 1320 | |
| ggggtgagag tgtgtggagt aaggacattc agaataaata tctgctgctc tgctcaccaa | 1380 | |
| ttgctgctgg cagcctctcc cgtc | 1404 | |

<210> SEQ ID NO 77
<211> LENGTH: 1610
<212> TYPE: DNA
<213> ORGANISM: Homo sapiens

<400> SEQUENCE: 77

| | | |
|---|---|---|
| gcatcagaaa ccagcacacc agagcaccag ggcggggggc ttctccgcag caagtttcca | 60 | |
| aacaagcccct cagtgaacat cattgaagcg tgactgcctg tctgcaggga gaaggattcc | 120 | |
| attttcttc tcagctggtc cccaggccca cgggcacagg gagagggaca actgcagcag | 180 | |
| tggggaggag gcacagctag ctgcacagtt ctctcttctc cttgtcctag tcagatgaag | 240 | |
| gaggctgcac tacaaaccca aattctgcaa aaaaataaa aataagccac aaaactaaaa | 300 | |
| ggcctggccc cattctggaa aaggcaaagc tgcatgagac acagccttct gcctcctcgc | 360 | |
| ctctcctgga ctggcttcct ctttgagaaa atgcacaaag ccctgggaga tgacaagcac | 420 | |
| aaggactgac tcaagctgtg tctttcagac caaggaacat cagagaagct gtggggctgc | 480 | |
| ctgccaggca ggatcatggc tgccatcaag ccttttctgg atccagccat caaggacatg | 540 | |
| tttgtggtgt gatgcacact tttgcaagcg tgtaagatgt tacctggttt gtctcttttg | 600 | |
| gaaaacaaaa atcagaaggc tgcattctag agggcagaga aattcccccg aagactgagc | 660 | |
| tggttgcctg catcctctat cttctttgac ccttatgact gaaagatcat cagttttggaa | 720 | |
| ggtactggtc caatttattt aggaagtatc tcttggagtt tcagaaatgc tagcttggac | 780 | |
| aactgaaaag tcacatcaca gctggcattc tgggggctac caaaacaccc cttctggagt | 840 | |
| agaagctgct ggaaggcagg cctgagccat tcaccacgga caggaagagc agctctggct | 900 | |
| atcaccactg gcctctgggg tcttcatatc ttgccatctc atccagggtt ccatgaaagt | 960 | |
| tacccagggt cctcatgtcc ttccttagag cctgagtggt gtgaggtgac aggtctctct | 1020 | |
| ctccactgcc ccttttctggt ttaaaaaaat ggtgcttgat gagggaaggt agactcttcc | 1080 | |
| ctaggactga cgagttacgg ctgccagatg cctgcatggg aagaggtgga catctgcatc | 1140 | |

```
ttccattggt ggtcaaggat gggtgtggga gaaccacacc tagtgcaagc ctggtactca    1200
gtaaatattt gttgaaatga atgataagag cattggtccc caagccagag agccagaagc    1260
catcacccaa tgaccgcccc ttccttccgg tctacaagag ctctcaaggc tgggtctgcc    1320
accactctgc tttgcccaag tgtgacgcag ctggggagga gagacaggat aaagggcaga    1380
tgtcagcaat actaagggct tcctcatggg agggcatgag gctccactca ttgtcttgtg    1440
acttccatcc ctgctgaatg gggctgcaag gccaaggctc cttaggggag aggtccttac    1500
ctctgatcca cttagagcaa taaccacttt ttaaatgtaa aataaaaaga caaatgaaaa    1560
ggcaaaaaaa aaaaaaaaaa aaaaaaaaa aaaaaaaaa aaaaaaaaa                  1610

<210> SEQ ID NO 78
<211> LENGTH: 1356
<212> TYPE: DNA
<213> ORGANISM: Homo sapiens

<400> SEQUENCE: 78
ttctcccgca accttccctt cgctccctcc cgtcccccc agctcctagc ctccgactcc      60 ctcccccct cacgcccgcc ctctcgcctt cgccgaacca agtggatta attacacgct      120 ttctgtttct ctccgtgctg ttctctcccg ctgtgcgcct gcccgcctct cgctgtcctc    180 tctcccctc gccctctctt cggcccccc cttcacgtt cactctgtct ctcccactat      240 ctctgcccc ctctatcctt gatacaacag ctgacctcat ttcccgatac cttttccccc     300
ccgaaaagta caacatctgg cccgcccag cccgaagaca gcccgtcctc cctgggacaat   360 cagacgaatt ctcccccccc ccccaaaaaa aaaagccatc ccccgctct gccccgtcgc    420 acattcggcc cccgcgactc ggccagagcg gcgctggcag aggagtgtcc ggcaggaggg   480
ccaacgcccg ctgttcggtt tgcgacacgc agcagggagg tgggcggcag cgtcgccggc   540
ttccagacac caatgggaat cccaatgggg aagtcgatgc tggtgcttct caccttcttg   600
gccttcgcct cgtgctgcat tgctgcttac cgccccagtg agaccctgtg cggcggggag   660
ctggtggaca ccctccagtt cgtctgtggg gaccgcggct tctacttcag caggcccgca   720
agccgtgtga gccgtcgcag ccgtggcatc gttgaggagt gctgtttccg cagctgtgac   780
ctggccctcc tggagacgta ctgtgctacc ccgccaagt ccgagaggga cgtgtcgacc    840
cctccgaccg tgcttccgga caacttcccc agatacccg tgggcaagtt cttccaatat    900
gacacctgga agcagtccac ccagcgcctg cgcaggggcc tgcctgccct cctgcgtgcc   960
cgccggggtc acgtgctcgc caaggagctc gaggcgttca gggaggccaa acgtcaccgt   1020
cccctgattg ctctacccac ccaagacccc gcccacgggg gcgcccccc agagatggcc   1080 agcaatcgga agtgagcaaa actgccgcaa gtctgcagcc cggcgccacc atcctgcagc   1140
ctcctcctga ccacggacgt ttccatcagg ttccatcccg aaaatctctc ggttccacgt   1200
ccccctgggg cttctcctga cccagtcccc gtgcccgcc tccccgaaac aggctactct    1260
cctcggcccc ctccatcggg ctgaggaagc acagcagcat cttcaaacat gtacaaaatc   1320
gattggcttt aaacacccctt cacatacccct cccccc                           1356

<210> SEQ ID NO 79
<211> LENGTH: 2330
<212> TYPE: DNA
<213> ORGANISM: Homo sapiens

<400> SEQUENCE: 79
gaattcggca cgagcgacgc ggcccagagg ccaggaacat tccgcgcgtg gaccagccgg    60
```

```
gccagggcga tgctgcgggt gcggtgtctg cgcggcggga gccgcggcgc cgaggcggtg        120
cactacatcg gatctcggct tggacgaacc ttgacaggat gggtgcagcg aactttccag        180
agcacccagg cagctacggc ttcctcccgg aactcctgtg cagctgacga caaagccact        240
gagcctctgc ccaaggactg ccctgtctct tcttacaacg aatgggaccc cttagaggaa        300
gtgatagtgg gcagagcaga aaacgcctgt gttccaccgt tcaccatcga ggtgaaggcc        360
aacacatatg aaaagtactg gccatttttac cagaagcaag gagggcatta ttttcccaaa        420
gatcatttga aaaaggctgt tgctgaaatt gaagaaatgt gcaatatttt aaaaacggaa        480
ggagtgacag taaggaggcc tgaccccatt gactggtcat tgaagtataa aactcctgat        540
tttgagtcta cgggttttata cagtgcaatg cctcgagaca tcctgatagt tgtgggcaat        600
gagattatcg aggctcccat ggcatggcgt tcacgcttct ttgagtaccg agcgtacagg        660
tcaattatca aagactactt ccaccgtggc gccaagtgga acagctcc taagcccaca         720 atggctgatg agctttataa ccaggattat cccatccact ctgtagaaga cagacacaaa        780
ttggctgctc agggaaaatt tgtgacaact gagtttgagc catgctttga tgctgctgac        840
ttcattcgag ctggaagaga tattttttgca cagagaagcc aggttacaaa ctacctaggc        900
attgaatgga tgcgtaggca tcttgctcca gactacagag tgcatatcat ctccttttaaa        960 gatcccaatc ccatgcatat tgatgctacc ttcaacatca ttggacctgg tattgtgctt       1020
tccaaccctg accgaccatg tcaccagatt gatcttttca agaaagcagg atggactatc       1080
attactcctc caacaccaat catcccagac gatcatccac tctggatgtc atccaaatgg       1140
ctttccatga atgtcttaat gctagatgaa aaacgtgtta tggtggatgc caatgaagtt       1200
ccaattcaaa agatgtttga aaagctgggt atcactacca ttaaagttaa cattcgtaat       1260
gccaattccc tgggaggagg cttccattgc tggacctgcg atgtccggcg ccgaggcacc       1320
ctacagtcct acttggactg aacaggcctg atggagcttg tggctggcct cagatacacc       1380
taagaagctt aggggcaagg ttcattctcc tgctttaaaa agtgcatgaa ctgtagtgct       1440
ttaaacaatc atctccttaa caggggtcgt aagcctggtt tgcttctatt acttttctttt      1500 gacataaaga aaataacttc tgctaggtat tactctctac tcctaaagtt atttactatt       1560
tggcttcaag tataaaattt tggtgaatgt gtaccaagaa aaaattagtc acctgagtaa       1620
cttggccact aataattaac catctacctc tgttttttaat tttctttcca aaaggcagct       1680
tgaaatgttg gtcctaatct taattttttt tcctcttcta tagacttgag aatgttttc        1740 tctaaatgag agaaagactt agaatgtaca cagatccaaa atagaatcag attatctctt       1800
tttttctaaa ggagagaaag acttagaaca tacacagatc ctaagtagaa ccaggtaatt       1860 gtctctttt ctaataagga atttgggtaa tttttaattt tttgtttttt aaaaaataac         1920
ctagactatg caaaacatca aagtgaattt tccatgaatg ttttttaatat tctcatctca       1980 acattgtgat atatgctact aaaaaccttt tcatatacat cttacctcat ttcaagtgaa       2040 ttatttttaat ctttttctct ctttccaaaa atttacagga atgtttagtg taattggatt      2100
tcgctatcag ttcccatcct taagttttga tattcaatat ctgatagata cactgcatct       2160
ttggtcatct aagatttgtt tacaaatgtg caaattattt agagcataga ctttataagc       2220
attaaaaaaa actaatggag gtaaaaccta aatgcgatgt gaaataattt tagtgttgat       2280
actgtatgtg tattttttatt ctaataaact tttgtgttcc agattgaaaa                 2330
```

<210> SEQ ID NO 80
<211> LENGTH: 2436
<212> TYPE: DNA

<213> ORGANISM: Homo sapiens

<400> SEQUENCE: 80

```
ggctcccaca gtgggtggcg gaaaacaact ttcagagctt tgtaaatgcc agttgtgccc      60
atcctcagct gctaaaagga agaagcattt ttgctgttag cccagatggc tttgtgtgtg     120
atgattttcc caaccccag atcacggttc agccagaaac acagtcggca ataaaaggtt      180
ccaatttgag tttcatctgc tcagctgcca gcagcagtga ttccccaatg acttttgctt    240
ggaaaaaaga caatgaacta ctgcatgatg ctgaaatgga aaattatgca cacctccggg    300
cccaaggtgg cgaggtgatg gagtatacca ccatccttcg gctgcgcgag gtggaatttg    360
ccagtgaggg gaaatatcag tgtgtcatct ccaatcactt tggttcatcc tactctgtca    420
aagccaagct tacagtaaat atgcttccct cattcaccaa gacccccatg gatctcacca    480
tccgagctgg ggccatggca cgcttggagt gtgctgctgt ggggcaccca gccccccaga    540
tagcctggca gaaggatggg ggcacagact cccagctgc acgggagaga cgcatgcatg    600
tgatgcccga ggatgacgtg ttctttatcg tggatgtgaa gatagaggac attggggtat    660
acagctgcac agctcagaac agtgcaggaa gtatttcagc aaatgcaact ctgactgtcc    720
tagaaacacc atcattttg cggccactgt tggaccgaac tgtaaccaag ggagaaacag     780
ccgtcctaca gtgcattgct ggaggaagcc ctccccctaa actgaactgg accaaagatg    840
atagcccatt ggtggtaacc gagaggcact ttttgcagc aggcaatcag cttctgatta    900
ttgtggactc agatgtcagt gatgctggga atacacatg tgagatgtct aacacccttg    960
gcactgagag aggaaacgtg cgcctcagtg tgatccccac tccaacctgc gactcccctc   1020
agatgacagc cccatcgtta gacgatgacg gatgggccac tgtgggtgtc gtgatcatag    1080
ccgtggtttg ctgtgtggtg ggcacgtcac tcgtgtgggt ggtcatcata taccacacaa    1140
ggcggaggaa tgaagattgc agcattacca cacagatga gaccaacttg ccagcagata    1200
ttcctagtta tttgtcatct cagggaacgt tagctgacag gcaggatggg tacgtgtctt    1260
cagaaagtgg aagccaccac cagtttgtca catcttcagg tgctggattt ttcttaccac    1320
aacatgacag tagtgggacc tgccatattg acaaatagca tgaagctgat gtggaagctg    1380
ccacagatct gttcctttgt ccgttttttgg gatccacagg ccctatgtat ttgaagggaa    1440
atgtgtatgg ctcagatcct tttgaaacat atcatacagg ttgcagtcct gacccaagaa    1500
cagtttttaat ggaccactat gagcccagtt acataaagaa aaaggagtgc tacccatgtt   1560
ctcatccttc agaagaatcc tgcgaacgga gcttcagtaa tatatcgtgg ccttcacatg   1620
tgaggaagct acttaacact agttactctc acaatgaagg acctggaatg aaaaatctgt   1680
gtctaaacaa gtcctctta gattttagtg caaatccaga gccagcgtcg gttgcctcga    1740
gtaattcttt catgggtacc tttggaaaag ctctcaggag acctcaccta gatgcctatt    1800
caagctttgg acagccatca gattgtcagc caagagcctt ttatttgaaa gctcattctt    1860
ccccagactt ggactctggg tcagaggaag atgggaaaga aaggacagat tttcaggaag    1920
aaaatcacat ttgtacccttt aaacagactt tagaaaacta caggactcca aattttcagt   1980
cttatgactt ggacacatag actgaatgag accaaaggaa aagcttaaca tactacctca   2040
agtgaacttt tatttaaaag agagagaatc ttatgttttt taaatggagt tatgaatttt    2100
aaaaggataa aaatgcttta tttatacaga tgaaccaaaa ttacaaaaag ttatgaaaat    2160
ttttatactg ggaatgatgc tcatataaga ataccttttt aaactatttt ttaactttgt    2220
tttatgcaaa aaagtatctt acgtaaatta atgatataaa tcatgattat tttatgtatt    2280
```

| | |
|---|---:|
| tttataatgc cagatttctt tttatggaaa atgagttact aaagcatttt aaataatacc | 2340 |
| tgccttgtac cattttttaa atagaagtta cttcattata ttttgcacat tatatttaat | 2400 |
| aaaatgtgtc aatttgaaaa aaaaaaaaaa aaaaaa | 2436 |

<210> SEQ ID NO 81
<211> LENGTH: 2121
<212> TYPE: DNA
<213> ORGANISM: Homo sapiens

<400> SEQUENCE: 81

| | |
|---|---:|
| ctgctcgcgg ccgccaccgc cgggccccgg ccgtccctgg ctcccctcct gcctcgagaa | 60 |
| gggcagggct tctcagaggc ttggcgggaa aaaagaacgg agggagggat cgcgctgagt | 120 |
| ataaaagccg gttttcgggg ctttatctaa ctcgctgtag taattccagc gagaggcaga | 180 |
| gggagcgagc gggcggccgg ctagggtgga agagccgggc gagcagagct gcgctgcggg | 240 |
| cgtcctggga agggagatcc ggagcgaata ggggcttcg cctctggccc agccctcccg | 300 |
| cttgatcccc caggccagcg gtccgcaacc cttgccgcat ccacgaaact ttgcccatag | 360 |
| cagcgggcgg gcactttgca ctggaactta caacacccga gcaaggacgc gactctcccg | 420 |
| acgcggggag gctattctgc ccatttgggg acacttcccc gccgctgcca ggacccgctt | 480 |
| ctctgaaagg ctctccttgc agctgcttag acgctggatt tttttcgggt agtggaaaac | 540 |
| cagcagcctc ccgcgacgat gcccctcaac gttagcttca ccaacaggaa ctatgacctc | 600 |
| gactacgact cggtgcagcc gtatttctac tgcgacgagg aggagaactt ctaccagcag | 660 |
| cagcagcaga gcgagctgca gccccggcg cccagcgagg atatctggaa gaaattcgag | 720 |
| ctgctgccca cccgcccct gtcccctagc cgccgctccg ggctctgctc gccctcctac | 780 |
| gttgcggtca caccttctc ccttcgggga acaacgacg gcggtggcgg gagcttctcc | 840 |
| acggccgacc agctggagat ggtgaccgag ctgctgggag agacatggt gaaccagagt | 900 |
| ttcatctgcg acccggacga cgagaccttc atcaaaaaca tcatcatcca ggactgtatg | 960 |
| tggagcggct tctcggccgc cgccaagctc gtctcagaga agctggcctc ctaccaggct | 1020 |
| gcgcgcaaag acagcggcag cccgaacccc gcccgcggcc acagcgtctg ctccacctcc | 1080 |
| agcttgtacc tgcaggatct gagcgccgcc gcctcagagt gcatcgaccc ctcggtggtc | 1140 |
| ttcccctacc ctctcaacga cagcagctcg cccaagtcct gcgcctcgca agactccagc | 1200 |
| gccttctctc cgtcctcgga ttctctgctc tcctcgacgg agtcctcccc gcagggcagc | 1260 |
| cccgagcccc tggtgctcca tgaggagaca ccgccaccca ccagcagcga ctctgaggag | 1320 |
| gaacaagaag atgaggaaga atcgatgtt gtttctgtgg aaaagaggca ggctcctggc | 1380 |
| aaaaggtcag agtctggatc accttctgct ggaggccaca gcaaacctcc tcacagccca | 1440 |
| ctggtcctca gaggtgcca cgtctccaca catcagcaca actacgcagc gcctccctcc | 1500 |
| actcggaagg actatcctgc tgccaagagg gtcaagttgg acagtgtcag agtcctgaga | 1560 |
| cagatcagca caaccgaaa atgcaccagc cccaggtcct cggacaccga ggagaatgtc | 1620 |
| aagaggcgaa cacacaacgt cttggagcgc agaggagga acgagctaaa cggagctttt | 1680 |
| tttgccctgc gtgaccagat cccggagttg gaaaacaatg aaaaggcccc caaggtagtt | 1740 |
| atccttaaaa aagccacagc atacatcctg tccgtccaag cagaggagca aaagctcatt | 1800 |
| tctgaagagg acttgttgcg gaaacgacga gaacagttga acacaaaact tgaacagcta | 1860 |
| cggaactctt gtgcgtaagg aaaagtaagg aaaacgattc cttctaacag aaatgtcctg | 1920 |
| agcaatcacc tatgaacttg tttcaaatgc atgatcaaat gcaacctcac aaccttggct | 1980 |

-continued

| | |
|---|---|
| gagtcttgag actgaaagat ttagccataa tgtaaactgc ctcaaattgg actttgggca | 2040 |
| taaaagaact ttttatgct taccatcttt ttttttcctt aacagattt gtatttaaga | 2100 |
| attgttttta aaaattta a | 2121 |

<210> SEQ ID NO 82
<211> LENGTH: 2121
<212> TYPE: DNA
<213> ORGANISM: Homo sapiens

<400> SEQUENCE: 82

| | |
|---|---|
| ctgctcgcgg ccgccaccgc cgggccccgg ccgtccctgg ctcccctcct gcctcgagaa | 60 |
| gggcagggct tctcagaggc ttggcgggaa aaagaacgg agggagggat cgcgctgagt | 120 |
| ataaaagccg gttttcgggg ctttatctaa ctcgctgtag taattccagc gagaggcaga | 180 |
| gggagcgagc gggcggccgg ctagggtgga agagccgggc gagcagagct gcgctgcggg | 240 |
| cgtcctggga agggagatcc ggagcgaata gggggcttcg cctctggccc agccctcccg | 300 |
| cttgatcccc caggccagcg gtccgcaacc cttgccgcat ccacgaaact ttgcccatag | 360 |
| cagcgggcgg gcactttgca ctggaactta caacacccga gcaaggacgc gactctcccg | 420 |
| acgcggggag gctattctgc ccatttgggg acacttcccc gccgctgcca ggacccgctt | 480 |
| ctctgaaagg ctctccttgc agctgcttag acgctggatt tttttcgggt agtggaaaac | 540 |
| cagcagcctc ccgcgacgat gccctcaac gttagcttca ccaacaggaa ctatgacctc | 600 |
| gactacgact cggtgcagcc gtatttctac tgcgacgagg aggagaactt ctaccagcag | 660 |
| cagcagcaga gcgagctgca gccccggcg cccagcgagg atatctggaa gaaattcgag | 720 |
| ctgctgccca ccccgccct gtccctagc cgccgctccg ggctctgctc gccctcctac | 780 |
| gttgcggtca caccccttctc ccttcgggga gacaacgacg gcggtggcgg gagcttctcc | 840 |
| acggccgacc agctggagat ggtgaccgag ctgctgggag agacatggt gaaccagagt | 900 |
| ttcatctgcg acccggacga cgagaccttc atcaaaaaca tcatcatcca ggactgtatg | 960 |
| tggagcggct tctcggccgc cgccaagctc gtctcagaga agctggcctc ctaccaggct | 1020 |
| gcgcgcaaag acagcggcag cccgaacccc gcccgcggcc acagcgtctg ctccacctcc | 1080 |
| agcttgtacc tgcaggatct gagcgccgcc gcctcagagt gcatcgaccc ctcggtggtc | 1140 |
| ttcccctacc ctctcaacga cagcagctcg cccaagtcct gcgcctcgca agactccagc | 1200 |
| gccttctctc cgtcctcgga ttctctgctc tcctcgacgg agtcctcccc gcagggcagc | 1260 |
| cccgagcccc tggtgctcca tgaggagaca ccgccaccca ccagcagcga ctctgaggag | 1320 |
| gaacaagaag atgaggaaga atcgatgtt gttctctgtgg aaaagaggca ggctcctggc | 1380 |
| aaaaggtcag agtctggatc accttctgct ggaggccaca gcaaacctcc tcacagccca | 1440 |
| ctggtcctca agaggtgcca cgtctccaca catcagcaca actacgcagc gcctccctcc | 1500 |
| actcggaagg actatcctgc tgccaagagg gtcaagttgg acagtgtcag agtcctgaga | 1560 |
| cagatcagca caaccgaaa atgcaccagc cccaggtcct cggacaccga ggagaatgtc | 1620 |
| aagaggcgaa cacacaacgt cttggagcgc cagaggagga cgagctaaa cggagcttt | 1680 |
| tttgccctgc gtgaccagat cccggagttg gaaaacaatg aaaaggcccc caaggtagtt | 1740 |
| atccttaaaa aagccacagc atacatcctg tccgtccaag cagaggagca aaagctcatt | 1800 |
| tctgaagagg acttgttgcg gaaacgacga gaacagttga acacaaaact tgaacagcta | 1860 |
| cggaactctt gtgcgtaagg aaaagtaagg aaaacgattc cttctaacag aaatgtcctg | 1920 |
| agcaatcacc tatgaacttg tttcaaatgc atgatcaaat gcaacctcac aaccttggct | 1980 |

-continued

```
gagtcttgag actgaaagat ttagccataa tgtaaactgc ctcaaattgg actttgggca    2040
taaaagaact ttttatgct taccatcttt ttttttcttt taacagatttt gtatttaaga    2100 attgttttta aaaattttta a                                              2121
```

<210> SEQ ID NO 83
<211> LENGTH: 3597
<212> TYPE: DNA
<213> ORGANISM: Homo sapiens

<400> SEQUENCE: 83

```
ggcgaatgga gcaggggcgc gcagataatt aaagatttac acacagctgg aagaaatcat      60
agagaagccg gcgtggtgg ctcatgccta taatcccagc acttttggag gctgaggcgg      120
gcagatcact tgagatcagg agttcgagac cagcctggtg ccttggcatc tcccaatggg     180
gtggctttgc tctgggctcc tgttccctgt gagctgcctg gtcctgctgc aggtggcaag     240
ctctgggaac atgaaggtct tgcaggagcc acctgcgtc tccgactaca tgagcatctc      300
tacttgcgag tggaagatga atggtcccac caattgcagc accgagctcc gcctgttgta    360
ccagctggtt tttctgctct ccgaagccca cacgtgtatc cctgagaaca cggaggcgc     420 ggggtgcgtg tgccacctgc tcatggatga cgtggtcagt gcggataact atacactgga    480
cctgtgggct gggcagcagc tgctgtggaa gggctccttc aagcccagcg agcatgtgaa    540
acccagggcc ccaggaaacc tgacagttca caccaatgtc tccgacactc tgctgctgac    600
ctggagcaac ccgtatcccc ctgacaatta cctgtataat catctcacct atgcagtcaa    660
catttggagt gaaaacgacc cggcagattt cagaatctat aacgtgacct acctagaacc    720
ctccctccgc atcgcagcca gcaccctgaa gtctgggatt tcctacaggg cacgggtgag    780
ggcctgggct cagtgctata acaccacctg gagtgagtgg agccccagca ccaagtggca    840
caactcctac agggagccct tcgagcagca cctcctgctg ggcgtcagcg tttcctgcat    900
tgtcatcctg gccgtctgcc tgttgtgcta tgtcagcatc accaagatta agaaagaatg    960
gtgggatcag attcccaacc cagcccgcag ccgcctcgtg gctataataa tccaggatgc    1020
tcaggggtca cagtgggaga agcggtcccg aggccaggaa ccagccaagt gcccacactg    1080
gaagaattgt cttaccaagc tcttgccctg ttttctggag cacaacatga aaagggatga    1140
agatcctcac aaggctgcca aagagatgcc tttccaggc tctggaaaat cagcatggtg     1200
cccagtggag atcagcaaga cagtcctctg gccagagagc atcagcgtgg tgcgatgtgt    1260
ggagttgttt gaggccccgg tggagtgtga ggaggaggag gaggtagagg aagaaaaagg    1320
gagcttctgt gcatcgcctg agagcagcag ggatgacttc caggagggaa gggagggcat    1380
tgtggcccgg ctaacagaga gcctgttcct ggacctgctc ggagaggaga atggggcctt    1440
ttgccagcag gacatggggg agtcatgcct tcttccacct tcgggaagta cgagtgctca    1500
catgccctgg gatgagttcc caagtgcagg gccaaggag gcacctccct ggggcaagga     1560
gcagcctctc cacctggagc caagtcctcc tgccagcccg acccagagtc cagacaacct    1620
gacttgcaca gagacgcccc tcgtcatcgc aggcaaccct gcttaccgca gcttcagcaa    1680
ctccctgagc cagtcaccgt gtccagagag ctgggtcca gacccactgc tggccagaca     1740
cctggaggaa gtagaacccg agatgccctg tgtcccccag ctctctgagc caaccactgt    1800
gccccaacct gagccagaaa cctgggagca gatcctccgc gaaatgtcc tccagcatgg     1860 ggcagctgca gccccgtct cggccccac cagtggctat caggagtttg tacatgcggt     1920
ggagcagggt ggcacccagg ccagtgcggt ggtgggcttg ggtccccag gagaggctgg     1980
```

-continued

```
ttacaaggcc ttctcaagcc tgcttgccag cagtgctgtg tccccagaga aatgtgggtt    2040
tggggctagc agtggggaag aggggtataa gcctttccaa gacctcattc ctggctgccc    2100
tggggaccct gccccagtcc ctgtcccctt gttcaccttt ggactggaca gggagccacc    2160
tcgcagtccg cagagctcac atctcccaag cagctcccca gagcacctgg gtctggagcc    2220 ggggaaaag gtagaggaca tgccaaagcc cccacttccc caggagcagg ccacagaccc    2280
ccttgtggac agcctgggca gtggcattgt ctactcagcc cttacctgcc acctgtgcgg    2340
ccacctgaaa cagtgtcatg gccaggagga tggtggccag accctgtca tggccagtcc    2400 ttgctgtggc tgctgctgtg agacaggtc ctcgccccct acaacccccc tgagggcccc    2460
agacccctct ccaggtgggg ttccactgga ggccagtctg tgtccggcct ccctggcacc    2520
ctcgggcatc tcagagaaga gtaaatcctc atcatccttc catcctgccc ctggcaatgc    2580
tcagagctca agccagaccc caaaatcgt gaactttgtc tccgtgggac ccacatacat    2640
gagggtctct taggtgcatg tcctcttgtt gctgagtctg cagatgagga ctagggctta    2700
tccatgcctg ggaaatgcca cctcctggaa ggcagccagg ctggcagatt ccaaaagac    2760 ttgaagaacc atggtatgaa ggtgattggc cccactgacg ttggcctaac actgggctgc    2820
agagactgga ccccgcccag cattgggctg ggctcgccac atcccatgag agtagagggc    2880
actgggtcgc cgtgccccac ggcaggcccc tgcaggaaaa ctgaggccct tgggcacctc    2940
gacttgtgaa cgagttgttg gctgctccct ccacagcttc tgcagcagac tgtccctgtt    3000
gtaactgccc aaggcatgtt ttgcccacca gatcatggcc cacgtggagg cccacctgcc    3060
tctgtctcac tgaactagaa gccgagccta gaaactaaca cagccatcaa gggaatgact    3120
tgggcggcct tgggaaatcg atgagaaatt gaacttcagg gagggtggtc attgcctaga    3180
ggtgctcatt catttaacag agcttcctta ggttgatgct ggaggcagaa tcccggctgt    3240 caagggtgt tcagttaagg ggagcaacag aggacatgaa aaattgctat gactaaagca    3300
gggacaattt gctgccaaac acccatgccc agctgtatgg ctgggggctc ctcgtatgca    3360
tggaaccccc agaataaata tgctcagcca ccctgtgggc cggcaatcc agacagcagg    3420 cataaggcac cagttaccct gcatgttggc ccagacctca ggtgctaggg aaggcgggaa    3480
ccttgggttg agtaatgctc gtctgtgtgt tttagtttca tcacctgtta tctgtgtttg    3540
ctgaggagag tggaacagaa ggggtggagt tttgtataaa taaagtttct ttgtctc       3597
```

<210> SEQ ID NO 84
<211> LENGTH: 2709
<212> TYPE: DNA
<213> ORGANISM: Homo sapiens

<400> SEQUENCE: 84

```
gggaatagca gaataggagc aagccagcac tagtcagcta actaagtgac tcaaccaagg     60 cctttttcc ttgttatctt tgcagatact tcatttcttt agcgtttctg gagattacaa    120
catcctgcgg ttccgtttct gggaactttta ctgatttatc tccccctca cacaaataag    180 cattgattcc tgcatttctg aagatctcaa gatctggact actgttgaaa aaatttccag    240
tgaggctcac ttatgtctgt aaagatggga aaaaatca agaacattgt tctactaaaa    300
ggattagagg tcatcaatga ttatcatttt agaatggtta agtccttact gagcaacgat    360
ttaaaactta atttaaaaat gagagaagag tatgacaaaa ttcagattgc tgacttgatg    420
gaagaaaagt tccgaggtga tgctggtttg ggcaaactaa taaaaatttt cgaagatata    480
ccaacgcttg aagacctggc tgaaactctt aaaaaagaaa agttaaaagt aaaaggacca    540
```

```
gccctatcaa gaaagaggaa gaaggaagtg catgctactt cacctgcacc ctccacaagc      600
agcactgtca aaactgaagg agcagaggca actcctggag ctcagaaaag aaaaaaatca      660
accaaagaaa aggctggacc caaagggagt aaggtgtccg aggaacagac tcagcctccc      720
tctcctgcag gagccggcat gtccacagcc atgggccgtt ccccatctcc caagacctca      780
ttgtcagctc cacccaacag ttcttcaact gagaacccga aaacagtggc caaatgtcag      840
gtaactccca gaagaaatgt tctccaaaaa cgcccagtga tagtgaaggt actgagtaca      900
acaaagccat ttgaatatga accccagaa atggagaaaa aataatgtt tcatgctaca        960 gtggctacac agacacagtt cttccatgtg aaggttttaa acaccagctt gaaggagaaa     1020
ttcaatggaa agaaaatcat catcatatca gattatttgg aatatgatag tctcctagag     1080
gtcaatgaag aatctactgt atctgaagct ggtcctaacc aaacgtttga ggttccaaat     1140
aaaatcatca acagagcaaa ggaaactctg aagattgata ttcttcacaa acaagcttca     1200
ggaaatattg tatatggggt atttatgcta cataagaaaa cagtaaatca gaagaccaca     1260
atctacgaaa ttcaggatga tagaggaaaa atggatgtag tggggacagg acaatgtcac     1320
aatatcccct gtgaagaagg agataagctc cagcttttct gctttcgact tagaaaaaag     1380
aaccagatgt caaaactgat ttcagaaatg catagtttta tccagataaa gaaaaaaaca     1440
aacccgagaa acaatgaccc caagagcatg aagctacccc aggaacagcg tcagcttcca     1500
tatccttcag aggccagcac aaccttccct gagagccatc ttcggactcc tcagatgcca     1560
ccaacaactc catccagcag tttcttcacc aagaaaagtg aagacacaat ctccaaaatg     1620
aatgacttca tgaggatgca gatactgaag gaagggagtc attttccagg accgttcatg     1680
accagcatag gcccagctga gagccatccc cacactcctc agatgcctcc atcaacacca     1740
agcagcagtt tcttaaccac gttgaaacca agactgaaga ctgaacctga agaagtttcc     1800
atagaagaca gtgcccagag tgacctcaaa gaagtgatgg tgctgaacgc aacagaatca     1860
tttgtatatg agcccaaaga gcagaagaaa atgtttcatg ccacagtggc aactgagaat     1920
gaagtcttcc gagtgaaggt ttttaatatt gacctaaagg agaagttcac cccaaagaag     1980
atcattgcca tagcaaatta tgtttgccgc aatgggttcc tggaggtata tcctttcaca     2040
cttgtggctg atgtgaatgc tgaccgaaac atggagatcc caaaggatt gattagaagt      2100 gccagcgtaa ctcctaaaat caatcagctt tgctcacaaa ctaaggaag ttttgtgaat       2160 ggggtgtttg aggtacataa gaaaaatgta aggggtgaat tcacttatta tgaaatacaa     2220
gataatacag ggaagatgga agtggtggtg catggacgac tgaacacaat caactgtgag     2280
gaaggagata aactgaaact caccagcttt gaattggcac cgaaaagtgg gaataccggg     2340
gagttgagat ctgtaattca tagtcacatc aaggtcatca agaccaggaa aaacaagaaa     2400
gacatactca atcctgattc aagtatggaa acttcaccag acttttttctt ctaaaatctg     2460 gatgtcattg acgataatgt ttatggagat aaggtctaag tccctaaaaa aatgtacata     2520
tacctggttg aaatacaaca ctatacatac acaccaccat atatactagc tgttaatcct     2580
atggaatggg ggtattggga gtgcttttt aattttcat agtttttttt taataaaatg       2640
gcatattttg catctacaac ttctataata agaaaaaata aataaacatt atctttttg      2700 tgaaaaaaa                                                             2709
```

<210> SEQ ID NO 85
<211> LENGTH: 777
<212> TYPE: DNA
<213> ORGANISM: Homo sapiens

<400> SEQUENCE: 85

```
ttcttcaaac cctcctcttc cctgtgttct cctacagaga ttgctgattt ctccttaagc      60
aagagattca ctgccgctaa gcatggctca gaccaactcg ttcttcatgc tgatctcctc     120
cctgatgttc ctgtctctga gccaaggcca agaggcccag acagagttgc cccaggcccg     180
gatcagctgc ccagaaggca ccaatgccta tcgctcctac tgctactact ttaatgaaga     240
ccgtgagacc tgggttgatg cagatctcta ttgccagaac atgaattcgg caacctggt      300
gtctgtgctc acccaggccg agggtgcctt tgtggcctca ctgattaagg agagtggcac     360
tgatgacttc aatgtctgga ttggcctcca tgacccaaa aagaaccgcc gctggcactg      420
gagcagtggg tccctggtct cctacaagtc ctggggcatt ggagccccaa gcagtgttaa     480
tcctggctac tgtgtgagcc tgacctcaag cacaggattc cagaaatgga aggatgtgcc     540
ttgtgaagac aagttctcct ttgtatgcaa gttcaaaaac tagaggcagc tggaaaatac     600
atgtctagaa ctgatccagc aattacaacg gagtcaaaaa ttaaaccgga ccatctctcc     660
aactcaactc aacctggaca ctctcttctc tgctgagttt gccttgttaa tcttcaatag     720
ttttacctac cccagtcttt ggaaccctaa ataataaaaa taaacatgtt ttccact        777
```

<210> SEQ ID NO 86
<211> LENGTH: 2043
<212> TYPE: DNA
<213> ORGANISM: Homo sapiens

<400> SEQUENCE: 86

```
gtgcttaggc actgcagttg agtggctcac aaggagctaa aatttcacta atgcgtattc      60
agtgggtggt tctggttttgc ctgattttttg cctctgggca tggctgtttc agcctgagag    120
gctgttccaa gaatgttgct ttactaggag ctcatgccgc tggtggtaa atatgaagta      180
cagcagtgca acagaccagt tttactccaa ggaaaccctg tagagatgac agcaatggtt     240
ggtgatttct gcctcaatta tgaaagtgat ctggtgttac agggccagag aagactaggg     300
gagttcgggt tttctagacc aaacagacac tcagtcctgg gcctggaggt ctctgcagtg     360
aggtgctgcc acagacagag ccaccttaac tcctcaggac aaccagtggc ttccgacaca     420
cactatgcac tggagggcaa gcagctctca gcttgggagc aactgaggat ggtgaacagc     480
ctgggcaagg agtgctctga ggctaagacc ctgaacagca ggaaccgaag tgcagctccc     540
cacttcaggt aatgtgattc taccctttgc ctgagaaaca tatccatcct aattgccatg     600
tgctcagctg gaccactaga gggagccatc ctgtaacggg tgaggtcaac ctaacaaatg     660
gtatcagtcg agtattgatc ggaggccaac gcaagaagtt accagtagcc tatttcagat     720
ttattaaaaa acacataggt aacgagtcag agctttggct aggaatgatt tggaaaagaa     780
ctgaaggcat aattccacag gacattcaca gttgtgtgct agagacagag aggagcagga     840
aagtgtttta gaagcatttg cggtggacaa tggaaggccc ggcttcatcg tattcctgtt     900
tgctgatcca catctgctgg aaggtggaca gagaggccag gatggagcca ccgatccaga     960
cagagtattt gcgctccgga ggggcaatga tctgtcagtc aagatgaaaa agaatggtca    1020
ttaatgtcat cattagtgca gtcgttagtg cggtaggaca gagcctggat gttctaccat    1080
ggcctagttt cttgttcagc agggacacag gcttgtctgt tagatgccaa ttgtgtccta    1140
attgtgtcat gttcttggca ggaccgccag agggagccca ggatttagaa attcttcagt    1200
ggtttcatgg atgccagcag actccatccc tggaaaagag acacaggcca tggtccttaa    1260
gtggagagta aaacccaggc tagacatgga agaccagact tgaacatctg gatgatcttg    1320
```

```
cagtggactg aggctgggaa gacataataa tctaggaacc acctgtctga gagacaaaag   1380
ggtcttgtta tgctctatgt cttcctgcct gccttctaat gaggaaggcc tgctgcagca   1440
tcctgaggtg tgggctacaa cagaaatgct tttggtcttg ggcaaccgt cacttgtctc    1500
```
```
catgttctgg aggctggctt gatatggaag aagacaatga ctccccttcc caggaaaagg   1560
gcgtttgttg cctaccgatg aaggatggct ggaacagggt ctctgggcag cggaaacgtt   1620
catttccgat ggtgatcact tgcccatcag gcaactcgta actcttctca agggaggatg   1680
aggatgcggc agtggccatc tcattttcaa agtccagagc tacataacac agtttctcct   1740
tgatgtcccg gacaatctca cgctcagctg tcaaccagat acaaacattg tggcaaacat   1800
tagggtctgc acaggtggca aagattcacc tgccctactg cagtctctcc ctcaagacat   1860
gtgccatcaa aaaatgtgtc agttcaatat tctgcaatcc aaaatccaca atgataatga   1920
cgtagtaggg ccaccaggga accacctctg ttcctaggac agtgtctcat gcatagtagg   1980
ccctcagcat gcattgtctg ggaaatgcat aacaagaata aaatgagcta gctagagaaa   2040
ggc                                                                 2043

<210> SEQ ID NO 87
<211> LENGTH: 1501
<212> TYPE: DNA
<213> ORGANISM: Homo sapiens

<400> SEQUENCE: 87
agcgagtcct tcttttcctg actgcagctc ttttcatttt gccatccttc tccagctcca     60
tgatggttct gcaggtttct gcggcccccc ggacagtggc tctgacggcg ttactgatgg    120
tgctgctcac atctgtggtc cagggcaggg ccactccaga gaattacgtg taccagggac    180
ggcaggaatg ctacgcgttt aatgggacac agcgcttcct ggagagatac atctacaacc    240
gggaggagta cgcgcgcttc gacagcgacg tgggggagtt ccgggcggtg acggagctgg    300
ggcggcctgc tgcggagtac tggaacagcc agaaggacat cctggaggag aagcgggcag    360
tgccggacag ggtatgcaga cacaactacg agctggacga ggccgtgacc ctgcagcgcc    420
gagtccagcc taaggtgaac gtttcccct ccaagaaggg gccctgcag caccacaacc      480
```
```
tgcttgtctg ccacgtgaca gatttctacc caggcagcat tcaagtccga tggttcctga    540
atggacagga ggaaacagct ggggtcgtgt ccaccaacct gatccgtaat ggagactgga    600
ccttccagat cctggtgatg ctggaaatga cccccagca gggagacgtc tacatctgcc    660
aagtggagca caccagcctg acagtcctg tcaccgtgga gtggaaggca cagtctgatt     720
ctgcccagag taagacattg acgggagctg ggggcttcgt gctggggctc atcatctgtg    780
gagtgggcat cttcatgcac aggaggagca agaaagttca acgaggatct gcataaacag    840
ggttcctgac ctcaccgaaa agactaatgt gccttagaac aagcatttgc tgtgttttgt    900
taacacctgg ttccaggaca gaccctcagc ttcccaagag gatactgctg ccaagaagtt    960
gctctgaagt cagtttctat cgttctgctc tttgattcaa agcactgttt ctctcactgg   1020
gcctccaacc atgttccctt cttcttagca ccacaaataa tcaaaaccca acataagtgt   1080 ttgcttcct ttaaaatat gcatcaaatc gtctctcatt acttttctct gagggtttta    1140
gtaaacagta ggagttaata agaagttca ttttggttta cacgtaggaa agaagagaag   1200
catcaaagtg gagatatgtt aactattgta taatgtggcc tgttatacat gacactcttc   1260
tgaattgact gtatttcagt gagctgcccc caaatcaagt ttagtgccct catccattta   1320
tgtctcagac cgctattctt aactattcaa tggtgagcag actgcaaatc tgcctgatag   1380
```

```
gacccatatt cccacagcac taattcaaca tatatcttac tgagagcatg ttttatcatt    1440
accattaaga agttaaatga acatcagaat ttaaaatcat aaatataatc taatacactt    1500
t                                                                     1501
```

<210> SEQ ID NO 88
<211> LENGTH: 1096
<212> TYPE: DNA
<213> ORGANISM: Homo sapiens

<400> SEQUENCE: 88

```
atgatcctaa acaaagctct gctgctgggg gccctcgctc tgaccaccgt gatgagcccc      60
tgtggaggtg aagacattgt ggctgaccac gttgcctctt gtggtgtaaa cttgtaccag     120
ttttacggtc cctctggcca gtacacccat gaatttgatg agatgagca gttctacgtg      180 gacctggaga ggaaggagac tgcctggcgg tggcctgagt tcagcaaatt tggaggtttt     240
gacccgcagg gtgcactgag aaacatggct gtggcaaaac acaacttgaa catcatgatt     300
aaacgctaca actctaccgc tgctaccaat gaggttcctg aggtcacagt gttttccaag     360
tctcccgtga cactgggtca gcccaacacc ctcatttgtc ttgtggacaa catctttcct     420
cctgtggtca acatcacatg gctgagcaat gggcagtcag tcacagaagg tgtttctgag     480
accagcttcc tctccaagag tgatcattcc ttcttcaaga tcagttacct caccttcctc     540
ccttctgctg atgagattta tgactgcaag gtggagcact ggggcctgga ccagcctctt     600
ctgaaacact gggagcctga gattccagcc cctatgtcag agctcacaga gactgtggtc     660
tgtgccctgg ggttgtctgt gggcctcatg ggcattgtgg tgggcactgt cttcatcatc     720
caaggcctgc gttcagttgg tgcttccaga caccaagggc cattgtgaat cccatcctgg     780
aagggaaggt gcatcgccat ctacaggagc agaagaatgg acttgctaaa tgacctagca     840
ctattctctg gcccgattta tcatatccct tttctcctcc aaatatttct cctctcacct     900
tttctctggg acttaagctg ctatatcccc tcagagctca caaatgcctt tacattcttt     960
ccctgacctc ctgatttttt ttttcttttc tcaaatgtta cctacaatac atgcctgggg    1020
taagccaccc ggctacctaa ttcctcagta acctccatct aaaatctcca aggaagcaat    1080
aaattccttt tatgag                                                    1096
```

<210> SEQ ID NO 89
<211> LENGTH: 1100
<212> TYPE: DNA
<213> ORGANISM: Homo sapiens

<400> SEQUENCE: 89

```
ctaaagctgg gttggtagct cctacctact gtgtggcaag aaggtatggg tcatgaacag      60
aaccaaggag ctgcgctgct acagatgtta ccacttctgt ggctgctacc ccactcctgg     120
gccgtccctg aagctcctac tccaatgtgg ccagatgacc tgcaaaacca cacattcctg     180
cacacagtgt actgccagga tgggagtccc agtgtgggac tctctgaggc ctacgacgag     240
gaccagcttt tcttcttcga cttttcccag aacactcggg tgcctcgcct gcccgaattt     300
gctgactggg ctcaggaaca gggagatgct cctgccattt tatttgacaa agagttctgc     360
gagtggatga tccagcaaat agggccaaaa cttgatggga aaatcccggt gtccagaggg     420
tttcctatcg ctgaagtgtt cacgctgaag cccctggagt ttggcaagcc caacactttg     480
gtctgttttg tcagtaatct cttcccaccc atgctgacag tgaactggca gcatcattcc     540
gtccctgtgg aaggatttgg gcctactttt gtctcagctg tcgatggact cagcttccag     600
```

```
gccttttctt acttaaactt cacaccagaa ccttctgaca ttttctcctg cattgtgact      660
cacgaaattg accgctacac agcaattgcc tattgggtac cccggaacgc actgccctca      720
gatctgctgg agaatgtgct gtgtggcgtg gcctttggcc tgggtgtgct gggcatcatc      780
gtgggcattg ttctcatcat ctacttccgg aagccttgct caggtgactg attcttccag      840
accagagttt gatgccagca gcttcggcca tccaaacaga ggatgctcag atttctcaca      900
tcctgcccag gatctcctct tagggtagaa gaagtctctg gacatccct ggggtgtgtg       960 tgtagatttc ccacctgggg actctgctgt ccctgggctt gcatcccagg gatcccagag     1020
tggcctgcct atcacaacca catcccttcc ccccacaagg caataaatct catttcttta     1080
aaaaaaaaaa aaaaaaaaa                                                  1100

<210> SEQ ID NO 90
<211> LENGTH: 3526
<212> TYPE: DNA
<213> ORGANISM: Homo sapiens

<400> SEQUENCE: 90
ccacgcgtcc ggacaggctt aagcatggcc aagaagcttg agagaagaaa aatttcagaa       60
aaattgtctc aatttgacta gaatatcaat gaaccaggaa aactgaagca ccttccctaa      120
agaaaacttg ggtatacaat tactccacag acagagctga gggttttta cccaaatcag       180 tcactggatt ttgctgcctg atacgtgaat cttcttggaa tttttctcat gtggatctaa      240
ggggaatgct ttattatggc tgctgttgtc aacagaacg acctagtatt tgaatttgct       300
agtaacgtca tggaggatga acgacagctt ggtgatccag ctattttttcc tgccgtaatt      360 gtgaacatg ttcctggtgc tgatattctc aatagttatg ccggtctagc ctgtgtggaa       420
gagcccaatg acatgattac tgagagttca ctggatgttg ctgaagaaga aatcatagac       480
gatgatgatg atgacatcac ccttacagtt gaagcttctt gtcatgacgg ggatgaaaca      540
attgaaacta ttgaggctgc tgaggcactc ctcaatatgg attcccctgg ccctatgctg      600
gatgaaaaac gaataaataa taatatattt agttcacctg aagatgacat ggttgttgcc      660
ccagtcaccc atgtgtccgt cacattagat gggattcctg aagtgatgga acacagcag       720 gtgcaagaaa aatatgcaga ctcaccggga gcctcatcac cagaacagcc taagaggaaa      780
aaaggaagaa aaactaaacc accacgacca gattccccag ccactacgcc aaatatatct      840
gtgaagaaga aaacaaaga tggaagggga acacaattt atctttggga gttttactg       900 gcactgctcc aggacaaggc tacttgtcct aaatacatca gtggaccca gcgagagaaa       960 ggcattttta aattggtgga ttctaaagca gtgtccaggt tgtgggggaa gcacaaaaac     1020
aaacctgata tgaattatga gaccatggga gagcactca ggtactatta ccaaaggggt      1080
attctggcaa aagtggaagg tcagcgcttg gtgtatcagt ttaaagaaat gccaaaagat      1140
cttatatata taaatgatga ggatccaagt tccagcatag agtcttcaga tccatcacta     1200
tcttcatcag ccacttcaaa taggaatcaa accagccggt cgagagtatc ttcaagtcca     1260
ggggtaaaag gaggagccac tacagttcta aaaccaggga attctaaagc tgcaaaaccc     1320
aaagatcctg tggaagttgc acaaccatca gaagttttga ggacagtgca gcccacgcag     1380
tctccatatc ctacccagct cttccggact gttcatgtag tacagccagt acaggctgtc     1440
ccagagggag aagcagctag aaccagtacc atgcaggatg aaacattaaa ttcttccgtt     1500
cagagtatta ggactataca ggctccaacc caagttccag tggttgtgtc tcctaggaat     1560
cagcagttgc atacagtaac actccaaaca gtgccactca caacagttat agccagcaca     1620
```

```
gatccatcag caggtactgg atctcagaag tttattttac aagccattcc atcatcacag    1680
cccatgacag tactgaaaga aaatgtcatg ctgcagtcac aaaaggcggg ctctcctcct    1740
tcaattgtct tgggccctgc ccaggttcag caggtcctta ctagcaatgt tcagaccatt    1800
tgcaatggaa ccgtcagtgt ggcttcctct ccatccttca gtgctactgc acctgtggtg    1860 acctttctc ctcgcagttc acagctggtt gctcacccac ctggcactgt aatcacttca    1920
gttatcaaaa ctcaagaaac aaaaactctt acacaggaag tagagaaaaa ggaatctgaa    1980
gatcatttga aagagaacac tgagaaaacg gagcagcagc cacagcctta tgtgatggta    2040
gtgtccagtt ccaatggatt tacttctcag gtagctatga aacaaaacga actgctggaa    2100
cccaactctt tttagttaat ataccaaagc ttatgaataa ttgtttgtta attgaacatt    2160
ttcaattata tgcagactga ctgattctaa gataaattct aaggaggttt ctaattttgt    2220
aattgttaaa aatagagtta attttgactt tgttagatga gggaggaaaa ctcaactgtt    2280
tctctttgtt atctaaatgt ttcagaattc aatcgtgaag gaacaggcat tttacactat    2340
gaagacattc ttttgagatt tttatttcag ttgctatatc ataagcattt ttaaagtttc    2400
ttttctaatt ttacattgta ttagattttc tgattctttt gtaaatacag aacttaaata    2460
gaaggcaaca ggaaatttat ataggaacta ttttcattcc acttgtgtaa gttaagtctt    2520
gactctttca aatgcaaaaa acctatttta tgctttgtta aaattatggt gtcacttaga    2580
ttgactttag ttgactgcac tatataatat agaactatga atatgtagaa taacatgaaa    2640
aattggaggt gctggtggta tggctgaccc tgtttcagaa gcaggatagt ataaaagcat    2700
cagcctaaga atggcactcc cactaactag ctatgtaatc ttgacctctt tgggctttag    2760
ttcctctcat aaaaggaaga gatgtattgg attagactag attatcacca ctttctcttc    2820
tagttctaat ttttttaatt ctaataccta tattttcaag ttatgtcaat taaatcatta    2880
tcaggttatt tcctaatgta agaatagcta aaatgttgca gagaaataag tgacccaaca    2940
aaatttattc atctgttatg ggtaagatct gccataaatt cttcctaaat aatttgttta    3000
ctaactcttt aggccactgt gctttgcggt ccattagtaa acttgtgttg ctaagtgcta    3060
aacagaatac tgctattttg agagagtcaa gactcttttct taagggccaa gaaagcaact    3120
tgagccttgg gctaatctgg ctgagtagtc agttataaaa gcataattgc tttatatttt    3180
ggatcatttt ttactggggg cggacttggg ggggttgca tacaaagata acatatatat    3240
ccaactttct gaaatgaaat gttttagat tacttttca actgtaaata atgtacattt      3300
aatgtcacaa gaaaaaatg tcttctgcaa atttttctagt ataacagaaa ttttgtaga    3360 tgaaaaaaat cattatgttt agaggtctaa tgctatgttt tcatattaca gagtgaattt    3420
gtatttaaac aaaaatttaa attttggaat cctctaaaca ttttttgtatc tttaattggt    3480 ttattattaa ataaatcata taaaaattct caaaaaaaaa aaaaaa                   3526
```

<210> SEQ ID NO 91
<211> LENGTH: 1968
<212> TYPE: DNA
<213> ORGANISM: Homo sapiens

<400> SEQUENCE: 91

```
aattccgccg ggcgcttaga acagaggctt gcacaggtgg agatgtggaa gtctgtagtg      60
ggccatgatg tgtctgtttc cgtgggagacc cagggtgatg attgggacac agatcctgac    120
tttgtgaatg acatctctga aaaggagcaa cgatggggag ccaagaccat cgaggggtct    180
ggacgcacag aacacatcaa catccaccag ctgaggaaca agtatcaga ggagcatgat     240
```

| | | | |
|---|---|---|---|
| gttctcagga | agaaagagat | ggagtcaggg cccaaagcat cccatggcta tggaggtcgg | 300 |
| tttggagtag | aaagagaccg | aatggacaag agtgcagtgg gccatgagta tgttgccgag | 360 |
| gtggagaagc | actcttctca | gacggatgct gccaaaggct ttgggggcaa gtacggagtt | 420 |
| gagagggaca | gggcagacaa | gtcagcagtc ggctttgatt ataaaggaga agtggagaag | 480 |
| catacatctc | agaaagatta | ctctcgtggc tttggtggcc ggtacggggt ggagaaggat | 540 |
| aaatgggaca | aagcagctct | gggatatgac tacaagggag agacggagaa acacgagtcc | 600 |
| cagagagatt | atgccaaggg | ctttggtggc cagtatggaa tccagaagga ccgagtggat | 660 |
| aagagcgctg | tcggcttcaa | tgaaatggag cccccgacca cagcttataa gaagacgacg | 720 |
| cccatagaag | ccgcttctag | tggtgcccgt gggctgaagg cgaaatttga gtccatggct | 780 |
| gaggagaaga | ggaagcgaga | ggaagaggag aaggcacagc aggtggccag gaggcaacag | 840 |
| gagcgaaagg | ctgtgacaaa | gaggagccct gaggctccac agccagtgat agctatggaa | 900 |
| gagccagcag | taccggcccc | actgcccaag aaaatctcct cagaggcctg gcctccagtt | 960 |
| gggactcctc | catcatcaga | gtctgagcct gtgagaacca gcagggaaca cccagtgccc | 1020 |
| ttgctgccca | ttaggcagac | tctcccggag gacaatgagg agcccccagc tctgccccct | 1080 |
| aggactctgg | aaggcctcca | ggtggaggaa gagccagtgt acgaagcaga gcctgagcct | 1140 |
| gagcccgagc | ctgagcccga | gcctgagaat gactatgagg acgttgagga gatggacagg | 1200 |
| catgagcagg | aggatgaacc | agaggggac tatgaggagg tgctcgagcc tgaagattct | 1260 |
| tctttttctt | ctgctctggc | tggatcatca ggctgcccgg ctggggctgg ggctggggct | 1320 |
| gtggctctgg | ggatctcagc | tgtggctcta tatgattacc aaggagaggg aagtgatgag | 1380 |
| ctttcctttg | atccggacga | cgtaatcact gacattgaga tggtggacga gggctggtgg | 1440 |
| cggggacgtt | gccatggcca | cttttggactc ttccctgcaa attatgtcaa gcttctggag | 1500 |
| tgactagagc | tcactgtcta | ctgcaactgt gatttcccat gtccaaagtg gctctgctcc | 1560 |
| accccctccc | tattcctgat | gcaaatgtct aaccagatga gtttctggac agacttccct | 1620 |
| ctcctgcttc | attaagggct | tggggcagag acagcatggg gaaggaggtc cccttcccca | 1680 |
| agagtcctct | ctatcctgga | tgagctcatg aacatttctc ttgtgttcct gactccttcc | 1740 |
| caatgaacac | ctctctgcca | ccccaagctc tgctctcctc ctctgtgagc tctgggcttc | 1800 |
| ccagtttgtt | tacccgggaa | agtacgtcta gattgtgtgg tttgcctcat tgtgctattt | 1860 |
| gcccactttc | cttccctgaa | gaaatatctg tgaaccttct ttctgttcag tcctaaaatt | 1920 |
| cgaaataaag | tgagactatg | gttcacctgt aaaaaaaaaa aaggaatt | 1968 |

<210> SEQ ID NO 92
<211> LENGTH: 2088
<212> TYPE: DNA
<213> ORGANISM: Homo sapiens

<400> SEQUENCE: 92

| | | | |
|---|---|---|---|
| gaattcggca | cgagcgcgcg | gcgaatctca acgctgcgcc gtctgcgggc gcttccgggc | 60 |
| caccagtttc | tctgctttcc | accctggcgc ccccagccc tggctcccca gctgcgctgc | 120 |
| cccgggcgtc | cacgccctgc | gggcttagcg ggttcagtgg gctcaatctg cgcagcgcca | 180 |
| cctccatgtt | gaccaagcct | ctacaggggc ctcccgcgcc ccccgggacc cccacgccgc | 240 |
| cgccaggagg | caaggatcgg | gaagcgttcg aggccgagta tcgactcggc cccctcctgg | 300 |
| gtaagggggg | ctttggcacc | gtcttcgcag gacaccgcct cacagatcga ctccaggtgg | 360 |
| ccatcaaagt | gattccccgg | aatcgtgtgc tgggctggtc ccccttgtca gactcagtca | 420 |

```
catgcccact cgaagtcgca ctgctatgga aagtgggtgc aggtggtggg caccctggcg    480
tgatccgcct gcttgactgg tttgagacac aggaaggctt catgctggtc ctcgagcggc    540
cttgccccgc ccaggatctc tttgactata tcacagagaa gggcccactg ggtgaaggcc    600
caagccgctg cttctttggc caagtagtgg cagccatcca gcactgccat tcccgtggag    660
ttgtccatcg tgacatcaag gatgagaaca tcctgataga cctacgccgt ggctgtgcca    720
aactcattga ttttggttct ggtgccctgc ttcatgatga ccctacact gactttgatg    780
ggacaagggt gtacagcccc cagagtggaa tctctcgaca ccagtaccat gcactcccgg    840
ccactgtctg gtcactgggc atcctcctct atgacatggt gtgtgggac attccctttg    900
agagggacca ggagattctg gaagctgagc tccacttccc agcccatgtc tccccagact    960
gctgtgccca atccgccgg tgcctggccc ccaaaccttc ttcccgaccc tcactggaag    1020
agatcctgct ggaccctgg atgcaaacac cagccgagga tgttaccct caaccctcc     1080
aaaggaggcc ctgccccttt ggcctggtcc ttgctaccct aagcctggcc tggcctggcc    1140
tggcccccaa tggtcagaag agccatccca tggccatgtc acagggatag atggacattt    1200
gttgacttgg ttttacaggt cattaccagt cattaaagtc cagtattact aaggtaaggg    1260
attgaggatc aggggttaga agacataaac caagtttgcc cagttcctt cccaatccta     1320
caaaggagcc ttcctccag aacctgtggt ccctgatttt ggagggaa cttcttgctt       1380
ctcattttgc taaggaagtt tattttggtg aagttgttcc cattttgagc cccgggactc    1440
ttatttgat gatgtgtcac cccacattgg cacctcctac taccaccaca caaacttagt    1500
tcatatgctt ttacttgggc aagggtgctt tccttccaat accccagtag cttttatttt    1560
agtaaaggga cccttttcccc tagcctaggg tcccatattg ggtcaagctg cttacctgcc    1620
tcagcccagg attttttatt ttgggggagg taatgccctg ttgttacccc aaggcttctt    1680
ttttttttt ttttttttg gtgagggga ccctactttg ttatcccaag tgctcttatt       1740
ctggtgagaa gaaccttaat tccataattt gggaaggaat ggaagatgga caccaccgga    1800
caccaccaga caataggatg ggatggatgg ttttttgggg gatgggctag gggaaataag    1860
gcttgctgtt tgttttcctg gggcgctccc tccaattttg cagattttg caacctcctc     1920
ctgagccggg attgtccaat tactaaaatg taaataatca cgtattgtgg ggaggggagt    1980
tccaagtgtg ccctccttt ttttcctgcc tggattattt aaaaagccat gtgtggaaac      2040
ccactattta ataaaagtaa tagaatcaga aaaaaaaaaa aaaaaaa                  2088
```

<210> SEQ ID NO 93
<211> LENGTH: 415
<212> TYPE: DNA
<213> ORGANISM: Homo sapiens

<400> SEQUENCE: 93

```
ccgctgcgtg ttttcctctt gatcgggaac tcctgcttct ccttgcctcg aaatggaccc    60
caactgctcc tgctcgcctg ttggctcctg tgcctgtgcc ggctcctgca aatgcaaaga    120
gtgcaaatgc acctcctgca agaagagctg ctgctcctgc tgccctgtgg gctgtgcmaa    180
gtgtgcccag ggctgcatct gcaaagggac gtcagacaag tgcagctgct gtgcctgatg    240
ccaggacagc tgtgctctca gatgtaaata gagcaaccta tataaacctg gatttttttt    300
tttttttttt tgtacaaccc tgacccgttt gctacatctt ttttctatg aaatatgtga     360
atggcaataa attcatctag actaaaaaaa aaaaaaaaaa aaaaaaaaaa aaaaa          415
```

<210> SEQ ID NO 94

<211> LENGTH: 5725
<212> TYPE: DNA
<213> ORGANISM: Homo sapiens

<400> SEQUENCE: 94

| | | | | | |
|---|---|---|---|---|---|
| cctggaggag | ggctctggaa | gtcacgtcag | gttggctctt | caggttcatt | tccatagttc | 60 |
| cctgcggcct | ctgccttggg | gagttatgtt | ttgttaccga | gatccgcgct | accagattgc | 120 |
| accgggctg | atttggggc | tgggaatttg | ccattctgct | gtacagacac | tgattttttt | 180 |
| ttcttcttt | taaaaagcaa | ggtttgtttt | cattttggat | tttaggtgat | gggcaagtca | 240 |
| gaaagtcaga | tggatataac | tgatatcaac | actccaaagc | caagaagaa | acagcgatgg | 300 |
| actcgactgg | agatcagcct | ctcggtcctt | gtcctgctcc | tcaccatcat | agctgtgaga | 360 |
| atgatcgcac | tctatgcaac | ctacgatgat | ggtatttgca | agtcatcaga | ctgcataaaa | 420 |
| tcagctgctc | gactgatcca | aaacatggat | gccaccactg | agccttgtag | agacttttc | 480 |
| aaatatgctt | gcggaggctg | gttgaaacgt | aatgtcattc | ccgagaccag | ctcccgttac | 540 |
| ggcaactttg | acatttttaag | agatgaacta | gaagtcgttt | tgaaagatgt | ccttcaagaa | 600 |
| cccaaaactg | aagatatagt | agcagtgcag | aaagcaaaag | cattgtacag | gtcttgtata | 660 |
| aatgaatctg | ctattgatag | cagaggtgga | gaacctctac | tcaaactgtt | accagacata | 720 |
| tatgggtggc | cagtagcaac | agaaaactgg | gagcaaaaat | atggtgcttc | ttggacagct | 780 |
| gaaaaagcta | ttgcacaact | gaattctaaa | tatgggaaaa | aagtccttat | taatttgttt | 840 |
| gttggcactg | atgataagaa | ttctgtgaat | catgtaattc | atattgacca | acctcgactt | 900 |
| ggcctccctt | ctagagatta | ctatgaatgc | actggaatct | ataagagggc | ttgtacagca | 960 |
| tatgtggatt | ttatgatttc | tgtggccaga | ttgattcgtc | aggaagaaag | attgcccatc | 1020 |
| gatgaaaacc | agcttgcttt | ggaaatgaat | aaagttatgg | aattggaaaa | agaaattgcc | 1080 |
| aatgctacgg | ctaaacctga | agatcgaaat | gatccaatgc | ttctgtataa | caagatgaga | 1140 |
| ttggcccaga | tccaaaataa | cttttcacta | gagatcaatg | gaagccatt | cagctggttg | 1200 |
| aatttcacaa | atgaaatcat | gtcaactgtg | aatattagta | ttacaaatga | ggaagatgtg | 1260 |
| gttgtttatg | ctccagaata | tttaaccaaa | cttaagccca | ttcttaccaa | atattctgcc | 1320 |
| agagatcttc | aaaatttaat | gtcctggaga | ttcataatgg | atcttgtaag | cagcctcagc | 1380 |
| cgaacctaca | aggagtccag | aaatgctttc | cgcaaggccc | tttatggtac | aacctcagaa | 1440 |
| acagcaactt | ggagacgttg | tgcaaactat | gtcaatggga | atatggaaaa | tgctgtgggg | 1500 |
| aggctttatg | tggaagcagc | atttgctgga | gagagtaaac | atgtggtcga | ggatttgatt | 1560 |
| gcacagatcc | gagaagtttt | tattcagact | ttagatgacc | tcacttggat | ggatgccgag | 1620 |
| acaaaaaaga | gagctgaaga | aaaggcctta | gcaattaaag | aaaggatcgg | ctatcctgat | 1680 |
| gacattgttt | caaatgataa | caaactgaat | aatgagtacc | tcgagttgaa | ctacaaagaa | 1740 |
| gatgaatact | tcgagaacat | aattcaaaat | ttgaaattca | gccaaagtaa | acaactgaag | 1800 |
| aagctccgag | aaaaggtgga | caaagatgag | tggataagtg | gagcagctgt | agtcaatgca | 1860 |
| ttttactctt | caggaagaaa | tcagatagtc | ttcccagccg | gcattctgca | gccccccttc | 1920 |
| tttagtgccc | agcagtccaa | ctcattgaac | tatgggggca | tcggcatggt | cataggacac | 1980 |
| gaaatcaccc | atggcttcga | tgacaatggc | agaaacttta | caaagatgg | agacctcgtt | 2040 |
| gactggtgga | ctcaacagtc | tgcaagtaac | tttaaggagc | aatcccagtg | catggtgtat | 2100 |
| cagtatggaa | acttttcctg | ggacctggca | ggtggacagc | accttaatgg | aattaataca | 2160 |
| ctgggagaaa | acattgctga | taatggaggt | cttggtcaag | catacagagc | ctatcagaat | 2220 |

```
tatattaaaa agaatggcga agaaaaatta cttcctggac ttgacctaaa tcacaaacaa    2280 ctattttct  tgaactttgc acaggtgtgg tgtggaacct ataggccaga gtatgcggtt    2340
aactccatta aaacagatgt gcacagtcca ggcaatttca ggattattgg actttgcag    2400 aactctgcag agttttcaga agcctttcac tgccgcaaga attcatacat gaatccagaa    2460
aagaagtgcc gggtttggtg atcttcaaaa gaagcattgc agcccttggc tagacttgcc    2520
aacaccacag aaatggggaa ttctctaatc gaaagaaaat gggccctagg ggtcactgta    2580
ctgacttgag ggtgattaac agagagggca ccatcacaat acagataaca ttaggttgtc    2640
ctagaaaggg tgtggaggga ggaagggggt ctaaggtcta tcaagtcaat catttctcac    2700
tgtgtacata atgcttaatt tctaaagata atattactgt ttatttctgt ttctcatatg    2760
gtctaccagt ttgctgatgt ccctagaaaa caatgcaaaa cctttgaggt agaccaggat    2820
ttctaatcaa aagggaaaag aagatgttga agaatagagt taggcaccag aagaagagta    2880
ggtgacacta tagtttaaaa cacattgcct aactactagt ttttactttt atttgcaaca    2940
tttacagtcc ttcaaaatcc ttccaaagaa ttcttataca cattggggcc ttggagctta    3000
catagtttta aactcatttt tgccatacat cagttattca ttctgtgatc atttatttta    3060
agcactctta aagcaaaaaa tgaatgtcta aaattgtttt ttgttgtacc tgctttgact    3120
gatgctgaga ttcttcaggc ttcctgcaat tttctaagca atttcttgct ctatctctca    3180
aaacttggta tttttcagag atttatataa atgtaaaaat aataattttt atatttaatt    3240
attaactaca tttatgagta actattatta taggtaatca atgaatattg aagtttcagc    3300
ttaaaataaa cagttgtgaa ccaagatcta taaagcgata tacagatgaa aatttgagac    3360
tatttaaact tataaatcat attgatgaaa agatttaagc acaaacttta gggtaaaaat    3420
tgcgattgga cagttgtcta gagatatata tacttgtggt tttcaaattg gacttttcaaa   3480 attaaatctg tccctgagag tgtctctgat aaaagggcaa atctgcacct atgtagctct    3540
gcatctcctg tcttttcagg tttgtcatca gatggaaata ttttgataat aaattgaaat    3600
tgtgaactca ttgctcccta agactgtgac aactgtctaa ctttagaagt gcatttctga    3660
atagaaatgg gaggcctctg atggaccttc tagaattata agtcacaaag agttctggaa    3720
aagaactgtt tactgcttga taggaattca tcttttgagg cttctgttcc tctcttttcc    3780
tgttgtattg actattttcg ttcattactt gattaagatt ttacaaaaga ggagcacttc    3840
caaaattctt attttcccta acaaagatg aaagcaggga atttctatct aaatgatgag    3900
tattagttcc ctgtctcttg aaaaatgccc atttgccttt aaaaaaaaaa gttacagaaa    3960
tactataaca tatgtacata aattgcataa agcataagta tacagttcaa taaacttaac    4020
tttaactgaa caatggccct gtagccagca cctgtaagaa acagagcagt accagcgctc    4080
taaaagcacc tccttgtcac tttattactc ccagaacaac aactatcctg acttctaata    4140
tcattcacta gctttgcctg gttttgtctt ttatgcagat agaatcaatc agtatgtatt    4200
cttttgtgcc tggcttcttt ctctcagcct tacatttgtg agattcctct gtattgtgct    4260
gattgtggat cttttcattc tcattgcaga ataatgttct attgtgggac ttattacaat    4320
ttgttcatcc tattgttgat gggcacttga gaactttcca ttttggcgct attacaaata    4380
gtgcaactat gaatgtactg catgttacca tcttacttga gcctttaatg gacttatttc    4440
ttcaaatcct tccaaaaatt attataagca ttgaaattat agtttcaagc caactgtgga    4500
tacccttacc ctttcctcct ttatcacaac caccgttaca agtatactta tatttccta    4560 aaatacattt aaaacttacc taagtgacat ttgtagttgg agtaatagga gcttccagct    4620
```

| | |
|---|---|
| ctaataaaac agctgtctct aacttatttt atttccatca tgtcagagca ggtgaagagc | 4680 |
| cagaagtgaa gagtgactag tacaaattat aaaaagccac tagactcttc actgttagct | 4740 |
| ttttaaaaca ttaggctccc atccctatgg aggaacaact ctccagtgcc tggatcccct | 4800 |
| ctgtctacaa atataagatt ttctgggcct aaaggataga tcaaagtcaa aaatagcaat | 4860 |
| gcctccctat ccctcacaca tccagacatc atgaatttta catggtactc ttgttgagtt | 4920 |
| ctatagagcc ttctgatgtc tctaaagcac taccgattct ttggagttgt cacatcagat | 4980 |
| aagacatatc tctaattcca tccataaatc cagttctact atggctgagt tctggtcaaa | 5040 |
| gaaagaaagt ttagaagctg agacacaaag ggttgggagc tgatgaaact cacaaatgat | 5100 |
| ggtaggaaga agctctcgac aatacccgtt ggcaaggagt ctgcctccat gctgcagtgt | 5160 |
| tcgagtggat tgtaggtgca agatggaaag gattgtaggt gcaagctgtc cagagaaaag | 5220 |
| agtccttgtt ccagccctat tctgccactc ctgacagggt gaccttgggt atttgcaata | 5280 |
| ttcctttggg cctctgcttc tctcacctaa aaaaagagaa ttagattata ttggtggttc | 5340 |
| tcagcaagag aaggagtatg tgtccaatgc tgccttccca tgaatctgtc tcccagttat | 5400 |
| gaatcagtgg gcaggataaa ctgaaaactc ccatttaagt gtctgaatcg agtgagacaa | 5460 |
| aattttagtc caaataacaa gtaccaaagt tttatcaagt ttgggtctgt gctgctgtta | 5520 |
| ctgttaacca tttaagtggg gcaaaacctt gctaattttc tcaaaagcat ttatcattct | 5580 |
| tgttgccaca gctggagctc tcaaactaaa agacatttgt tattttggaa agaagaaaga | 5640 |
| ctctattctc aaagtttcct aatcagaaat tttatcagt ttccagtctc aaaaatacaa | 5700 |
| aataaaaaca aacgttttta atact | 5725 |

<210> SEQ ID NO 95
<211> LENGTH: 3259
<212> TYPE: DNA
<213> ORGANISM: Homo sapiens

<400> SEQUENCE: 95

| | |
|---|---|
| gacgcgcgcc gggagccggc ggccgggcca gccggcgccg gggcccagtg cgccgcgctc | 60 |
| gcagccggta gcgcgccagc cgtaggcgtc gctcggcagc cgcggggccc taggcgtgcc | 120 |
| ggggaggggg cgagggcggc caggcgcctg ccgccccgga ggcaggatga gcatcgagat | 180 |
| cccggcggga ctgacggagc tgctgcaggg cttcacggtg gaggtgctga ggcaccagcc | 240 |
| cgcggacctg ctggagttcg cgctgcagca cttcacccgc ctgcagcagg agaacgagcg | 300 |
| caaaggcacc gcgcgcttcg gccatgaggg caggacctgg ggggacctgg gcgccgctgc | 360 |
| cgggggcggc accccagca aggggtcaa cttcgccgag gagcccatgc agtccgactc | 420 |
| cgaggacggg gaggaggagg aggcggcgcc cgcggacgca gggcgttca atgctccagt | 480 |
| aataaaccga ttcacaaggc gtgcctcagt atgtgcagaa gcttataatc ctgatgaaga | 540 |
| agaagatgat gcagagtcca ggattataca tccaaaaact gatgatcaaa gaaataggtt | 600 |
| gcaagaggct tgcaaagaca tcctgctgtt taagaatctg gatccggagc agatgtctca | 660 |
| agtattagat gccatgtttg aaaaattggt caaagatggg gagcatgtaa ttgatcaagg | 720 |
| tgacgatggt gacaactttt atgtaattga tagaggcaca tttgatattt atgtgaaatg | 780 |
| tgatggtgtt ggaagatgtg ttggtaacta tgataatcgt gggagtttcg gcgaactggc | 840 |
| cttaatgtac aatacacccca gagcagctac aatcactgct acctctcctg gtgctctgtg | 900 |
| gggtttggac agggtaaccct tcaggagaat aattgtgaaa acaatgccaa aaagagaaa | 960 |
| aatgtatgaa agctttattg agtcactgcc attccttaaa tctttggagt tttctgaacg | 1020 |

```
cctgaaagta gtagatgtga taggcaccaa agtatacaac gatggagaac aaatcattgc    1080
tcagggagat tcggctgatt cttttttcat tgtagaatct ggagaagtga aaattactat    1140
gaaaagaaag ggtaaatcag aagtggaaga gaatggtgca gtagaaatgc ctcgatgctc    1200 gcgggggacag tactttggag agcttgccct ggtaactaac aaacctcgag cagcttctgc    1260
ccacgccatt gggactgtca atgtttagc aatggatgtg caagcatttg aaaggcttct    1320
gggaccttgc atggaaatta tgaaaaggaa catcgctacc tatgaagaac agttagttgc    1380
cctgtttgga acgaacatgg atattgttga acccactgca tgaagcaaaa gtatggagca    1440
agacctgtag tgacaaaatt acacagtagt ggttagtcca ctgagaatgt gtttgtgtag    1500
atgccaagca ttttctgtga tttcaggttt tttccttttt ttacatttac aacgtatcaa    1560
taaacagtag tgatttaata gtcaataggc tttaacatca ctttctaaag agtagttcat    1620
aaaaaaatca acatactgat aaaatgactt tgtactccac aaaattatga ctgaaaggtt    1680
tattaaaatg attgtaatat atagaaagta tctgtgttta agaagataat taaaggatgt    1740
tatcataggc tatatgtgtt ttacttattc agactgataa tcatattagt gactatcccc    1800
atgtaagagg gcacttggca attaaacatg ctacacagca tggcatcact ttttttttata    1860 actcattaaa cacagtaaaa ttttaatcat ttttgtttta aagttttcta gcttgataag    1920
ttatgtgctg ccttggccta ttggtgaaat ggtataaaat atcatatgca gttttaaaac    1980
tttttatatt tttgcaataa agtacatttt gactttgttg gcataatgtc agtaacatac    2040
atattccagt ggttttatgg acaggcaatt tagtcattat gataataagg aaaacagtgt    2100
tttagatgag agatcattaa tgcatttttc cctcatcaag catatatctg ctttttttta    2160
ttttgcaatt ctctgtattc tatgtcttta aaaatttgat cttgacattt aatgtcacaa    2220
agttttgttt ttttaaaaag tgatttaaac ttaagatccg acatttttg tattctttaa    2280 gattttacac ctaaaaaatc tctcctatcc caaaaataat gtgggatcct tatcagcatg    2340
cccacagttt atttctttgt tcttcactag gcctgcataa tacagtccta tgtagacatc    2400
tgttcccttg ggtttccgtt cttttcttagg atggttgcca acccacaatc tcattgatca    2460
gcagccaata tgggtttgtt tggtttttt aattcttaaa aacatcctct agaggaatag    2520
aaacaaattt ttatgagcat aaccctatat aaagacaaaa tgaatttctg accttaccat    2580
atataccatt aggccttgcc attgctttaa tgtagactca tagttgaaat tagtgcagaa    2640
agaactcaga tgtactagat tttcattgtt cattgatatg ctcagtatgc tgccacataa    2700
gatgaattta attatattca accaaagcaa tatactctta catgatttct aggcccatg    2760 acccagtgtc tagagacatt aattctaacc agttgtttgc ttttaaatga gtgatttcat    2820
tttgggaaac aggtttcaaa tgaatatata tacatgggta aaattactct gtgctagtgt    2880
agtcttacta gagaatgttt atggtcccac ttgtatatga aaatgtggtt agaatgttaa    2940
ttggataatg tatatataag aagttaaagt atgtaaagta taacttcagc cacatttta    3000 gaacactgtt taacattttt gcaaaacctt cttgtaggaa aagagagctc tctacatgaa    3060
gatgacttgt tttatatttc agatttttatt ttaaaagcca tgtctgttaa acaagaaaaa    3120
acacaaaaga actccagatt cctggttcat cattctgtat tcttactcac tttttcaagt    3180
tatctatttt gttgcataaa ctaattgtta actattcatg gaacagcaaa cgcctgttta    3240
ataaagaact ttgaccaag                                                 3259
```

<210> SEQ ID NO 96
<211> LENGTH: 2376
<212> TYPE: DNA

<213> ORGANISM: Homo sapiens

<400> SEQUENCE: 96

```
cgagggcagc gccggtcggg agcgcagcgc ggcgcagctc ggcgcgcacg cggggagcgg      60
cgcgcgagtg gtcgggcctg gcggctggac gggcgcccct cgctgccccg cgcgctcccc     120
gccgcccccc atgagcgcag ccccgcgcgg cccgggtccg taggcggcgg ggcgcccccc     180
atgctgctgc agcccgcgcc gtgcgccccg agcgcgggct tcccgcggcc cctgccgcc      240
cccggcgcca tgcacggctc gcagaaggac accacgttca ccaagatctt cgtgggcggc     300
ctgccgtacc acactaccga cgcctcgctc aggaagtact tcgagggctt cggcgacatc     360
gaggaggccg tggtcatcac cgaccgccag acgggcaagt cccgcggcta cggcttcgtg     420
accatggccg accgggcggc agctgagagg gcttgcaaag acccgaaccc catcatcgac     480
ggccgcaagg ccaacgtgaa cctggcatat ctgggcgcca agccgcggag cctccagacg     540
ggctttgcca ttggggtgca gcagctgcac cccaccttga tccagcggac ttacgggctg     600
accccgcact acatctaccc accagccatc gtgcagccca gcgtggtgat cccagccgcc     660
cctgtcccgt cgctgtcctc gccctacatt gagtacacgc cggccagccc ggcctacgcc     720
cagtacccac cggccaccta tgaccagtac ccatacgccg cctcgcctgc cacggctgcc     780
agcttcgtgg gctacagcta ccctgccgcc gtgcccagg ccctctcagc cgcagcaccc      840
gcgggcacca ctttcgtgca gtaccaggcg ccgcagctgc agcctgacag gatgcagtga     900
ggggcgttcc tgccccgagg actgtggcat tgtcaccttc acagcagaca gagctgccag     960
gccatgatgg gctggcgaca gcccggctga gctttagtga ggtgccacca gcacccgtgc    1020
ctccgaagac cgctcgggca ttccgcctgc gccctgggac agcggagaga tggcttctct    1080
ttaatctagg tcccattgtg tcttgaggga ggactttaag aatgactgag aactatttaa    1140
agacgcaatc ccaggttcct tgcacaccat ggcagcctct tcttgcacct tctcctgcct    1200
ctccacactc caggttccct caggcttgtg tccccactgc tgcatcgtgg cggggtgtca    1260
cagaccctct gcagcccctg gctgccctgg actgtgcaga gatgcctgac tccagggaaa    1320
cctgaaagca agaagttaat ggactgttta ttgtaacttg atcctcccga gctgtgagcg    1380
cagtctgagg tgtgaggaca cggcctcctg ttggagtccc attttctcca tcagggcacg    1440
tgggcggctt cctcaagccc ggaggagctc ccaggcgcac aggggccgcc ggtaacaggg    1500
gccgccggcc aaaggcccct ttccagtcat agcactgaag ttgcaacttt ttcttgtaa     1560
ttgttttgct actaagataa tttcagaagt tcagtctatt ttttcagcgg atactgccgc    1620
caccaagaat ccaaaaccta tttttgactt ggagagactt gcttttgttg gttccgcccg    1680
tggagacgac gacagtgttt ctgtataata aagtgtctgc cggctcgcgg gccaggatcc    1740
tctcggtggg atgggcacca cagacaggag gcccctcagg cccgtgcggg ccactgtctg    1800
ctgccgcctg ccggggtggc agagtgagtt gtctcaggac cccgtcactg cgacgttgac    1860
actctctcct tccttccttc cccaactccc caaacactgt ggaagggaag aaggaagtga    1920
tccacagcat tcaggccact tggggtctag accatggtgg tgccagcctg ggggggggcag   1980
tggccctcag ctctgcccgc tggagcggtt gagtgcagaa gggtgcgcct cttccctcta    2040
cccccgcacc acctgctgtg tgccagcctg agacggttcc tgcctgtctt ggggttggt     2100
ggagggtgga ggcagttctg ccagccgtgg cagggctgct atggggcatc cagggctgtg    2160
ggggtctgga ggaggggaca tgaggtgaga ggtatcctgg ccgagggcgg ggggcagcgg    2220
ggggtctccc tccggaccta cctcagggag ctgagcgtgc aggcgctcca gggcaggcct    2280
```

```
gggacagagt caaggctcag agaataaagg tagctaatct catcataata tttttattag    2340
aatgttctga tgataaaaat aaaacttgtt ttcttt                              2376

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
gttgtaaaac gacggccagt g                                              21

<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98
cacacaggaa acagctatg                                                 19

<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99
tttttttttt tttttttttt v                                              21
```